US012165747B2

(12) United States Patent
Regev et al.

(10) Patent No.: US 12,165,747 B2
(45) Date of Patent: Dec. 10, 2024

(54) MOLECULAR SPATIAL MAPPING OF METASTATIC TUMOR MICROENVIRONMENT

(71) Applicants: The Broad Institute, Inc., Cambridge, MA (US); Massachusetts Institute of Technology, Cambridge, MA (US); Dana-Farber Cancer Institute, Inc., Boston, MA (US)

(72) Inventors: Aviv Regev, Cambridge, MA (US); Johanna Klughammer, Cambridge, MA (US); Daniel Abravanel, Boston, MA (US)

(73) Assignees: The Broad Institute, Inc., Cambridge, MA (US); Massachusetts Institute of Technology, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 368 days.

(21) Appl. No.: 17/156,392

(22) Filed: Jan. 22, 2021

(65) Prior Publication Data

US 2021/0358573 A1 Nov. 18, 2021

Related U.S. Application Data

(60) Provisional application No. 62/965,130, filed on Jan. 23, 2020.

(51) Int. Cl.

| | |
|---|---|
| ***G16B 45/00*** | (2019.01) |
| ***C12N 5/09*** | (2010.01) |
| ***C12Q 1/6841*** | (2018.01) |
| ***C12Q 1/6886*** | (2018.01) |
| ***G01N 33/50*** | (2006.01) |
| ***G16B 25/10*** | (2019.01) |
| ***G16H 30/40*** | (2018.01) |
| ***G16H 70/60*** | (2018.01) |

(52) U.S. Cl.

CPC ........... *G16B 45/00* (2019.02); *C12N 5/0693* (2013.01); *C12Q 1/6841* (2013.01); *C12Q 1/6886* (2013.01); *G01N 33/5023* (2013.01); *G16B 25/10* (2019.02); *G16H 30/40* (2018.01); *G16H 70/60* (2018.01); *C12Q 2600/158* (2013.01)

(58) Field of Classification Search

CPC ........ G16B 45/00; G16B 25/10; G16H 70/60; G16H 30/40; C12N 5/0693; C12Q 1/6841; C12Q 1/6886; C12Q 2600/158; G01N 33/5023

See application file for complete search history.

(56) References Cited

U.S. PATENT DOCUMENTS

| | | | |
|---|---|---|---|
| 4,737,323 | A | 4/1988 | Martin et al. |
| 4,837,028 | A | 6/1989 | Allen |
| 5,143,854 | A | 9/1992 | Fodor et al. |
| 5,288,644 | A | 2/1994 | Beavis et al. |
| 5,324,633 | A | 6/1994 | Fodor et al. |
| 5,432,049 | A | 7/1995 | Fischer et al. |
| 5,470,710 | A | 11/1995 | Weiss et al. |
| 5,492,806 | A | 2/1996 | Ormanac et al. |
| 5,503,980 | A | 4/1996 | Cantor |
| 5,510,270 | A | 4/1996 | Fodor et al. |
| 5,525,464 | A | 6/1996 | Drmanac et al. |
| 5,547,839 | A | 8/1996 | Dower et al. |
| 5,580,732 | A | 12/1996 | Grossman et al. |
| 5,580,737 | A | 12/1996 | Polisky et al. |
| 5,641,870 | A | 6/1997 | Rinderknecht et al. |
| 5,660,985 | A | 8/1997 | Pieken et al. |
| 5,661,028 | A | 8/1997 | Foote |
| 5,686,281 | A | 11/1997 | Roberts |
| 5,800,992 | A | 9/1998 | Fodor et al. |
| 5,811,097 | A | 9/1998 | Allison et al. |
| 5,843,728 | A | 12/1998 | Seed et al. |
| 5,851,828 | A | 12/1998 | Seed et al. |
| 5,858,358 | A | 1/1999 | June et al. |

(Continued)

FOREIGN PATENT DOCUMENTS

| | | |
|---|---|---|
| EP | 0404097 A2 | 12/1990 |
| EP | 0785280 A2 | 7/1997 |

(Continued)

OTHER PUBLICATIONS

Jin et al., In vivo Perturb-Seq reveals neuronal and glial abnormalities associated with Autism risk genes, bioRxiv, 2019 (Year: 2019).*
Zhong et al (Identification of key genes as potential biomarkers for TNBC using integrating genomic analysis, Mol. Med. Reports, 21 , pp. 557-566, 2019) (Year: 2019).*
Becht, et al., "Dimensionality Reduction for Visualizing Single-Cell Data Using UMAP", Nature Biotechnology, vol. 37, No. 1, Jan. 2019, 38-44.
Becht, et al., "Evaluation of UMAP as an Alternative to T-SNE for Single-Cell Data", bioRxiv, Apr. 10, 2018, 10 pages.

(Continued)

*Primary Examiner* — Mark Halvorson
*Assistant Examiner* — Dennis J Sullivan
(74) *Attorney, Agent, or Firm* — Foley & Lardner LLP; Sunit Talapatra

(57) ABSTRACT

The present invention discloses novel methods and uses thereof for producing molecular spatial maps of metastatic breast cancer (MBC) and ductal carcinoma in situ of the breast (DCIS). A specific list of genes are identified using single-cell RNA sequencing and single-nucleus RNA sequencing and are used for RNA visualization of MBC and DCIS tissue microenvironment. Unexpected subtypes of tumor cells are revealed, and methods for identifying molecular biomarkers for MBC in the bone and breast and DCIS are disclosed. Furthermore, methods for identifying therapeutic agents and uses thereof for treating MBC and DCIS as well as compositions thereof comprising such identified therapeutic agents are provided.

16 Claims, 49 Drawing Sheets

Specification includes a Sequence Listing.

(56) References Cited

U.S. PATENT DOCUMENTS

| | | | |
|---|---|---|---|
| 5,869,326 | A | 2/1999 | Hofmann |
| 5,883,223 | A | 3/1999 | Gray |
| 5,906,936 | A | 5/1999 | Eshhar et al. |
| 5,912,170 | A | 6/1999 | Seed et al. |
| 5,912,172 | A | 6/1999 | Eshhar et al. |
| 6,004,811 | A | 12/1999 | Seed et al. |
| 6,040,177 | A | 3/2000 | Riddell et al. |
| 6,284,240 | B1 | 9/2001 | Seed et al. |
| 6,352,694 | B1 | 3/2002 | June et al. |
| 6,392,013 | B1 | 5/2002 | Seed et al. |
| 6,410,014 | B1 | 6/2002 | Seed et al. |
| 6,479,626 | B1 | 11/2002 | Kim et al. |
| 6,489,458 | B2 | 12/2002 | Hackett et al. |
| 6,534,055 | B1 | 3/2003 | June et al. |
| 6,534,261 | B1 | 3/2003 | Cox et al. |
| 6,607,882 | B1 | 8/2003 | Cox et al. |
| 6,746,838 | B1 | 6/2004 | Choo et al. |
| 6,753,162 | B1 | 6/2004 | Seed et al. |
| 6,794,136 | B1 | 9/2004 | Eisenberg et al. |
| 6,797,514 | B2 | 9/2004 | Berenson et al. |
| 6,824,978 | B1 | 11/2004 | Cox et al. |
| 6,866,997 | B1 | 3/2005 | Choo et al. |
| 6,867,041 | B2 | 3/2005 | Berenson et al. |
| 6,887,466 | B2 | 5/2005 | June et al. |
| 6,903,185 | B2 | 6/2005 | Kim et al. |
| 6,905,680 | B2 | 6/2005 | June et al. |
| 6,905,681 | B1 | 6/2005 | June et al. |
| 6,905,874 | B2 | 6/2005 | Berenson et al. |
| 6,933,113 | B2 | 8/2005 | Case |
| 6,979,539 | B2 | 12/2005 | Cox et al. |
| 7,013,219 | B2 | 3/2006 | Case et al. |
| 7,030,215 | B2 | 4/2006 | Liu et al. |
| 7,144,575 | B2 | 12/2006 | June et al. |
| 7,148,203 | B2 | 12/2006 | Hackett et al. |
| 7,160,682 | B2 | 1/2007 | Hackett et al. |
| 7,175,843 | B2 | 2/2007 | June et al. |
| 7,220,719 | B2 | 5/2007 | Case et al. |
| 7,232,566 | B2 | 6/2007 | June et al. |
| 7,241,573 | B2 | 7/2007 | Choo et al. |
| 7,241,574 | B2 | 7/2007 | Choo et al. |
| 7,446,190 | B2 | 11/2008 | Sadelain et al. |
| 7,572,631 | B2 | 8/2009 | Berenson et al. |
| 7,585,849 | B2 | 9/2009 | Liu et al. |
| 7,595,376 | B2 | 9/2009 | Kim et al. |
| 7,741,465 | B1 | 6/2010 | Eshhar et al. |
| 7,985,739 | B2 | 7/2011 | Kay et al. |
| 8,021,867 | B2 | 9/2011 | Smith et al. |
| 8,034,334 | B2 | 10/2011 | Dudley et al. |
| 8,088,379 | B2 | 1/2012 | Robbins et al. |
| 8,119,361 | B2 | 2/2012 | Smith et al. |
| 8,119,381 | B2 | 2/2012 | Smith et al. |
| 8,124,369 | B2 | 2/2012 | Smith et al. |
| 8,129,134 | B2 | 3/2012 | Smith et al. |
| 8,133,697 | B2 | 3/2012 | Smith et al. |
| 8,163,514 | B2 | 4/2012 | Smith et al. |
| 8,211,422 | B2 | 7/2012 | Eshhar et al. |
| 8,227,432 | B2 | 7/2012 | Hackett et al. |
| 8,399,645 | B2 | 3/2013 | Campana et al. |
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 8,637,307 | B2 | 1/2014 | June et al. |
| 8,697,854 | B2 | 4/2014 | Schendel et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,181,527 | B2 | 11/2015 | Sentman |
| 9,233,125 | B2 | 1/2016 | Davila et al. |
| 10,059,990 | B2 | 8/2018 | Boyden et al. |
| 2004/0171156 | A1 | 9/2004 | Hartley et al. |
| 2004/0224402 | A1 | 11/2004 | Bonyhadi et al. |
| 2010/0104509 | A1 | 4/2010 | King et al. |
| 2011/0265198 | A1 | 10/2011 | Gregory et al. |
| 2012/0017290 | A1 | 1/2012 | Cui et al. |
| 2012/0219947 | A1 | 8/2012 | Yurkovetsky et al. |
| 2012/0244133 | A1 | 9/2012 | Rosenberg et al. |
| 2013/0071414 | A1 | 3/2013 | Dotti et al. |
| 2013/0236946 | A1 | 9/2013 | Gouble |
| 2015/0368342 | A1 | 12/2015 | Wu et al. |
| 2015/0368360 | A1 | 12/2015 | Liang et al. |
| 2016/0046724 | A1 | 2/2016 | Brogdon et al. |
| 2016/0060691 | A1 | 3/2016 | Giresi et al. |
| 2016/0129109 | A1 | 5/2016 | Davila et al. |
| 2016/0166613 | A1 | 6/2016 | Spencer et al. |
| 2016/0175359 | A1 | 6/2016 | Spencer et al. |
| 2016/0208323 | A1 | 7/2016 | Bernstein et al. |
| 2017/0047193 | A1 | 2/2017 | Jiang et al. |
| 2017/0211142 | A1 | 7/2017 | Smargon et al. |
| 2017/0283504 | A1 | 10/2017 | Wiltzius et al. |
| 2017/0321251 | A1 | 11/2017 | Nolan |
| 2018/0085444 | A1 | 3/2018 | Morgan et al. |
| 2018/0100201 | A1 | 4/2018 | Garraway et al. |
| 2018/0320224 | A1 | 11/2018 | Gaublomme et al. |
| 2018/0340939 | A1 | 11/2018 | Gaublomme et al. |
| 2019/0218276 | A1 | 7/2019 | Regev et al. |
| 2019/0241967 | A1* | 8/2019 | Baker .................. C12Q 1/6886 |
| 2019/0263912 | A1 | 8/2019 | Haber et al. |
| 2019/0285644 | A1 | 9/2019 | Regev et al. |
| 2019/0314398 | A1* | 10/2019 | Simone ................ C12N 15/113 |
| 2021/0047694 | A1 | 2/2021 | Regev et al. |

FOREIGN PATENT DOCUMENTS

| | | | | |
|---|---|---|---|---|
| EP | 0373203 | B2 | 2/2007 | |
| EP | 3587731 | A1 * | 1/2020 | ............. E21C 37/16 |
| WO | 92/15322 | A1 | 9/1992 | |
| WO | 93/11161 | A1 | 6/1993 | |
| WO | 95/21265 | A1 | 8/1995 | |
| WO | 96/31622 | A1 | 10/1996 | |
| WO | 96/40281 | A2 | 12/1996 | |
| WO | 97/10365 | A1 | 3/1997 | |
| WO | 97/27317 | A1 | 7/1997 | |
| WO | WO-97/49450 | A1 | 12/1997 | |
| WO | WO-98/52609 | A1 | 11/1998 | |
| WO | 03/020763 | A2 | 3/2003 | |
| WO | 03/057171 | A2 | 7/2003 | |
| WO | 2004/033685 | A1 | 4/2004 | |
| WO | 2004/044004 | A2 | 5/2004 | |
| WO | 2004/074322 | A1 | 9/2004 | |
| WO | 2005/113595 | A2 | 12/2005 | |
| WO | 2005/114215 | A2 | 12/2005 | |
| WO | 2006/000830 | A2 | 1/2006 | |
| WO | 2006/125962 | A2 | 11/2006 | |
| WO | 2008/038002 | A2 | 4/2008 | |
| WO | 2008/039818 | A2 | 4/2008 | |
| WO | WO-2009/012418 | A2 | 1/2009 | |
| WO | 2011/146862 | A1 | 11/2011 | |
| WO | 2012/058460 | A2 | 5/2012 | |
| WO | 2012/079000 | A1 | 6/2012 | |
| WO | 2013/039889 | A1 | 3/2013 | |
| WO | 2013/040371 | A2 | 3/2013 | |
| WO | 2013/044225 | A1 | 3/2013 | |
| WO | 2013/154760 | A1 | 10/2013 | |
| WO | 2013/166321 | A1 | 11/2013 | |
| WO | 2013/176915 | A1 | 11/2013 | |
| WO | 2014/011987 | A1 | 1/2014 | |
| WO | 2014/018863 | A1 | 1/2014 | |
| WO | 2014/047561 | A1 | 3/2014 | |
| WO | 2014/059173 | A2 | 4/2014 | |
| WO | 2014/083173 | A1 | 6/2014 | |
| WO | 2014/085802 | A1 | 6/2014 | |
| WO | 2014/093622 | A2 | 6/2014 | |
| WO | 2014/133567 | A1 | 9/2014 | |
| WO | 2014/133568 | A1 | 9/2014 | |
| WO | 2014/134165 | A1 | 9/2014 | |
| WO | 2014/172606 | A1 | 10/2014 | |
| WO | 2014/184744 | A1 | 11/2014 | |
| WO | 2014/191128 | A1 | 12/2014 | |
| WO | 2014/204725 | A1 | 12/2014 | |
| WO | WO-2014/210353 | A2 | 12/2014 | |

(56) References Cited

FOREIGN PATENT DOCUMENTS

| | | | | |
|---|---|---|---|---|
| WO | 2015/057834 | A1 | 4/2015 | |
| WO | 2015/057852 | A1 | 4/2015 | |
| WO | 2015/120096 | A2 | 8/2015 | |
| WO | 2015/142675 | A2 | 9/2015 | |
| WO | 2015/158671 | A1 | 10/2015 | |
| WO | 2015/187528 | A1 | 12/2015 | |
| WO | 2016/000304 | A1 | 1/2016 | |
| WO | 2016/011210 | A2 | 1/2016 | |
| WO | 2016/014789 | A2 | 1/2016 | |
| WO | WO-2016001006 | A1 * | 1/2016 | ............. B01L 3/508 |
| WO | WO-2016/040476 | A1 | 3/2016 | |
| WO | 2016/070061 | A1 | 5/2016 | |
| WO | 2016/106236 | A1 | 6/2016 | |
| WO | WO-2016/168584 | A1 | 10/2016 | |
| WO | 2016/191756 | A1 | 12/2016 | |
| WO | 2016/196388 | A1 | 12/2016 | |
| WO | 2017/004916 | A1 | 1/2017 | |
| WO | 2017/011804 | A1 | 1/2017 | |
| WO | 2017/070395 | A1 | 4/2017 | |
| WO | WO-2017/070605 | A1 | 4/2017 | |
| WO | 2017/132291 | A1 | 8/2017 | |
| WO | 2017/156336 | A1 | 9/2017 | |
| WO | WO-2017/164936 | A1 | 9/2017 | |
| WO | 2017/211900 | A1 | 12/2017 | |
| WO | 2018/028647 | A1 | 2/2018 | |
| WO | 2018/191520 | A1 | 10/2018 | |
| WO | 2018/191558 | A1 | 10/2018 | |
| WO | 2018/213708 | A1 | 11/2018 | |
| WO | 2018/213726 | A1 | 11/2018 | |
| WO | 2019/005884 | A1 | 1/2019 | |
| WO | 2019/005886 | A1 | 1/2019 | |
| WO | 2019/018423 | A1 | 1/2019 | |
| WO | 2019/018440 | A1 | 1/2019 | |
| WO | 2019/060746 | A1 | 3/2019 | |
| WO | 2019/071048 | A1 | 4/2019 | |
| WO | 2019/094984 | A1 | 5/2019 | |
| WO | 2019/126709 | A1 | 6/2019 | |
| WO | 2019/126716 | A1 | 6/2019 | |
| WO | 2019/126762 | A2 | 6/2019 | |
| WO | WO-2019241273 | A1 * | 12/2019 | ............. A61K 45/06 |
| WO | WO-2019246499 | A1 * | 12/2019 | ........... A61K 31/015 |
| WO | 2020/033601 | A1 | 2/2020 | |
| WO | 2020/077236 | A1 | 4/2020 | |
| WO | 2020/131862 | A1 | 6/2020 | |

OTHER PUBLICATIONS

Bielecki, et al., "Skin Inflammation Driven by Differentiation of Quiescent Tissue-resident ILCs Into a Spectrum of Pathogenic Effectors", bioRxiv, Nov. 12, 2018, 43 pages.

Chen, et al., "RNA Imaging. Spatially Resolved, Highly Multiplexed RNA Profiling in Single Cells", Science, vol. 348, No. 6233, Apr. 24, 2015, 14 pages.

Du Verle, et al., "CellTree: An R/bioconductor Package to Infer the Hierarchical Structure of Cell Populations from Single-Cell RNA-Seq Data", BMC Bioinformatics, vol. 17, Article No. 363, 2016, 17 pages.

Wang, et al., "The Allen Mouse Brain Common Coordinate Framework: A 3D Reference Atlas", Cell, vol. 181, No. 4, May 14, 2020, 936-953.

Lamb, Justin "The Connectivity Map: A New Tool for Biomedical Research", Nature Reviews Cancer, vol. 7, No. 1, Jan. 2007, 54-60.

Lamb, et al., "The Connectivity Map: Using Gene-Expression Signatures to Connect Small Molecules, Genes, and Disease", Science, vol. 313, Issue 5795, Sep. 29, 2006, 1929-1935.

Shekhar, et al., "Comprehensive Classification of Retinal Bipolar Neurons by Single-Cell Transcriptomics", Cell, vol. 166, No. 5, Aug. 25, 2016, 57 pages.

Stegmaier, et al., "Gene Expression-Based High-Throughput Screening (Ge-Hts) and Application to Leukemia Differentiation", Nature Genetics, vol. 36, No. 3, Mar. 2004, 257-263.

Vickovic, et al., "High-Definition Spatial Transcriptomics for in Situ Tissue Profiling", Nature Methods, vol. 16, No. 10, Oct. 2019, 987-990.

Bartunek et al., Avian stem cell factor (SCF): production and characterization of the recombinant His-tagged SCF of chicken and its neutralizing antibody, Cytokine, Jan. 1996, vol. 8, Issue 1 (pp. 14-20).

Burlingame et al., "Mass spectrometry," Analytical Chemistry, Aug. 15, 1998, vol. 70, No. 16 (pp. 647-716).

Dellinger et al., "Streamlined process for the chemical synthesis of RNA using 2'-O-thionocarbamate-protected nucleoside phosphoramidites in the solid phase," Journal of the American Chemical Society, Aug. 3, 2011, vol. 133, No. 30 (p. 11540-11556).

Gruber et al., "The Vienna RNA Websuite," Nucleic Acids Research, Apr. 19, 2008, vol. 36 (pp. W70-W74).

Hobbs et al., "Polynucleotides containing 2'-amino-2'-deoxyribose and 2'-azido-2'-deoxyribose," Biochemistry, 1973, vol. 12, No. 25 (pp. 5138-5145).

Howard et al., "Acute subdural hematomas: an age-dependent clinical entity," Journal of Neurosurgery, vol. 71, No. 6 (pp. 858-863).

Junker et al., "CD70: a new tumor specific biomarker for renal cell carcinoma," The Journal of Urology, Jun. 2005, vol. 173, No. 6 (pp. 2150-2153).

Levy-Nissenbaum et al., Nanotechnology and aptamers: applications in drug delivery, Trends in Biotechnology, Aug. 2008, vol. 26, No. 8 (pp. 442-449).

Liautard et al., "Specific Inhibition of IL-6 Signalling with Monoclonal Antibodies Against the gp130 Receptor," Cytokine, Apr. 1997, vol. 9, No. 4 (pp. 223-241).

Morocz et al., "Brain edema development after MRI-guided focused ultrasound treatment," Journal of Magnetic Resonance Imaging, Jan.-Feb. 1998, vol. 8, No. 1 (pp. 136-142).

Moussatov et al., "A Possible Approach to The Treatment of Polycystic Ovarian Syndrome Using Focused Ultrasound," Ultrasonics, 1998, vol. 36, No. 8 (pp. 893-900).

Nixon et al., "Engineered protein inhibitors of proteases," Current Opinion in Drug Discovery & Development, Mar. 1, 2006, vol. 9, No. 2 (pp. 261-268).

Parris et al., "Additive effect of the AZGP1, PIP, S100A8 and UBE2C molecular biomarkers improves outcome prediction in breast carcinoma," International Journal of Cancer, 2014, vol. 134 (pp. 1617-1629).

Powell et al. "Compendium of Excipients for Parenteral Formulations," PDA Journal of Pharmaceutical Science and Technology, Sep./Oct. 1998, vol. 52, No. 2 (pp. 238-311).

Scaringe et al., "Advanced 5'-silyl-2'-orthoester approach to RNA oligonucleotide synthesis," Methods in Enzymology, 2000, vol. 317 (pp. 3-18).

Scaringe et al., "Novel RNA Synthesis Method Using 5'-O-Silyl-2'-O-orthoester Protecting Groups," Journal of the American Chemical Society, 1998, vol. 120, No. 45 (pp. 11820-11821).

Twyman et al., "Glutamate Receptor Antibodies Activate a Subset of Receptors and Reveal an Agonist Binding Site," Neuron, Apr. 1995, vol. 14 (pp. 755-762).

Abudayyeh et al., C2c2 is a single-component programmable RNA-guided RNA targeting CRISPR effector, Science, Aug. 5, 2016, vol. 353, No. 6299 (23 pages).

Agathanggelou et al., "Expression of immune regulatory molecules in Epstein-Barr virus—associated nasopharyngeal carcinomas with prominent lymphoid stroma. Evidence for a functional interaction between epithelial tumor cells and infiltrating lymphoid cells," American Journal of Pathology, Oct. 1995, vol. 147, No. 4 (pp. 1152-1160).

Allerson et al., "Fully 2'-Modified Oligonucleotide Duplexes with Improved in Vitro Potency and Stability Compared to Unmodified Small Interfering RNA," American Chemical Society, Journal of Medicinal Chemistry, Feb. 2005, vol. 48 (pp. 901-904).

Altman et al., "Phenotypic Analysis of Antigen-specific T Lymphocytes," Science, Oct. 4, 1996, vol. 274, No. 5284 (pp. 94-96).

Andersen et al., "Parallel detection of antigen-specific T cell responses by combinatorial encoding of MHC multimers", Nature Protocols, vol. 7, No. 5, 2012 (pp. 891-902).

(56) References Cited

OTHER PUBLICATIONS

Appleby et al. "New technologies for ultra-high throughput genotyping in plants", Methods in Molecular Biology, Plant Genomics, vol. 513 (pp. 19-39).
Baba et al., "Highly Enhanced Expression of CD70 on Human T-Lymphotropic Virus Type 1-Carrying T-Cell Lines and Adult T-Cell Leukemia Cells," Journal of Virology, Apr. 2008, vol. 82, No. 8 (pp. 3843-3852).
Bartel et al., "MicroRNAs: Genomics, Biogenesis, Mechanism, and Function," Cell, Jan. 23, 2004, vol. 116, No. 2 (pp. 281-297).
Berdeja et al., "Durable Clinical Responses in Heavily Pretreated Patients with Relapsed/Refractory Multiple Myeloma: Updated Results from a Multicenter Study of bb2121 Anti-Bcma CAR T Cell Therapy," Blood 2017, vol. 130 (pp. 740).
Besser et al., "Clinical responses in a phase II study using adoptive transfer of short-term cultured tumor infiltration lymphocytes in metastatic melanoma patients," Clinical Cancer Research, May 1, 2010, vol. 16, No. 9 (pp. 2646-2655).
Binz et al., "Engineering novel binding proteins from nonimmunoglobulin domains," Nature Biotechnology, 2005, vol. 23 (pp. 1257-1268).
Bird, Robert E. et al., "Single-Chain Antigen-Binding Proteins," Science, Oct. 1988, vol. 242 (pp. 423-426).
Blei et al., "Latent Dirichlet Allocation," Journal of Machine Learning Research 3, 2003 (pp. 993-1022).
Boch, et al., "Breaking the Code of DNA Binding Specificity of TAL-Type III Effectors," Science, vol. 326, Dec. 11, 2009 (pp. 1509-1512).
Bondeson et al., "Targeted Protein Degradation by Small Molecules," Annual Review of Pharmacology and Toxicology, Jan. 6, 2017, vol. 57 (pp. 107-123).
Boni et al., "Adoptive transfer of allogeneic tumor-specific T cells mediates effective regression of large tumors across major histocompatibility barriers," Blood, Dec. 1, 2008, vol. 112, No. 12 (pp. 4746-4754).
Bramsen et al., "Development of Therapeutic-Grade Small Interfering RNAs by Chemical Engineering," Frontiers in Genetics, Aug. 20, 2012, vol. 3, Article 154 (pp. 22).
Brown et al., "Propellant-Driven Aerosols of Proteins," Aerosol Science and Technology, Jan. 1996, vol. 24 (pp. 45-55).
Budde et al., "Combining a CD20 Chimeric Antigen Receptor and an Inducible Caspase 9 Suicide Switch to Improve the Efficacy and Safety of T Cell Adoptive Immunotherapy for Lymphoma," PLoS One, 2013, vol. 8, No. 12, e82742 (10 pages).
Buenrostro et al. "Transposition of native chromatin for fast and sensitive epigenomic profiling of open chromatin, DNA-binding proteins and nucleosome position," Nature Methods, Dec. 2013, vol. 10, No. 12 (pp. 1213-1218).
Buenrostro et al., "Single-cell chromatin accessibility reveals principles of regulatory variation," Nature, Jul. 23, 2015, vol. 523, No. 7561 (pp. 486-490).
Cao et al., "Comprehensive single-cell transcriptional profiling of a multicellular organism," Science, Aug. 18, 2017, vol. 357, No. 6352 (pp. 661-667).
Carlson et al., "Identification of Amino Acids in the Glutamate Receptor, GluR3, Important for Antibody-binding and Receptor-specific Activation," The Journal of Biological Chemistry, Apr. 25, 1997, vol. 272, No. 17 (pp. 11295-11301).
Carr et al., "Genome Engineering," Nature Biotechnology, Dec. 2009, vol. 27, No. 12 (pp. 1151-1162).
Cermak et al., "Efficient Design and Assembly of Custom Talen and Other Tal Effector-Based Constructs for DNA Targeting", Nucleic Acids Research, 2011, vol. 39, No. 12 (pp. 1-11).
Chahlavi et al., "Glioblastomas Induce T-Lymphocyte Death by Two Distinct Pathways Involving Gangliosides and CD70," Cancer Research, Jun. 15, 2005, vol. 65, No. 12 (pp. 5428-5438).
Charman, "Lipids, Lipophilic Drugs, and Oral Drug Delivery-Some Emerging Concepts," Journal of Pharmaceutical Sciences, 2000, vol. 89, No. 8 (pp. 967-978).
Chen et al., "Dynamic Imaging of Genomic Loci in Living Human Cells by an Optimized CRISPR/Cas System," Cell, 2013, vol. 155 (pp. 1479-1491).
Chen et al., "Effects of Interleukin-1a, Interleukin-1 Receptor Antagonist, and Neutralizing Antibody on Proinflammatory Cytokine Expression by Human Squamous Cell Carcinoma Lines," Cancer Research, Aug. 15, 1998, vol. 58, (pp. 3668-3676).
Chen et al., "Spatially Resolved, Highly Multiplexed RNA Profiling in Single Cells," Science, Apr. 2015, vol. 348, No. 6233 (15 pages).
Chen et al., "Expansion Microscopy," Science, Jan. 30, 2015, vol. 47, No. 6221 (pp. 543-548).
Chung et al., "Polycistronic RNA polymerase II expression vectors for RNA interference based on BIC/miR-155," Nucleic Acids Research, 2006, vol. 34, No. 7 (14 pages).
Cooper et al., "T-cell clones can be rendered specific for CD19: toward the selective augmentation of the graft-versus-B-lineage leukemia effect," Blood, Feb. 15, 2003, vol. 101, No. 4 (pp. 1637-1644).
Cotten et al., "2'-O-methyl, 2'-O-ethyl oligoribonucleotides and phosphorothioate oligodeoxyribonucleotides as inhibitors of the in vitro U7 snRNP-dependent mRNA processing event," Nucleic Acids Research, vol. 19, Issue 10, May 11, 1991 (pp. 2629-2635).
Cox et al., "RNA editing with CRISPR-Cas13," Science, Nov. 24, 2017, vol. 358, No. 6366 (pp. 1019-1027).
Cusanovich et al., "Multiplex single-cell profiling of chromatin accessibility by combinatorial cellular indexing" Science, May 22, 2015, vol. 348, No. 6237 (pp. 910-914).
Dar et al.—Abstract 1540: Allogeneic chimeric antigen receptor T cells targeting B cell maturation antigen American Association of Cancer Research, Poster Presentations—Proffered Abstracts, Jul. 1, 2018 (3 pages).
Deng et al., "An Agonist Murine Monoclonal Antibody to the Human c-Mpl Receptor Stimulates Megakaryocytopoiesis," Blood, Sep. 1998, vol. 92, No. 6 (pp. 1981-1988).
Deng et al., "CASFISH: CRISPR/Cas9-mediated in situ labeling of genomic loci in fixed cells," Proceedings of the National Academy of Sciences, USA, Sep. 22, 2015, vol. 112, No. 38 (pp. 11870-11875).
Di Stasi et al., "Inducible apoptosis as a safety switch for adoptive cell therapy," Clinical Trial, New England Journal of Medicine, Nov. 3, 2011, vol. 365, No. 18 (pp. 1673-1683).
Dudley et al., "Adoptive Cell Transfer Therapy Following Non-Myeloablative but Lymphodepleting Chemotherapy for the Treatment of Patients with Refractory Metastatic Melanoma", Journal of Clinical Oncology, Apr. 1, 2005, vol. 23, No. 10, (pp. 2346-2357).
Dudley et al., "Cancer regression and autoimmunity in patients after clonal repopulation with antitumor lymphocytes," Science, 2002, vol. 298, No. 5594 (pp. 850-854).
East-Seletsky et al., "Two distinct RNase activities of CRISPR-C2c2 enable guide-RNA processing and RNA detection," Nature, Oct. 13, 2016, vol. 538, No. 7624 (pp. 270-273).
Friedman et al., "Effective Targeting of Multiple BCMA-Expressing Hematological Malignancies by Anti-BCMA CART Cells," Human Gene Therapy, May 2018, vol. 29, No. 5 (pp. 585-601).
Gangadharan et al., "Prolactin induced protein (PIP) is a potential biomarker for early stage and malignant breast cancer," Breast, 2018, vol. 39 (pp. 101-109).
Gebauer and Skerra, "Engineered protein scaffolds as next-generation antibody therapeutics," Current Opinion in Chemical Biology, Jun. 2009, vol. 13, No. 3 (pp. 245-255).
Geiss et al., "Direct multiplexed measurement of gene expression with color-coded probe pairs," Nature Biotechnology, 2008, vol. 26, No. 3 (pp. 317-325).
Genbank identifier NM_006139.
Georgiadis et al., "Long Terminal Repeat CRISPR-CAR-Coupled 'Universal' T Cells Mediate Potent Anti-leukemic Effects," Molecular Therapy, May 2, 2018 Vol. 26, No. 5 (pp. 1215-1227).
Gierahn et al., "Seq-Well: Portable, Low-Cost RNA Sequencing of Single Cells at High Throughput," Nature Methods, Apr. 2017, vol. 14, No. 4 (9 pages).
Gill et al., "Biopharmaceutical drug discovery using novel protein scaffolds," Current Opinion in Biotechnology, 2006, vol. 17, No. 6 (653-658).

(56) References Cited

OTHER PUBLICATIONS

Greco et al., "Improving the safety of cell therapy with the TK-suicide gene," Frontiers in Pharmacology, May 5, 2015, vol. 6, No. 95 (13 pages).
Guo et al., "Droplet microfluidics for high-throughput biological assays" Lab Chip, 2012, vol. 12 (pp. 2146-2155).
Habib et al., "Div-Seq: Single-nucleus RNA-Seq reveals dynamics of rare adult newborn neurons," Science, Aug. 26, 2016, vol. 353, No. 6302 (pp. 925-928).
Habib et al., "Massively parallel single-nucleus RNA-seq with DroNc-seq," Nature Methods, Oct. 2017, vol. 14, No. 10 (pp. 955-958).
Harrop et al., "Antibodies to TR2 (Herpesvirus Entry Mediator), a New Member of the TNF Receptor Superfamily, Block T Cell Proliferation, Expression of Activation Markers, and Production of Cytokines," Journal of Immunology, 1998, vol. 161, No. 4 (pp. 1786-1794).
Hashimshony, et al., "CEL-Seq: Single-Cell RNA-Seq by Multiplexed Linear Amplification," Cell Reports, 2012, vol. 2, No. 3 (pp. 666-673).
Head et al., "Library construction for next-generation sequencing: Overviews and challenges," Biotechniques, 2014, vol. 56, No. 2 (pp. 61-77).
Hendel et al., "Chemically modified guide RNAs enhance CRISPR-Cas genome editing in human primary cells," Nature Biotechnology Sep. 2015, vol. 33, No. 9 (pp. 985-989).
Hicke et al., "Escort aptamers: a delivery service for diagnosis and therapy," The Journal of Clinical Investigation, Oct. 2000, vol. 106, No. 8 (pp. 923-928).
Hinrichs et al., "Exploiting the curative potential of adoptive T-cell therapy for cancer," Immunological Reviews, Jan. 2014, vol. 257, No. 1 (pp. 56-71).
Hollinger et al., "Diabodies": Small bivalent and bispecific antibody fragments, Proceedings of the National Academy of Sciences, USA, Jul. 1993, vol. 90 (pp. 6444-6448).
Houot et al., "T-cell-based immunotherapy: adoptive cell transfer and checkpoint inhibition," Cancer Immunology Research, 2015, vol. 3, No. 10 (pp. 1115-1122).
Hsu et al., "Development and Applications of CRISPR-Cas9 for Genome Engineering," Cell, 2014, vol. 157 (pp. 1262-1278).
Hughes et al., "Highly Efficient, Massively-Parallel Single-Cell RNA-Seq Reveals Cellular States and Molecular Features of Human Skin Pathology," bioRxiv, 689273, this version posted Jul. 2, 2019 (51 pages).
Hughes et al., "Transfer of a TCR gene derived from a patient with a marked antitumor response conveys highly active T-cell effector functions," Human Gene Therapy, Apr. 2005, vol. 16, No. 4 (pp. 457-472).
Hunter et al., "High Levels of Soluble Immunoregulatory Receptors in Patients with Waldenstro M's Macroglobulinemia," Blood, Nov. 16, 2004, vol. 104, No. 11 (2 pages).
Huston et al., "Protein engineering of antibody binding sites: recovery of specific activity in an anti- digoxin single-chain Fv analogue produced in *Escherichia coli*," Proceedings of the National Academy of Sciences, USA, 1988, vol. 85 (pp. 5879-5883).
Imelfort et al., "De novo sequencing of plant genomes using second-generation technologies," Briefings in Bioinformatics, 2009, vol. 10, No. 6 (pp. 609-618).
Inoue et al., "An inducible translocation strategy to rapidly activate and inhibit small GTPase signaling pathways," Nature Methods, Jun. 2005, vol. 2, No. 6 (pp. 415-418).
Irving et al., "Engineering Chimeric Antigen Receptor T-Cells for Racing in Solid Tumors: Don't Forget the Fuel," Frontiers in Immunology, Apr. 3, 2017, vol. 8, Article 267 (19 pages).
Islam, et al., "Characterization of the single-cell transcriptional landscape by highly multiplex RNA-seq," Genome Research, 2011, vol. 21, No. 7 (pp. 1160-1167).
Jensen et al., "Design and Implementation of Adoptive Therapy with Chimeric Antigen Receptor-Modified T Cells," Immunological Reviews, Jan. 2014, vol. 257, No. 1 (32 pages).
Jin et al., "CD70, a novel target of CAR T-cell therapy for gliomas," Neuro-Oncology Jan. 10 2018, vol. 20, No. 1 (pp. 55-65).
Johnson et al., "Gene therapy with human and mouse T-cell receptors mediates cancer regression and targets normal tissues expressing cognate antigen," Blood, Jul. 2009, vol. 114, No. 3 (pp. 535-546).
Kalisky et al., "Genomic Analysis at the Single-Cell Level," Annual Review of Genetics, 2011, vol. 45 (pp. 431-445).
Kalisky et al., "Single-cell genomics," Nature Methods, Apr. 2011, vol. 8, No. 4 (pp. 311-314).
Kalos et al., "T Cells with Chimeric Antigen Receptors Have Potent Antitumor Effects and Can Establish Memory in Patients with Advanced Leukemia," Science Translational Medicine, Aug. 10, 2011, vol. 3, No. 95 (12 pages).
Kamta et al. "Advancing Cancer Therapy with Present and Emerging Immuno-Oncology Approaches," Frontiers in Oncology, Apr. 18, 2017, vol. 7, No. 64 (15 pages).
Keefe et al., "Aptamers as therapeutics," Nature Reviews, Jul. 2010, vol. 9 (pp. 537-550).
Kelley et al., "Versatility of chemically synthesized guide RNAs for CRISPR-Cas9 genome editing," Journal of Biotechnology, Sep. 2016, vol. 233, 10 (pp. 74-83).
Kim et al., "Chimeric restriction endonuclease.," Proceedings of the National Academy of Sciences, USA, Feb. 1994, vol. 91, No. 3 (pp. 883-887).
Kim et al., "Hybrid restriction enzymes: zinc finger fusions to Fok I cleavage domain," Proceedings of the National Academy of Sciences, USA, Feb. 6, 1996, vol. 93, No. 3 (pp. 1156-1160).
Klein et al., "Droplet barcoding for single-cell transcriptomics applied to embryonic stem cells," Cell, May 21, 2015, vol. 161 (pp. 1187-1201).
Kleinstiver et al., "Engineered CRISPR-Cas9 nucleases with altered PAM specificities," Nature, Jul. 23, 2015, vol. 523, No. 7561 (pp. 481-485).
Kochenderfer et al., "Construction and Preclinical Evaluation of an Anti-CD19 Chimeric Antigen Receptor," Journal of Immunotherapy, Sep. 2009, vol. 32, No. 7 (26 pages).
Kolmar, "Alternative binding proteins: biological activity and therapeutic potential of cystine-knot miniproteins," The FEBS Journal, 2008, 275 (pp. 2684-2690).
Kooreman et al., "Autologous iPSC-Based Vaccines Elicit Anti-tumor Responses In Vivo," Cell Stem Cell, Apr. 5, 2018, vol. 22, No. 4 (pp. 501-513).
Lagos-Quintana et al., "Identification of Novel Genes Coding for Small Expressed RNAs," Science, Oct. 26, 2001, vol. 294 (pp. 853-858).
Lagos-Quintana et al., "Identification of tissue-specific microRNAs from mouse," Current Biology, Apr. 30, 2002, vol. 12, (pp. 735-739).
Lagos-Quintana et al., "New microRNAs from mouse and human," RNA, 2003, vol. 9 (pp. 175-179).
Lai et al., "Modular PROTAC Design for the Degradation of Oncogenic BCR-ABL," Angewandte Chemie International Edition [Engl] Jan. 11, 2016, vol. 55, No. 2 (pp. 807-810).
Lau et al., "An abundant class of tiny RNAs with probable regulatory roles in Caenorhabditis elegans," Science, Oct. 26, 2001, vol. 294 (pp. 858-862).
Le Mercier et al., "Beyond CTLA-4 and PD-1, the generation Z of negative checkpoint regulators," Frontiers in Immunology, Aug. 21, 2015, vol. 6, Article 418 (15 pages).
Lee et al., "An Extensive Class of Small RNAs in Caenorhabditis elegans," Science, Oct. 26, 2001, vol. 294 (pp. 862-864).
Lee et al., "Highly multiplexed subcellular RNA sequencing in situ," Science, Mar. 21, 2014, vol. 343, No. 6177 (pp. 1360-1363).
Lee et al., "Synthetically modified guide RNA and donor DNA are a versatile platform for CRISPR- Cas9 engineering," Elife, May 2, 2017, vol. 6 e25312 (17 pages).
Legut et al., "CRISPR-mediated TCR replacement generates superior anticancer transgenic T cells," Blood, 2018, vol. 131, No. 3 (pp. 311-322).
Li et al., "Adoptive cell therapy with CD4+ T helper 1 cells and CD8+ cytotoxic T cells enhances complete rejection of an established tumour, leading to generation of endogenous memory responses

(56) References Cited

OTHER PUBLICATIONS to non-targeted tumour epitopes," Clinical Translational Immunology, Oct. 20, 2017, vol. 6, No. 10 e160 (10 pages).
Li et al., "Engineering CRISPR-Cpf1 crRNAs and mRNAs to maximize genome editing efficiency," Nature Biomedical Engineering, May 2017, vol. 1, No. 5 (21 pages).
Lim et al., "The microRNAs of Caenorhabditis elegans," Genes & Development, Apr. 15, 2003, vol. 17, No. 8 (pp. 991-1008).
Lim et al., "Vertebrate microRNA genes," Science, Mar. 7, 2003, vol. 299, No. 5612 (p. 1540).
Lu et al., "Demethylation of the Same Promoter Sequence Increases CD70 Expression in Lupus T Cells and T Cells Treated with Lupus-Inducing Drugs," The Journal of Immunology, May 15, 2005, vol. 174, No. 10 (pp. 6212-6219).
Macosko et al., "Highly Parallel Genome-wide Expression Profiling of Individual Cells Using Nanoliter Droplets," Cell, May 21, 2015, vol. 161 (pp. 1202-1214).
Maher et al., "Human T-lymphocyte cytotoxicity and proliferation directed by a single chimeric TCRzeta /CD28 receptor," Nature Biotechnology, Jan. 2002, vol. 20, No. 1 (pp. 70-75).
Margulies, et al. "Genome sequencing in microfabricated high-density picolitre reactors", NATURE, Sep. 15, 2005, vol. 437, No. 7057, pp. 376-380.
Martin-Orozco et al., "T helper 17 cells promote cytotoxic T cell activation in tumor immunity," Immunity, Nov. 20, 2009, vol. 31, No. 5 (pp. 787-798).
Maruyama et al., "Targetability of novel immunoliposomes modified with amphipathic poly( ethylene glycol) s conjugated at their distal terminals to monoclonal antibodies," Biochimica et Biophysica Acta, 1995, vol. 1234 (pp. 74-80).
Matsuda et al., "Controlled expression of transgenes introduced by in vivo electroporation," Proceedings of the National Academy of Sciences, Jan. 16, 2007, vol. 104, No. 3 (pp. 1027-1032).
Maus et al., "Adoptive immunotherapy for cancer or viruses," Annual Review of Immunology, 2014, vol. 32 (pp. 189-225).
Mettananda et al., "Editing an alpha-globin enhancer in primary human hematopoietic stem cells as a treatment for beta-thalassemia," Nature Communications, Sep. 4, 2017, vol. 8, No. 1 (11 pages).
Miyamoto et al., "Rapid and orthogonal logic gating with a gibberellin-induced dimerization system," Nature Chemical Biology, 2012, vol. 8, No. 5 (pp. 465-470).
Morgan et al., "Cancer Regression in Patients After Transfer of Genetically Engineered Lymphocytes," Science, Oct. 6, 2006, vol. 314, No. 5796 (pp. 126-129).
Morozova et al., "Applications of next-generation sequencing technologies in functional genomics," Genomics, 2008. Vol., 92 (pp. 255-264).
Moscou, et al., "A Simple Cipher Governs DNA Recognition by TAL Effectors," Science, Dec. 11, 2009, vol. 326, No. 11 (p. 1501).
Mouhieddine et al., "Immunotherapy in Multiple Myeloma: The Era of CAR T Cell Therapy," Hematologist, Apr. 2018, vol. 15, issue 3 (8 pages).
Muller et al., "VEGF and the Fab fragment of a humanized neutralizing antibody: crystal structure of the complex at 2.4 A resolution and mutational analysis of the interface," Structure, 1998, vol. 6, No. 9 (pp. 1153-1167).
Muranski et al., "Tumor-specific Th17-polarized cells eradicate large established melanoma," Blood, Jul. 15, 2008, vol. 112, No. 2 (pp. 362-373).
Nakamura et al., "Codon usage tabulated from the international DNA sequence databases: status for the year 2000," Nucleic Acids Research, 2000, vol. 28, No. 1 (p. 292).
Nicholson et al., "Construction and characterisation of a functional CD19 specific single chain Fv fragment for immunotherapy of B lineage leukaemia and lymphoma," Molecular Immunology, November-Dec. 1997, vol. 34, Nos. 16-17 (pp. 1157-1165).
Nowak et al., "Survey and Summary—Guide RNA engineering for versatile Cas9 functionality," Nucleic Acids Research, Oct. 12, 2016, vol. 44, No. 20 (pp. 9555-9564).
Nygren, "Alternative binding proteins: Affibody binding proteins developed from a small three-helix bundle scaffold," The FEBS Journal, 2008, vol. 275 (pp. 2668-2676).
Padalia et al., Abstract 2551: Allogeneic CRISPR engineered anti CD70 Car T cells demonstrate potent preclinical activity against both solid and hematological cancer cells, American Association of Cancer Research, Poster Presentations—Proffered Abstracts, Jul. 1, 2018 (3 pages).
Paige et al., "RNA mimics of green fluorescent protein," Science, Jul. 29, 2011, vol. 333, No. 6042 (pp. 642-646).
Park et al., "CD70 as a target for chimeric antigen receptor T cells in head and neck squamous cell carcinoma," Oral Oncology Mar. 2018, vol. 78 (pp. 145-150).
Parker et al., "Scheme for ranking potential HLA-A2 binding peptides based on independent binding of individual peptide side-chains," The Journal of Immunology, Jan. 1, 1994, vol. 152, No. 1 (pp. 163-175).
Piazza et al., "Immunotherapy of Respiratory Syncytial Virus Infection in Cotton Rats(Sigmodon fulviventer) Using IgG in a Small-Particle Aerosol," The Journal of Infectious Diseases, vol. 166 (pp. 1422-1424).
Picelli et al. "Full-length RNA-seq from single cells using Smart-seq2," Nature Protocols, Jan. 2014, vol. 9, No. 1 (pp. 171-181).
Pitard et al., "Production and characterization of monoclonal antibodies against the leukemia inhibitory factor low affinity receptor, gp190," Journal of Immunological Methods, 1997, vol. 205 pages (177-190).
Platt et al., "CRISPR-Cas9 Knockin Mice for Genome Editing and Cancer Modeling," Cell, 2014, vol. 159 (pp. 440-455).
Poirot et al., "Multiplex genome edited T-cell manufacturing platform for 'off-the-shelf' adoptive T- cell immunotherapies," Cancer Research, Sep. 15, 2015, vol. 75, No. 18 (pp. 3853-3864).
Prat et al., "Agonistic monoclonal antibodies against the Met receptor dissect the biological responses to HGF," Journal of Cell Science, 1998, vol. 111 (pp. 237-247).
Qasim et al., "Molecular remission of infant B-ALL after infusion of universal TALEN gene-edited Car T cells," Cancer, Science Translational Medicine, Jan. 25, 2017, vol. 9 (pp. 1-8).
Rahdar et al., "Synthetic CRISPR RNA-Cas9-guided genome editing in human cells," Proceedings of the American Academy of Sciences, U.S.A. Nov. 16, 2015 (pages E7110-E7117).
Rajasagi et al., "Systematic Identification of Personal Tumor-specific Neoantigens in Chronic Lymphocytic Leukemia," Blood, Jun. 2, 2014, vol. 124, No. 3 (pp. 453-462).
Ramos et al., "An inducible caspase 9 suicide gene to improve the safety of mesenchymal stromal cell therapies," Stem Cells, Jun. 2010, vol. 28, No. 6 (pp. 1107-1115).
Ramskold et al., "Full-length mRNA-Seq from single-cell levels of RNA and individual circulating tumor cells," Nature Biotechnology, Aug. 2012, vol. 30, No. 8 (777-782).
Ren et al., "Multiplex Genome Editing to Generate Universal Car T Cells Resistant to PD1 Inhibition," Clinical Cancer Research, May 1, 2017, vol. 23, No. 9 (pp. 2255-2266).
Restifo et al., "Adoptive Immunotherapy for Cancer: Harnessing the T Cell Response", Nature Reviews Immunology, Mar. 22, 2012, vol. 12, No. 4 (pp. 269-281).
Rodriques et al., "Slide-seq: A Scalable Technology for Measuring Genome-Wide Expression at High Spatial Resolution," Science, 2019, vol. 363, No. 6434 (pp. 1463-1467).
Rohloff et al. "Nucleic acid ligands with protein-like side chains: modified aptamers and their use as diagnostic and therapeutic agents," Molecular Therapy-Nucleic Acids, 2014, vol. 3, e201 (13 pages).
Ronaghi et al., "Real-time DNA sequencing using detection of pyrophosphate release," Analytical Biochemistry, 1996, vol. 242, Article 0432 (pp. 84-89).
Rosenberg et al., "Adoptive cell transfer as personalized immunotherapy for human cancer," Cancer Immunology and Immunotherapy, Apr. 2015, vol. 348, Issue 6230 (pp. 62-69).
Rosenberg et al., "Scaling single cell transcriptomics through split pool barcoding," bioRxiv preprint first posted online Feb. 2, 2017 (13 pages).

(56) References Cited

OTHER PUBLICATIONS

Rosenberg et al., "Single-cell profiling of the developing mouse brain and spinal cord with split- pool barcoding," Science, Single Cell Genomics, 2018, vol. 360 (pp. 176-182).
Sadelain et al., "Eliminating Cells Gone Astray," New England Journal of Medicine, Nov. 3, 2011, vol. 365, No. 18 (pp. 1735-1737).
Saudek et al., "A preliminary trial of the programmable implantable medication system for insulin delivery," New England Journal of Medicine, Aug. 31, 1989, vol. 321 (pp. 574-579).
Schena et al., "Parallel human genome analysis: Microarray-based expression monitoring of 1000 genes," Proceedings of the National Academy of Science, Oct. 1996, vol. 93 (pp. 10614- 10619).
Sharma et al., "Antisense oligonucleotides: modifications and clinical trials," Medical Chemistry Journal, 2014, 5 (pp. 1454-1471).
Shendure et al., "Accurate Multiplex Polony Sequencing of an Evolved Bacterial Genome," Science, vol. 309, Sep. 9, 2005, vol. 309 (pp. 1728-1732).
Shmakov et al., "Discovery and Functional Characterization of Diverse Class 2 CRISPR-Cas Systems," Molecular Cell, Nov. 1, 2015, vol. 60, No. 3 (pp. 385-397).
Silverman et al., "Multivalent avimer proteins evolved by exon shuffling of a family of human receptor domains," Nature Biotechnology, 2005, vol. 23, No. 12 (pp. 1556-1561).
Skerra et al., "Alternative binding proteins: Anticalins-harnessing the structural plasticity of the lipocalin ligand pocket to engineer novel binding activities," The FEBS Journal, 2008, vol. 275 (pp. 2677-2683).
Skerra et al., "Alternative non-antibody scaffolds for molecular recognition." Current Opinion in Biotechnology, 2007, vol. 18 (pp. 295-303).
Skerra, "Engineered protein scaffolds for molecular recognition," Journal of Molecular Recognition, 2000, vol. 13 (pp. 167-187).
Smargon et al., "Cas13b Is a Type VI-B CRISPR-Associated RNA-Guided RNases Differentially Regulated by Accessory Proteins Csx27 and Csx28," Molecular Cell Feb. 16, 2017, vol. 65, No. 4 (pp. 618-630).
Sproat et al., "New synthetic routes to synthons suitable for 2'-O-allyloligoribonucleotide assembly," Nucleic Acids Research, vol. 19, No. 4 (pp. 733-737).
Stanley et al., "Radio-Wave Heating of Iron Oxide Nanoparticles Can Regulate Plasma Glucose in Mice," Science, May 4, 2012 Vol. 336, No. 6081 (pp. 604-608).
Stumpp et al., "DARPins: a new generation of protein therapeutics," Drug Discovery Today, Aug. 2008, vol. 13, Nos. 15/16 (pp. 695-701).
Swiech et al., "In vivo interrogation of gene function in the mammalian brain using CRISPR-Cas9," Nature Biotechnology, 2014, vol. 33 (pp. 102-106) [Including Supplemental information, 4 pages].
Tang et al., "RNA-Seq analysis to capture the transcriptome landscape of a single cell," Nature Protocols, Mar. 2010 Vol. 5, No. 3 (pp. 516-535).
Tang, et al., "mRNA-Seq whole-transcriptome analysis of a single cell," Nature Methods, May 2009, vol. 6, No. 5 (pp. 377-382).
Tran-Huu-Hue et al., "Practical Systems for the Generation of High Power Continuous Wave-Non Focused Ultrasound in the MHz Range," ACUSTICA, acta acustica, 1997, vol. 83 (pp. 1103-1106).
Tuerk et al., "Systematic evolution of ligands by exponential enrichment: RNA ligands to bacteriophage T4 Dna polymerase," Science, Aug. 3, 1990, vol. 249, Issue 4968 (pp. 505-510).
Urbaniak et al., "Prolactin-induced protein (PIP)-characterization and role in breast cancer progression," American Journal of Cancer Research, 2018, vol. 8, No. 11 (pp. 2150-2164).
Vitak et al., "Sequencing thousands of single-cell genomes with combinatorial indexing," Nature Methods, Mar. 2017, vol. 14, No. 3 (pp. 302-308).
Von Essen, "Constitutive and ligand-induced TCR degradation," Journal of Immunology, vol. 173, No. 1 (pp. 384-393).
Wang, Wei, "Lyophilization and development of solid protein pharmaceuticals", International Journal of Pharmaceutics, Aug. 2000, vol. 203, Issues 1-2 (pp. 1-60).
Watson et al., "SHP-1: the next checkpoint target for cancer immunotherapy?" Biochemical Society Transactions, Apr. 15, 2016, vol. 44, No. 2 (pp. 356-362).
Wu et al., "Remote control of therapeutic T cells through a small molecule-gated chimeric receptor," Science, Oct. 16, 2015, vol. 350, No. 6258 (pp. 1-21).
Xia et al., "Multiplexed detection of RNA using MERFISH and branched DNA amplification," Scientific Reports, 2019, vol. 9 (13 pages).
Yan et al., "Cas13d Is a Compact RNA-Targeting Type VI CRISPR Effector Positively Modulated by a WYL-Domain-Containing Accessory Protein," Molecular Cell, Apr. 19, 2018, vol. 70, No. 2 (pp. 327-339).
Yoon et al., "Antibodies to Domains II and III of the IL-1 Receptor Accessory Protein Inhibit IL-1f Activity But Not Binding: Regulation of IL-1 Responses Is Via Type I Receptor, Not the Accessory Protein," Journal of Immunology, 2019, vol. 160, No. 7 (pp. 3170-3179).
Zacharakis et al., "Immune recognition of somatic mutations leading to complete durable regression in metastatic breast cancer," Nature Medicine, Jun. 2018, vol. 24, No. 6 (pp. 724-730).
Zapata et al., "Engineering linear F(ab')2 fragments for efficient production in Escherichia coli and enhanced antiproliferative activity," Protein Engineering, 1995, vol. 8, No. 10 (pp. 1057-1062).
Zhang et al., "Efficient Construction of Sequence-Specific TAL Effectors for Modulating Mammalian Transcription," Nature Biotechnology, Feb. 2011, vol. 29, No. 2 (pp. 149-154).
Zheng et al. "Haplotyping germline and cancer genomes with high-throughput linked-read sequencing" Nature Biotechnology, Feb. 1, 2016, vol. 34, No. 3 (pp. 303-311) [with Supplemental Material].
Zheng et al., "Massively parallel digital transcriptional profiling of single cells," Nature Communications, Jan. 16, 2017, vol. 8, No. 14049 (12 pages).
Zhou et al., "Aptamer-targeted cell-specific RNA interference," Silence, Feb. 1, 2010, vol. 1, No. 4 (10 pages).
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry, Jan. 25, 2018, vol. 61, No. 2 (pp. 462-481).
Zhou et al., "Long-term outcome after haploidentical stem cell transplant and infusion of T cells expressing the inducible caspase 9 safety transgene," Blood, Jun. 19, 2014, vol. 123, No. 25 (pp. 3895-3905).
Zhu et al., "Inhibition of Vascular Endothelial Growth Factor-induced Receptor Activation with Anti- Kinase Insert Domain-containing Receptor Single-Chain Antibodies from a Phage Display Library," Cancer Research, Aug. 1998, vol. 58 (pp. 3209-3214).
Zilionis et al., "Single-cell barcoding and sequencing using droplet microfluidics," Nature Protocols, 2017, vol. 12, No. 1 (pp. 44-73).
Zuker et al., "Optimal computer folding of large RNA sequences using thermodynamics and auxiliary information," Nucleic Acids Research, Jan. 10, 1981, vol. 9, No. 1 (pp. 133-148).
Doyon et al., "Enhancing zinc-finger-nuclease activity with improved obligate heterodimeric architectures," Nature Methods, Jan. 2011, vol. 8, No. 1 (pp. 74-79).
Dumais et al., "Indexing by Latent Semantic Analysis," Journal of the American Society for Information Science, 1990, vol. 41, No. 6 (pp. 391-407).
Eyquem et al., "Targeting a CAR to the TRAC Locus with CRISPR/Cas9 Enhances Tumour Rejection," Nature, Mar. 2, 2017, vol. 543, No. 7643 (pp. 113-117).
Lee et al., "Learning the parts of objects by non-negative matrix factorization," Nature, Oct. 21, 1999, vol. 401, No. 6755 (pp. 788-791).
Schneider et al., "DNA sequencing with nanopores," Nature Biotechnology, Apr. 10, 2012, vol. 30, No. 4 (pp. 326-328).

(56) References Cited

OTHER PUBLICATIONS

Ward et al., "Binding activities of a repertoire of single immunoglobulin variable domains secreted from *Escherichia coli*," Nature, Oct. 1989, vol. 341 (pp. 544-546).

* cited by examiner

Literature/interest/focus genes

- Relevant aspects of MBC biology
- General well known cell type (ct) markers
- Focus on resistance and ER signaling FIG. 14
CODEX/MIBI panels
- Translation from protein-world to RNA-world leads to expansion (e.g. Cytokeratin, Collagen)
- Emphasis on immune cells and processes
- codex_fixed is assigned priority 0, codex_frozen and mibi_fixed priority 1
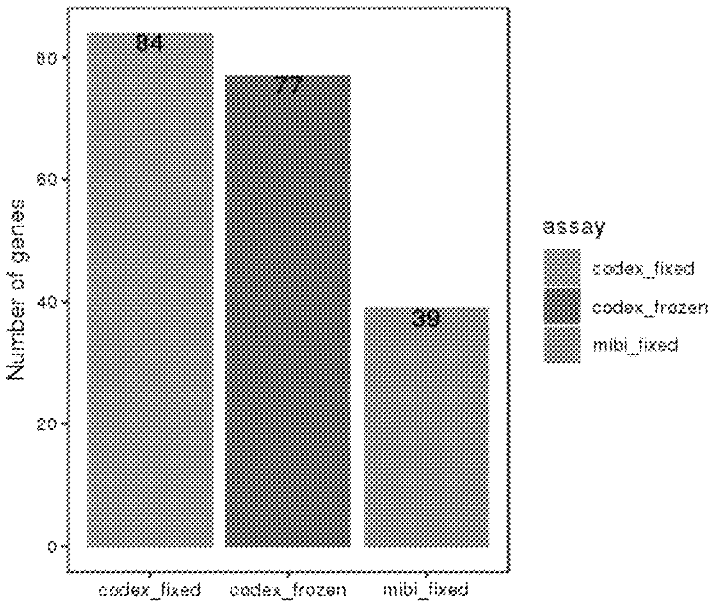
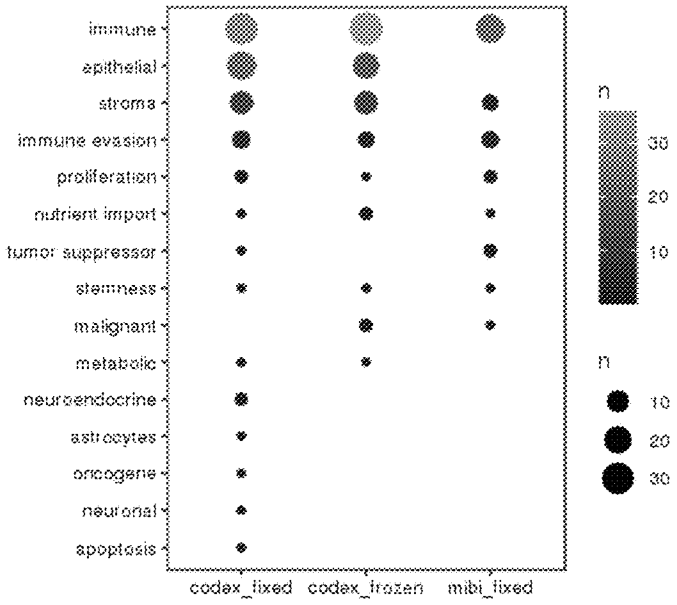

pam50 model for breast cancer subtyping

- 50 genes that classify 5 subtypes (LumA, LumB, Her2, Basal, Normal)
- Developed for and on primary breast cancer bulk data
- ~ 50 % of the malignant cells get assigned unambiguously Data driven cell type predictive genes

- Use support vector classification (SVM) to predict cell types based on gene expression
- Compare performance to random forest (RF) classifier
- Use model weights to select genes with highest predictive value
- Assess loss in accuracy (cross-validation) when using reduced gene sets

FIG. 26

Fibroblasts

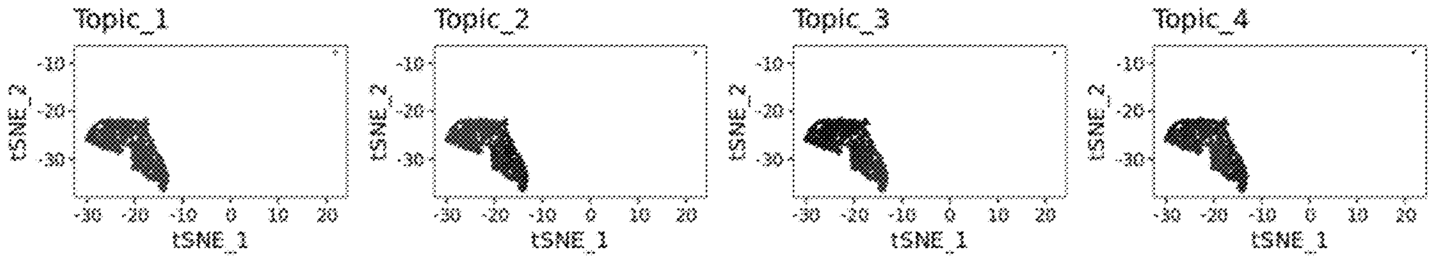

Selected topics:
1,2,3,4

| topic | Term | Overlap | Adjusted.P.value | Genes |
|---|---|---|---|---|
| 1 | sequestering of actin monomers (GO:0042989) | 3/11 | 1.933964e-04 | GSN;TMSB4X;TMSB10 |
| 2 | muscle contraction (GO:0006936) | 7/138 | 4.009811e-07 | ACTA2;MYL6;TPM2;MYH11;MYL9;ACTG2;MYLK |
| 3 | extracellular matrix organization (GO:0030198) | 13/230 | 1.406165e-15 | LUM;COL11A1;MMP2;COL12A1;DCN;MFAP5;COMP;COL1A1;COL3A1;COL1A2;MMP13;SPP1;COL10A1 |
| 4 | cellular response to cytokine stimulus (GO:0071345) | 11/457 | 1.694293e-08 | CXCL13;IGHG4;IGHG1;CCL21;BGN;CCL2;VIM;CCL19;TIMP1;MMP9;DCN |

T cells

| topic | Term | Overlap | Adjusted.P.value | Genes |
|---|---|---|---|---|
| 1 | nuclear-transcribed mRNA catabolic process, nonsense-mediated decay (GO:0000184) | 5/113 | 1.679794e-04 | RPL13;RPSA;EIF3E;PABPC1;RPL18 |
| 2 | regulation of natural killer cell chemotaxis (GO:2000501) | 4/8 | 3.392546e-08 | CCL5;CCL4;CCL3;XCL1 |
| 3 | type I interferon signaling pathway (GO:0060337) | 4/66 | 1.693518e-04 | ISG15;HLA-A;IFIT1;IFIT3 |

Selected topics:
2,3

Filtering (
mean norm. expression > 0.15
*OR*
variability > 0.025
*OR*
categories > 1
)

*AND*

(
mean norm. expression > 1.5 & <4
*OR*
variability > 0.25
*OR*
priority == 1
*OR*
categories > 1
)

300 genes

Expression of selected genes across all cell types

FIG. 37 Excursion on generalizability

- Comparison to earlier data set from the same cohort
- Frozen (single nucleus) data
- 3 samples (different patients)
- Different chemistry (v2 vs v3)
- Different biology
- → Bigger overlap in selected genes compared to fresh

Data driven expression predictive genes

- Use regularized support vector regression (SVR) to model expression of each gene based on all other genes
  - All genes/ variable genes
  - All cell types together/ cell types separately
- Use model weights to select genes with highest predictive value
- Test selected genes in well performing neural net based approach

Neural net based prediction of expression

- Predict all variable genes across all cell types using only the data driven cell type predictive genes to get a performance baseline

FIG. 46

Cell type wise statistics

| gene | labels | mean_raw | sd_raw | median_raw | max_raw | min_raw | perc_expr_raw | N_expr_raw | mean_norm | sd_norm | median_norm | max_norm | min_norm | perc_expr_norm | N_expr_norm |
|---|---|---|---|---|---|---|---|---|---|---|---|---|---|---|---|
| HLA-B | B_cell | 18.970446 | 23.799533 | 7 | 313 | 0 | 0.9764777 | 1619 | 2.927938 | 0.7800969 | 3.028404 | 5.324837 | 0 | 0.9764777 | 1619 |
| HLA-B | Endothelial_cells | 16.253656 | 26.316181 | 9 | 451 | 0 | 0.9603009 | 2298 | 3.197122 | 0.9585465 | 3.296752 | 5.364225 | 0 | 0.9603009 | 2298 |
| HLA-B | Epithelial_cells | 31.508163 | 34.994116 | 6 | 387 | 0 | 0.8360291 | 22174 | 2.089291 | 1.3252704 | 2.278165 | 5.532898 | 0 | 0.8360291 | 22174 |
| HLA-B | Fibroblasts | 6.116592 | 10.437063 | 3 | 89 | 0 | 0.8116592 | 181 | 2.093954 | 1.2694166 | 2.121967 | 4.581749 | 0 | 0.8116592 | 181 |
| HLA-B | Macrophage | 22.429352 | 27.397635 | 12 | 228 | 0 | 0.9692833 | 1420 | 3.314967 | 0.8829259 | 3.460489 | 5.349409 | 0 | 0.9692833 | 1420 |
| HLA-B | Monocyte | 17.000000 | 16.007772 | 12 | 88 | 0 | 0.9801980 | 198 | 3.249717 | 0.7857381 | 3.380996 | 4.655546 | 0 | 0.9801980 | 198 |
| HLA-B | NK_cell | 10.757705 | 7.600902 | 9 | 108 | 0 | 0.9948630 | 3486 | 3.779097 | 0.6351783 | 3.844152 | 5.416768 | 0 | 0.9948630 | 3486 |
| HLA-B | T_cells | 9.602515 | 6.850924 | 8 | 84 | 0 | 0.9936437 | 6253 | 3.594400 | 0.6754359 | 3.651689 | 5.476862 | 0 | 0.9936437 | 6253 |
| HLA-B | iPS_cells | 3.236753 | 5.322194 | 2 | 78 | 0 | 0.7022043 | 3313 | 1.001149 | 0.8403541 | 1.006916 | 4.413509 | 0 | 0.7022043 | 3313 |

stats per cell type (raw data)

stats per cell type (normalized data)

cells with >= 1 UMI cells with normalized expression >0.1

FIG. 47

Statistics across the entire data set expression in bulk data cells >=1 UMI

| type | method | N_listed | variability | N_expr_all | perc_expr_all | mean.TPM.Mets | cluster_0.7 | cluster_0.6 | cluster_order | priority |
|---|---|---|---|---|---|---|---|---|---|---|
| immune | codex_frozen\|codex_fixed | 2 | 0.3329212 | 53984 | 0.878494 | 1628.638 | 11 | 15 | 27 | 1 |

Selection categories stats across entire data set gene-gene correlation

% cells with |z-score| >1

% cells >=1 UMI

FIG. 48

Reduce complexity

- For each gene, only keep stats for the highest expressing cell type according to mean normalized expression.
- For MBC interest genes only choose among malignant cell types.

| gene | labels | mean_raw | sd_raw | median_raw | max_raw | min_raw | perc_expr_raw | N_expr_raw | mean_norm | sd_norm | median_norm | max_norm | min_norm | perc_expr_norm | N_expr_norm |
|---|---|---|---|---|---|---|---|---|---|---|---|---|---|---|---|
| CD163 | Monocyte | 1.3663366 | 2.0331715 | 1 | 12 | 0 | 0.5198020 | 105 | 0.9091792 | 1.0157318 | 0.7255274 | 3.582547 | 0 | 0.5198020 | 105 |
| CD19 | B_cell | 0.3582316 | 0.6026203 | 0 | 3 | 0 | 0.2973503 | 303 | 0.3235321 | 0.8243686 | 0.0000000 | 2.713868 | 0 | 0.2973503 | 303 |
| CD3D | T_cells | 2.1468298 | 1.7787883 | 2 | 26 | 0 | 0.8461783 | 5325 | 2.0030310 | 0.9995366 | 2.2254490 | 4.151919 | 0 | 0.8461783 | 5325 |
| DCN | Fibroblasts | 15.5246637 | 23.2667274 | 5 | 130 | 0 | 0.6905830 | 154 | 2.4670225 | 1.8623124 | 2.9796595 | 5.791456 | 0 | 0.6905830 | 154 |
| EPCAM | Epithelial_cells | 5.5094445 | 9.0276962 | 3 | 182 | 0 | 0.7799646 | 20687 | 1.2654198 | 0.8366833 | 1.4015614 | 4.293349 | 0 | 0.7799646 | 20687 |
| PECAM1 | Endothelial_cells | 2.3903051 | 3.2805986 | 1 | 40 | 0 | 0.6949436 | 1663 | 1.3472775 | 1.0044776 | 1.5826264 | 4.350673 | 0 | 0.6949436 | 1663 |

MOLECULAR SPATIAL MAPPING OF METASTATIC TUMOR MICROENVIRONMENT

CROSS-REFERENCE TO RELATED APPLICATIONS

This application claims the benefit of U.S. Provisional Application No. 62/965,130, filed Jan. 23, 2020. The entire contents of the above-identified application are hereby fully incorporated herein by reference.

STATEMENT REGARDING FEDERALLY SPONSORED RESEARCH

This invention was made with government support under grant number AI133524 awarded by the National Institutes of Health. The government has certain rights in the invention.

REFERENCE TO AN ELECTRONIC SEQUENCE LISTING

The contents of the electronic sequence listing ("BROD-4970US_ST25.txt"; Size is 61,000 bytes and it was created on Jan. 21, 2021) is herein incorporated by reference in its entirety.

TECHNICAL FIELD

The present invention is generally directed to methods of producing molecular spatial maps of the metastatic tumor microenvironment. It also relates to compositions for treating breast cancer metastasis and ductal carcinoma in situ of the breast.

BACKGROUND

Cancer metastasis is responsible for more than 90% of cancer deaths. The microenvironment of metastatic tumor tissue is molecularly, structurally, and functionally distinct from that of primary tumor tissue. Thorough understanding of metastatic tumor microenvironment is critical not only for early diagnosis of cancer metastasis, but also for predicting, treating, and preventing the occurrence of metastatic disease.

As a highly complex malignant disease, breast cancer is prone to metastasize to a variety of tissues including the bone, brain, breast, liver, and lung. Information obtained from molecular profiling of metastatic breast cancer (MBC) at tissue level is limited. A more in-depth molecular dissection in conjunction with spatial mapping of a heterogeneous population of molecules and cells in MBC metastatic microenvironment are urgently needed for developing effective methods and compositions for identifying biomarkers and therapeutic agents for treating MBC.

On the other hand, ductal carcinoma in situ of the breast (DCIS) is a noninvasive condition in which abnormal cells are located in the lining of a breast duct. Although DCIS in many patients is curable, some DCIS diseases do develop into invasive and metastatic breast cancer. Identifying molecular features of DCIS and therapeutic approaches for preventing DCIS from becoming invasive is urgently needed.

Citation or identification of any document in this application is not an admission that such a document is available as prior art to the present invention.

SUMMARY

In certain embodiments, methods and compositions are provided for producing molecular spatial mapping of metastatic tumor tissue microenvironment and identifying therapeutic agents for treating metastatic cancers. In a preferred embodiment, the metastatic tumor tissue is a metastatic breast cancer (MBC) tumor tissue. In some aspects, the methods disclose a distinct list of genes specifically useful for performing RNA visualization of metastatic tumor tissues of MBC. In some aspects, provided are methods of selecting the distinct list of genes to be used for molecular spatial mapping of tissues.

In some embodiments, the molecular spatial mapping provides in-depth information about cell types, cell state, cell location, and the expression levels of genes in different locations, in different types of cells, and in different cell states in the metastatic tumor tissue microenvironment.

In some embodiments, the metastatic tissues of MBC include, but are not limited to, the bone, brain, breast, lung, liver, lymph node, stomach, spleen, pancreas, kidney, ovary, uterus, or any combination thereof.

In some embodiments, methods disclosed herein use RNA in situ sequencing or RNA in situ hybridization for visualizing the RNA molecules selected specifically for MBC tissues and signaling pathways of interest for molecular spatial mapping of MBC tumor tissue microenvironment.

In some embodiments, methods are provided for selecting RNA molecules that can be used for molecular spatial mapping of MBC tumor tissue microenvironment. The methods comprise steps of running topic modeling on each of the cell types separately for T cells, natural killer (NK) cells, B cells, plasma cells, monocytes, macrophages, fibroblasts, endothelial cell, and epithelial (malignant) cells, running GO-term enrichment (biological processes) on top list of driving genes per topic, selecting topic of interest, and selecting genes that lead to enrichment of the respective GO-terms. As a result, a list of genes that can be used for RNA visualization are obtained.

In certain embodiments, method of identifying therapeutic targets of MBC is provided. The therapeutic targets identified using such method can be used for developing, screening, and evaluating therapeutic agents for treating MBC. The method includes selecting one or more genes that have high expression levels in comparison to that in normal tissues and have function related to inhibiting apoptosis, stimulating angiogenesis, promoting cell proliferation, inhibiting cytotoxic immune cells, inhibiting antigen presenting cells, stimulating regulatory T cells and immunotolerance, and degrading extracellular matrix.

In certain embodiments, methods are provided for treating MBC by using agents that are capable of inhibiting the function or expression of genes identified aforementioned as the therapeutic targets for MBC. In some aspects, the agents can be small molecules, antibodies or antibody fragments thereof, or genome editing systems. In some aspects, the genome editing systems capable of inhibiting the therapeutic targets can be CRISPR-Cas genome editing system, zinc finger nucleases (ZFNs), or transcription activator-like effector nucleases (TALEN).

In some embodiments, methods are disclosed for screening therapeutic agents for treating MBC. These methods use cells that express the therapeutic targets and test candidate compounds for their ability to inhibit the expression or function of therapeutic targets identified in the present invention. In some aspects, the therapeutic targets can be small molecules, antibodies or antibody fragments thereof, or genome editing systems.

In some embodiments, a pharmaceutical composition is provided for treating MBC. The pharmaceutical composition includes the therapeutic agents identified in the present invention and a pharmaceutically acceptable carrier or excipient.

In some embodiments, a method is disclosed for identifying biomarkers for a metastatic tumor of breast cancer. The method includes selecting genes that are differentially expressed in the metastatic tumor in comparison to that in normal tissues, or selecting cells that are present in the metastatic tumor but absent in normal counterpart tissues. As a result, the genes and/or cells selected using such method can be used as biomarkers for MBC. The metastatic tumor can be in the bone, breast, lung, brain, liver, spleen, pancreas, stomach, kidney, ovary, lymph nodes, colon, and uterus.

In certain embodiments, the present invention discloses surprising discoveries of novel subtypes of malignant cells in the metastatic tumor tissue microenvironment of MBC. These new subtypes of malignant cells include stem-like malignant cells (see, Table 1) and neural-like malignant cells. In some aspects, the majority of stem-like malignant cells are in active cycling phases. These newly identified subtypes of malignant cells not only provide an insight of metastatic microenvironment, but also provide potential therapeutic targets for MBC.

In certain embodiments, the present invention also discloses a method for identifying molecular biomarker for MBC in tissues such as the bone and breast. In a preferred embodiment, single-nucleus RNA sequencing (snRNA-seq) is used for molecular profiling of bone or breast metastases, and it is surprisingly found that single-nucleus RNA sequencing achieves substantially better coverage of molecular features than single-cell RNA sequencing (scRNA-seq) does.

In certain embodiments, a method for producing molecular spatial mapping for a tissue environment is provided. The tissue can be a healthy or diseased tissue. The diseased tissue can be of malignant disease, autoimmune disease, inflammatory disease, or any diseases that impair the function, physiology, or structure of a tissue. In some embodiments, the method includes performing single-cell RNA sequencing or single-nucleus RNA sequencing and selecting a set of differentially expressed genes for clustering cells and performing RNA visualization. The method can provide an insight into the heterogeneity of cells in the tissue, including the physical location of each cell, cell state, and expression of each gene in cells of the same type but at different physical locations. Therefore, this method provides a powerful tool for physiology studies, biomarker discovery, therapeutic target identification, and therapeutic agent screening and evaluation.

In certain embodiments, a method of distinguishing cell types in ductal carcinoma in situ of the breast (DCIS) using gene expression profile is provided. The cell types include epithelial cells, endothelial cells, smooth muscle cells, adipocytes, T cells, macrophages, and fibroblasts. A list of genes are selected from gene expression data obtained using scRNA-seq and snRNA-seq, and are used for differentiate the types of cells in DCIS tissues with the help of dimension reduction techniques.

In some embodiments, a method of identifying subpopulations of epithelial cells in DCIS tissues is provide. This method comprises detecting the expression pattern of PIP, ESR1, PGR, ERBB2, and EGFR genes. In some aspects, it is disclosed that the epithelial cells in DCIS comprise at least two subpopulations. The first subpopulation is characterized by the expression of PIP, and the second subpopulation is characterized by no or low levels of expression of PIP in comparison to normal ductal tissue of the breast.

In some embodiments, an epithelial cell derived from DCIS tissues is provided. This type cell is characterized by expression of PIP gene or gene products, and the expression of one or more of genes or gene products comprising ESR1, PGR, ERBB2, and EGFR.

In some embodiments, an epithelial cell derived from DCIS tissues is provided. This type cell is characterized by no or lower levels of expression of PIP gene or gene products in comparison to that in normal ductal tissue of the breast, and the expression of one or more of genes or gene products comprising ESR1, PGR, and ERBB2.

In some embodiments, a method is provided for producing a molecular spatial map for visualizing tissue microenvironment of DCIS. In some aspects, the method includes performing RNA visualization on a DCIS tissue for one or more RNA molecules herein, whereby a molecular spatial map for the DCIS tissue microenvironment is obtained. In some aspects, the tissue microenvironment of DCIS comprises a heterogeneous population of cells. In some aspects, the molecular spatial map comprises information about cell types, cell state, and cell location in DCIS tissues. In some aspects, the molecular spatial map further comprises information about expression levels of one or more genes in one or more locations, one or more cell types, and one or more cell states in the DCIS tissue microenvironment. In some aspects, the RNA visualization is realized using RNA in situ sequencing methods or RNA in situ hybridization methods.

In some embodiments, a method of identifying therapeutic agent for preventing DCIS from becoming invasive is provided. In some aspects, this method includes identifying genes highly expressed in the second subpopulation of epithelial cells in DCIS tissues and selecting therapeutic agents that are capable of inhibiting the expression or function of the identified genes. In some aspects, the method includes identifying genes which expressions are inhibited in the second subpopulation of epithelial cells in DCIS tissues according to any one of the preceding claims; and selecting therapeutic agents that are capable of enhancing or increasing the expression or function of the identified genes. Thus, the growth of second subpopulation of epithelial cells or the volume of DCIS tumor is reduced or inhibited, and the invasiveness of DCIS tumor is prevented.

In some embodiments, a method of treating a patient with DCIS is provided. This method includes administering a therapeutically effective amount of therapeutic agent or agents identified in the present invention to the patient, whereby the DCIS is prevented from developing invasiveness and metastasis.

In some embodiments, a stem-like epithelial malignant cell in metastatic tumor tissue is disclosed. This cell is characterized by the expression of genes comprising according to Table 1. In some aspects, the majority of stem-like epithelial malignant cells (>70%) are in cycling phase (G1/S and G2/M phases).

In some embodiments, a neural-like epithelial malignant cell in metastatic tumor tissue is disclosed.

In some embodiments, a method of identifying molecular biomarker for metastatic breast cancer in the bone and breast is provided. This method includes performing snRNA-seq of the bone tumor tissue, wherein the snRNA-seq produces substantially more RNA sequences than scRNA-seq does. It further includes selecting differentially expressed genes in comparison to corresponding normal tissues (bone or breast), whereby the differentially expressed genes can be used as molecular biomarkers for metastatic breast cancer in the bone or in the breast.

In another aspect, the present invention provides for a method of detecting one or more breast cancer tumor specific cell types, detecting in a tumor sample obtained from a subject in need thereof the expression, activity and/or function of one or more signature genes selected from Table 1 or the Figures.

In another aspect, the present invention provides for a method of treating breast cancer in a subject in need thereof comprising administering to the subject a therapeutically effective amount of one or more agents capable of modulating the expression, activity and/or function of one or more signature genes selected from Table 1 or the Figures. In certain embodiments, the one or more signature genes are upregulated or specifically expressed in malignant epithelial cells or epithelial stem cells. In certain embodiments, the one or more agents comprise immune cells specific for one or more signature genes, small molecules, antibodies or antibody fragments thereof, genetic modifying agents, and any combinations thereof. In certain embodiments, the one or more agents are capable of targeting or binding to one or more cell surface exposed signature genes. In certain embodiments, the one or more agents are capable of targeting or binding to one or more receptors or ligands specific for a cell surface exposed signature gene. In certain embodiments, the one or more agents are capable of targeting or binding to one or more secreted signature genes. In certain embodiments, the one or more agents are capable of targeting or binding to one or more receptors or ligands specific for a secreted signature gene. In certain embodiments, the immune cell comprises a CAR T cell or a T cell expressing an endogenous or exogenous TCR. In certain embodiments, the genetic modifying agent comprises a CRISPR system or IscB system.

In another aspect, the present invention provides for a kit comprising one or more reagents for detecting the one or more signature genes selected from Table 1 or the figures herein. In certain embodiments, the reagents are for determining spatial location of cells and/or transcripts.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 14. Bar graph showing the number of genes in codex on a fixed sample, codex on a frozen sample and MIBI on a fixed sample. Dot plot showing the number of cells expressing a cell type specific gene and the expression level in each of the data types.

The single cells do not cluster by pam50 subtypes for about 50% of the single cells.

Figure 17:
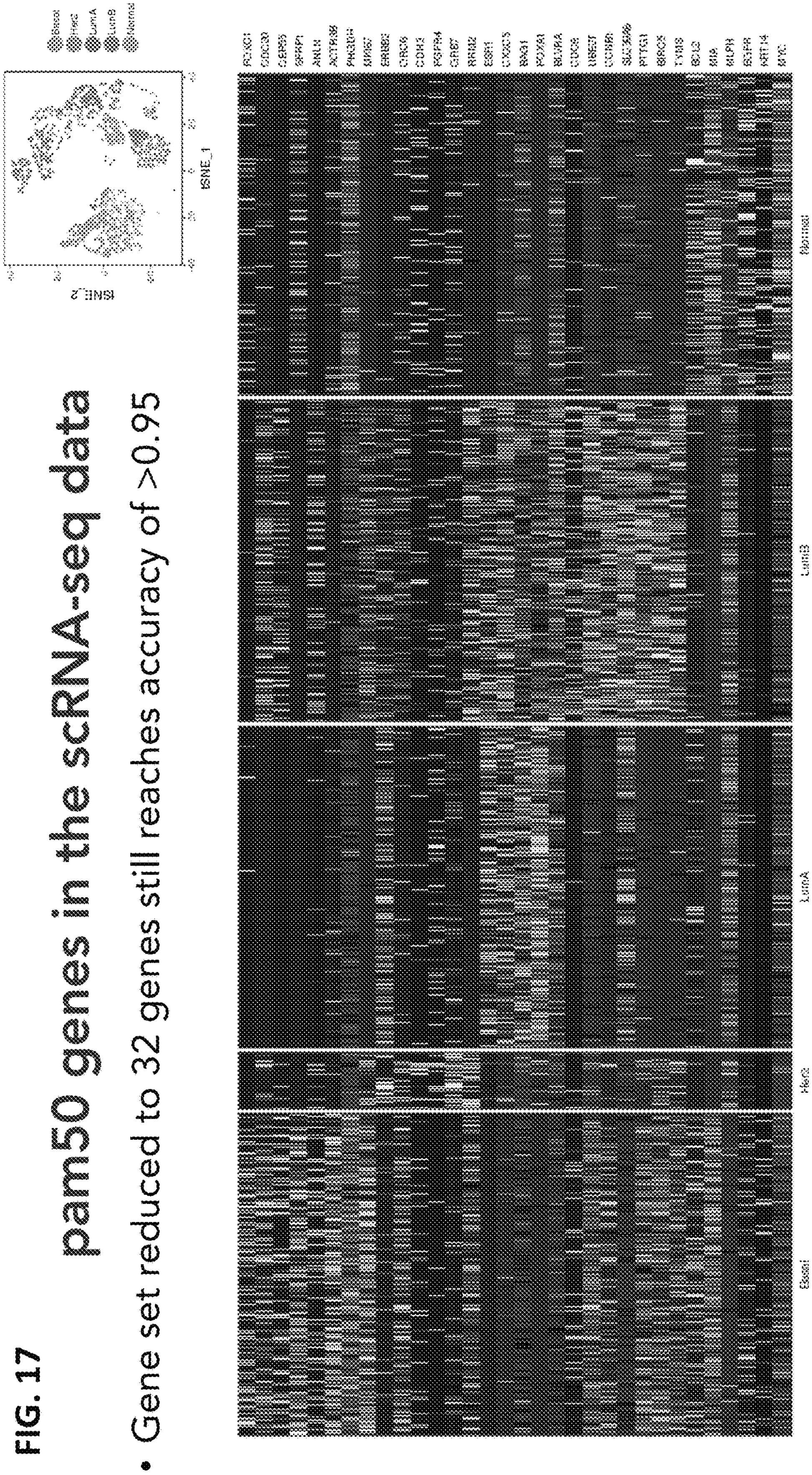

FIG. 17. Heat map showing expression of pam50 genes in single cells from MBC and labeled by the cell type.

Figure 18:
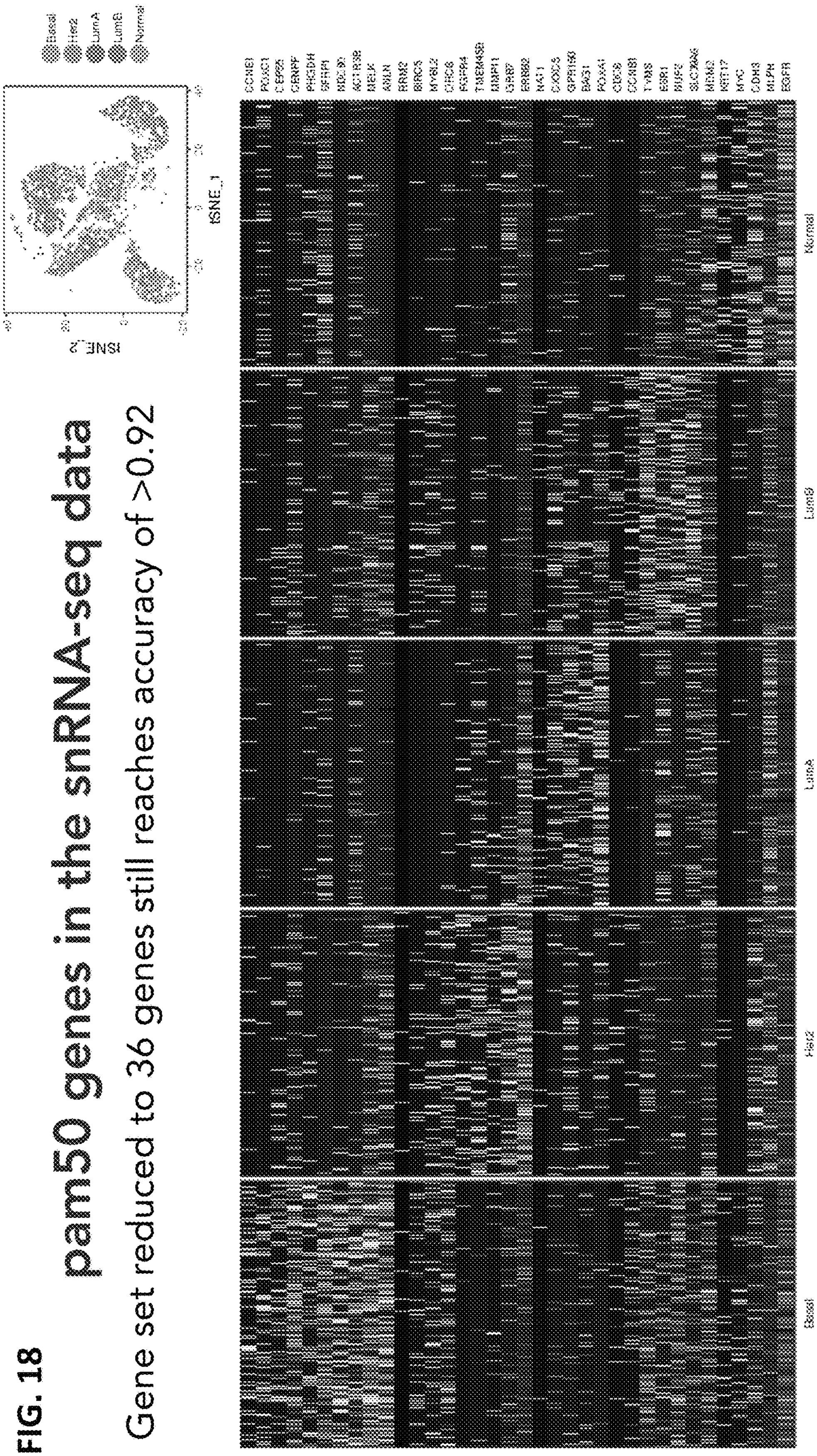

FIG. 18. Heat map showing expression of pam50 genes in single nuclei from MBC and labeled by the cell type.

Figure 19:
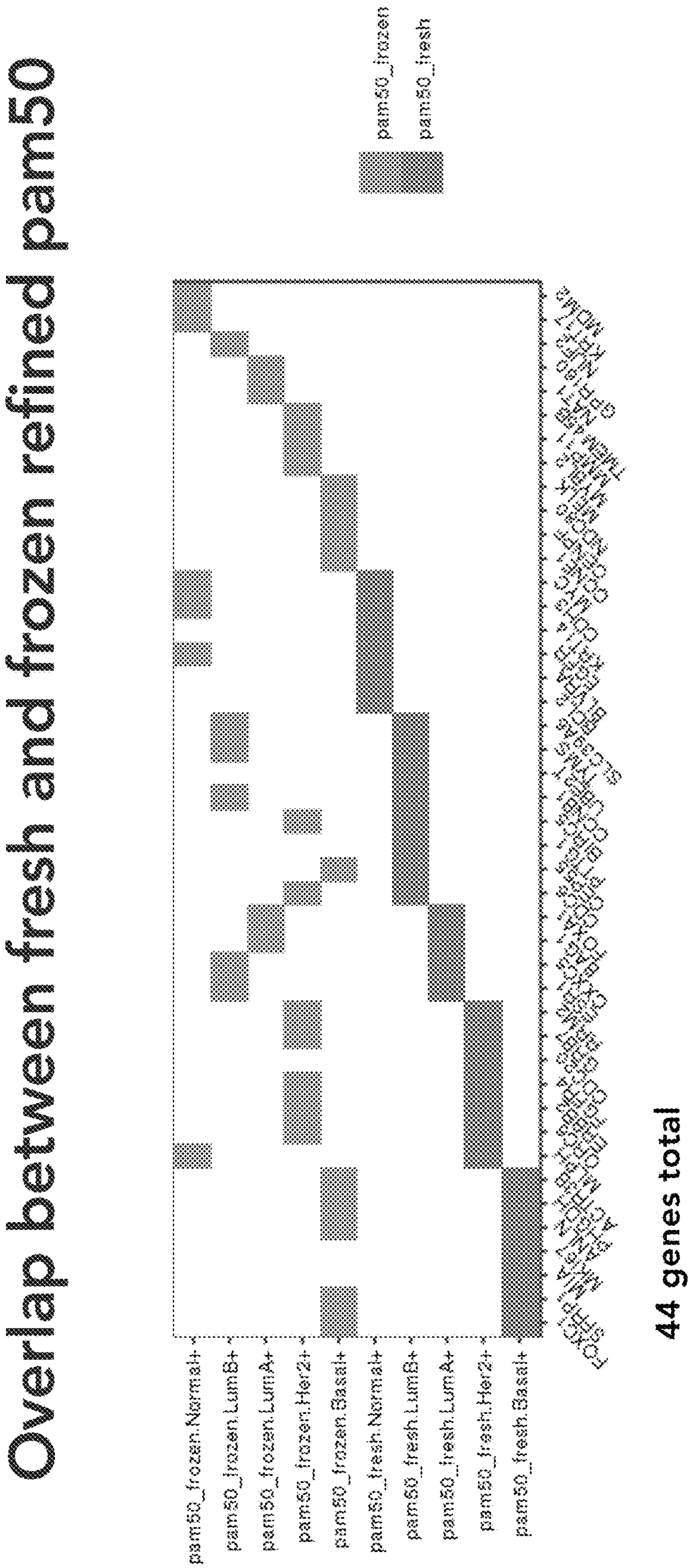

FIG. 19. Graph showing expression of pam50 genes in breast cancer subtypes in fresh and frozen tissues.

Figure 20:
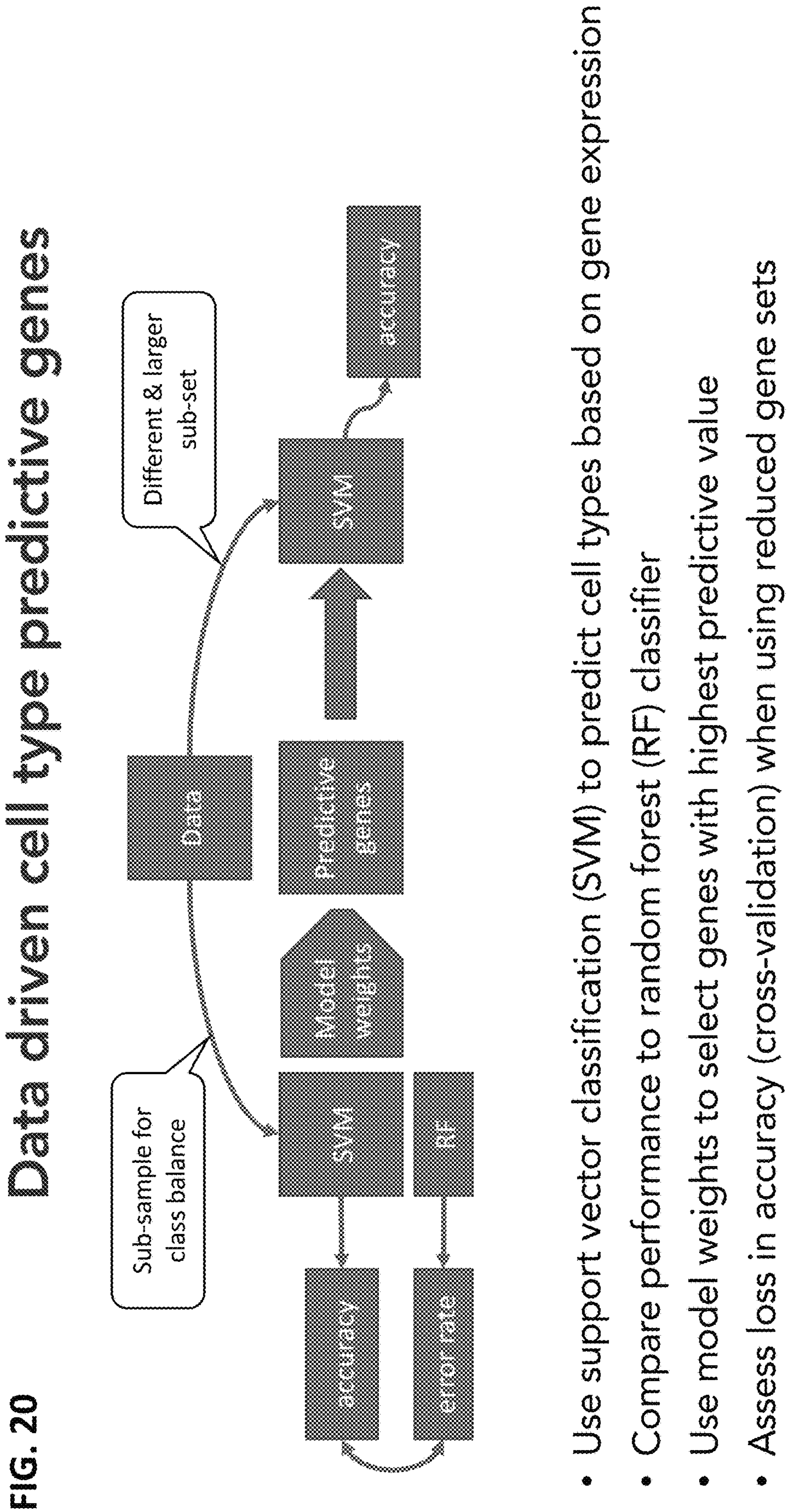

FIG. 20. Schematic showing a data driven method to identify genes that can be used to predict cell types.

Figure 21:
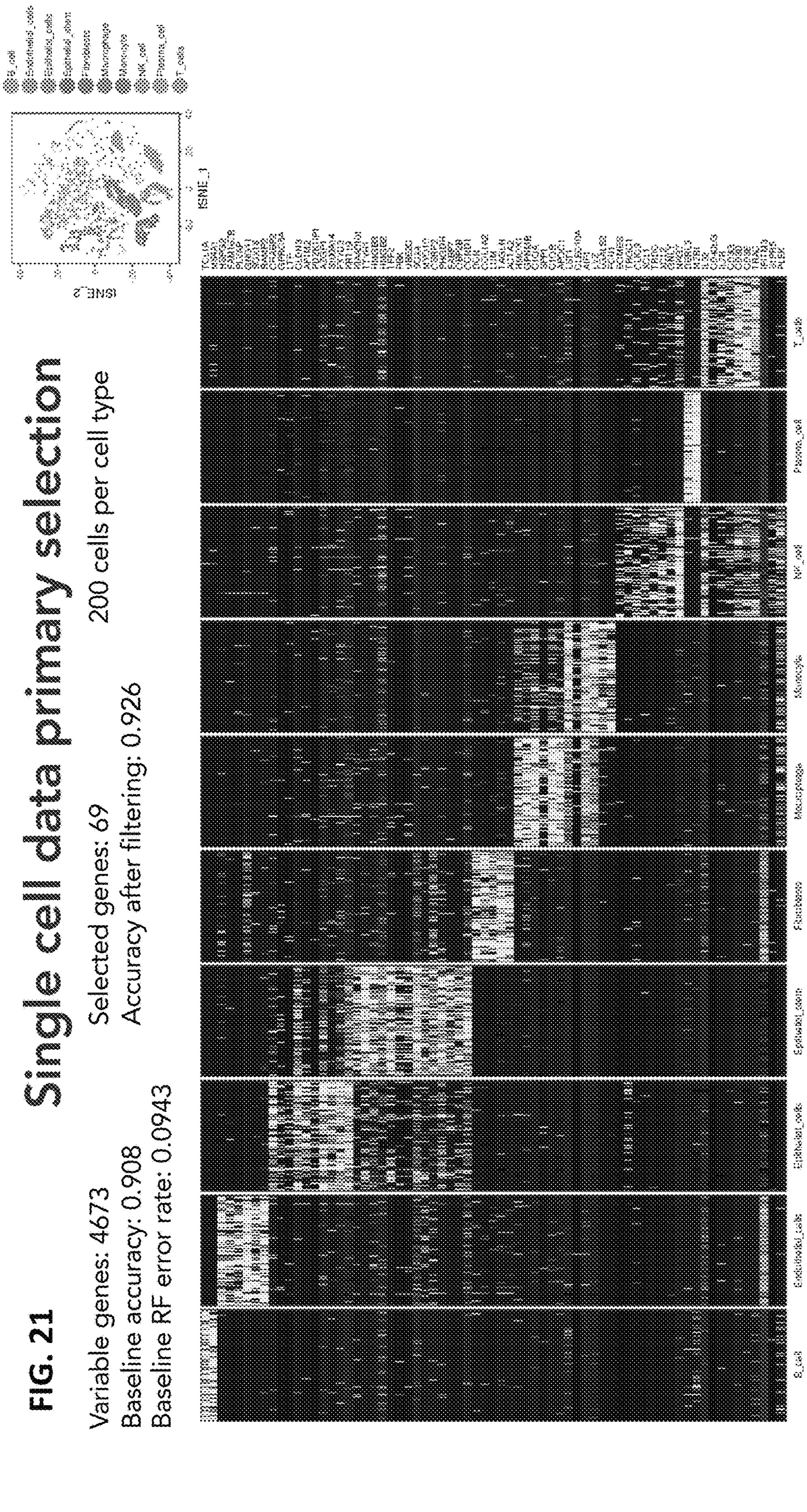

FIG. 21. Heatmap showing cell type specific gene expression in single cells from MBC.

Figure 22:
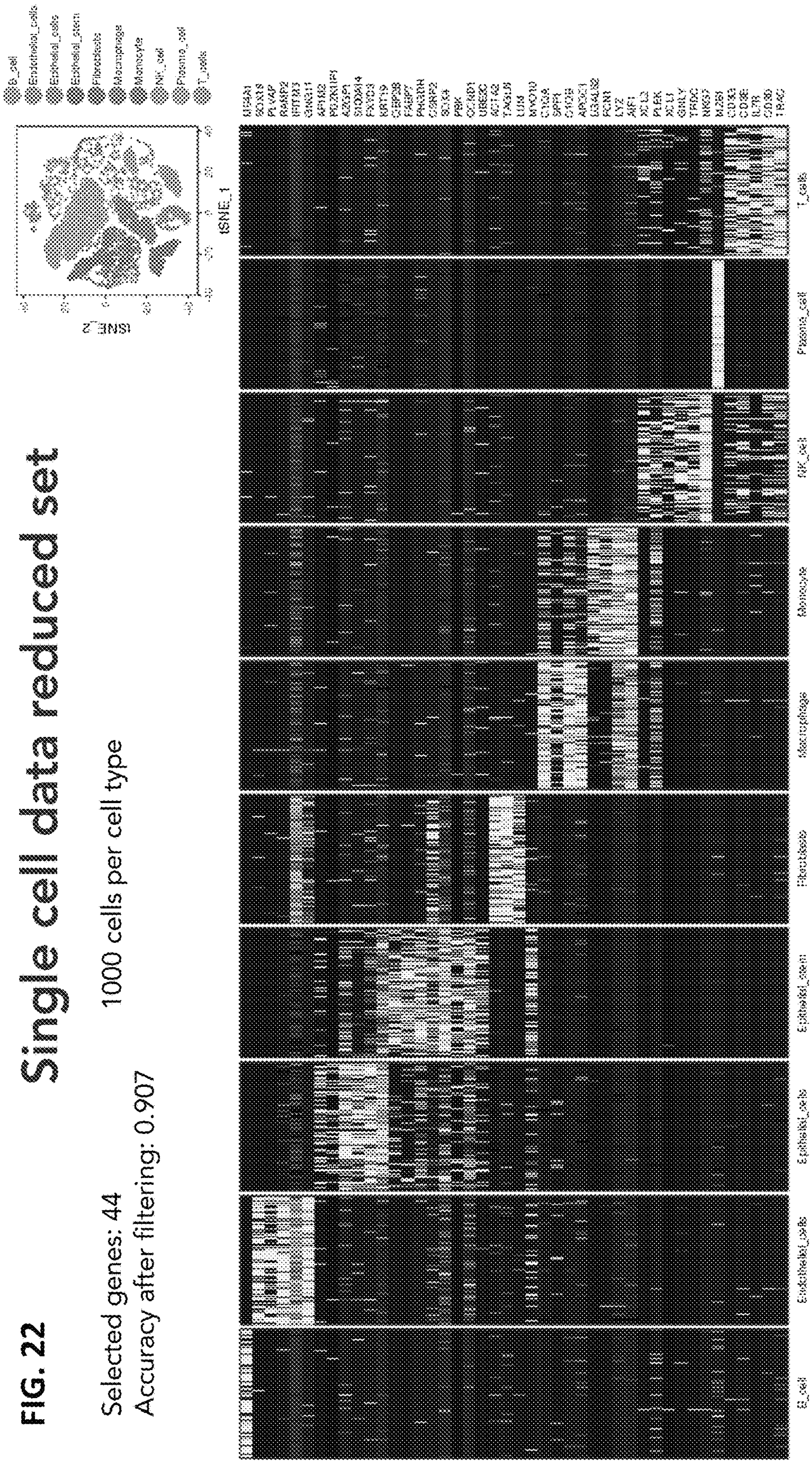

FIG. 22. Heatmap showing cell type specific gene expression in single cells from MBC using 44 genes.

Figure 23:
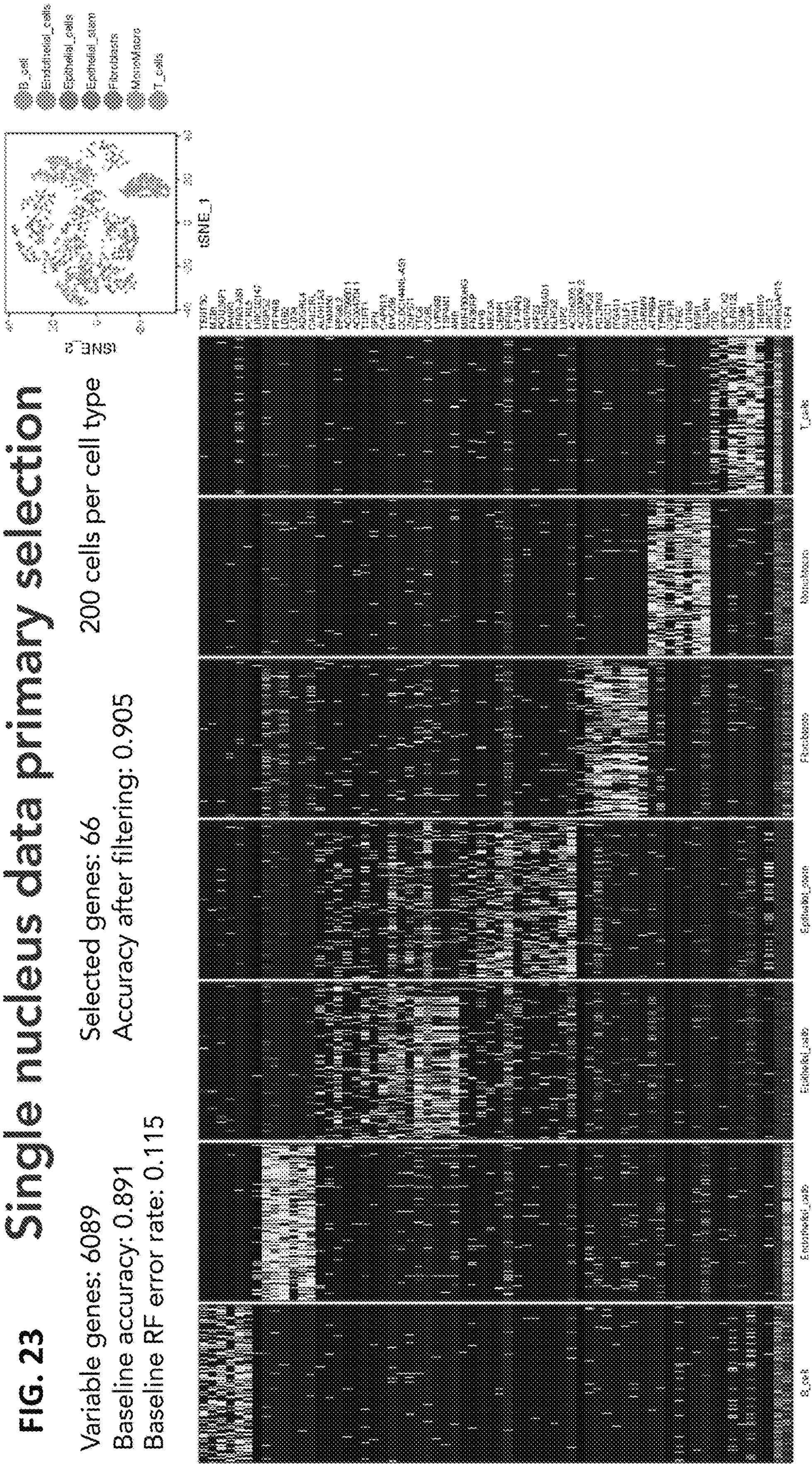

FIG. 23. Heatmap showing cell type specific gene expression in single nuclei from MBC.

Figure 24:
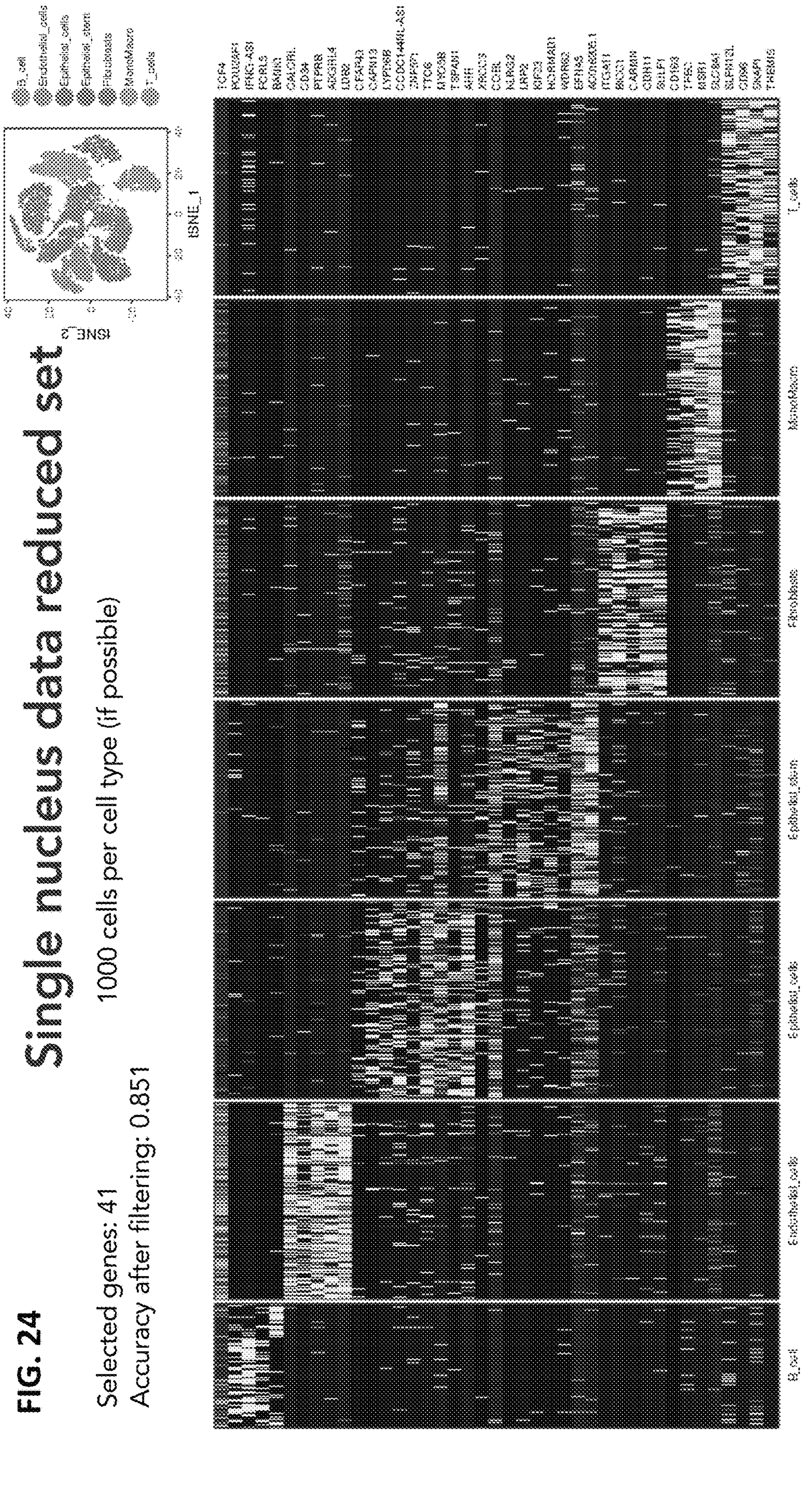

FIG. 24. Heatmap showing cell type specific gene expression in single nuclei from MBC using 41 genes.

Figure 25:
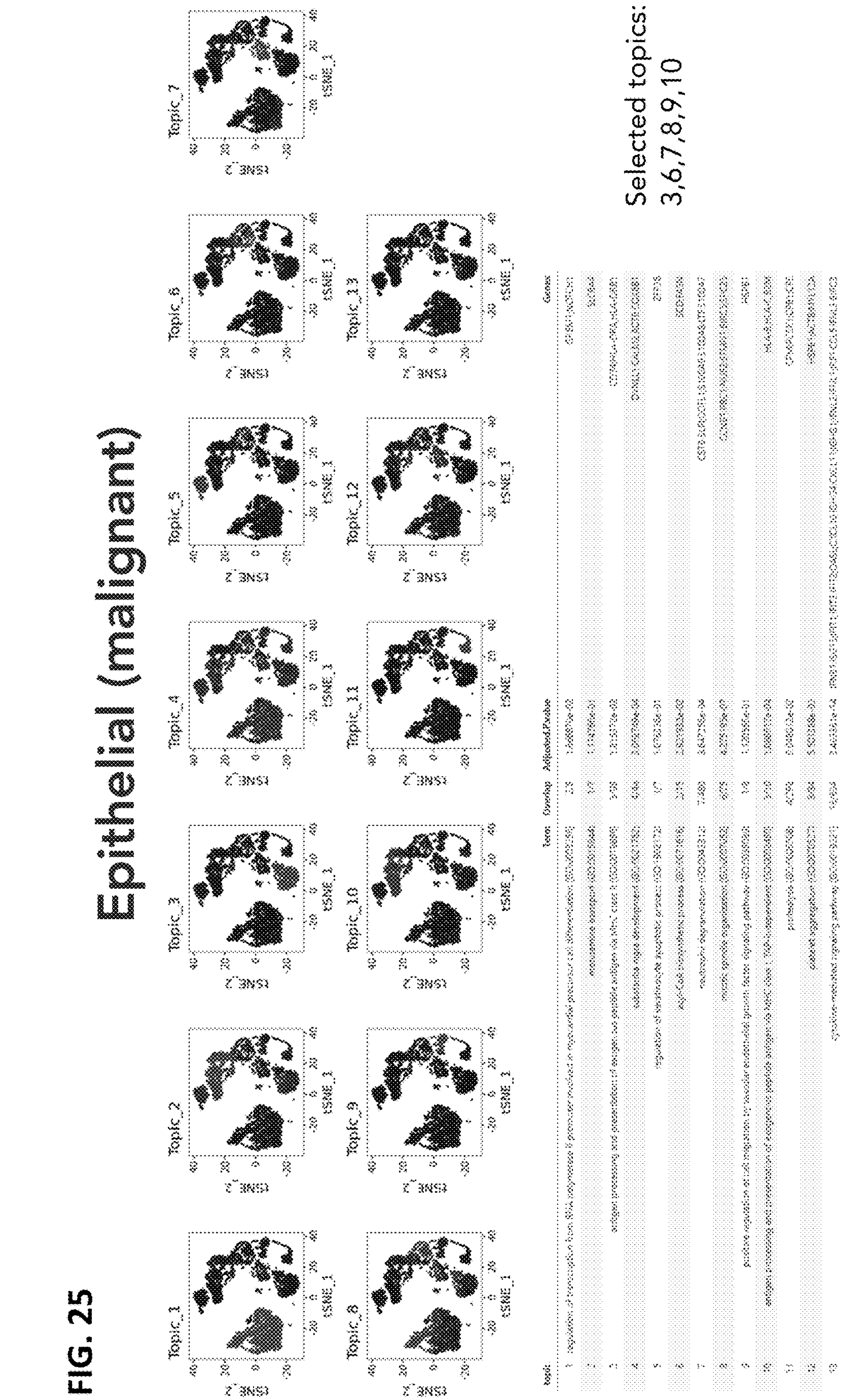

FIG. 25. tSNE plots showing malignant cell topics (gene programs) projected on the single cells. Representative genes and GO terms are shown for each topic. Selected topics are indicated.

FIG. 26. tSNE plots showing fibroblast topics (gene programs) projected on the single cells. Representative genes and GO terms are shown for each topic. Selected topics are indicated.

Figure 27:
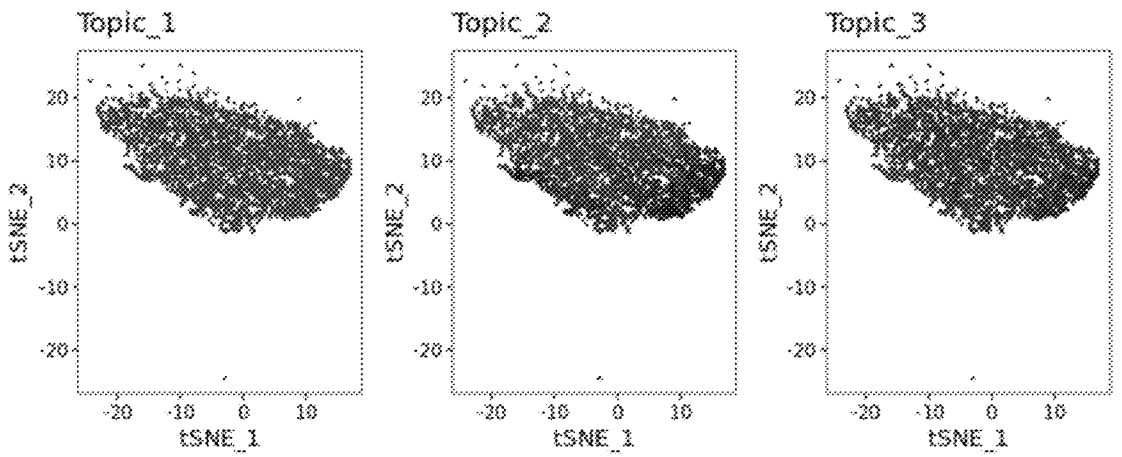

FIG. 27. tSNE plots showing T cell topics (gene programs) projected on the single cells. Representative genes and GO terms are shown for each topic. Selected topics are indicated.

Genes from the topics can be selected for identifying cell types in a spatial analysis.

Figure 28:
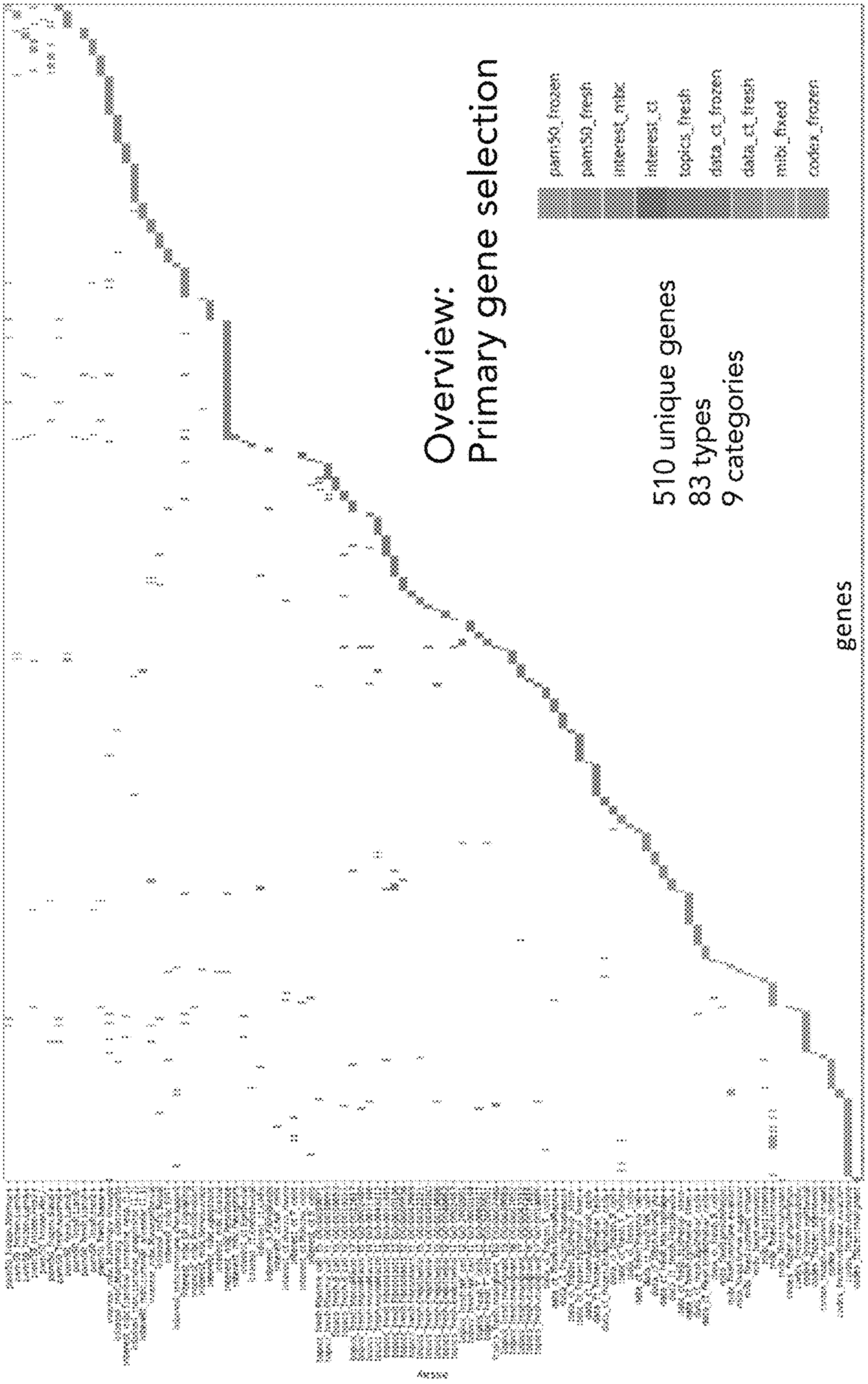

FIG. 28. Graph showing genes identified in the primary selection for each assay type.

Figure 29:
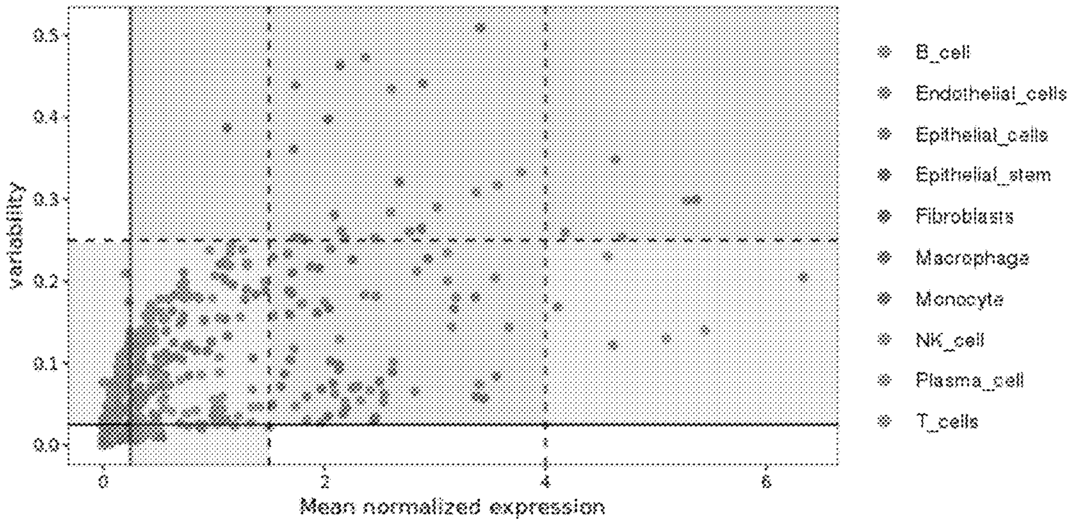

FIG. 29. Schematic showing filtering to obtain the 300 genes for use in spatial analysis (Table 1). Graph showing gene variability and mean normalized expression for the indicated cell types.

Figure 30:
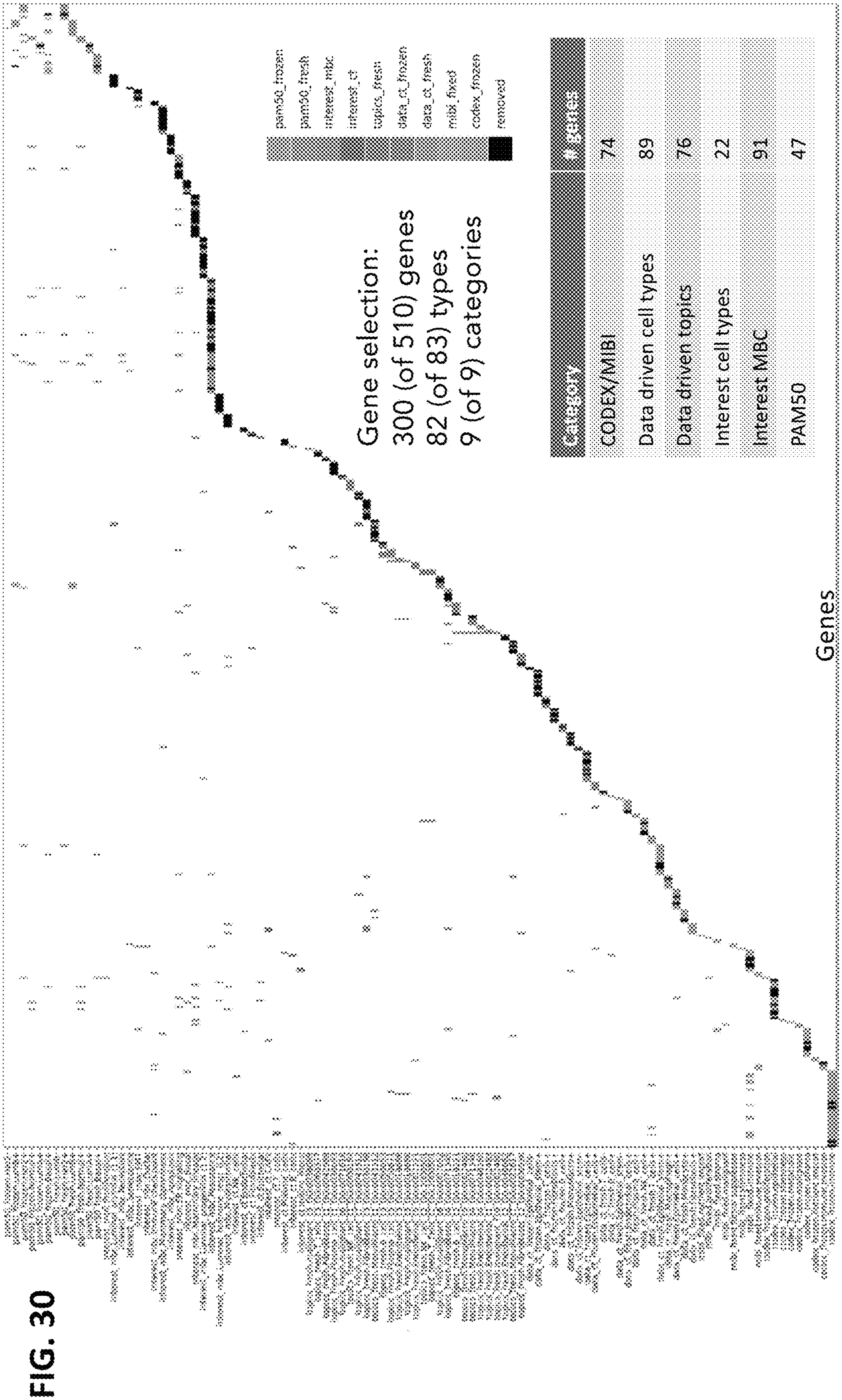

FIG. 30. Graph showing the 300 genes selected for use in spatial analysis (Table 1). The source of the selected genes are shown in the table.

Figure 31:
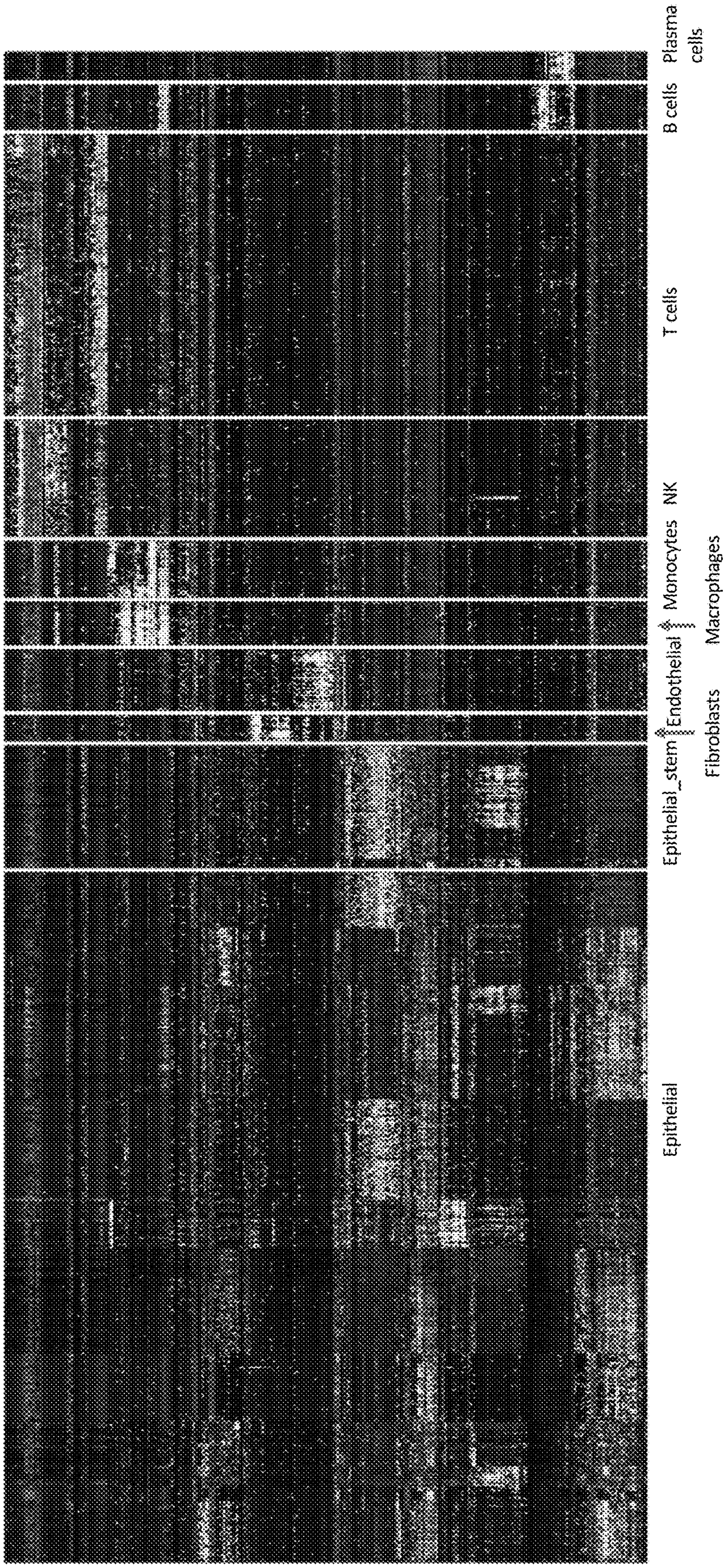

FIG. 31. Heatmap showing the expression of the selected genes (y-axis) in single cells (x-axis).

Figure 32:
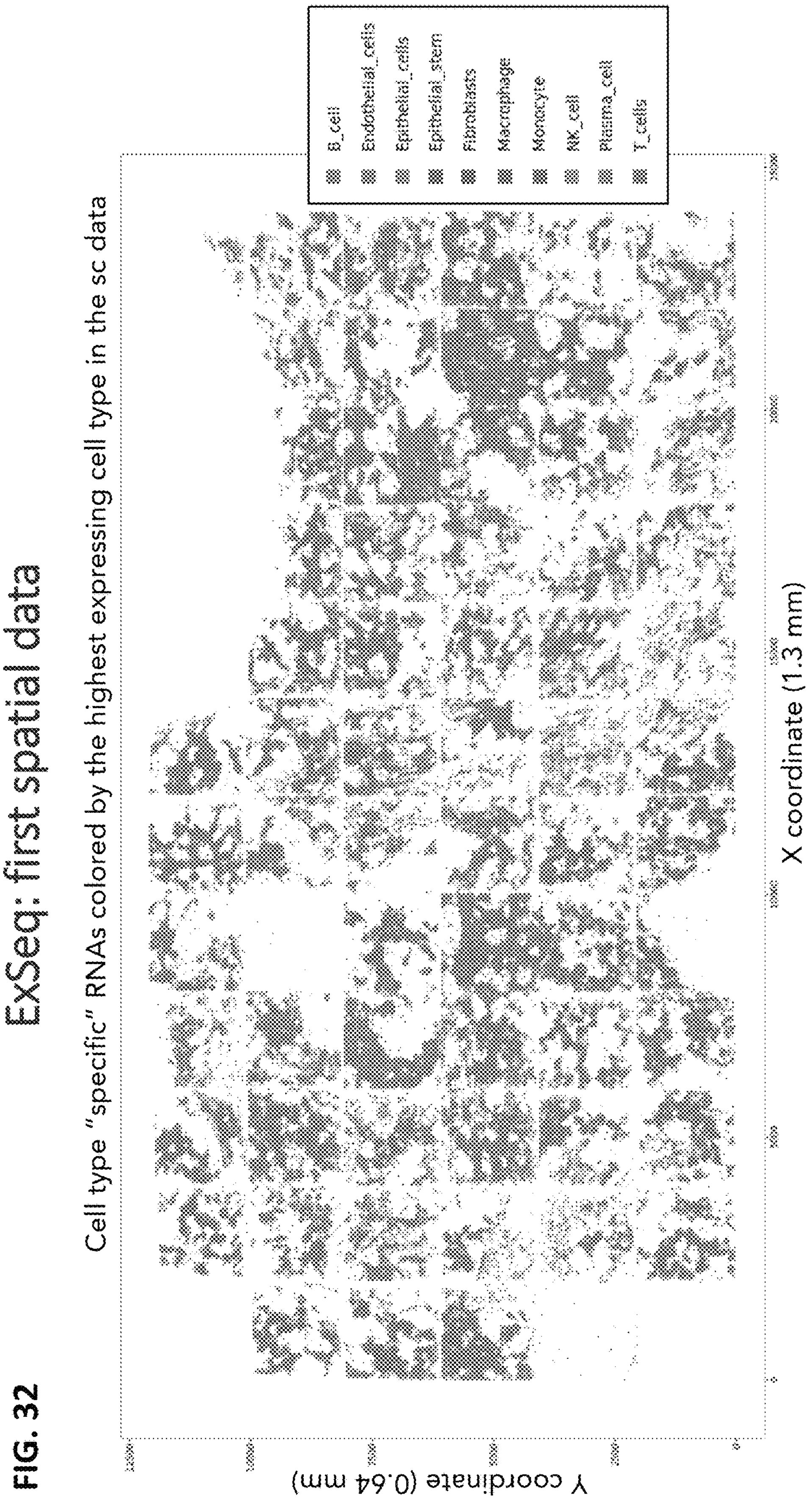

FIG. 32. ExSeq spatial data in breast cancer tissue using cell type specific markers.

Figure 33:
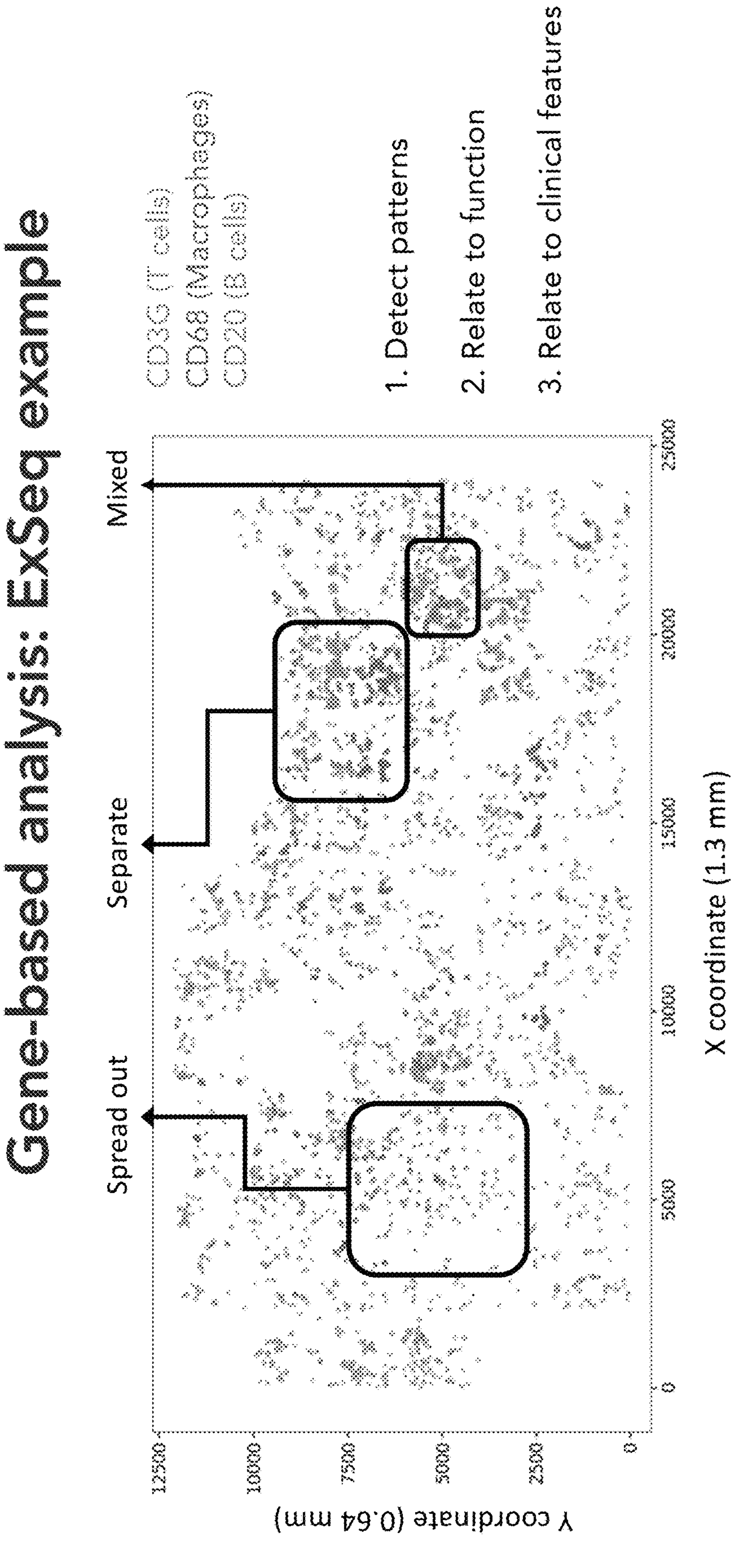

FIG. 33. ExSeq spatial data analysis of T cells, macrophages and B cells using indicated cell specific markers. Mixed, separate and spread out populations can be observed.

Figure 34:
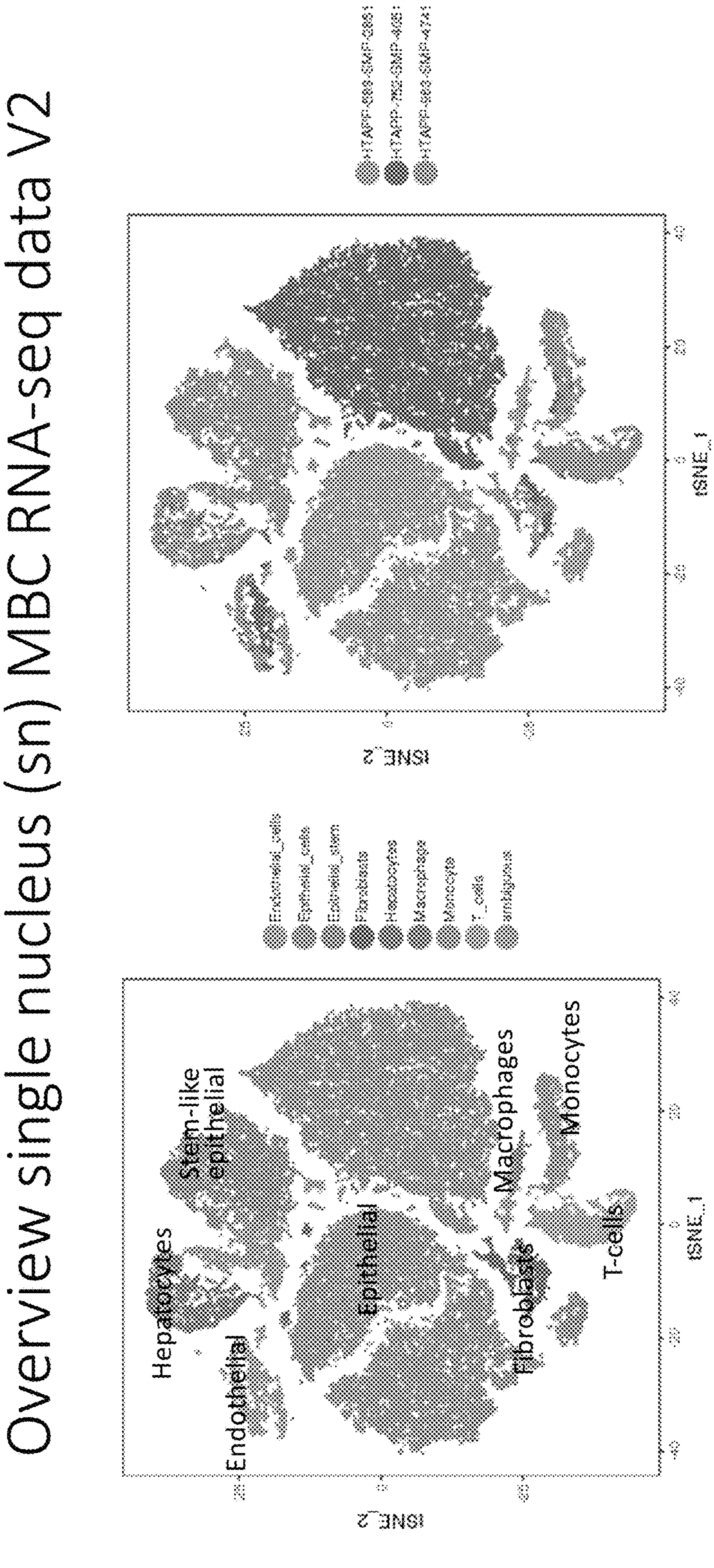

FIG. 34. tSNE plots of single cells using single nucleus RNA-seq labeled by cell type and sample.

Figure 35:
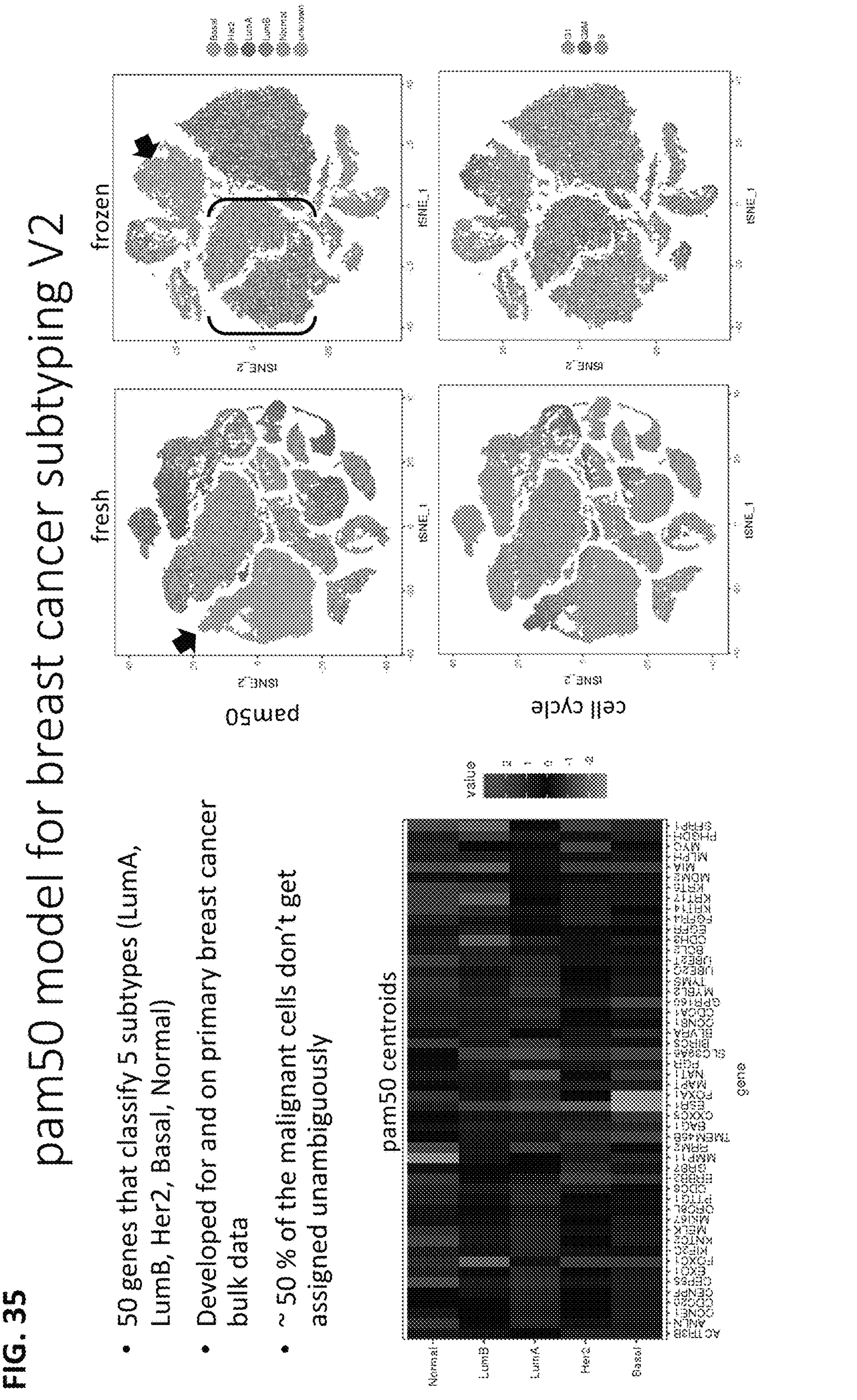

FIG. 35. Heatmap showing expression of pam50 genes in the breast cancer subtypes. tSNE plots of single cells from fresh and frozen tissue with pam50 subtypes and cell cycle projected.

Figure 36:
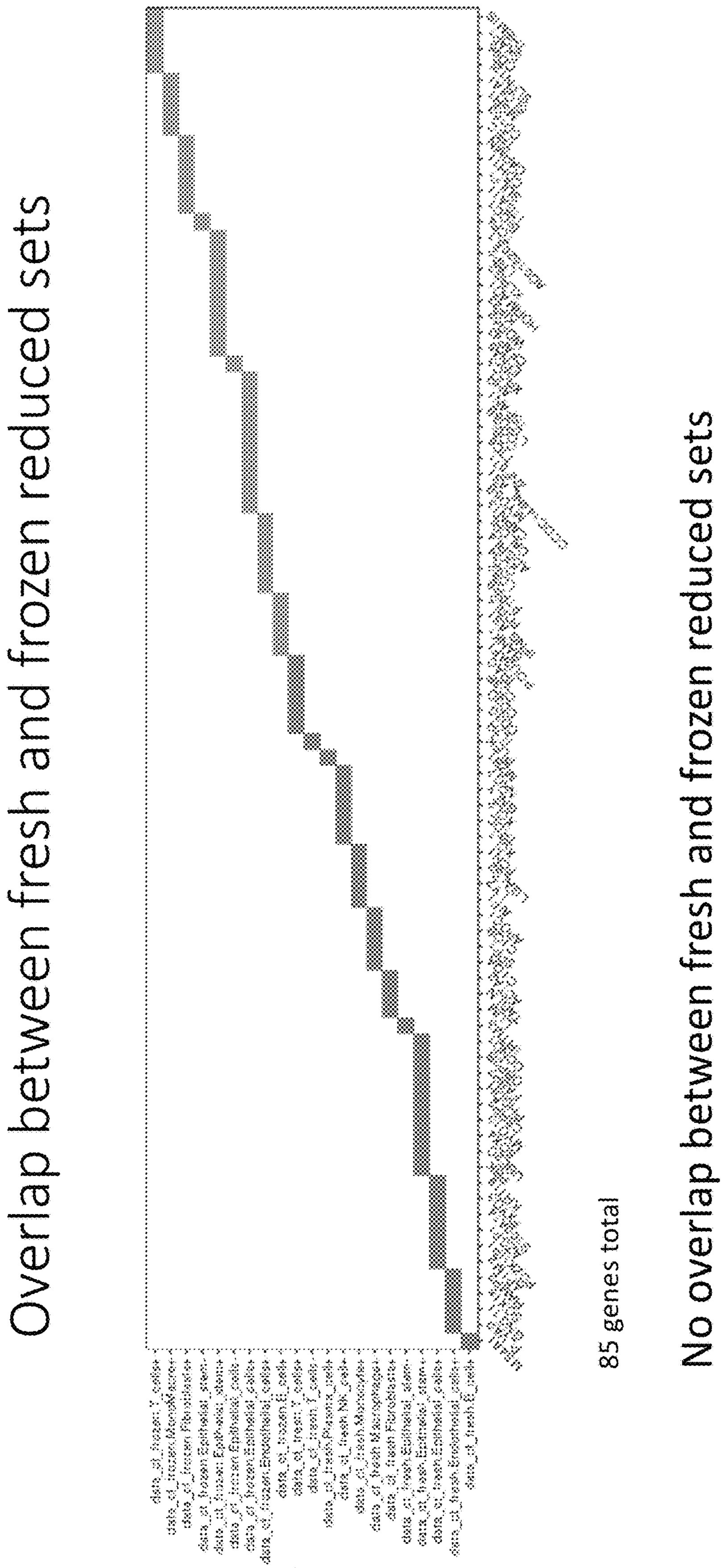

FIG. 36. Graph showing expression of an 85 reduced gene set in breast cancer subtypes in fresh and frozen tissues.

Figure 37:
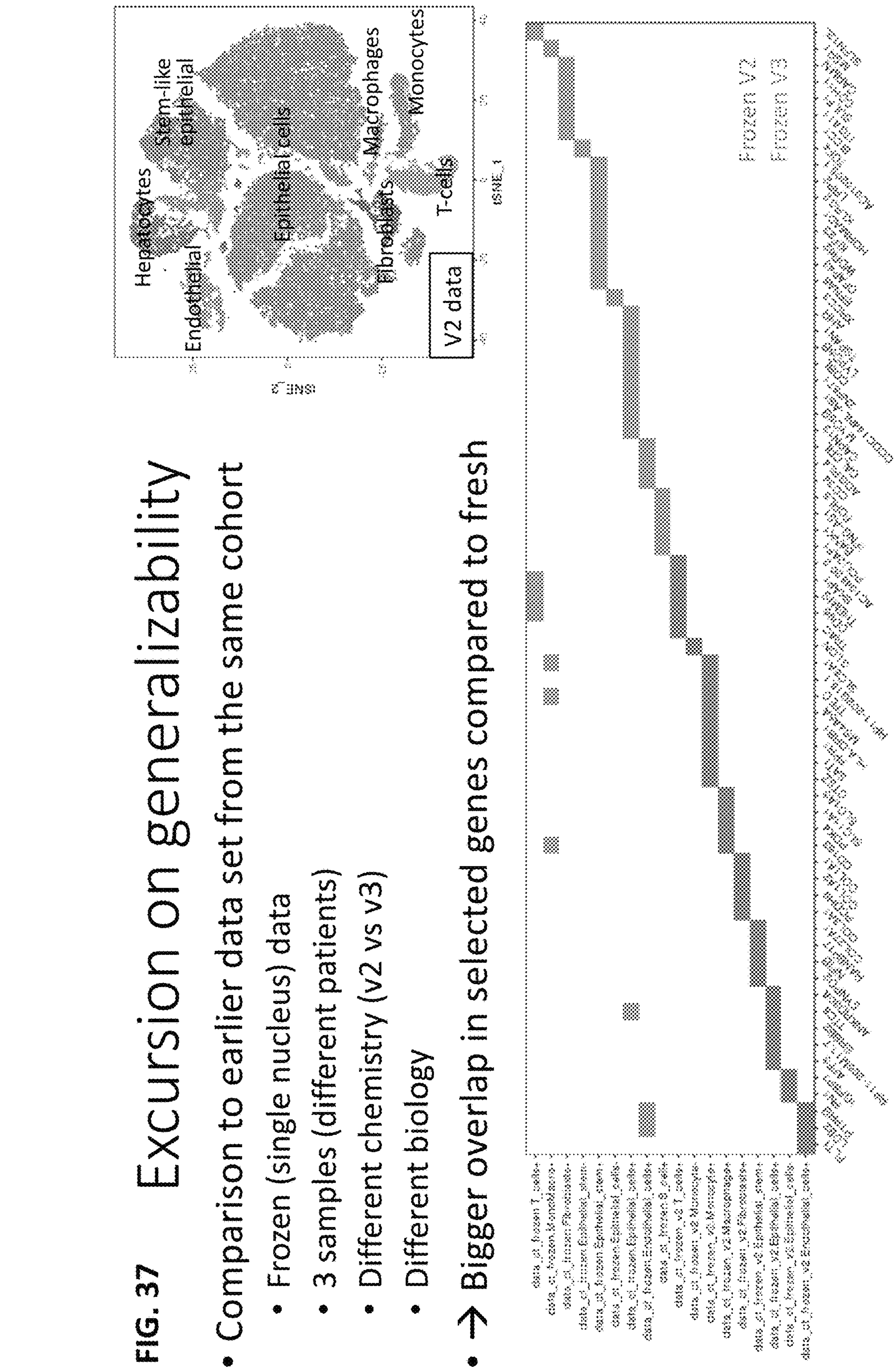

FIG. 37. Graph showing expression of selected gene set in breast cancer subtypes in version 2 and 3 chemistry frozen tissues.

Figure 38:
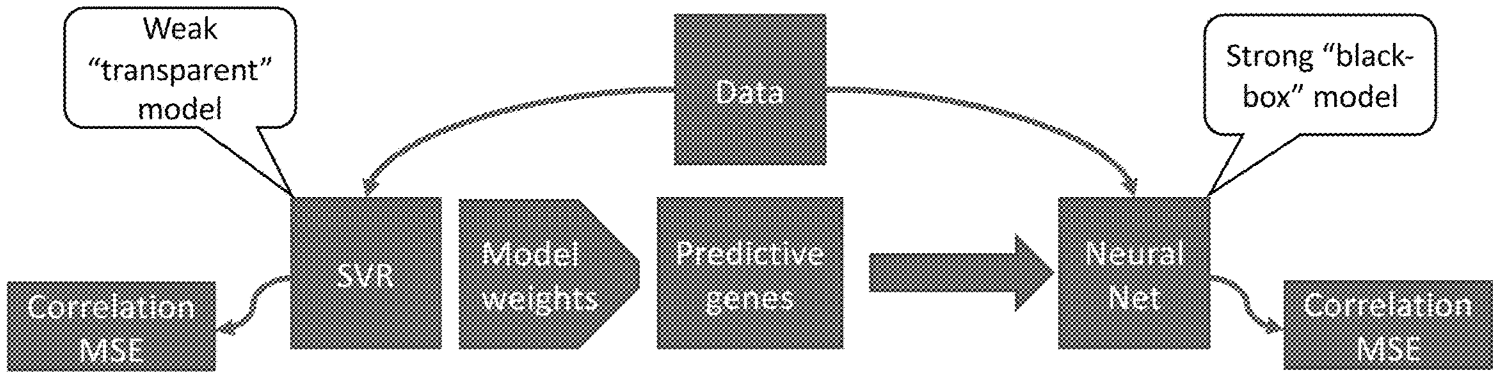

FIG. 38. Schematic showing a data driven method to identify genes that can be used to predict cell types.

Figure 39:
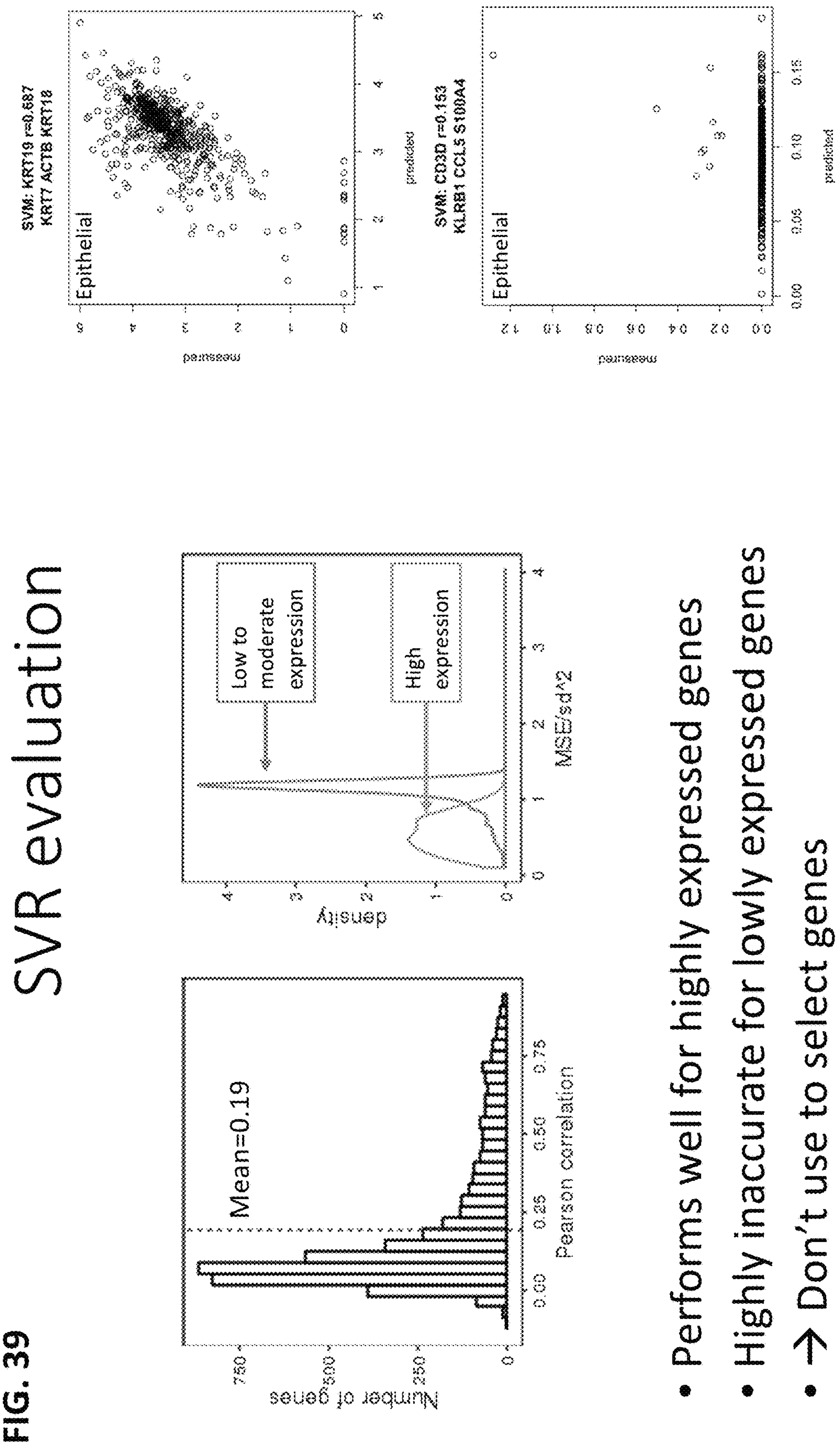

FIG. 39. Graphs showing prediction and measured gene for epithelial cells using SVR evaluation of highly and lowly expressed genes.

Figure 40:
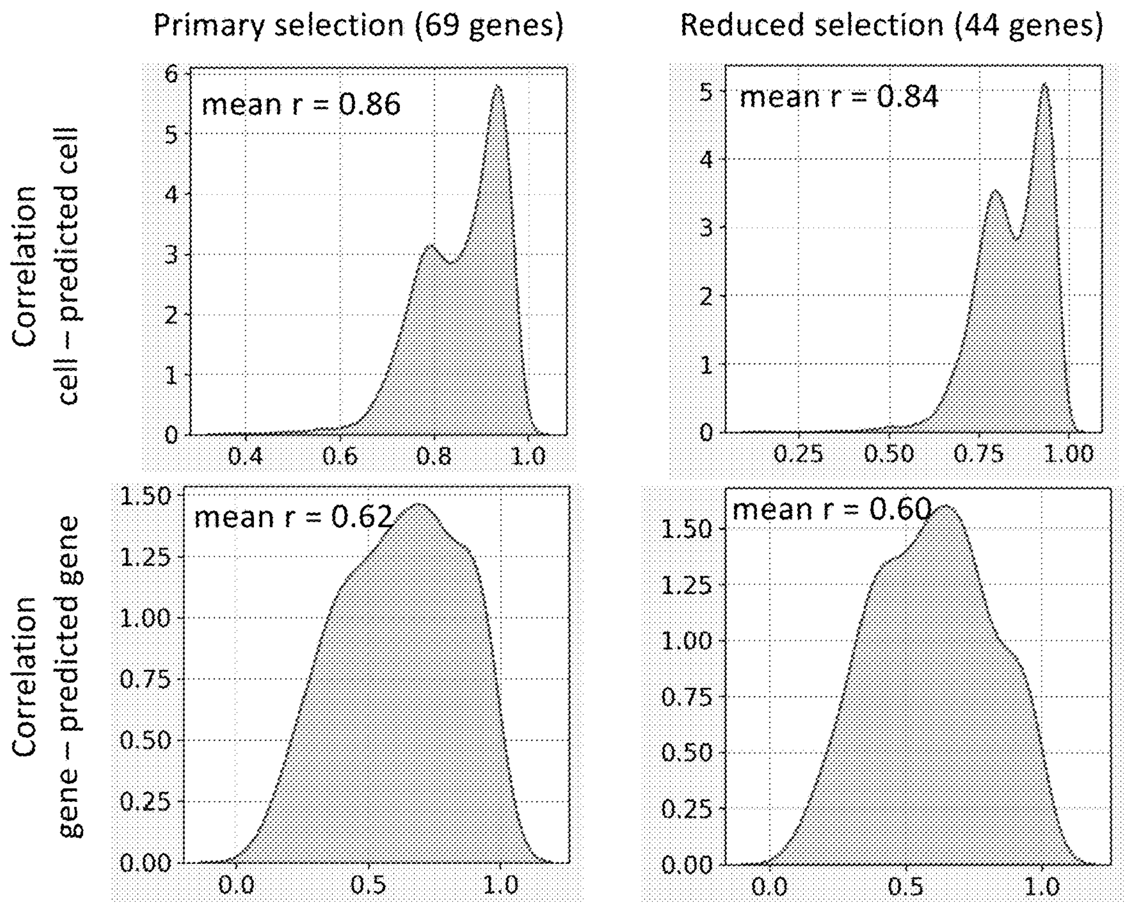

FIG. 40. Graphs showing neural net based prediction of expression.

Figure 41:
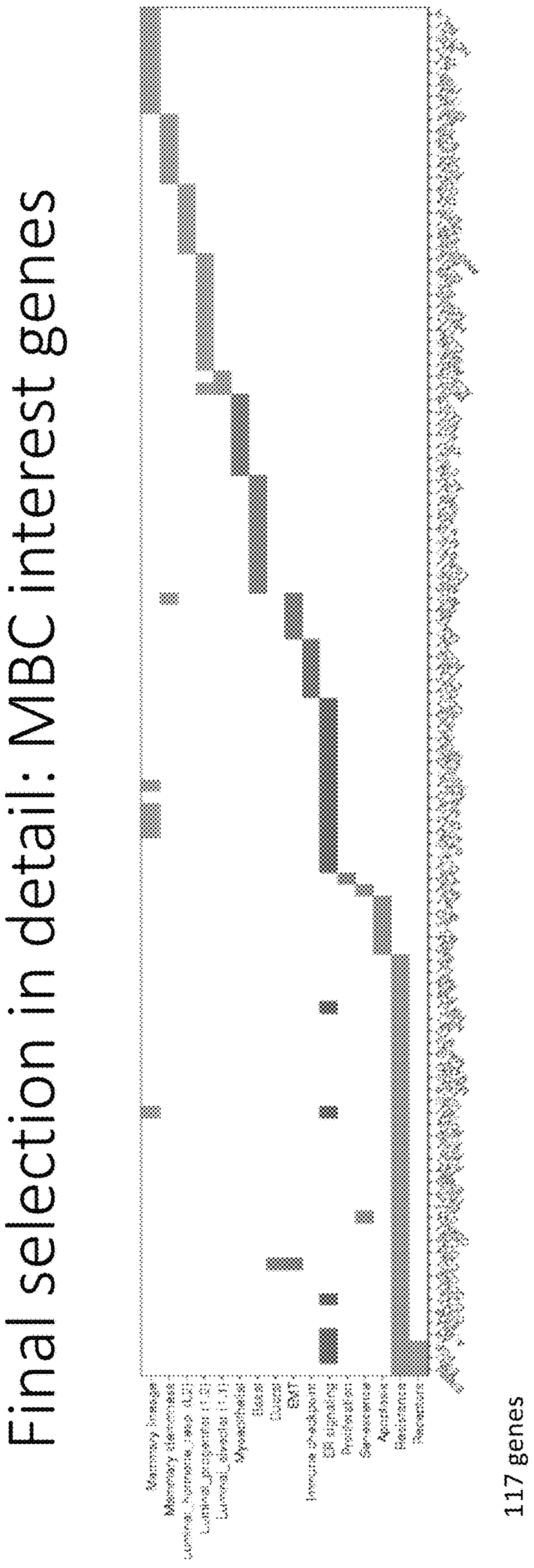

FIG. 41. Graph showing expression of 117 MBC interest genes in the indicated pathways and lineages.

Figure 42:
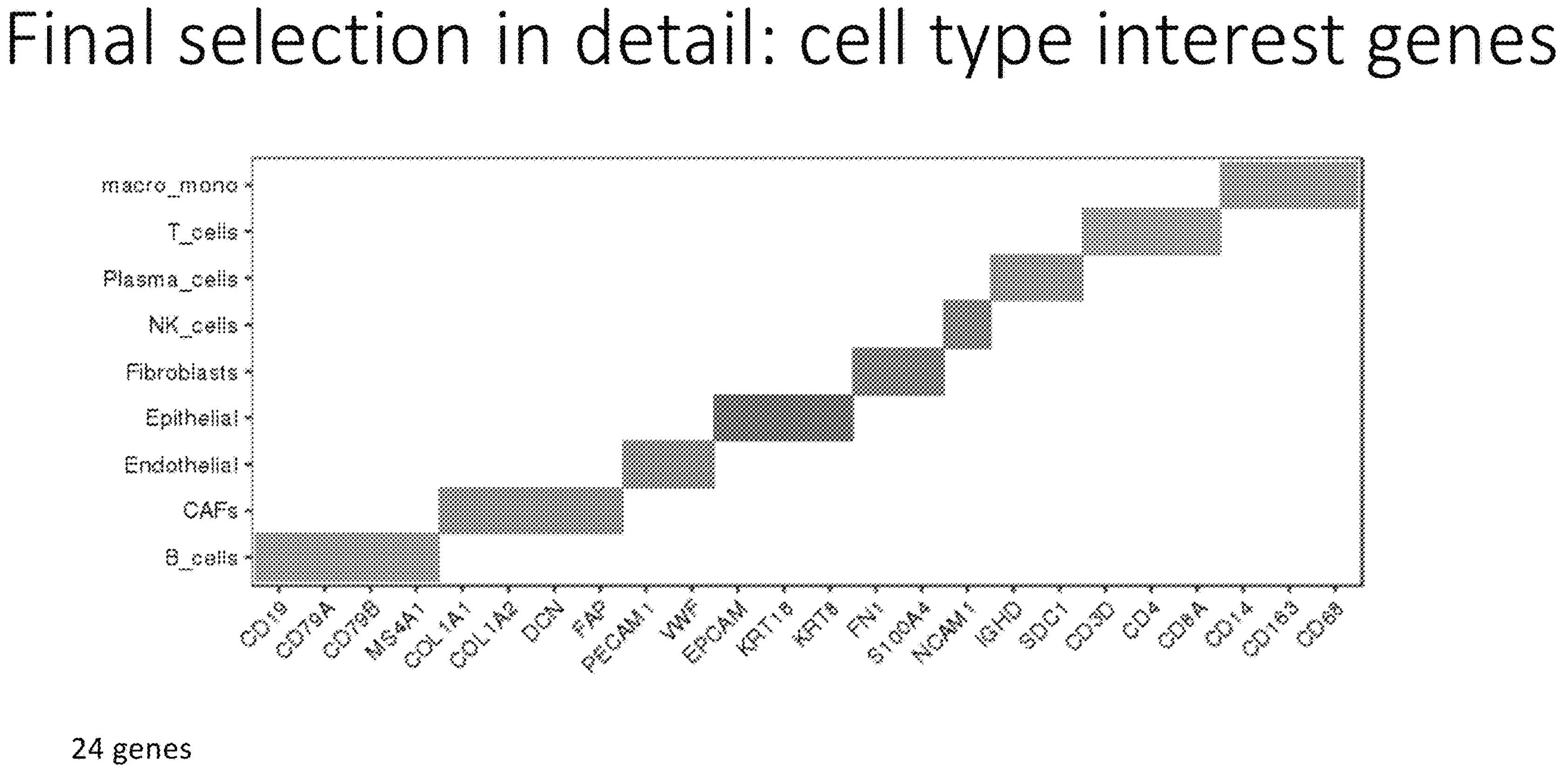

FIG. 42. Graph showing expression of 24 cell type interest genes in the indicated cell types.

Figure 43:
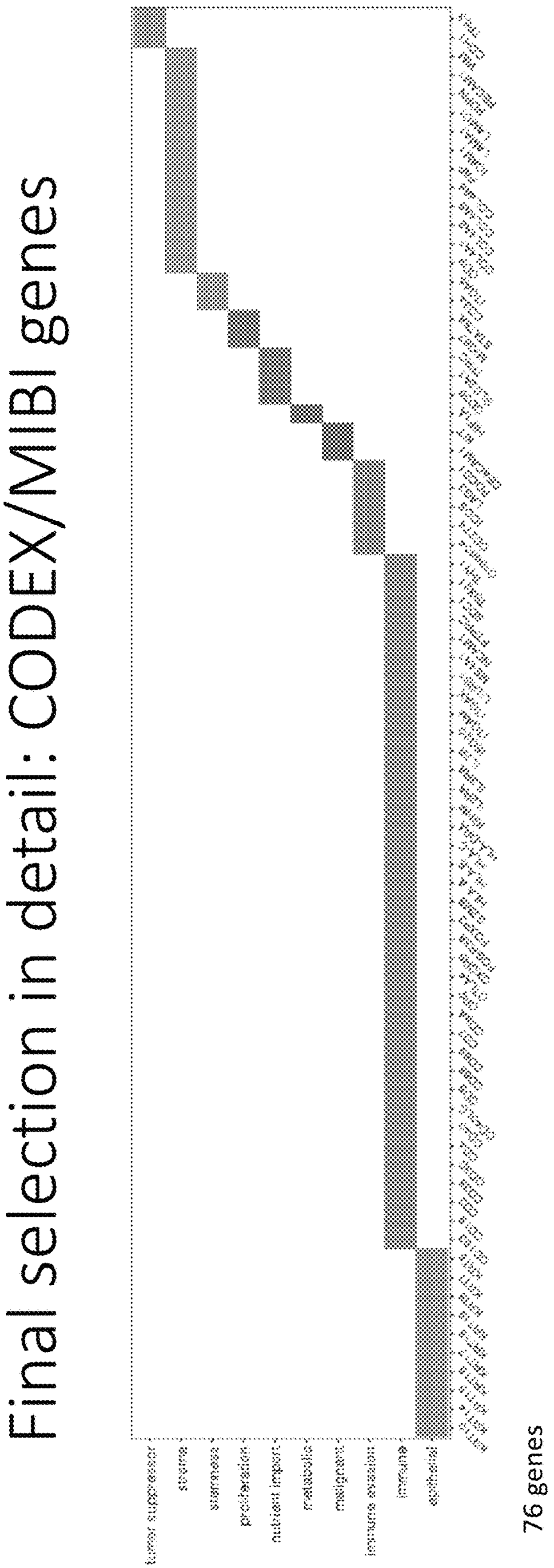

FIG. 43. Graph showing expression of 76 CODEX/MIBI genes in the indicated pathways and lineages.

Figure 44:
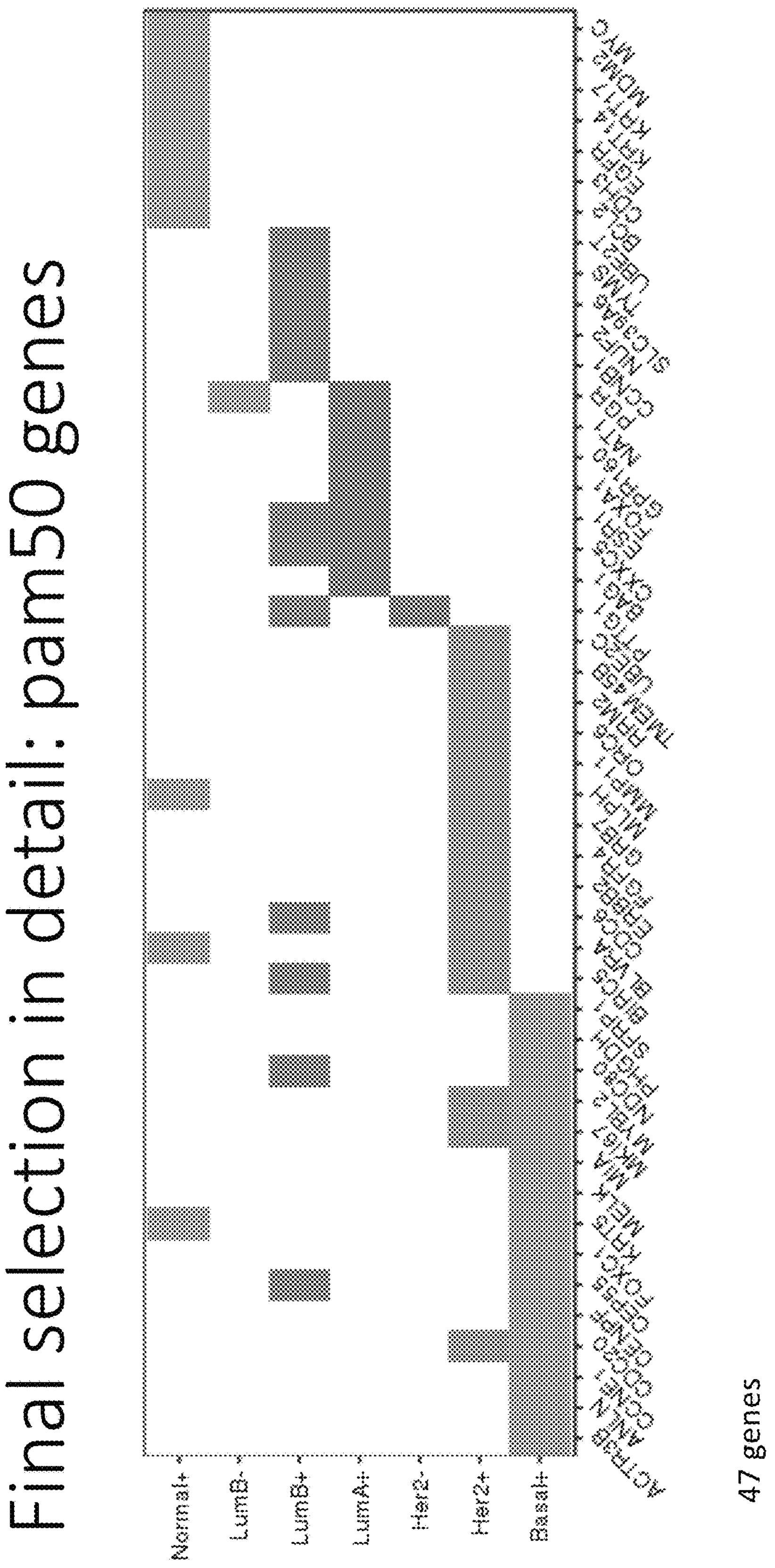

FIG. 44. Graph showing expression of 47 pam50 genes in the indicated breast cancer subtype.

Figure 45:
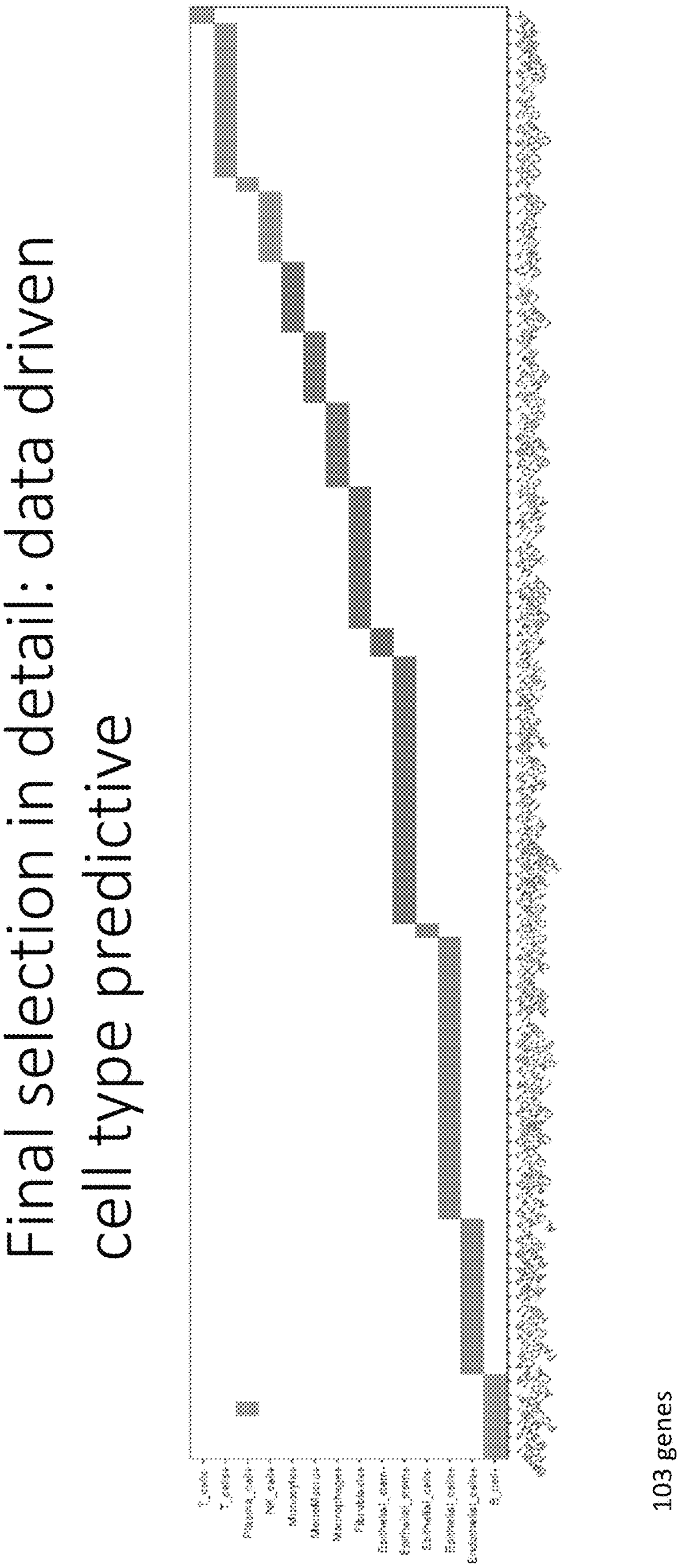

FIG. 45. Graph showing expression of 103 data driven cell type predictive genes in the indicated cell types.

FIG. 46. Table showing MBC cell type wise statistics.

FIG. 47. Table showing statistics across the entire data set.

FIG. 48. Table showing statistics with reduced complexity.

Figure 49:
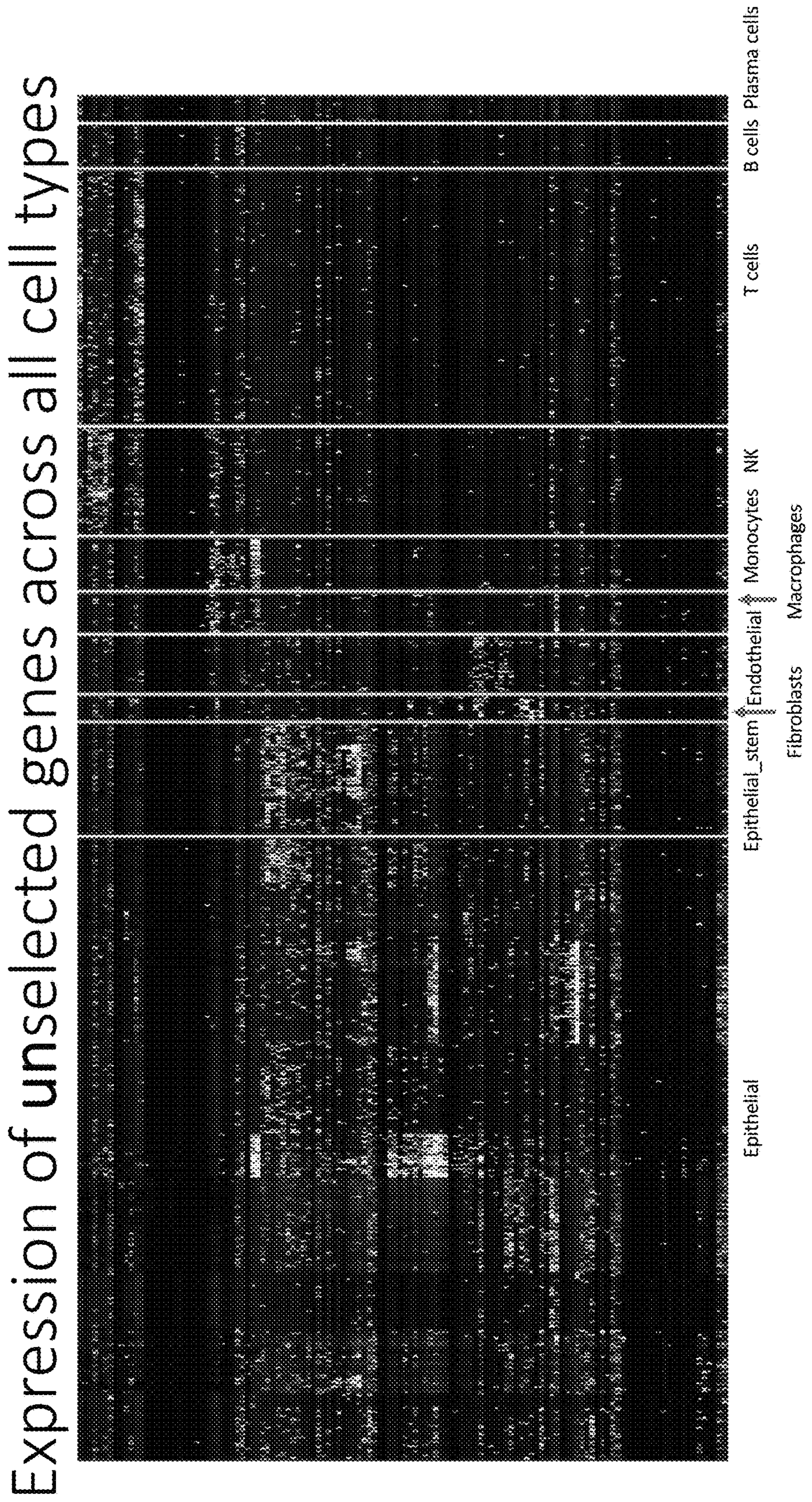

FIG. 49. Heatmap showing expression of unselected genes across all cell types.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, the applicant, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murine, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

As used herein, the term "cell state" refers to a specific state of the cell, such as but not limited to an activated cell, such as activated immune cell, resting cell, such as a resting immune cell, a dividing cell, quiescent cell, or a cell during any stages of the cell cycle.

As used herein, the term "gene expression profile" refers to a measurement of expression levels of a set of genes or all genes in a nucleus, a cell, or a tissue at any given moment. Gene expression profiling measures pre-RNA or mRNA levels, showing the pattern of genes expressed by a cell at the transcription level. This often means measuring relative pre-RNA or mRNA amounts in two or more experimental conditions, then assessing which conditions resulted in specific genes being expressed.

As used herein, a "gene expression profile" or a "signature" may encompass any gene or genes, protein or proteins, or epigenetic element(s) whose expression profile or whose occurrence is associated with a specific cell type, subtype, or cell state of a specific cell type or subtype within a population of cells.

As used herein, "gene targets" refer to any gene or genes that are directly or indirectly associated with cellular functions comprising apoptosis, angiogenesis, immunity, immunotolerance, antigen presentation, extracellular matrix integrity, immunocytotoxicity, and any combination thereof, and have differentially expressed in tumors in comparison to that in normal tissues.

As used herein, the terms "dimensionality reduction" or "dimension reduction" refers to the process of reducing the number of random variables under consideration, via obtaining a set "uncorrelated" principle variables.

As used herein, the term "metric" refers to a mathematical function that associates a real nonnegative number analogous to distance with each pair of elements in a set such that the number is zero only if the two elements are identical, the number is the same regardless of the order in which the two elements are taken, and the number associated with one pair of elements plus that associated with one member of the pair and a third element is equal to or greater than the number associated with the other member of the pair and the third element.

As used herein, an antibody is a type of immunoglobulin molecule, a protein made by plasma cells in response to an antigen (a substance that causes the body to make a specific immune response). Each antibody can bind to only one specific antigen. Some antibodies destroy antigens directly. Others make it easier for white blood cells to destroy the antigen.

As used herein, a therapeutic agent is defined as a small molecule, a biologic, an antibody, or any chemical entity that possesses therapeutic effect for a disease or diseases.

The heterogeneous population of cells may be derived from a section of a tissue or a tumor from a subject. Accordingly, the term "cell population" or "population" can denote a set of cells having one or more characteristics in common, which may be, for example, source derivation.

As used herein, a "subpopulation" of cells preferably refers to a particular subset of cells of a particular cell type or cell state which can be distinguished or are uniquely identifiable and set apart from other cells of this cell type. As used herein, cell subtype and cell subpopulation are used interchangeably.

As used herein, barcoding that may be used in the present invention may be performed based on any of the compositions or methods disclosed in patent publication WO 2014047561 A1, Compositions and methods for labeling of agents, incorporated herein in its entirety. Not being bound by a theory, amplified sequences from single cells or nuclei can be sequenced together and resolved based on the barcode associated with each cell or nuclei.

All publications, published patent documents, and patent applications cited herein are hereby incorporated by reference to the same extent as though each individual publication, published patent document, or patent application was specifically and individually indicated as being incorporated by reference.

Overview

The present invention provides methods and uses thereof for producing molecular spatial maps for the tissue microenvironment of MBC and DCIS. Specific set of genes (i.e., markers) are provided herein for performing such molecular spatial mapping using RNA visualization methods. Methods are disclosed to select the specific set of genes from gene expression data obtained using scRNA-seq or snRNA-seq. The molecular spatial map of tissue microenvironment provides rich information including, but not limited to, cell types, cell states, and cell locations in a tissue. It further provides information about the expression levels of a given gene in one or more cell types, one or more cell states, and one or more spatial locations. Thus, the methods disclosed herein can provide a comprehensive body of information for a tissue microenvironment in MBC or DCIS.

The present invention also provides methods and compositions for treating MBC. In some aspects, methods are provided for identifying therapeutic targets for MBC or DCIS. These targets can be genes or gene products involved in a variety of cellular functions including apoptosis, angiogenesis, cell proliferation, immune environment, immunity, immunotolerance, and integrity of extracellular matrix. In some aspects, the present invention further provides methods that teach identifying therapeutic agents that are capable of modulating the expression and/or function of these target genes. Using these agents, one with ordinary skill of the art can develop compositions for treating MBC and/or DCIS. Furthermore, pharmaceutical compositions can also be developed using the therapeutic agents identified in the present invention for treating MBC and preventing DCIS from becoming invasive and metastatic.

The present invention also discloses a stem-like epithelial malignant cell identified in metastatic tumor tissue of MBC, and a neural-like epithelial malignant cell in metastatic tumor tissue.

The present invention also provides a gene expression profile for distinguishing cell types comprising epithelial cells, such as epithelial malignant cells and stem-like epithelial malignant cells, endothelial cells, smooth muscle cells, adipocytes, T cells, macrophages, and fibroblasts, in tissues from MBC. The method includes detecting the expression of one or more of the genes presented in Table 1. The method may include using a dimension reduction method for clustering the cell types. The method further includes targeting malignant cell specific genes for therapeutic purposes. The genes may be targeted by a variety of therapeutic agents (e.g., antibodies, CAR T cells, or T cells expressing an endogenous or exogenous T cell receptor (TCR)).

The present invention further discloses an epithelial cell derived from DCIS and characterized by expression of PIP gene or gene products, and the expression of one or more of genes or gene products comprising ESR1, PGR, ERBB2, and EGFR. Moreover, it also discloses an epithelial cell derived from ductal carcinoma in situ of the breast and characterized by no or low levels of expression of PIP gene or gene products in comparison to the normal breast ductal tissue, and the expression of one or more of genes or gene products comprising ESR1, PGR, and ERBB2.

The present invention also provides a gene expression profile for distinguishing cell types comprising epithelial cells, endothelial cells, smooth muscle cells, adipocytes, T cells, macrophages, and fibroblasts, in tissues of DCIS. The method includes detecting the expression of one or more of the genes presented herein. The method may include using a dimension reduction method for clustering the cell types. The method further includes targeting malignant cell specific genes for therapeutic purposes. The genes may be targeted by a variety of therapeutic agents (e.g., antibodies, CAR T cells, or T cells expressing an endogenous or exogenous T cell receptor (TCR)).

Gene Signatures and Biological Programs

Applicants have discovered and selected a novel gene set, gene signatures or biological programs (topics) for cell types in the tumor microenvironment of metastatic breast cancer (MBC).

TABLE 1

| Example Genes | | | | | | | |
|---|---|---|---|---|---|---|---|
| gene | labels | mean_raw | sd_raw | median_raw | max_raw | min_raw | perc_expr_raw |
| BANK1 | B_cell | 0.79 | 0.93 | 1 | 5 | 0 | 0.54 |
| CD19 | B_cell | 0.36 | 0.60 | 0 | 3 | 0 | 0.30 |
| CD40 | B_cell | 0.36 | 0.62 | 0 | 4 | 0 | 0.30 |
| CD69 | B_cell | 4.45 | 4.62 | 3 | 27 | 0 | 0.81 |
| CD74 | B_cell | 25.67 | 11.72 | 24 | 220 | 2 | 1.00 |
| CD79A | B_cell | 3.56 | 2.36 | 3 | 14 | 0 | 0.95 |
| CD79B | B_cell | 2.46 | 2.17 | 2 | 20 | 0 | 0.88 |
| CR2 | B_cell | 0.05 | 0.24 | 0 | 2 | 0 | 0.05 |
| CXCR5 | B_cell | 0.20 | 0.48 | 0 | 5 | 0 | 0.17 |
| CXXC5 | B_cell | 0.41 | 0.70 | 0 | 6 | 0 | 0.32 |
| HLA-DRB5 | B_cell | 1.91 | 1.90 | 1 | 21 | 0 | 0.75 |
| JUNB | B_cell | 5.28 | 4.81 | 4 | 31 | 0 | 0.86 |
| MS4A1 | B_cell | 1.93 | 1.71 | 2 | 13 | 0 | 0.82 |
| RPL13 | B_cell | 27.84 | 12.81 | 27 | 154 | 2 | 1.00 |
| RPL18 | B_cell | 8.98 | 4.78 | 8 | 64 | 1 | 1.00 |
| RPSA | B_cell | 6.38 | 4.46 | 6 | 73 | 0 | 0.99 |
| TCL1A | B_cell | 2.61 | 2.79 | 2 | 33 | 0 | 0.78 |
| ADGRL4 | Endothelial_cells | 1.60 | 2.36 | 1 | 22 | 0 | 0.60 |
| CALCRL | Endothelial_cells | 1.34 | 2.14 | 1 | 19 | 0 | 0.52 |
| CD34 | Endothelial_cells | 1.47 | 2.59 | 1 | 36 | 0 | 0.50 |
| CD36 | Endothelial_cells | 0.81 | 1.91 | 0 | 17 | 0 | 0.28 |
| COL4A1 | Endothelial_cells | 2.25 | 4.77 | 1 | 69 | 0 | 0.55 |
| COL4A2 | Endothelial_cells | 2.14 | 4.81 | 1 | 94 | 0 | 0.55 |
| GNG11 | Endothelial_cells | 7.67 | 9.73 | 5 | 161 | 0 | 0.93 |
| GSN | Endothelial_cells | 2.59 | 4.71 | 1 | 60 | 0 | 0.63 |
| HSPB1 | Endothelial_cells | 7.08 | 9.66 | 4 | 160 | 0 | 0.92 |
| HSPG2 | Endothelial_cells | 3.88 | 5.03 | 2 | 59 | 0 | 0.80 |
| IFITM3 | Endothelial_cells | 12.91 | 15.62 | 8 | 256 | 0 | 0.96 |
| IL3RA | Endothelial_cells | 0.39 | 0.89 | 0 | 10 | 0 | 0.25 |
| LAMC1 | Endothelial_cells | 0.29 | 0.74 | 0 | 11 | 0 | 0.20 |
| LDB2 | Endothelial_cells | 1.45 | 2.06 | 1 | 19 | 0 | 0.60 |
| MYL6 | Endothelial_cells | 12.23 | 16.16 | 8 | 262 | 0 | 0.97 |
| PECAM1 | Endothelial_cells | 2.39 | 3.28 | 1 | 40 | 0 | 0.69 |
| PLVAP | Endothelial_cells | 3.47 | 6.23 | 1 | 73 | 0 | 0.60 |
| PTPRB | Endothelial_cells | 0.95 | 1.49 | 0 | 15 | 0 | 0.49 |
| RAMP2 | Endothelial_cells | 7.07 | 9.62 | 4 | 129 | 0 | 0.86 |
| SOX18 | Endothelial_cells | 2.20 | 3.39 | 1 | 32 | 0 | 0.63 |
| TMSB10 | Endothelial_cells | 38.40 | 49.11 | 23 | 616 | 0 | 0.99 |
| TP53 | Endothelial_cells | 0.21 | 0.55 | 0 | 7 | 0 | 0.16 |
| ACTA2 | Epithelial_cells | 0.10 | 1.62 | 0 | 167 | 0 | 0.05 |
| AGR2 | Epithelial_cells | 8.09 | 18.66 | 1 | 502 | 0 | 0.56 |
| AKT1 | Epithelial_cells | 0.34 | 0.83 | 0 | 19 | 0 | 0.22 |
| AP1M2 | Epithelial_cells | 1.58 | 2.62 | 0 | 26 | 0 | 0.49 |
| AR | Epithelial_cells | 0.86 | 1.75 | 0 | 27 | 0 | 0.35 |
| AZGP1 | Epithelial_cells | 21.54 | 32.64 | 9 | 362 | 0 | 0.78 |
| BAG1 | Epithelial_cells | 2.32 | 4.08 | 1 | 73 | 0 | 0.60 |
| BRAF | Epithelial_cells | 0.10 | 0.34 | 0 | 5 | 0 | 0.09 |

TABLE 1-continued

| Example Genes | | | | | | | |
|---|---|---|---|---|---|---|---|
| CAPN13 | Epithelial_cells | 0.20 | 0.63 | 0 | 12 | 0 | 0.13 |
| CD9 | Epithelial_cells | 9.73 | 12.33 | 6 | 225 | 0 | 0.86 |
| CDH1 | Epithelial_cells | 0.65 | 1.39 | 0 | 34 | 0 | 0.33 |
| CDH3 | Epithelial_cells | 0.11 | 0.54 | 0 | 14 | 0 | 0.07 |
| CDK7 | Epithelial_cells | 0.22 | 0.54 | 0 | 6 | 0 | 0.18 |
| CDKN2A | Epithelial_cells | 1.39 | 6.89 | 0 | 192 | 0 | 0.25 |
| CLDN4 | Epithelial_cells | 4.27 | 8.24 | 2 | 211 | 0 | 0.68 |
| CLU | Epithelial_cells | 13.01 | 22.58 | 3 | 526 | 0 | 0.63 |
| COBL | Epithelial_cells | 0.24 | 0.65 | 0 | 12 | 0 | 0.17 |
| COL4A5 | Epithelial_cells | 0.10 | 0.36 | 0 | 10 | 0 | 0.08 |
| CRABP2 | Epithelial_cells | 13.53 | 20.94 | 5 | 254 | 0 | 0.70 |
| EPCAM | Epithelial_cells | 5.51 | 9.03 | 3 | 182 | 0 | 0.78 |
| ERBB2 | Epithelial_cells | 0.79 | 3.79 | 0 | 124 | 0 | 0.30 |
| ERBB3 | Epithelial_cells | 0.93 | 1.53 | 0 | 26 | 0 | 0.44 |
| ERBB4 | Epithelial_cells | 0.22 | 0.80 | 0 | 15 | 0 | 0.12 |
| ESR1 | Epithelial_cells | 0.71 | 2.10 | 0 | 56 | 0 | 0.27 |
| FASN | Epithelial_cells | 1.15 | 4.76 | 0 | 137 | 0 | 0.31 |
| FGFR4 | Epithelial_cells | 0.17 | 0.60 | 0 | 11 | 0 | 0.11 |
| FN1 | Epithelial_cells | 0.22 | 1.28 | 0 | 72 | 0 | 0.08 |
| FOS | Epithelial_cells | 10.99 | 14.28 | 6 | 236 | 0 | 0.78 |
| FOXA1 | Epithelial_cells | 2.19 | 3.88 | 0 | 37 | 0 | 0.48 |
| FXYD3 | Epithelial_cells | 10.09 | 15.81 | 4 | 343 | 0 | 0.82 |
| GATA3 | Epithelial_cells | 6.03 | 9.57 | 2 | 163 | 0 | 0.62 |
| GPR160 | Epithelial_cells | 1.27 | 2.19 | 0 | 33 | 0 | 0.45 |
| GRB7 | Epithelial_cells | 0.32 | 2.35 | 0 | 64 | 0 | 0.13 |
| IGF1R | Epithelial_cells | 0.24 | 0.78 | 0 | 16 | 0 | 0.15 |
| KRAS | Epithelial_cells | 0.64 | 1.40 | 0 | 42 | 0 | 0.34 |
| KRT10 | Epithelial_cells | 3.39 | 4.89 | 2 | 85 | 0 | 0.70 |
| KRT14 | Epithelial_cells | 0.40 | 6.99 | 0 | 568 | 0 | 0.05 |
| KRT17 | Epithelial_cells | 2.33 | 19.82 | 0 | 1147 | 0 | 0.08 |
| KRT18 | Epithelial_cells | 19.55 | 37.69 | 8 | 931 | 0 | 0.88 |
| KRT19 | Epithelial_cells | 32.47 | 53.22 | 13 | 965 | 0 | 0.95 |
| KRT7 | Epithelial_cells | 8.81 | 19.83 | 2 | 494 | 0 | 0.69 |
| KRT8 | Epithelial_cells | 15.16 | 33.88 | 6 | 795 | 0 | 0.91 |
| LRP2 | Epithelial_cells | 0.17 | 0.77 | 0 | 26 | 0 | 0.10 |
| LTF | Epithelial_cells | 4.63 | 23.26 | 0 | 615 | 0 | 0.27 |
| LYPD6B | Epithelial_cells | 0.71 | 1.48 | 0 | 32 | 0 | 0.31 |
| MAPK13 | Epithelial_cells | 0.92 | 1.60 | 0 | 26 | 0 | 0.43 |
| MAPK3 | Epithelial_cells | 0.42 | 0.90 | 0 | 12 | 0 | 0.27 |
| MDM2 | Epithelial_cells | 0.35 | 0.84 | 0 | 16 | 0 | 0.23 |
| MLPH | Epithelial_cells | 2.22 | 3.21 | 1 | 38 | 0 | 0.56 |
| MUC1 | Epithelial_cells | 2.67 | 4.43 | 1 | 69 | 0 | 0.54 |
| MYB | Epithelial_cells | 0.23 | 0.59 | 0 | 6 | 0 | 0.17 |
| MYO5B | Epithelial_cells | 0.17 | 0.50 | 0 | 7 | 0 | 0.13 |
| NAT1 | Epithelial_cells | 0.61 | 2.26 | 0 | 98 | 0 | 0.17 |
| NF1 | Epithelial_cells | 0.20 | 0.51 | 0 | 7 | 0 | 0.16 |
| NR3C1 | Epithelial_cells | 0.70 | 1.58 | 0 | 19 | 0 | 0.29 |
| PDZK1IP1 | Epithelial_cells | 1.32 | 5.13 | 0 | 186 | 0 | 0.34 |
| PGR | Epithelial_cells | 0.05 | 0.30 | 0 | 6 | 0 | 0.03 |
| PI3 | Epithelial_cells | 0.24 | 2.38 | 0 | 101 | 0 | 0.03 |
| PTEN | Epithelial_cells | 0.43 | 0.88 | 0 | 16 | 0 | 0.27 |

TABLE 1-continued

| Example Genes | | | | | | | |
|---|---|---|---|---|---|---|---|
| S100A14 | Epithelial_cells | 7.35 | 12.31 | 2 | 170 | 0 | 0.67 |
| S100A8 | Epithelial_cells | 2.88 | 26.93 | 0 | 953 | 0 | 0.08 |
| S100A9 | Epithelial_cells | 3.85 | 26.80 | 0 | 743 | 0 | 0.11 |
| SIAH2 | Epithelial_cells | 1.29 | 2.57 | 0 | 35 | 0 | 0.42 |
| SLC39A6 | Epithelial_cells | 3.59 | 6.60 | 1 | 111 | 0 | 0.58 |
| SLPI | Epithelial_cells | 8.48 | 35.73 | 0 | 1156 | 0 | 0.36 |
| SPDEF | Epithelial_cells | 2.39 | 3.55 | 1 | 52 | 0 | 0.58 |
| TAGLN | Epithelial_cells | 0.51 | 5.19 | 0 | 258 | 0 | 0.08 |
| TFF1 | Epithelial_cells | 15.14 | 48.93 | 0 | 1250 | 0 | 0.43 |
| TFF3 | Epithelial_cells | 45.81 | 107.17 | 3 | 1796 | 0 | 0.60 |
| TIMP1 | Epithelial_cells | 3.13 | 5.28 | 1 | 108 | 0 | 0.61 |
| TMEM45B | Epithelial_cells | 0.08 | 0.49 | 0 | 16 | 0 | 0.06 |
| TSPAN1 | Epithelial_cells | 4.05 | 8.29 | 0 | 112 | 0 | 0.48 |
| TTC6 | Epithelial_cells | 0.15 | 0.47 | 0 | 8 | 0 | 0.12 |
| XBP1 | Epithelial_cells | 19.33 | 25.99 | 9 | 376 | 0 | 0.81 |
| ACTG2 | Epithelial_stem | 0.22 | 1.52 | 0 | 44 | 0 | 0.09 |
| ACTR3B | Epithelial_stem | 1.07 | 1.59 | 0 | 16 | 0 | 0.50 |
| ALDH1A3 | Epithelial_stem | 0.02 | 0.16 | 0 | 2 | 0 | 0.02 |
| ANLN | Epithelial_stem | 0.16 | 0.47 | 0 | 5 | 0 | 0.12 |
| AURKA | Epithelial_stem | 0.92 | 4.77 | 0 | 166 | 0 | 0.27 |
| BCL2 | Epithelial_stem | 0.61 | 0.99 | 0 | 9 | 0 | 0.37 |
| BIRC5 | Epithelial_stem | 1.52 | 3.08 | 0 | 53 | 0 | 0.44 |
| CCNB1 | Epithelial_stem | 0.91 | 2.90 | 0 | 62 | 0 | 0.28 |
| CCND1 | Epithelial_stem | 10.41 | 12.56 | 7 | 162 | 0 | 0.88 |
| CCNE1 | Epithelial_stem | 0.14 | 0.43 | 0 | 5 | 0 | 0.11 |
| CCNE2 | Epithelial_stem | 0.16 | 0.51 | 0 | 7 | 0 | 0.12 |
| CD24 | Epithelial_stem | 7.47 | 8.44 | 5 | 106 | 0 | 0.91 |
| CD44 | Epithelial_stem | 1.82 | 2.50 | 1 | 27 | 0 | 0.62 |
| CDC20 | Epithelial_stem | 0.80 | 2.16 | 0 | 37 | 0 | 0.30 |
| CDC6 | Epithelial_stem | 0.22 | 0.73 | 0 | 24 | 0 | 0.15 |
| CDK4 | Epithelial_stem | 1.38 | 1.84 | 1 | 34 | 0 | 0.63 |
| CDK6 | Epithelial_stem | 0.32 | 0.66 | 0 | 6 | 0 | 0.24 |
| CEACAM1 | Epithelial_stem | 0.36 | 0.94 | 0 | 28 | 0 | 0.22 |
| CENPF | Epithelial_stem | 1.70 | 4.12 | 0 | 106 | 0 | 0.40 |
| CEP55 | Epithelial_stem | 0.24 | 0.67 | 0 | 8 | 0 | 0.16 |
| CSRP2 | Epithelial_stem | 2.62 | 3.32 | 2 | 38 | 0 | 0.72 |
| CTCF | Epithelial_stem | 0.29 | 0.61 | 0 | 7 | 0 | 0.23 |
| EFNA5 | Epithelial_stem | 0.31 | 0.71 | 0 | 10 | 0 | 0.22 |
| EGFR | Epithelial_stem | 0.27 | 0.65 | 0 | 7 | 0 | 0.19 |
| EIF3E | Epithelial_stem | 8.26 | 7.11 | 7 | 74 | 0 | 0.95 |
| ELF5 | Epithelial_stem | 0.88 | 1.23 | 0 | 11 | 0 | 0.49 |
| FABP7 | Epithelial_stem | 6.92 | 13.55 | 2 | 184 | 0 | 0.71 |
| FAT1 | Epithelial_stem | 0.16 | 0.42 | 0 | 4 | 0 | 0.14 |
| FGFR1 | Epithelial_stem | 0.12 | 0.39 | 0 | 6 | 0 | 0.10 |
| FGFR2 | Epithelial_stem | 0.99 | 1.46 | 0 | 14 | 0 | 0.48 |
| FOXC1 | Epithelial_stem | 0.39 | 0.77 | 0 | 6 | 0 | 0.27 |
| ISG15 | Epithelial_stem | 9.43 | 14.43 | 4 | 166 | 0 | 0.81 |
| ITGA6 | Epithelial_stem | 0.26 | 0.57 | 0 | 6 | 0 | 0.21 |
| KIF23 | Epithelial_stem | 0.25 | 0.75 | 0 | 11 | 0 | 0.16 |
| KIT | Epithelial_stem | 0.41 | 0.80 | 0 | 9 | 0 | 0.28 |
| KRT15 | Epithelial_stem | 2.03 | 3.69 | 1 | 44 | 0 | 0.52 |

TABLE 1-continued

| Example Genes | | | | | | | |
|---|---|---|---|---|---|---|---|
| KRT5 | Epithelial_stem | 0.78 | 2.03 | 0 | 34 | 0 | 0.29 |
| LAMA1 | Epithelial_stem | 0.26 | 0.61 | 0 | 6 | 0 | 0.20 |
| MELK | Epithelial_stem | 0.18 | 0.53 | 0 | 6 | 0 | 0.14 |
| MIA | Epithelial_stem | 10.68 | 15.42 | 6 | 337 | 0 | 0.86 |
| MKI67 | Epithelial_stem | 1.57 | 2.98 | 0 | 45 | 0 | 0.42 |
| MYBL2 | Epithelial_stem | 0.34 | 0.89 | 0 | 15 | 0 | 0.20 |
| MYC | Epithelial_stem | 1.38 | 1.90 | 1 | 28 | 0 | 0.57 |
| MYLK | Epithelial_stem | 0.13 | 0.57 | 0 | 19 | 0 | 0.09 |
| MYO10 | Epithelial_stem | 1.29 | 1.50 | 1 | 11 | 0 | 0.61 |
| NDC80 | Epithelial_stem | 0.21 | 0.66 | 0 | 14 | 0 | 0.14 |
| NDRG2 | Epithelial_stem | 6.38 | 6.23 | 5 | 53 | 0 | 0.87 |
| NOTCH1 | Epithelial_stem | 3.65 | 4.75 | 2 | 64 | 0 | 0.74 |
| NUF2 | Epithelial_stem | 0.77 | 1.65 | 0 | 23 | 0 | 0.32 |
| OBP2B | Epithelial_stem | 2.34 | 3.38 | 1 | 44 | 0 | 0.62 |
| ORC6 | Epithelial_stem | 0.54 | 0.96 | 0 | 17 | 0 | 0.34 |
| PABPC1 | Epithelial_stem | 17.49 | 14.39 | 14 | 87 | 0 | 0.96 |
| PBK | Epithelial_stem | 1.03 | 2.04 | 0 | 33 | 0 | 0.40 |
| PDPN | Epithelial_stem | 0.02 | 0.14 | 0 | 2 | 0 | 0.02 |
| PHGDH | Epithelial_stem | 4.14 | 4.15 | 3 | 53 | 0 | 0.85 |
| PIK3CA | Epithelial_stem | 0.13 | 0.38 | 0 | 4 | 0 | 0.12 |
| PRLR | Epithelial_stem | 0.45 | 0.78 | 0 | 7 | 0 | 0.32 |
| PTTG1 | Epithelial_stem | 2.30 | 4.36 | 1 | 70 | 0 | 0.57 |
| RB1 | Epithelial_stem | 0.15 | 0.40 | 0 | 4 | 0 | 0.13 |
| RRM2 | Epithelial_stem | 0.93 | 2.21 | 0 | 50 | 0 | 0.34 |
| SFRP1 | Epithelial_stem | 1.36 | 2.11 | 1 | 23 | 0 | 0.52 |
| SLC2A1 | Epithelial_stem | 0.85 | 1.93 | 0 | 27 | 0 | 0.36 |
| SNAI2 | Epithelial_stem | 0.09 | 0.35 | 0 | 4 | 0 | 0.08 |
| SOX10 | Epithelial_stem | 1.41 | 1.84 | 1 | 30 | 0 | 0.59 |
| SOX4 | Epithelial_stem | 29.22 | 30.66 | 20 | 252 | 0 | 0.93 |
| STMN1 | Epithelial_stem | 11.57 | 11.63 | 8 | 103 | 0 | 0.95 |
| TCF4 | Epithelial_stem | 0.04 | 0.22 | 0 | 3 | 0 | 0.04 |
| TFF2 | Epithelial_stem | 7.34 | 8.86 | 5 | 75 | 0 | 0.85 |
| THY1 | Epithelial_stem | 0.02 | 0.16 | 0 | 2 | 0 | 0.02 |
| TPM2 | Epithelial_stem | 0.59 | 1.00 | 0 | 10 | 0 | 0.37 |
| TTYH1 | Epithelial_stem | 9.64 | 8.47 | 8 | 62 | 0 | 0.88 |
| TYMS | Epithelial_stem | 1.13 | 1.92 | 0 | 22 | 0 | 0.45 |
| UBE2C | Epithelial_stem | 3.31 | 7.46 | 0 | 134 | 0 | 0.49 |
| UBE2T | Epithelial_stem | 2.07 | 3.43 | 1 | 63 | 0 | 0.60 |
| VIM | Epithelial_stem | 5.02 | 9.95 | 1 | 130 | 0 | 0.65 |
| ZEB1 | Epithelial_stem | 0.00 | 0.06 | 0 | 1 | 0 | 0.00 |
| BGN | Fibroblasts | 5.30 | 7.00 | 3 | 51 | 0 | 0.75 |
| BICC1 | Fibroblasts | 0.32 | 0.71 | 0 | 4 | 0 | 0.21 |
| CDH11 | Fibroblasts | 0.55 | 1.12 | 0 | 6 | 0 | 0.27 |
| COL1A1 | Fibroblasts | 17.21 | 40.71 | 3 | 349 | 0 | 0.65 |
| COL1A2 | Fibroblasts | 13.77 | 28.79 | 3 | 234 | 0 | 0.65 |
| COL3A1 | Fibroblasts | 11.89 | 25.26 | 2 | 235 | 0 | 0.64 |
| DCN | Fibroblasts | 15.52 | 23.27 | 5 | 130 | 0 | 0.69 |
| FAP | Fibroblasts | 0.54 | 1.21 | 0 | 9 | 0 | 0.26 |
| IGFBP5 | Fibroblasts | 0.74 | 1.97 | 0 | 17 | 0 | 0.26 |
| LGALS1 | Fibroblasts | 11.33 | 13.86 | 6 | 76 | 0 | 0.90 |
| LUM | Fibroblasts | 23.70 | 48.21 | 4 | 378 | 0 | 0.64 |

TABLE 1-continued

| Example Genes | | | | | | | |
|---|---|---|---|---|---|---|---|
| MMP11 | Fibroblasts | 1.33 | 5.80 | 0 | 59 | 0 | 0.24 |
| MT2A | Fibroblasts | 4.97 | 9.09 | 2 | 56 | 0 | 0.68 |
| MYL9 | Fibroblasts | 6.84 | 11.10 | 4 | 62 | 0 | 0.77 |
| SULF1 | Fibroblasts | 0.32 | 0.81 | 0 | 5 | 0 | 0.20 |
| APOC1 | Macrophage | 51.81 | 90.53 | 17 | 736 | 0 | 0.92 |
| APOE | Macrophage | 131.05 | 196.08 | 52 | 1821 | 0 | 0.96 |
| BLVRA | Macrophage | 0.69 | 1.19 | 0 | 9 | 0 | 0.38 |
| C1QA | Macrophage | 25.62 | 27.35 | 17 | 183 | 0 | 0.92 |
| C1QB | Macrophage | 29.17 | 33.43 | 17 | 242 | 0 | 0.93 |
| CD274 | Macrophage | 0.03 | 0.18 | 0 | 2 | 0 | 0.02 |
| CD4 | Macrophage | 0.72 | 1.07 | 0 | 8 | 0 | 0.43 |
| CD63 | Macrophage | 14.69 | 17.69 | 8 | 153 | 0 | 0.95 |
| CD68 | Macrophage | 7.90 | 10.20 | 4 | 105 | 0 | 0.90 |
| CSTB | Macrophage | 7.82 | 14.60 | 4 | 210 | 0 | 0.88 |
| CTSL | Macrophage | 4.83 | 7.34 | 2 | 65 | 0 | 0.79 |
| FTL | Macrophage | 429.41 | 552.78 | 254 | 5234 | 2 | 1.00 |
| GPNMB | Macrophage | 8.04 | 12.02 | 4 | 103 | 0 | 0.83 |
| HLA-DPA1 | Macrophage | 22.24 | 26.92 | 13 | 232 | 0 | 0.93 |
| HLA-DRA | Macrophage | 57.07 | 69.19 | 31 | 479 | 0 | 0.97 |
| IL2RA | Macrophage | 0.06 | 0.28 | 0 | 3 | 0 | 0.05 |
| ITGAX | Macrophage | 0.31 | 0.63 | 0 | 4 | 0 | 0.23 |
| LGMN | Macrophage | 7.45 | 11.78 | 4 | 161 | 0 | 0.83 |
| MSR1 | Macrophage | 2.01 | 2.89 | 1 | 33 | 0 | 0.64 |
| STAT5A | Macrophage | 0.11 | 0.35 | 0 | 3 | 0 | 0.10 |
| TFEC | Macrophage | 0.33 | 0.69 | 0 | 6 | 0 | 0.24 |
| TFRC | Macrophage | 0.23 | 0.68 | 0 | 6 | 0 | 0.14 |
| TMSB4X | Macrophage | 142.30 | 144.83 | 90 | 1124 | 0 | 1.00 |
| AHR | Monocyte | 0.25 | 0.54 | 0 | 2 | 0 | 0.20 |
| AIF1 | Monocyte | 8.49 | 7.43 | 7 | 49 | 0 | 0.95 |
| C10orf54 | Monocyte | 0.95 | 1.22 | 1 | 7 | 0 | 0.53 |
| CCL2 | Monocyte | 5.49 | 12.83 | 0 | 82 | 0 | 0.38 |
| CCL3 | Monocyte | 11.50 | 17.13 | 4 | 89 | 0 | 0.72 |
| CD14 | Monocyte | 8.38 | 10.27 | 4 | 52 | 0 | 0.85 |
| CD163 | Monocyte | 1.37 | 2.03 | 1 | 12 | 0 | 0.52 |
| CST3 | Monocyte | 21.54 | 19.94 | 15 | 103 | 0 | 0.97 |
| FCGR3A | Monocyte | 3.80 | 5.25 | 2 | 41 | 0 | 0.75 |
| FCN1 | Monocyte | 0.87 | 2.58 | 0 | 21 | 0 | 0.25 |
| HIF1A | Monocyte | 0.73 | 1.16 | 0 | 6 | 0 | 0.41 |
| HLA-DRB1 | Monocyte | 30.64 | 34.56 | 17.5 | 181 | 0 | 0.92 |
| ICAM1 | Monocyte | 0.37 | 0.68 | 0 | 3 | 0 | 0.27 |
| JUN | Monocyte | 4.90 | 6.87 | 2 | 38 | 0 | 0.76 |
| LGALS2 | Monocyte | 0.56 | 1.96 | 0 | 19 | 0 | 0.20 |
| LILRB1 | Monocyte | 0.33 | 0.70 | 0 | 5 | 0 | 0.24 |
| LST1 | Monocyte | 3.52 | 4.21 | 2 | 30 | 0 | 0.82 |
| LYZ | Monocyte | 17.26 | 32.28 | 6 | 274 | 0 | 0.83 |
| MMP12 | Monocyte | 0.19 | 2.54 | 0 | 36 | 0 | 0.01 |
| MMP9 | Monocyte | 0.76 | 3.00 | 0 | 25 | 0 | 0.15 |
| NFKBIA | Monocyte | 3.01 | 5.66 | 1 | 46 | 0 | 0.65 |
| SPP1 | Monocyte | 20.54 | 71.92 | 0 | 844 | 0 | 0.43 |
| CCL4 | NK__cell | 9.31 | 11.90 | 6 | 226 | 0 | 0.90 |
| CCL5 | NK__cell | 8.36 | 6.64 | 8 | 45 | 0 | 0.87 |

TABLE 1-continued

| Example Genes | | | | | | | |
|---|---|---|---|---|---|---|---|
| CD7 | NK_cell | 2.84 | 2.88 | 2 | 37 | 0 | 0.79 |
| GNLY | NK_cell | 8.61 | 12.32 | 2 | 137 | 0 | 0.55 |
| GZMB | NK_cell | 2.01 | 3.44 | 0 | 66 | 0 | 0.49 |
| HLA-A | NK_cell | 8.22 | 5.20 | 7 | 97 | 0 | 0.99 |
| HLA-B | NK_cell | 10.76 | 7.60 | 9 | 108 | 0 | 0.99 |
| HLA-C | NK_cell | 6.96 | 4.33 | 6 | 56 | 0 | 0.99 |
| HLA-E | NK_cell | 2.92 | 2.23 | 3 | 25 | 0 | 0.89 |
| NCAM1 | NK_cell | 0.10 | 0.32 | 0 | 3 | 0 | 0.09 |
| NKG7 | NK_cell | 10.29 | 6.98 | 9 | 61 | 0 | 0.97 |
| PLEK | NK_cell | 0.67 | 0.93 | 0 | 6 | 0 | 0.44 |
| PTPRC | NK_cell | 1.25 | 1.26 | 1 | 10 | 0 | 0.67 |
| SKAP1 | NK_cell | 0.34 | 0.60 | 0 | 5 | 0 | 0.28 |
| TBX21 | NK_cell | 0.25 | 0.54 | 0 | 4 | 0 | 0.21 |
| TRDC | NK_cell | 1.49 | 1.90 | 1 | 22 | 0 | 0.58 |
| XCL1 | NK_cell | 0.91 | 1.95 | 0 | 31 | 0 | 0.35 |
| CD38 | Plasma_cell | 2.56 | 2.44 | 2 | 16 | 0 | 0.79 |
| DERL3 | Plasma_cell | 11.27 | 12.49 | 8 | 128 | 0 | 0.97 |
| FCRL5 | Plasma_cell | 1.18 | 1.54 | 1 | 22 | 0 | 0.62 |
| IGHG1 | Plasma_cell | 531.06 | 822.02 | 11 | 7000 | 0 | 0.89 |
| IGHG4 | Plasma_cell | 250.50 | 539.22 | 4 | 5535 | 0 | 0.79 |
| IGHM | Plasma_cell | 887.65 | 2087.77 | 8 | 11340 | 0 | 0.85 |
| IGKC | Plasma_cell | 4611.98 | 5428.05 | 366 | 22641 | 0 | 0.99 |
| ISG20 | Plasma_cell | 3.48 | 2.82 | 3 | 16 | 0 | 0.89 |
| MZB1 | Plasma_cell | 31.06 | 20.75 | 27 | 157 | 1 | 1.00 |
| POU2AF1 | Plasma_cell | 1.24 | 1.37 | 1 | 8 | 0 | 0.63 |
| SDC1 | Plasma_cell | 1.31 | 1.48 | 1 | 11 | 0 | 0.64 |
| B2M | T_cells | 46.20 | 17.82 | 44 | 181 | 0 | 1.00 |
| CD2 | T_cells | 1.89 | 1.88 | 1 | 20 | 0 | 0.77 |
| CD3D | T_cells | 2.15 | 1.78 | 2 | 26 | 0 | 0.85 |
| CD3E | T_cells | 1.35 | 1.22 | 1 | 9 | 0 | 0.73 |
| CD3G | T_cells | 0.82 | 0.98 | 1 | 8 | 0 | 0.54 |
| CD40LG | T_cells | 0.26 | 0.60 | 0 | 7 | 0 | 0.19 |
| CD5 | T_cells | 0.15 | 0.41 | 0 | 4 | 0 | 0.14 |
| CD8A | T_cells | 0.45 | 0.91 | 0 | 8 | 0 | 0.26 |
| CD96 | T_cells | 0.24 | 0.51 | 0 | 4 | 0 | 0.20 |
| CTLA4 | T_cells | 0.03 | 0.21 | 0 | 4 | 0 | 0.02 |
| FOXP3 | T_cells | 0.02 | 0.19 | 0 | 5 | 0 | 0.02 |
| ICOS | T_cells | 0.16 | 0.52 | 0 | 12 | 0 | 0.12 |
| IL32 | T_cells | 5.20 | 4.35 | 4 | 41 | 0 | 0.94 |
| IL7R | T_cells | 1.11 | 1.61 | 0 | 14 | 0 | 0.49 |
| LAG3 | T_cells | 0.14 | 0.50 | 0 | 13 | 0 | 0.11 |
| PDCD1 | T_cells | 0.07 | 0.30 | 0 | 7 | 0 | 0.06 |
| S100A4 | T_cells | 5.01 | 4.76 | 4 | 48 | 0 | 0.86 |
| THEMIS | T_cells | 0.16 | 0.41 | 0 | 4 | 0 | 0.14 |
| TRAC | T_cells | 3.57 | 3.04 | 3 | 31 | 0 | 0.91 |
| ZNF571 | T_cells | 0.01 | 0.12 | 0 | 2 | 0 | 0.01 |

TABLE 1-continued

| Example Genes | | | | | | | |
|---|---|---|---|---|---|---|---|
| gene | N__expr__raw | mean__norm | sd__norm | median__norm | max__norm | min__norm | perc__expr__norm |
| BANK1 | 549 | 1.02 | 0.99 | 1.42 | 3.32 | 0.00 | 0.54 |
| CD19 | 303 | 0.52 | 0.82 | 0.00 | 2.71 | 0.00 | 0.30 |
| CD40 | 307 | 0.53 | 0.83 | 0.00 | 3.12 | 0.00 | 0.30 |
| CD69 | 828 | 2.37 | 1.36 | 2.61 | 4.80 | 0.00 | 0.81 |
| CD74 | 1019 | 4.63 | 0.37 | 4.66 | 5.63 | 1.74 | 1.00 |
| CD79A | 967 | 2.54 | 0.80 | 2.68 | 4.35 | 0.00 | 0.95 |
| CD79B | 895 | 2.09 | 0.95 | 2.27 | 4.51 | 0.00 | 0.88 |
| CR2 | 47 | 0.08 | 0.36 | 0.00 | 2.57 | 0.00 | 0.05 |
| CXCR5 | 175 | 0.29 | 0.66 | 0.00 | 3.11 | 0.00 | 0.17 |
| CXXC5 | 327 | 0.57 | 0.85 | 0.00 | 2.93 | 0.00 | 0.32 |
| HLA-DRB5 | 768 | 1.73 | 1.09 | 2.01 | 3.80 | 0.00 | 0.75 |
| JUNB | 880 | 2.61 | 1.28 | 2.90 | 4.95 | 0.00 | 0.86 |
| MS4A1 | 836 | 1.84 | 1.00 | 2.02 | 3.96 | 0.00 | 0.82 |
| RPL13 | 1019 | 4.69 | 0.33 | 4.73 | 5.42 | 2.73 | 1.00 |
| RPL18 | 1019 | 3.54 | 0.42 | 3.61 | 4.50 | 1.86 | 1.00 |
| RPSA | 1004 | 3.12 | 0.65 | 3.24 | 4.23 | 0.00 | 0.99 |
| TCL1A | 796 | 1.97 | 1.19 | 2.28 | 4.62 | 0.00 | 0.78 |
| ADGRL4 | 1424 | 1.03 | 0.95 | 1.19 | 3.52 | 0.00 | 0.60 |
| CALCRL | 1256 | 0.87 | 0.92 | 0.80 | 3.66 | 0.00 | 0.52 |
| CD34 | 1198 | 0.87 | 0.95 | 0.46 | 3.80 | 0.00 | 0.50 |
| CD36 | 682 | 0.57 | 0.99 | 0.00 | 4.11 | 0.00 | 0.28 |
| COL4A1 | 1315 | 1.08 | 1.11 | 1.05 | 4.33 | 0.00 | 0.55 |
| COL4A2 | 1318 | 1.05 | 1.08 | 1.04 | 4.43 | 0.00 | 0.55 |
| GNG11 | 2214 | 2.54 | 0.93 | 2.73 | 4.65 | 0.00 | 0.93 |
| GSN | 1496 | 1.24 | 1.11 | 1.34 | 4.61 | 0.00 | 0.63 |
| HSPB1 | 2210 | 2.46 | 0.93 | 2.61 | 4.85 | 0.00 | 0.92 |
| HSPG2 | 1923 | 1.84 | 1.11 | 2.04 | 4.82 | 0.00 | 0.80 |
| IFITM3 | 2309 | 3.11 | 0.83 | 3.27 | 5.09 | 0.00 | 0.96 |
| IL3RA | 601 | 0.32 | 0.61 | 0.00 | 3.21 | 0.00 | 0.25 |
| LAMC1 | 485 | 0.25 | 0.55 | 0.00 | 3.42 | 0.00 | 0.20 |
| LDB2 | 1431 | 1.02 | 0.94 | 1.12 | 3.91 | 0.00 | 0.60 |
| MYL6 | 2318 | 3.02 | 0.79 | 3.14 | 4.83 | 0.00 | 0.97 |
| PECAM1 | 1663 | 1.35 | 1.00 | 1.58 | 4.35 | 0.00 | 0.69 |
| PLVAP | 1436 | 1.34 | 1.23 | 1.46 | 4.46 | 0.00 | 0.60 |
| PTPRB | 1171 | 0.77 | 0.88 | 0.00 | 3.27 | 0.00 | 0.49 |
| RAMP2 | 2054 | 2.30 | 1.10 | 2.60 | 4.30 | 0.00 | 0.86 |
| SOX18 | 1512 | 1.22 | 1.06 | 1.39 | 4.09 | 0.00 | 0.63 |
| TMSB10 | 2380 | 4.18 | 0.71 | 4.26 | 5.90 | 0.00 | 0.99 |
| TP53 | 392 | 0.19 | 0.47 | 0.00 | 2.69 | 0.00 | 0.16 |
| ACTA2 | 1229 | 0.03 | 0.20 | 0.00 | 4.25 | 0.00 | 0.05 |
| AGR2 | 14729 | 1.11 | 1.19 | 0.84 | 4.97 | 0.00 | 0.56 |
| AKT1 | 5890 | 0.14 | 0.31 | 0.00 | 2.55 | 0.00 | 0.22 |
| AP1M2 | 13126 | 0.53 | 0.63 | 0.00 | 3.56 | 0.00 | 0.49 |
| AR | 9154 | 0.31 | 0.51 | 0.00 | 3.17 | 0.00 | 0.35 |
| AZGP1 | 20810 | 2.16 | 1.39 | 2.50 | 6.42 | 0.00 | 0.78 |
| BAG1 | 15791 | 0.71 | 0.71 | 0.66 | 3.84 | 0.00 | 0.60 |
| BRAF | 2418 | 0.05 | 0.19 | 0.00 | 2.68 | 0.00 | 0.09 |
| CAPN13 | 3437 | 0.08 | 0.25 | 0.00 | 3.02 | 0.00 | 0.13 |
| CD9 | 22863 | 1.82 | 0.95 | 1.97 | 4.65 | 0.00 | 0.86 |

TABLE 1-continued

| Example Genes | | | | | | | |
|---|---|---|---|---|---|---|---|
| CDH1 | 8681 | 0.25 | 0.42 | 0.00 | 2.88 | 0.00 | 0.33 |
| CDH3 | 1861 | 0.04 | 0.19 | 0.00 | 2.65 | 0.00 | 0.07 |
| CDK7 | 4705 | 0.10 | 0.27 | 0.00 | 2.63 | 0.00 | 0.18 |
| CDKN2A | 6554 | 0.27 | 0.62 | 0.00 | 4.09 | 0.00 | 0.25 |
| CLDN4 | 18135 | 1.01 | 0.89 | 0.99 | 5.19 | 0.00 | 0.68 |
| CLU | 16744 | 1.54 | 1.40 | 1.61 | 6.11 | 0.00 | 0.63 |
| COBL | 4487 | 0.10 | 0.27 | 0.00 | 2.98 | 0.00 | 0.17 |
| COL4A5 | 2215 | 0.05 | 0.19 | 0.00 | 2.44 | 0.00 | 0.08 |
| CRABP2 | 18568 | 1.74 | 1.30 | 2.15 | 4.90 | 0.00 | 0.70 |
| EPCAM | 20687 | 1.27 | 0.84 | 1.40 | 4.29 | 0.00 | 0.78 |
| ERBB2 | 8050 | 0.23 | 0.44 | 0.00 | 3.98 | 0.00 | 0.30 |
| ERBB3 | 11763 | 0.38 | 0.52 | 0.00 | 3.28 | 0.00 | 0.44 |
| ERBB4 | 3258 | 0.08 | 0.26 | 0.00 | 2.86 | 0.00 | 0.12 |
| ESR1 | 7252 | 0.25 | 0.48 | 0.00 | 2.94 | 0.00 | 0.27 |
| FASN | 8251 | 0.29 | 0.56 | 0.00 | 4.37 | 0.00 | 0.31 |
| FGFR4 | 2832 | 0.06 | 0.22 | 0.00 | 2.65 | 0.00 | 0.11 |
| FN1 | 2203 | 0.07 | 0.29 | 0.00 | 3.87 | 0.00 | 0.08 |
| FOS | 20721 | 1.74 | 1.13 | 2.02 | 4.65 | 0.00 | 0.78 |
| FOXA1 | 12804 | 0.60 | 0.72 | 0.00 | 3.70 | 0.00 | 0.48 |
| FXYD3 | 21762 | 1.67 | 1.02 | 1.84 | 5.00 | 0.00 | 0.82 |
| GATA3 | 16346 | 1.16 | 1.05 | 1.29 | 3.94 | 0.00 | 0.62 |
| GPR160 | 11893 | 0.44 | 0.57 | 0.00 | 3.50 | 0.00 | 0.45 |
| GRB7 | 3493 | 0.09 | 0.29 | 0.00 | 3.20 | 0.00 | 0.13 |
| IGF1R | 4029 | 0.11 | 0.29 | 0.00 | 3.03 | 0.00 | 0.15 |
| KRAS | 8996 | 0.25 | 0.42 | 0.00 | 3.37 | 0.00 | 0.34 |
| KRT10 | 18676 | 0.96 | 0.75 | 1.07 | 4.12 | 0.00 | 0.70 |
| KRT14 | 1288 | 0.06 | 0.31 | 0.00 | 4.74 | 0.00 | 0.05 |
| KRT17 | 2040 | 0.18 | 0.69 | 0.00 | 5.74 | 0.00 | 0.08 |
| KRT18 | 23218 | 2.19 | 1.13 | 2.47 | 5.33 | 0.00 | 0.88 |
| KRT19 | 25241 | 2.77 | 1.05 | 2.92 | 5.46 | 0.00 | 0.95 |
| KRT7 | 18303 | 1.30 | 1.10 | 1.29 | 4.62 | 0.00 | 0.69 |
| KRT8 | 24130 | 2.06 | 0.97 | 2.14 | 5.50 | 0.00 | 0.91 |
| LRP2 | 2584 | 0.07 | 0.25 | 0.00 | 3.31 | 0.00 | 0.10 |
| LTF | 7283 | 0.52 | 1.02 | 0.00 | 5.96 | 0.00 | 0.27 |
| LYPD6B | 8114 | 0.27 | 0.48 | 0.00 | 3.36 | 0.00 | 0.31 |
| MAPK13 | 11380 | 0.36 | 0.49 | 0.00 | 3.29 | 0.00 | 0.43 |
| MAPK3 | 7252 | 0.18 | 0.35 | 0.00 | 2.63 | 0.00 | 0.27 |
| MDM2 | 6019 | 0.16 | 0.37 | 0.00 | 3.40 | 0.00 | 0.23 |
| MLPH | 14787 | 0.70 | 0.73 | 0.64 | 3.85 | 0.00 | 0.56 |
| MUC1 | 14429 | 0.73 | 0.79 | 0.56 | 4.22 | 0.00 | 0.54 |
| MYB | 4475 | 0.11 | 0.29 | 0.00 | 2.61 | 0.00 | 0.17 |
| MYO5B | 3423 | 0.07 | 0.22 | 0.00 | 2.68 | 0.00 | 0.13 |
| NAT1 | 4573 | 0.20 | 0.52 | 0.00 | 3.98 | 0.00 | 0.17 |
| NF1 | 4338 | 0.10 | 0.26 | 0.00 | 2.71 | 0.00 | 0.16 |
| NR3C1 | 7601 | 0.25 | 0.46 | 0.00 | 3.53 | 0.00 | 0.29 |
| PDZK1IP1 | 8906 | 0.35 | 0.61 | 0.00 | 3.90 | 0.00 | 0.34 |
| PGR | 888 | 0.03 | 0.15 | 0.00 | 2.07 | 0.00 | 0.03 |
| PI3 | 888 | 0.04 | 0.27 | 0.00 | 3.91 | 0.00 | 0.03 |
| PTEN | 7168 | 0.19 | 0.39 | 0.00 | 3.70 | 0.00 | 0.27 |
| S100A14 | 17813 | 1.30 | 1.08 | 1.44 | 4.55 | 0.00 | 0.67 |
| S100A8 | 2222 | 0.18 | 0.73 | 0.00 | 6.37 | 0.00 | 0.08 |

TABLE 1-continued

| Example Genes | | | | | | | |
|---|---|---|---|---|---|---|---|
| S100A9 | 2793 | 0.24 | 0.86 | 0.00 | 6.16 | 0.00 | 0.11 |
| SIAH2 | 11209 | 0.41 | 0.59 | 0.00 | 3.92 | 0.00 | 0.42 |
| SLC39A6 | 15490 | 0.86 | 0.91 | 0.70 | 4.64 | 0.00 | 0.58 |
| SLPI | 9585 | 0.74 | 1.25 | 0.00 | 6.27 | 0.00 | 0.36 |
| SPDEF | 15439 | 0.74 | 0.72 | 0.74 | 3.56 | 0.00 | 0.58 |
| TAGLN | 2092 | 0.09 | 0.41 | 0.00 | 4.83 | 0.00 | 0.08 |
| TFF1 | 11475 | 1.04 | 1.48 | 0.00 | 6.96 | 0.00 | 0.43 |
| TFF3 | 15823 | 1.88 | 1.88 | 1.57 | 6.97 | 0.00 | 0.60 |
| TIMP1 | 16074 | 0.87 | 0.87 | 0.78 | 5.57 | 0.00 | 0.61 |
| TMEM45B | 1461 | 0.03 | 0.16 | 0.00 | 2.44 | 0.00 | 0.05 |
| TSPAN1 | 12780 | 0.79 | 0.95 | 0.00 | 4.71 | 0.00 | 0.48 |
| TTC6 | 3109 | 0.07 | 0.22 | 0.00 | 2.93 | 0.00 | 0.12 |
| XBP1 | 21490 | 2.09 | 1.30 | 2.50 | 5.33 | 0.00 | 0.81 |
| ACTG2 | 412 | 0.08 | 0.33 | 0.00 | 4.26 | 0.00 | 0.09 |
| ACTR3B | 2340 | 0.48 | 0.56 | 0.00 | 3.13 | 0.00 | 0.50 |
| ALDH1A3 | 108 | 0.01 | 0.11 | 0.00 | 2.46 | 0.00 | 0.02 |
| ANLN | 579 | 0.08 | 0.24 | 0.00 | 2.07 | 0.00 | 0.12 |
| AURKA | 1259 | 0.30 | 0.62 | 0.00 | 3.85 | 0.00 | 0.27 |
| BCL2 | 1766 | 0.33 | 0.48 | 0.00 | 3.10 | 0.00 | 0.37 |
| BIRC5 | 2092 | 0.57 | 0.75 | 0.00 | 3.58 | 0.00 | 0.44 |
| CCNB1 | 1340 | 0.33 | 0.63 | 0.00 | 3.46 | 0.00 | 0.28 |
| CCND1 | 4141 | 1.95 | 1.00 | 2.15 | 5.20 | 0.00 | 0.88 |
| CCNE1 | 512 | 0.08 | 0.25 | 0.00 | 2.48 | 0.00 | 0.11 |
| CCNE2 | 561 | 0.09 | 0.28 | 0.00 | 2.64 | 0.00 | 0.12 |
| CD24 | 4289 | 1.79 | 0.80 | 1.91 | 4.47 | 0.00 | 0.91 |
| CD44 | 2945 | 0.73 | 0.67 | 0.76 | 3.10 | 0.00 | 0.62 |
| CDC20 | 1395 | 0.32 | 0.59 | 0.00 | 3.28 | 0.00 | 0.30 |
| CDC6 | 719 | 0.12 | 0.31 | 0.00 | 3.32 | 0.00 | 0.15 |
| CDK4 | 2956 | 0.65 | 0.60 | 0.69 | 3.13 | 0.00 | 0.63 |
| CDK6 | 1135 | 0.17 | 0.34 | 0.00 | 2.48 | 0.00 | 0.24 |
| CEACAM1 | 1027 | 0.17 | 0.36 | 0.00 | 2.53 | 0.00 | 0.22 |
| CENPF | 1901 | 0.53 | 0.77 | 0.00 | 3.50 | 0.00 | 0.40 |
| CEP55 | 765 | 0.12 | 0.31 | 0.00 | 2.66 | 0.00 | 0.16 |
| CSRP2 | 3383 | 0.98 | 0.79 | 1.00 | 3.88 | 0.00 | 0.72 |
| CTCF | 1074 | 0.16 | 0.33 | 0.00 | 2.48 | 0.00 | 0.23 |
| EFNA5 | 1038 | 0.16 | 0.34 | 0.00 | 2.80 | 0.00 | 0.22 |
| EGFR | 915 | 0.14 | 0.31 | 0.00 | 1.99 | 0.00 | 0.19 |
| EIF3E | 4475 | 2.04 | 0.70 | 2.14 | 4.11 | 0.00 | 0.95 |
| ELF5 | 2308 | 0.46 | 0.54 | 0.00 | 2.80 | 0.00 | 0.49 |
| FABP7 | 3349 | 1.35 | 1.18 | 1.26 | 5.63 | 0.00 | 0.71 |
| FAT1 | 673 | 0.10 | 0.26 | 0.00 | 1.90 | 0.00 | 0.14 |
| FGFR1 | 457 | 0.06 | 0.22 | 0.00 | 1.91 | 0.00 | 0.10 |
| FGFR2 | 2282 | 0.46 | 0.53 | 0.00 | 2.43 | 0.00 | 0.48 |
| FOXC1 | 1252 | 0.20 | 0.36 | 0.00 | 2.38 | 0.00 | 0.27 |
| ISG15 | 3825 | 1.68 | 1.11 | 1.76 | 4.87 | 0.00 | 0.81 |
| ITGA6 | 969 | 0.15 | 0.34 | 0.00 | 2.36 | 0.00 | 0.21 |
| KIF23 | 748 | 0.13 | 0.34 | 0.00 | 3.21 | 0.00 | 0.16 |
| KIT | 1312 | 0.22 | 0.40 | 0.00 | 2.80 | 0.00 | 0.28 |
| KRT15 | 2458 | 0.67 | 0.77 | 0.47 | 3.76 | 0.00 | 0.52 |
| KRT5 | 1362 | 0.30 | 0.56 | 0.00 | 3.04 | 0.00 | 0.29 |
| LAMA1 | 924 | 0.15 | 0.34 | 0.00 | 2.59 | 0.00 | 0.20 |

TABLE 1-continued

| Example Genes | | | | | | | |
|---|---|---|---|---|---|---|---|
| MELK | 643 | 0.10 | 0.29 | 0.00 | 2.51 | 0.00 | 0.14 |
| MIA | 4062 | 1.94 | 1.05 | 2.07 | 4.89 | 0.00 | 0.86 |
| MKI67 | 1961 | 0.53 | 0.73 | 0.00 | 2.97 | 0.00 | 0.42 |
| MYBL2 | 963 | 0.15 | 0.34 | 0.00 | 2.33 | 0.00 | 0.20 |
| MYC | 2695 | 0.63 | 0.65 | 0.58 | 3.31 | 0.00 | 0.57 |
| MYLK | 441 | 0.07 | 0.25 | 0.00 | 3.56 | 0.00 | 0.09 |
| MYO10 | 2877 | 0.64 | 0.61 | 0.66 | 2.98 | 0.00 | 0.61 |
| NDC80 | 681 | 0.11 | 0.30 | 0.00 | 3.18 | 0.00 | 0.14 |
| NDRG2 | 4115 | 1.70 | 0.82 | 1.89 | 3.67 | 0.00 | 0.87 |
| NOTCH1 | 3488 | 1.12 | 0.81 | 1.26 | 3.65 | 0.00 | 0.74 |
| NUF2 | 1522 | 0.33 | 0.56 | 0.00 | 3.20 | 0.00 | 0.32 |
| OBP2B | 2932 | 0.85 | 0.80 | 0.83 | 3.47 | 0.00 | 0.62 |
| ORC6 | 1627 | 0.28 | 0.45 | 0.00 | 2.56 | 0.00 | 0.34 |
| PABPC1 | 4528 | 2.68 | 0.71 | 2.83 | 4.09 | 0.00 | 0.96 |
| PBK | 1875 | 0.44 | 0.64 | 0.00 | 3.23 | 0.00 | 0.40 |
| PDPN | 80 | 0.01 | 0.09 | 0.00 | 2.36 | 0.00 | 0.02 |
| PHGDH | 3993 | 1.38 | 0.79 | 1.50 | 3.49 | 0.00 | 0.85 |
| PIK3CA | 553 | 0.08 | 0.23 | 0.00 | 1.98 | 0.00 | 0.12 |
| PRLR | 1496 | 0.24 | 0.39 | 0.00 | 2.47 | 0.00 | 0.32 |
| PTTG1 | 2673 | 0.76 | 0.82 | 0.61 | 3.63 | 0.00 | 0.57 |
| RB1 | 620 | 0.08 | 0.25 | 0.00 | 2.50 | 0.00 | 0.13 |
| RRM2 | 1617 | 0.38 | 0.62 | 0.00 | 3.68 | 0.00 | 0.34 |
| SFRP1 | 2470 | 0.57 | 0.63 | 0.47 | 3.07 | 0.00 | 0.52 |
| SLC2A1 | 1706 | 0.36 | 0.56 | 0.00 | 3.07 | 0.00 | 0.36 |
| SNAI2 | 370 | 0.05 | 0.21 | 0.00 | 2.41 | 0.00 | 0.08 |
| SOX10 | 2776 | 0.62 | 0.59 | 0.69 | 2.82 | 0.00 | 0.59 |
| SOX4 | 4408 | 2.94 | 1.06 | 3.20 | 5.04 | 0.00 | 0.93 |
| STMN1 | 4503 | 2.26 | 0.83 | 2.36 | 4.47 | 0.00 | 0.95 |
| TCF4 | 185 | 0.02 | 0.13 | 0.00 | 1.47 | 0.00 | 0.04 |
| TFF2 | 3992 | 1.69 | 0.89 | 1.91 | 3.99 | 0.00 | 0.85 |
| THY1 | 111 | 0.02 | 0.11 | 0.00 | 1.76 | 0.00 | 0.02 |
| TPM2 | 1755 | 0.31 | 0.46 | 0.00 | 2.63 | 0.00 | 0.37 |
| TTYH1 | 4173 | 2.05 | 0.88 | 2.29 | 3.76 | 0.00 | 0.88 |
| TYMS | 2108 | 0.49 | 0.63 | 0.00 | 3.32 | 0.00 | 0.45 |
| UBE2C | 2325 | 0.78 | 0.98 | 0.00 | 4.56 | 0.00 | 0.49 |
| UBE2T | 2844 | 0.78 | 0.77 | 0.74 | 3.86 | 0.00 | 0.60 |
| VIM | 3084 | 1.12 | 1.09 | 0.95 | 4.71 | 0.00 | 0.65 |
| ZEB1 | 16 | 0.00 | 0.04 | 0.00 | 1.46 | 0.00 | 0.00 |
| BGN | 168 | 1.98 | 1.31 | 2.27 | 4.19 | 0.00 | 0.75 |
| BICC1 | 47 | 0.29 | 0.62 | 0.00 | 2.80 | 0.00 | 0.21 |
| CDH11 | 61 | 0.41 | 0.72 | 0.00 | 2.80 | 0.00 | 0.27 |
| COL1A1 | 145 | 2.20 | 1.90 | 2.25 | 6.40 | 0.00 | 0.65 |
| COL1A2 | 145 | 2.17 | 1.83 | 2.53 | 5.87 | 0.00 | 0.65 |
| COL3A1 | 142 | 2.03 | 1.80 | 2.13 | 5.99 | 0.00 | 0.64 |
| DCN | 154 | 2.47 | 1.86 | 2.98 | 5.79 | 0.00 | 0.69 |
| FAP | 57 | 0.39 | 0.72 | 0.00 | 2.87 | 0.00 | 0.26 |
| IGFBP5 | 58 | 0.51 | 0.98 | 0.00 | 4.83 | 0.00 | 0.26 |
| LGALS1 | 201 | 2.88 | 1.26 | 3.16 | 5.30 | 0.00 | 0.90 |
| LUM | 143 | 2.45 | 2.06 | 2.77 | 5.94 | 0.00 | 0.64 |
| MMP11 | 53 | 0.49 | 1.01 | 0.00 | 4.31 | 0.00 | 0.24 |
| MT2A | 151 | 1.71 | 1.42 | 1.88 | 5.18 | 0.00 | 0.68 |

TABLE 1-continued

| Example Genes | | | | | | | |
|---|---|---|---|---|---|---|---|
| MYL9 | 172 | 2.13 | 1.42 | 2.34 | 4.79 | 0.00 | 0.77 |
| SULF1 | 44 | 0.30 | 0.65 | 0.00 | 2.70 | 0.00 | 0.20 |
| APOC1 | 1351 | 3.56 | 1.54 | 3.90 | 6.48 | 0.00 | 0.92 |
| APOE | 1410 | 4.61 | 1.47 | 4.96 | 7.27 | 0.00 | 0.96 |
| BLVRA | 561 | 0.46 | 0.66 | 0.00 | 2.84 | 0.00 | 0.38 |
| C1QA | 1354 | 3.38 | 1.30 | 3.63 | 5.73 | 0.00 | 0.92 |
| C1QB | 1360 | 3.45 | 1.29 | 3.74 | 5.77 | 0.00 | 0.93 |
| CD274 | 32 | 0.02 | 0.15 | 0.00 | 2.12 | 0.00 | 0.02 |
| CD4 | 628 | 0.56 | 0.73 | 0.00 | 2.93 | 0.00 | 0.43 |
| CD63 | 1391 | 2.89 | 0.89 | 3.10 | 4.51 | 0.00 | 0.95 |
| CD68 | 1317 | 2.26 | 0.93 | 2.47 | 4.21 | 0.00 | 0.90 |
| CSTB | 1284 | 2.14 | 1.07 | 2.24 | 5.08 | 0.00 | 0.88 |
| CTSL | 1163 | 1.69 | 1.05 | 1.88 | 4.83 | 0.00 | 0.79 |
| FTL | 1465 | 6.33 | 0.78 | 6.43 | 8.24 | 2.20 | 1.00 |
| GPNMB | 1213 | 2.08 | 1.16 | 2.33 | 4.91 | 0.00 | 0.83 |
| HLA-DPA1 | 1364 | 3.18 | 1.17 | 3.46 | 5.18 | 0.00 | 0.93 |
| HLA-DRA | 1419 | 4.11 | 1.16 | 4.31 | 6.20 | 0.00 | 0.97 |
| IL2RA | 74 | 0.06 | 0.30 | 0.00 | 2.58 | 0.00 | 0.05 |
| ITGAX | 341 | 0.26 | 0.53 | 0.00 | 3.24 | 0.00 | 0.23 |
| LGMN | 1217 | 2.06 | 1.15 | 2.31 | 4.56 | 0.00 | 0.83 |
| MSR1 | 943 | 1.10 | 0.96 | 1.20 | 4.21 | 0.00 | 0.64 |
| STAT5A | 143 | 0.10 | 0.33 | 0.00 | 2.68 | 0.00 | 0.10 |
| TFEC | 350 | 0.27 | 0.53 | 0.00 | 2.62 | 0.00 | 0.24 |
| TFRC | 212 | 0.18 | 0.50 | 0.00 | 3.14 | 0.00 | 0.14 |
| TMSB4X | 1463 | 5.36 | 0.56 | 5.45 | 6.75 | 0.00 | 1.00 |
| AHR | 41 | 0.25 | 0.54 | 0.00 | 2.57 | 0.00 | 0.20 |
| AIF1 | 191 | 2.62 | 0.87 | 2.76 | 4.17 | 0.00 | 0.95 |
| C10orf54 | 107 | 0.72 | 0.77 | 0.77 | 3.31 | 0.00 | 0.53 |
| CCL2 | 77 | 1.05 | 1.49 | 0.00 | 4.65 | 0.00 | 0.38 |
| CCL3 | 145 | 2.13 | 1.60 | 2.40 | 5.14 | 0.00 | 0.72 |
| CD14 | 171 | 2.26 | 1.26 | 2.55 | 4.47 | 0.00 | 0.85 |
| CD163 | 105 | 0.91 | 1.02 | 0.73 | 3.58 | 0.00 | 0.52 |
| CST3 | 196 | 3.41 | 0.96 | 3.61 | 5.01 | 0.00 | 0.97 |
| FCGR3A | 152 | 1.61 | 1.09 | 1.86 | 3.99 | 0.00 | 0.75 |
| FCN1 | 50 | 0.44 | 0.84 | 0.00 | 3.32 | 0.00 | 0.25 |
| HIF1A | 83 | 0.57 | 0.75 | 0.00 | 2.57 | 0.00 | 0.41 |
| HLA-DRB1 | 185 | 3.37 | 1.40 | 3.65 | 5.52 | 0.00 | 0.92 |
| ICAM1 | 55 | 0.32 | 0.57 | 0.00 | 2.86 | 0.00 | 0.27 |
| JUN | 153 | 1.72 | 1.21 | 1.83 | 4.45 | 0.00 | 0.76 |
| LGALS2 | 40 | 0.32 | 0.70 | 0.00 | 2.90 | 0.00 | 0.20 |
| LILRB1 | 49 | 0.28 | 0.54 | 0.00 | 2.22 | 0.00 | 0.24 |
| LST1 | 165 | 1.64 | 0.94 | 1.88 | 3.57 | 0.00 | 0.82 |
| LYZ | 168 | 2.50 | 1.52 | 2.60 | 5.56 | 0.00 | 0.83 |
| MMP12 | 3 | 0.03 | 0.30 | 0.00 | 3.65 | 0.00 | 0.01 |
| MMP9 | 31 | 0.29 | 0.76 | 0.00 | 3.53 | 0.00 | 0.15 |
| NFKBIA | 131 | 1.28 | 1.13 | 1.30 | 4.76 | 0.00 | 0.65 |
| SPP1 | 87 | 1.53 | 2.05 | 0.00 | 6.93 | 0.00 | 0.43 |
| CCL4 | 3163 | 3.16 | 1.39 | 3.38 | 6.48 | 0.00 | 0.90 |
| CCL5 | 3037 | 3.19 | 1.42 | 3.65 | 5.34 | 0.00 | 0.87 |
| CD7 | 2755 | 2.14 | 1.27 | 2.47 | 4.44 | 0.00 | 0.79 |
| GNLY | 1926 | 2.19 | 2.10 | 2.50 | 6.20 | 0.00 | 0.55 |

TABLE 1-continued

| Example Genes | | | | | | | |
|---|---|---|---|---|---|---|---|
| GZMB | 1704 | 1.34 | 1.48 | 0.00 | 5.57 | 0.00 | 0.49 |
| HLA-A | 3485 | 3.56 | 0.58 | 3.64 | 4.93 | 0.00 | 0.99 |
| HLA-B | 3486 | 3.78 | 0.64 | 3.84 | 5.42 | 0.00 | 0.99 |
| HLA-C | 3472 | 3.38 | 0.65 | 3.47 | 4.94 | 0.00 | 0.99 |
| HLA-E | 3112 | 2.37 | 0.99 | 2.62 | 4.23 | 0.00 | 0.89 |
| NCAM1 | 308 | 0.16 | 0.52 | 0.00 | 2.81 | 0.00 | 0.09 |
| NKG7 | 3403 | 3.67 | 0.90 | 3.85 | 5.11 | 0.00 | 0.97 |
| PLEK | 1551 | 0.89 | 1.04 | 0.00 | 3.33 | 0.00 | 0.44 |
| PTPRC | 2347 | 1.46 | 1.10 | 1.81 | 3.57 | 0.00 | 0.67 |
| SKAP1 | 978 | 0.52 | 0.86 | 0.00 | 3.39 | 0.00 | 0.28 |
| TBX21 | 724 | 0.38 | 0.77 | 0.00 | 3.40 | 0.00 | 0.21 |
| TRDC | 2021 | 1.42 | 1.30 | 1.79 | 4.74 | 0.00 | 0.58 |
| XCL1 | 1239 | 0.85 | 1.21 | 0.00 | 4.65 | 0.00 | 0.35 |
| CD38 | 507 | 0.76 | 0.53 | 0.80 | 2.58 | 0.00 | 0.79 |
| DERL3 | 618 | 1.74 | 0.70 | 1.77 | 3.77 | 0.00 | 0.97 |
| FCRL5 | 396 | 0.44 | 0.43 | 0.41 | 1.96 | 0.00 | 0.62 |
| IGHG1 | 570 | 3.40 | 2.79 | 2.00 | 7.53 | 0.00 | 0.89 |
| IGHG4 | 505 | 2.42 | 2.40 | 1.30 | 7.46 | 0.00 | 0.79 |
| IGHM | 545 | 2.63 | 2.60 | 1.79 | 8.46 | 0.00 | 0.85 |
| IGKC | 632 | 5.45 | 3.17 | 5.48 | 9.01 | 0.00 | 0.99 |
| ISG20 | 571 | 0.99 | 0.56 | 0.99 | 2.71 | 0.00 | 0.89 |
| MZB1 | 639 | 2.82 | 0.52 | 2.83 | 4.81 | 0.86 | 1.00 |
| POU2AF1 | 402 | 0.46 | 0.44 | 0.42 | 2.04 | 0.00 | 0.63 |
| SDC1 | 412 | 0.47 | 0.45 | 0.43 | 3.01 | 0.00 | 0.64 |
| B2M | 6292 | 5.28 | 0.38 | 5.31 | 6.51 | 0.00 | 1.00 |
| CD2 | 4862 | 1.80 | 1.12 | 2.02 | 4.28 | 0.00 | 0.77 |
| CD3D | 5325 | 2.00 | 1.00 | 2.23 | 4.15 | 0.00 | 0.85 |
| CD3E | 4579 | 1.54 | 1.03 | 1.82 | 3.96 | 0.00 | 0.73 |
| CD3G | 3379 | 1.05 | 1.03 | 1.34 | 3.66 | 0.00 | 0.54 |
| CD40LG | 1202 | 0.34 | 0.72 | 0.00 | 3.47 | 0.00 | 0.19 |
| CD5 | 867 | 0.24 | 0.61 | 0.00 | 3.26 | 0.00 | 0.14 |
| CD8A | 1651 | 0.56 | 0.97 | 0.00 | 3.74 | 0.00 | 0.26 |
| CD96 | 1279 | 0.36 | 0.73 | 0.00 | 3.16 | 0.00 | 0.20 |
| CTLA4 | 143 | 0.04 | 0.28 | 0.00 | 3.13 | 0.00 | 0.02 |
| FOXP3 | 109 | 0.03 | 0.24 | 0.00 | 2.92 | 0.00 | 0.02 |
| ICOS | 785 | 0.22 | 0.61 | 0.00 | 4.01 | 0.00 | 0.12 |
| IL32 | 5920 | 2.84 | 0.99 | 3.02 | 5.12 | 0.00 | 0.94 |
| IL7R | 3091 | 1.05 | 1.14 | 0.00 | 3.95 | 0.00 | 0.49 |
| LAG3 | 688 | 0.21 | 0.61 | 0.00 | 4.11 | 0.00 | 0.11 |
| PDCD1 | 362 | 0.11 | 0.44 | 0.00 | 3.50 | 0.00 | 0.06 |
| S100A4 | 5434 | 2.60 | 1.23 | 2.94 | 4.95 | 0.00 | 0.86 |
| THEMIS | 905 | 0.25 | 0.63 | 0.00 | 3.20 | 0.00 | 0.14 |
| TRAC | 5742 | 2.47 | 1.00 | 2.63 | 4.97 | 0.00 | 0.91 |
| ZNF571 | 93 | 0.02 | 0.21 | 0.00 | 2.66 | 0.00 | 0.01 |

TABLE 1-continued

| Example Genes | | | | | |
|---|---|---|---|---|---|
| gene | N_expr_norm | type | method | N_listed | variability |
| BANK1 | 549 | B_cell+ | data_ct_frozen | 1 | 0.03 |
| CD19 | 303 | B_cells\|immune | interest_ct\|codex_frozen | 2 | 0.02 |
| CD40 | 307 | immune | codex_frozen | 1 | 0.05 |
| CD69 | 828 | immune | codex_frozen | 1 | 0.18 |
| CD74 | 1019 | malignant_t3_GO:0019886\|Endothelial_t3_GO:0019886\|Plasma_cell_t5_GO:0050871 | topics_fresh | 3 | 0.35 |
| CD79A | 967 | B_cells | interest_ct | 1 | 0.05 |
| CD79B | 895 | B_cells\|B_cell_t3_GO:0050853 | interest_ct\|topics_fresh | 2 | 0.06 |
| CR2 | 47 | immune | codex_frozen\|mibi_fixed | 2 | 0.00 |
| CXCR5 | 175 | immune | codex_frozen | 1 | 0.01 |
| CXXC5 | 327 | LumA+\|LumB+ | pam50_fresh\|pam50_frozen | 2 | 0.15 |
| HLA-DRB5 | 768 | Endothelial_t3_GO:0019886 | topics_fresh | 1 | 0.12 |
| JUNB | 880 | B_cell_t2_GO:0019221 | topics_fresh | 1 | 0.44 |
| MS4A1 | 836 | B_cells\|immune\|B_cell+ | interest_ct\|mibi_fixed\|data_ct_fresh | 3 | 0.03 |
| RPL13 | 1019 | NK_cell_t1_GO:0000184 | topics_fresh | 1 | 0.25 |
| RPL18 | 1019 | NK_cell_t1_GO:0000184 | topics_fresh | 1 | 0.20 |
| RPSA | 1004 | NK_cell_t1_GO:0000184 | topics_fresh | 1 | 0.24 |
| TCL1A | 796 | B_cell+ | data_ct_fresh | 1 | 0.03 |
| ADGRL4 | 1424 | Endothelial_cells+ | data_ct_frozen | 1 | 0.03 |
| CALCRL | 1256 | Endothelial_cells+ | data_ct_frozen | 1 | 0.03 |
| CD34 | 1198 | stemness\|Endothelial_cells+ | mibi_fixed\|data_ct_frozen | 2 | 0.02 |
| CD36 | 682 | nutrient import\|Endothelial_t5_GO:0002221 | codex_frozen\|topics_fresh | 2 | 0.11 |
| COL4A1 | 1315 | stroma | codex_frozen | 1 | 0.04 |
| COL4A2 | 1318 | stroma | codex_frozen | 1 | 0.05 |
| GNG11 | 2214 | Endothelial_cells+ | data_ct_fresh | 1 | 0.06 |
| GSN | 1496 | Fibroblasts_t1_GO:0042989 | topics_fresh | 1 | 0.16 |
| HSPB1 | 2210 | malignant_t9_GO:0038089 | topics_fresh | 1 | 0.25 |
| HSPG2 | 1923 | Endothelial_cells+ | data_ct_fresh\|data_ct_frozen | 2 | 0.06 |
| IFITM3 | 2309 | Epithelial_stem− | data_ct_fresh | 1 | 0.20 |
| IL3RA | 601 | immune | codex_frozen | 1 | 0.02 |
| LAMC1 | 485 | stroma | mibi_fixed | 1 | 0.07 |
| LDB2 | 1431 | Endothelial_cells+ | data_ct_frozen | 1 | 0.03 |
| MYL6 | 2318 | Fibroblasts_t2_GO:0006936 | topics_fresh | 1 | 0.29 |
| PECAM1 | 1663 | Endothelial\|stroma | interest_ct\|codex_frozen\|mibi_fixed | 3 | 0.07 |
| PLVAP | 1436 | Endothelial_cells+ | data_ct_fresh | 1 | 0.03 |
| PTPRB | 1171 | Endothelial_cells+ | data_ct_frozen | 1 | 0.02 |
| RAMP2 | 2054 | Endothelial_cells+ | data_ct_fresh | 1 | 0.07 |
| SOX18 | 1512 | Endothelial_cells+ | data_ct_fresh | 1 | 0.04 |
| TMSB10 | 2380 | Fibroblasts_t1_GO:0042989 | topics_fresh | 1 | 0.26 |
| TP53 | 392 | Senescence\|tumor suppressor | interest_mbc\|mibi_fixed | 2 | 0.09 |
| ACTA2 | 1223 | Myoepithelial\|Fibroblasts+\|Fibroblasts_t2_GO:0006936 | interest_mbc\|data_ct_fresh\|topics_fresh | 3 | 0.05 |
| AGR2 | 14725 | Luminal_hormone_resp. (L2) | interest_mbc | 1 | 0.20 |
| AKT1 | 5886 | Resistance | interest_mbc | 1 | 0.09 |
| AP1M2 | 13126 | Epithelial_cells+ | data_ct_fresh | 1 | 0.16 |
| AR | 9151 | Resistance\|ER signaling | interest_mbc | 2 | 0.13 |
| AZGP1 | 20810 | Epithelial_cells+ | data_ct_fresh | 1 | 0.26 |
| BAG1 | 15791 | LumA+ | pam50_fresh\|pam50_frozen | 2 | 0.20 |
| BRAF | 2406 | Resistance | interest_mbc | 1 | 0.05 |
| CAPN13 | 3431 | Epithelial_cells+ | data_ct_frozen | 1 | 0.05 |
| CD9 | 22863 | stroma | codex_frozen | 1 | 0.25 |

TABLE 1-continued

Example Genes

| | | | | | |
|---|---|---|---|---|---|
| CDH1 | 8679 | Resistance\|Ductal\|EMT\|tumor suppressor | interest_mbc\|mibi_fixed | 4 | 0.13 |
| CDH3 | 1859 | Normal+ | pam50_fresh\|pam50_frozen | 2 | 0.03 |
| CDK7 | 4698 | Resistance | interest_mbc | 1 | 0.07 |
| CDKN2A | 6548 | Resistance\|Senescence | interest_mbc | 2 | 0.08 |
| CLDN4 | 18135 | Luminal_progenitor (1.2) | interest_mbc | 1 | 0.21 |
| CLU | 16744 | Endothelial_t4_GO:0048260 | topics_fresh | 1 | 0.23 |
| COBL | 4482 | Epithelial_cells+ | data_ct_frozen | 1 | 0.07 |
| COL4A5 | 2206 | stroma | codex_frozen | 1 | 0.04 |
| CRABP2 | 18567 | Epithelial_cells+ | data_ct_fresh | 1 | 0.25 |
| EPCAM | 20687 | Epithelial\|Mammary lineage | interest_ct\|interest_mbc | 2 | 0.24 |
| ERBB2 | 8046 | Receptors\|Resistance\|Her2+ | interest_mbc\|pam50_fresh\|pam50_frozen | 4 | 0.11 |
| ERBB3 | 11763 | Resistance | interest_mbc | 1 | 0.16 |
| ERBB4 | 3249 | Resistance | interest_mbc | 1 | 0.05 |
| ESR1 | 7247 | Receptors\|Resistance\|ER signaling\|LumA+\|LumB+ | interest_mbc\|pam50_fresh\|pam50_frozen | 5 | 0.10 |
| FASN | 8247 | malignant_t6_GO:0071616 | topics_fresh | 1 | 0.11 |
| FGFR4 | 2826 | Resistance\|Her2+ | interest_mbc\|pam50_fresh\|pam50_frozen | 3 | 0.05 |
| FN1 | 2193 | Fibroblasts\|EMT\|MonoMacro_t7_GO:0022617 | interest_ct\|interest_mbc\|topics_fresh | 3 | 0.07 |
| FOS | 20721 | ER signaling\|B_cell_t2_GO:0019221\|Plasma_cell_t1_GO:0038093 | interest_mbc\|topics_fresh | 3 | 0.44 |
| FOXA1 | 12801 | Resistance\|ER signaling\|Mammary lineage\|LumA+ | interest_mbc\|pam50_fresh\|pam50_frozen | 5 | 0.18 |
| FXYD3 | 21762 | Epithelial_cells+ | data_ct_fresh | 1 | 0.23 |
| GATA3 | 16345 | ER signaling\|Mammary lineage | interest_mbc | 2 | 0.24 |
| GPR160 | 11893 | LumA+ | pam50_fresh\|pam50_frozen | 2 | 0.15 |
| GRB7 | 3486 | Her2+ | pam50_fresh\|pam50_frozen | 2 | 0.06 |
| IGF1R | 4024 | Resistance | interest_mbc | 1 | 0.07 |
| KRAS | 8994 | Resistance | interest_mbc | 1 | 0.13 |
| KRT10 | 18676 | epithelial | codex_frozen | 1 | 0.24 |
| KRT14 | 1288 | Myoepithelial\|epithelial\|Normal+ | interest_mbc\|codex_frozen\|pam50_fresh\|pam50_frozen | 4 | 0.02 |
| KRT17 | 2040 | Basal\|epithelial\|Normal+ | interest_mbc\|codex_frozen\|pam50_fresh\|pam50_frozen | 4 | 0.04 |
| KRT18 | 23218 | Epithelial\|Luminal_hormone_resp. (L2)\|epithelial | interest_ct\|interest_mbc\|codex_frozen | 3 | 0.25 |
| KRT19 | 25241 | ER signaling\|Mammary lineage\|epithelial\|Epithelial_cells+ | interest_mbc\|codex_frozen\|data_ct_fresh | 4 | 0.26 |
| KRT7 | 18302 | Mammary lineage\|epithelial | interest_mbc\|codex_frozen | 2 | 0.22 |
| KRT8 | 24130 | Epithelial\|Luminal_hormone_resp. (L2)\|epithelial | interest_ct\|interest_mbc\|codex_frozen | 3 | 0.24 |
| LRP2 | 2578 | Epithelial_stem+ | data_ct_frozen | 1 | 0.04 |
| LTF | 7280 | Epithelial_cells+\|malignant_t7_GO:0043312 | data_ct_fresh\|topics_fresh | 2 | 0.10 |
| LYPD6B | 8109 | Epithelial_cells+ | data_ct_frozen | 1 | 0.11 |
| MAPK13 | 11379 | Resistance | interest_mbc | 1 | 0.14 |
| MAPK3 | 7250 | Resistance | interest_mbc | 1 | 0.11 |
| MDM2 | 6012 | Normal+ | pam50_fresh\|pam50_frozen | 2 | 0.10 |
| MLPH | 14785 | ER signaling\|Her2+\|Normal+ | interest_mbc\|pam50_fresh\|pam50_frozen | 3 | 0.18 |
| MUC1 | 14426 | ER signaling\|Mammary lineage | interest_mbc | 2 | 0.19 |
| MYB | 4468 | Mammary lineage\|Epithelial_stem+ | interest_mbc\|data_ct_frozen | 2 | 0.07 |
| MYO5B | 3416 | Epithelial_cells+ | data_ct_frozen | 1 | 0.05 |
| NAT1 | 4566 | LumA+ | pam50_fresh\|pam50_frozen | 2 | 0.07 |
| NF1 | 4324 | Resistance | interest_mbc | 1 | 0.08 |
| NR3C1 | 7586 | Resistance\|ER signaling | interest_mbc | 2 | 0.14 |
| PDZK1IP1 | 8906 | Epithelial_cells+ | data_ct_fresh | 1 | 0.11 |
| PGR | 886 | Receptors\|Resistance\|ER signaling\|LumB−\|LumA+ | interest_mbc\|pam50_fresh\|pam50_frozen | 5 | 0.02 |
| PI3 | 888 | Luminal_alveolar (1.1)\|Luminal_progenitor (1.2) | interest_mbc | 2 | 0.02 |
| PTEN | 7161 | Resistance | interest_mbc | 1 | 0.11 |
| S100A14 | 17813 | Epithelial_cells+ | data_ct_fresh | 1 | 0.22 |
| S100A8 | 2218 | Luminal_alveolar (1.1)\|malignant_t7_GO:0043312\|MonoMacro_t1_GO:0043312 | interest_mbc\|topics_fresh | 3 | 0.06 |

TABLE 1-continued

| Example Genes | | | | | |
|---|---|---|---|---|---|
| S100A9 | 2789 | Luminal__alveolar (1.1)\|malignant__t7__GO:0043312\|MonoMacro__t1__GO:0043312 | interest__mbc\|topics__fresh | 3 | 0.08 |
| SIAH2 | 11206 | ER signaling | interest__mbc | 1 | 0.15 |
| SLC39A6 | 15489 | LumB+ | pam50__fresh\|pam50__frozen | 2 | 0.18 |
| SLPI | 9582 | Luminal__progenitor (1.2)\|malignant__t7__GO:0043312 | interest__mbc\|topics__fresh | 2 | 0.12 |
| SPDEF | 15436 | ER signaling | interest__mbc | 1 | 0.20 |
| TAGLN | 2089 | Myoepithelial\|Fibroblasts+ | interest__mbc\|data__ct__fresh | 2 | 0.06 |
| TFF1 | 11473 | ER signaling | interest__mbc | 2 | 0.16 |
| TFF3 | 15821 | ER signaling | interest__mbc | 1 | 0.22 |
| TIMP1 | 16073 | Basal\|Fibroblasts__t4__GO:0071345\|B__cell__t2__GO:0019221 | interest__mbc\|topics__fresh | 3 | 0.18 |
| TMEM45B | 1455 | Her2+ | pam50__fresh\|pam50__frozen | 2 | 0.03 |
| TSPAN1 | 12778 | Epithelial__cells+ | data__ct__frozen | 1 | 0.18 |
| TTC6 | 3105 | Epithelial__cells+ | data__ct__frozen | 1 | 0.05 |
| XBP1 | 21490 | ER signaling\|Plasma__cell__t5__GO:0050871 | interest__mbc\|topics__fresh | 2 | 0.28 |
| ACTG2 | 412 | Myoepithelial\|Fibroblasts__t2__GO:0006936 | interest__mbc\|topics__fresh | 2 | 0.02 |
| ACTR3B | 2340 | Basal+ | pam50__fresh\|pam50__frozen | 2 | 0.11 |
| ALDH1A3 | 108 | Luminal__progenitor (1.2)\|Epithelial__cells+ | interest__mbc\|data__ct__frozen | 2 | 0.01 |
| ANLN | 579 | Basal+ | pam50__fresh\|pam50__frozen | 2 | 0.03 |
| AURKA | 1259 | Resistance | interest__mbc | 1 | 0.06 |
| BCL2 | 1766 | Apoptosis\|Normal+ | interest__mbc\|pam50__fresh\|pam50__frozen | 3 | 0.10 |
| BIRC5 | 2092 | LumB+\|Her2+\|malignant__t8__GO:0007052 | pam50__fresh\|pam50__frozen\|topics__fresh | 3 | 0.09 |
| CCNB1 | 1340 | LumB+\|malignant__t8__GO:0007052 | pam50__fresh\|pam50__frozen\|topics__fresh | 3 | 0.07 |
| CCND1 | 4141 | Resistance\|ER signaling\|Epithelial__stem+ | interest__mbc\|data__ct__fresh | 3 | 0.22 |
| CCNE1 | 512 | Resistance\|Basal+ | interest__mbc\|pam50__fresh\|pam50__frozen | 3 | 0.03 |
| CCNE2 | 561 | Resistance | interest__mbc | 1 | 0.03 |
| CD24 | 4289 | Mammary stemmness | interest__mbc | 1 | 0.25 |
| CD44 | 2945 | Mammary stemmness | interest__mbc | 1 | 0.21 |
| CDC20 | 1395 | Her2+\|Basal+ | pam50__fresh\|pam50__frozen | 2 | 0.06 |
| CDC6 | 719 | LumB+\|Her2+ | pam50__fresh\|pam50__frozen | 2 | 0.04 |
| CDK4 | 2956 | Resistance | interest__mbc | 1 | 0.18 |
| CDK6 | 1135 | Resistance | interest__mbc | 1 | 0.08 |
| CEACAM1 | 1027 | malignant | codex__frozen | 1 | 0.09 |
| CENPF | 1901 | Basal+ | pam50__fresh\|pam50__frozen | 2 | 0.08 |
| CEP55 | 765 | LumB+\|Basal+ | pam50__fresh\|pam50__frozen | 2 | 0.03 |
| CSRP2 | 3383 | Epithelial__stem+ | data__ct__fresh | 1 | 0.13 |
| CTCF | 1074 | Resistance | interest__mbc | 1 | 0.10 |
| EFNA5 | 1038 | Epithelial__stem+ | data__ct__frozen | 1 | 0.08 |
| EGFR | 915 | Resistance+Normal+ | interest__mbc\|pam50__fresh\|pam50__frozen | 3 | 0.05 |
| EIF3E | 4475 | NK__cell__t1__GO:0000184 | topics__fresh | 1 | 0.40 |
| ELF5 | 2308 | Luminal__progenitor (1.2) | interest__mbc | 1 | 0.13 |
| FABP7 | 3349 | Epithelial__stem+ | data__ct__fresh | 1 | 0.11 |
| FAT1 | 673 | Resistance | interest__mbc | 1 | 0.05 |
| FGFR1 | 457 | Resistance | interest__mbc | 1 | 0.05 |
| FGFR2 | 2282 | Resistance | interest__mbc | 1 | 0.09 |
| FOXC1 | 1252 | Basal+ | pam50__fresh\|pam50__frozen | 2 | 0.07 |
| ISG15 | 3825 | T__cells__t3__GO:0060337 | topics__fresh | 1 | 0.19 |
| ITGA6 | 969 | Mammary lineage\|stemness | interest__mbc\|codex__frozen | 2 | 0.08 |
| KIF23 | 748 | Epithelial__stem+ | data__ct__frozen | 1 | 0.04 |
| KIT | 1312 | Mammary lineage\|malignant | interest__mbc\|codex__frozen\|mibi__fixed | 3 | 0.04 |
| KRT15 | 2458 | ER signaling\|Mammary lineage\|epithelial | interest__mbc\|codex__frozen | 3 | 0.11 |
| KRT5 | 1362 | Myoepithelial\|epithelial\|Normalt+\|Basal+ | interest__mbc\|codex__frozen\|pam50__fresh\|pam50__frozen | 4 | 0.06 |
| LAMA1 | 924 | stroma | mibi__fixed | 1 | 0.03 |

TABLE 1-continued

<table>
<tr><th colspan="5">Example Genes</th></tr>
<tr><td>MELK</td><td>643</td><td>Basal+</td><td>pam50__fresh|pam50__frozen</td><td>2</td><td>0.03</td></tr>
<tr><td>MIA</td><td>4062</td><td>Basal+</td><td>pam50__fresh</td><td>1</td><td>0.16</td></tr>
<tr><td>MKI67</td><td>1961</td><td>Proliferation|proliferation|Basal+|Her2+</td><td>interest__mbc|codex__frozen|mibi__fixed|pam50__fresh|pam50__frozen</td><td>5</td><td>0.07</td></tr>
<tr><td>MYBL2</td><td>963</td><td>Basal+|Her2+</td><td>pam50__fresh|pam50__frozen</td><td>2</td><td>0.05</td></tr>
<tr><td>MYC</td><td>2695</td><td>Resistance|Normal+</td><td>interest__mbc|pam50__fresh|pam50__frozen</td><td>3</td><td>0.16</td></tr>
<tr><td>MYLK</td><td>441</td><td>Myoepithelial|Fibroblasts__t2__GO:0006936</td><td>interest__mbc|topics__fresh</td><td>2</td><td>0.05</td></tr>
<tr><td>MYO10</td><td>2877</td><td>Epithelial__stem+</td><td>data__ct__fresh</td><td>1</td><td>0.13</td></tr>
<tr><td>NDC80</td><td>681</td><td>LumB+|Basal+</td><td>pam50__fresh|pam50__frozen</td><td>2</td><td>0.04</td></tr>
<tr><td>NDRG2</td><td>4115</td><td>Luminal__progenitor (1.2)</td><td>interest__mbc</td><td>1</td><td>0.19</td></tr>
<tr><td>NOTCH1</td><td>3488</td><td>Mammary lineage</td><td>interest__mbc</td><td>1</td><td>0.13</td></tr>
<tr><td>NUF2</td><td>1522</td><td>LumBt+|malignant__t8__GO:0007052</td><td>pam50__fresh|pam50__frozen|topics__fresh</td><td>3</td><td>0.06</td></tr>
<tr><td>OBP2B</td><td>2932</td><td>Epithelial__stem+</td><td>data__ct__fresh</td><td>1</td><td>0.12</td></tr>
<tr><td>ORC6</td><td>1627</td><td>Her2+</td><td>pam50__fresh|pam50__frozen</td><td>2</td><td>0.06</td></tr>
<tr><td>PABPC1</td><td>4528</td><td>NK__cell__t1__GO:0000184</td><td>topics__fresh</td><td>1</td><td>0.32</td></tr>
<tr><td>PBK</td><td>1875</td><td>Epithelial__stem+</td><td>data__ct__fresh</td><td>1</td><td>0.07</td></tr>
<tr><td>PDPN</td><td>80</td><td>Mammary stemmness|stroma</td><td>interest__mbc|codex__frozen</td><td>2</td><td>0.01</td></tr>
<tr><td>PHGDH</td><td>3993</td><td>Basal+|Epithelial__stem+</td><td>pam50__fresh|pam50__frozen|data__ct__fresh</td><td>3</td><td>0.18</td></tr>
<tr><td>PIK3CA</td><td>553</td><td>Resistance</td><td>interest__mbc</td><td>1</td><td>0.05</td></tr>
<tr><td>PRLR</td><td>1496</td><td>Mammary lineage</td><td>interest__mbc</td><td>1</td><td>0.12</td></tr>
<tr><td>PTTG1</td><td>2673</td><td>LumB+|Her2-</td><td>pam50__fresh|pam50__frozen</td><td>2</td><td>0.12</td></tr>
<tr><td>RB1</td><td>620</td><td>Resistance</td><td>interest__mbc</td><td>1</td><td>0.07</td></tr>
<tr><td>RRM2</td><td>1617</td><td>Her2+</td><td>pam50__fresh|pam50__frozen</td><td>2</td><td>0.06</td></tr>
<tr><td>SFRP1</td><td>2470</td><td>Basalt+</td><td>pam50__fresh|pam50__frozen</td><td>2</td><td>0.11</td></tr>
<tr><td>SLC2A1</td><td>1706</td><td>nutrient import</td><td>codex__frozen</td><td>1</td><td>0.10</td></tr>
<tr><td>SNAI2</td><td>370</td><td>EMT</td><td>interest__mbc</td><td>1</td><td>0.04</td></tr>
<tr><td>SOX10</td><td>2776</td><td>Luminal__progenitor (1.2)</td><td>interest__mbc</td><td>1</td><td>0.11</td></tr>
<tr><td>SOX4</td><td>4408</td><td>Epithelial__stem+</td><td>data__ct__fresh</td><td>1</td><td>0.23</td></tr>
<tr><td>STMN1</td><td>4503</td><td>malignant__t8__GO:0007052</td><td>topics__fresh</td><td>1</td><td>0.23</td></tr>
<tr><td>TCF4</td><td>185</td><td>Mammary stemmness|Epithelial__stem−</td><td>interest__mbc|data__ct__frozen</td><td>2</td><td>0.08</td></tr>
<tr><td>TFF2</td><td>3992</td><td>Epithelial__stem+</td><td>data__ct__fresh</td><td>1</td><td>0.16</td></tr>
<tr><td>THY1</td><td>111</td><td>Basal|immune</td><td>interest__mbc|codex__frozen</td><td>2</td><td>0.03</td></tr>
<tr><td>TPM2</td><td>1755</td><td>Basal|Fibroblasts__t2__GO:0006936</td><td>interest__mbc|topics__fresh</td><td>2</td><td>0.09</td></tr>
<tr><td>TTYH1</td><td>4173</td><td>Epithelial__stem+</td><td>data__ct__fresh</td><td>1</td><td>0.17</td></tr>
<tr><td>TYMS</td><td>2108</td><td>LumB+</td><td>pam50__fresh|pam50__frozen</td><td>2</td><td>0.09</td></tr>
<tr><td>UBE2C</td><td>2325</td><td>Her2+|Epithelial__stem+</td><td>pam50__fresh|pam50__frozen|data__ct__fresh</td><td>3</td><td>0.08</td></tr>
<tr><td>UBE2T</td><td>2844</td><td>LumB+</td><td>pam50__fresh|pam50__frozen</td><td>2</td><td>0.12</td></tr>
<tr><td>VIM</td><td>3084</td><td>EMT|stroma|Fibroblasts__t4__GO:0071345</td><td>interest__mbc|codex__frozen|mibi__fixed|topics__fresh</td><td>4</td><td>0.39</td></tr>
<tr><td>ZEB1</td><td>16</td><td>EMT|Mammary stemmness</td><td>interest__mbc</td><td>2</td><td>0.03</td></tr>
<tr><td>BGN</td><td>168</td><td>Fibroblasts__t4__GO:0071345</td><td>topics__fresh</td><td>1</td><td>0.07</td></tr>
<tr><td>BICC1</td><td>47</td><td>Fibroblasts+</td><td>data__ct__frozen</td><td>1</td><td>0.01</td></tr>
<tr><td>CDH11</td><td>61</td><td>Fibroblasts+</td><td>data__ct__frozen</td><td>1</td><td>0.02</td></tr>
<tr><td>COL1A1</td><td>145</td><td>CAFs|Fibroblasts__t3__GO:0030198</td><td>interest__ct|topics__fresh</td><td>2</td><td>0.05</td></tr>
<tr><td>COL1A2</td><td>145</td><td>CAFs|Fibroblasts+|Fibroblasts__t3__GO:0030198</td><td>interest__ct|data__ct__fresh|topics__fresh</td><td>3</td><td>0.04</td></tr>
<tr><td>COL3A1</td><td>142</td><td>Fibroblasts__t3__GO:0030198</td><td>topics__fresh</td><td>1</td><td>0.04</td></tr>
<tr><td>DCN</td><td>154</td><td>CAFs|Fibroblasts+|Fibroblasts__t3__GO:0030198|Fibroblasts__t4__GO:0071345</td><td>interest__ct|data__ct__fresh|topics__fresh</td><td>4</td><td>0.03</td></tr>
<tr><td>FAP</td><td>57</td><td>CAFs|stroma</td><td>interest__ct|codex__frozen</td><td>2</td><td>0.01</td></tr>
<tr><td>IGFBP5</td><td>58</td><td>Endothelial__t2__GO:0048662</td><td>topics__fresh</td><td>1</td><td>0.07</td></tr>
<tr><td>LGALS1</td><td>201</td><td>Basal</td><td>interest__mbc</td><td>1</td><td>0.26</td></tr>
<tr><td>LUM</td><td>143</td><td>Fibroblasts+|Fibroblasts__t3__GO:0030198</td><td>data__ct__fresh|topics__fresh</td><td>2</td><td>0.03</td></tr>
<tr><td>MMP11</td><td>53</td><td>Her2+</td><td>pam50__fresh|pam50__frozen</td><td>2</td><td>0.03</td></tr>
</table>

TABLE 1-continued

| Example Genes | | | | | |
|---|---|---|---|---|---|
| MT2A | 151 | Basal | interest__mbc | 1 | 0.21 |
| MYL9 | 172 | Fibroblasts__t2__GO:0006936 | topics__fresh | 1 | 0.09 |
| SULF1 | 44 | Fibroblasts+ | data__ct__frozen | 1 | 0.02 |
| APOC1 | 1351 | Macrophage+ | data__ct__fresh | 1 | 0.08 |
| APOE | 1410 | Basal | interest__mbc | 1 | 0.12 |
| BLVRA | 561 | Normal+\|Her2+ | pam50__fresh\|pam50__frozen | 2 | 0.16 |
| C1QA | 1354 | Macrophage+ | data__ct__fresh | 1 | 0.06 |
| C1QB | 1360 | Macrophage+ | data__ct__fresh | 1 | 0.06 |
| CD274 | 32 | Immune checkpoint\|immune evasion | interest__mbc\|codex__frozen\|mibi__fixed | 3 | 0.01 |
| CD4 | 628 | T__cells\|immune | interest__ct\|codex__frozen\|mibi__fixed | 3 | 0.06 |
| CD63 | 1391 | Endothelial__t4__GO:0048260 | topics__fresh | 1 | 0.44 |
| CD68 | 1317 | macro__mono\|immune | interest__ct\|mibi__fixed | 2 | 0.07 |
| CSTB | 1284 | malignant__t7__GO:0043312 | topics__fresh | 1 | 0.46 |
| CTSL | 1163 | Endothelial__t5__GO:0002221 | topics__fresh | 1 | 0.10 |
| FTL | 1465 | MonoMacro__tl__GO:0043312 | topics__fresh | 1 | 0.21 |
| GPNMB | 1213 | Macrophage+ | data__ct__fresh | 1 | 0.08 |
| HLA-DPA1 | 1364 | MonoMacro__t4__GO:0071346 | topics__fresh | 1 | 0.17 |
| HLA-DRA | 1419 | immune\|malignant__t3__GO:0019886\|Endothelial__t3__GO:0019886\|Mono-Macro__t4__GO:0071346 | codex__frozen\|topics__fresh | 4 | 0.17 |
| IL2RA | 74 | immune | codex__frozen\|mibi__fixed | 2 | 0.01 |
| ITGAX | 341 | immune | codex__frozen\|mibi__fixed | 2 | 0.02 |
| LGMN | 1217 | Endothelial__t5__GO:0002221 | topics__fresh | 1 | 0.10 |
| MSR1 | 943 | MonoMacro+ | data__ct__frozen | 1 | 0.03 |
| STAT5A | 143 | proliferation | mibi__fixed | 1 | 0.04 |
| TFEC | 350 | MonoMacro+ | data__ct__frozen | 1 | 0.01 |
| TFRC | 212 | nutrient import | mibi__fixed | 1 | 0.08 |
| TMSB4X | 1463 | Fibroblasts__t1__GO:0042989\|B__cell__t2__GO:0019221 | topics__fresh | 2 | 0.30 |
| AHR | 41 | Epithelial__cells+ | data__ct__frozen | 1 | 0.05 |
| AIF1 | 191 | Monocyte+ | data__ct__fresh | 1 | 0.09 |
| C10orf54 | 107 | immune evasion | mibi__fixed | 1 | 0.10 |
| CCL2 | 77 | Fibroblasts__t4__GO:0071345\|MonoMacro__t4__GO:0071346 | topics__fresh | 2 | 0.03 |
| CCL3 | 145 | T__cells__t2__GO:2000501\|NK__cell__t2__GO:2000501 | topics__fresh | 2 | 0.10 |
| CD14 | 171 | macro__mono\|Endothelial__t5__GO:0002221 | interest__ct\|topics__fresh | 2 | 0.07 |
| CD163 | 105 | macro__mono\|immune\|MonoMacro+ | interest__ct\|mibi__fixed\|data__ct__frozen | 3 | 0.02 |
| CST3 | 196 | MonoMacro__t1__GO:0043312 | topics__fresh | 1 | 0.51 |
| FCGR3A | 152 | immune | codex__frozen | 1 | 0.07 |
| FCN1 | 50 | Monocyte+\|MonoMacro__tl__GO:0043312 | data__ct__fresh\|topics__fresh | 2 | 0.03 |
| HIF1A | 83 | metabolic | codex__frozen | 1 | 0.10 |
| HLA-DRB1 | 185 | malignant__t3__GO:0019886\|Endothelial__t3__GO:0019886\|MonoMacro__t4__GO:0071346 | topics__fresh | 3 | 0.18 |
| ICAM1 | 55 | stroma | codex__frozen | 1 | 0.05 |
| JUN | 153 | Plasma__cell__t1__GO:0038093 | topics__fresh | 1 | 0.36 |
| LGALS2 | 40 | Monocyte+ | data__ct__fresh | 1 | 0.03 |
| LILRB1 | 49 | immune | codex__frozen | 1 | 0.02 |
| LST1 | 165 | Monocyte+ | data__ct__fresh | 1 | 0.09 |
| LYZ | 168 | Monocyte+\|MonoMacro__t1__GO:0043312 | data__ct__fresh\|topics__fresh | 2 | 0.08 |
| MMP12 | 3 | stroma\|MonoMacro__t7__GO:0022617 | codex__frozen\|topics__fresh | 2 | 0.00 |
| MMP9 | 31 | Fibroblasts__t4__GO:0071345\|MonoMacro__t7__GO:0022617 | topics__fresh | 2 | 0.01 |
| NFKBIA | 131 | B__cell__t2__GO:0019221\|Plasma__cell__t1__GO:0038093 | topics__fresh | 2 | 0.18 |
| SPP1 | 87 | Macrophage+\|Fibroblasts__t3__GO:0030198\|MonoMacro__t7__GO:0022617 | data__ct__fresh\|topics__fresh | 3 | 0.05 |
| CCL4 | 3163 | T__cells__t2__GO:2000501\|NK__cell__t2__GO:2000501 | topics__fresh | 2 | 0.14 |
| CCL5 | 3037 | T__cells__t2__GO:2000501\|NK__cell__t2__GO:2000501 | topics__fresh | 2 | 0.18 |

TABLE 1-continued

Example Genes

| | | | | | |
|---|---|---|---|---|---|
| CD7 | 2755 | immune | codex__frozen | 1 | 0.13 |
| GNLY | 1926 | NK__cell+ | data__ct__fresh | 1 | 0.05 |
| GZMB | 1704 | immune | mibi__fixed | 1 | 0.05 |
| HLA-A | 3485 | immune\|T__cells__t3__GO:0060337\|MonoMacro__t5__GO:0002480 | codex__frozen\|topics__fresh | 3 | 0.32 |
| HLA-B | 3486 | immune\|malignant__t10__GO:0002480\|B__cell__t2__GO:0019221 | codex__frozen\|topics__fresh | 3 | 0.33 |
| HLA-C | 3472 | immune\|malignant__t10__GO:0002480 | codex__frozen\|topics__fresh | 2 | 0.31 |
| HLA-E | 3112 | Endothelial__t1__GO:0002483 | topics__fresh | 1 | 0.47 |
| NCAM1 | 308 | NK__cells\|immune | interest__ct\|codex__frozen\|mibi__fixed | 3 | 0.02 |
| NKG7 | 3403 | NK__cell+ | data__ct__fresh | 1 | 0.14 |
| PLEK | 1551 | T__cells− | data__ct__fresh | 1 | 0.09 |
| PTPRC | 2347 | immune | codex__frozen\|mibi__fixed | 5 | 0.20 |
| SKAP1 | 978 | T__cells+ | data__ct__frozen | 1 | 0.08 |
| TBX21 | 724 | immune | mibi__fixed | 1 | 0.02 |
| TRDC | 2021 | NK__cell+ | data__ct__fresh | 1 | 0.05 |
| XCL1 | 1239 | NK__cell+\|T__cells__t2__GO:2000501\|NK__cell__t2__GO:2000501 | data__ct__fresh\|opics__fresh | 3 | 0.04 |
| CD38 | 507 | immune | codex__frozen\|mibi__fixed | 2 | 0.04 |
| DERL3 | 618 | Plasma__cell+ | data__ct__fresh | 1 | 0.05 |
| FCRL5 | 396 | B__cell+ | data__ct__frozen | 1 | 0.02 |
| IGHG1 | 570 | Fibroblasts__t4__GO:0071345 | topics__fresh | 1 | 0.07 |
| IGHG4 | 505 | Fibroblasts__t4__GO:0071345 | topics__fresh | 1 | 0.07 |
| IGHM | 545 | immune\|Plasma__cell__t5__GO:0050871 | codex__frozen\|topics__fresh | 2 | 0.10 |
| IGKC | 632 | B__cell__t3__GO:0050853\|Plasma__cell__t1__GO:0038093\|Plasma__cell__t5__GO:0050871 | topics__fresh | 3 | 0.14 |
| ISG20 | 571 | immune | codex__frozen\|mibi__fixed | 2 | 0.18 |
| MZB1 | 639 | Plasma__cell+\|B__cell+ | data__ct__fresh\|data__ct__frozen | 2 | 0.07 |
| POU2AF1 | 402 | B__cell+ | data__ct__frozen | 1 | 0.02 |
| SDC1 | 412 | Plasma__cells\|immune | interest__ct\|mibi__fixed | 2 | 0.13 |
| B2M | 6292 | malignant__t10__GO:0002480\|Endothelial__t1__GO:0002483\|Endothelial__t4__GO:0048260\|MonoMacro__t4__GO:0071346\|MonoMacro__t5__G0:0002480\|B__cell__t2__GO:0019221 | topics__fresh | 6 | 0.30 |
| CD2 | 4862 | immune\|T__cells+ | codex__frozen\|data__ct__frozen | 2 | 0.17 |
| CD3D | 5325 | T__cells\|immune\|T__cells+ | interest__ct\|codex__frozen\|mibi__fixed\|data__ct__fresh | 4 | 0.17 |
| CD3E | 4579 | T__cells+ | data__ct__fresh | 1 | 0.16 |
| CD3G | 3379 | T__cells+ | data__ct__fresh | 1 | 0.11 |
| CD40LG | 1202 | immune\|T__cells+ | codex__frozen\|data__ct__fresh | 2 | 0.03 |
| CD5 | 867 | immune | codex__frozen | 1 | 0.03 |
| CD8A | 1651 | T__cells\|immune | interest__ct\|codex__frozen\|mibi__fixed | 3 | 0.07 |
| CD96 | 1279 | T__cells+ | data__ct__frozen | 1 | 0.05 |
| CTLA4 | 143 | Immune checkpoint\|immune | interest__mbc\|codex__frozen | 2 | 0.01 |
| FOXP3 | 109 | immune | codex__frozen\|mibi__fixed | 2 | 0.01 |
| ICOS | 785 | immune evasion | codex__frozen\|mibi__fixed | 2 | 0.02 |
| IL32 | 5920 | T__cells+ | data__ct__fresh | 1 | 0.21 |
| IL7R | 3091 | immune\|T__cells+ | codex__frozen\|data__ct__fresh | 2 | 0.09 |
| LAG3 | 688 | Immune checkpoint\|immune evasion | interest__mbc\|mibi__fixed | 2 | 0.04 |
| PDCD1 | 362 | Immune checkpoint\|immune evasion | interest__mbc\|codex__frozen\|mibi__fixed | 3 | 0.01 |
| S100A4 | 5434 | Fibroblasts | interest__ct | 1 | 0.28 |
| THEMIS | 905 | T__cells+ | data__ct__frozen | 1 | 0.03 |
| TRAC | 5742 | T__cells+ | data__ct__fresh | 1 | 0.18 |
| ZNF571 | 93 | Epithelial__cells+ | data__ct__frozen | 1 | 0.03 |

gene N__expr__all perc__expr__all mean.TPM.Mets cluster__0.7 cluster__0.6 cluster__order priority TABLE 1-continued

| Example Genes | | | | | | | |
|---|---|---|---|---|---|---|---|
| BANK1 | 1659 | 0.03 | 2.81 | NA | NA | 439 | 1.00 |
| CD19 | 976 | 0.02 | 2.76 | NA | NA | 438 | 1.00 |
| CD40 | 3615 | 0.06 | 6.40 | NA | NA | 437 | 1.00 |
| CD69 | 14388 | 0.23 | 7.83 | NA | NA | 20 | 1.00 |
| CD74 | 38320 | 0.62 | 1193.85 | 12 | 16 | 110 | 1.00 |
| CD79A | 3416 | 0.06 | 12.58 | NA | 3 | 442 | 0.00 |
| CD79B | 4367 | 0.07 | 9.86 | NA | 3 | 440 | 0.00 |
| CR2 | 95 | 0.00 | 1.93 | NA | NA | 435 | 1.00 |
| CXCR5 | 342 | 0.01 | 0.45 | NA | NA | 436 | 1.00 |
| CXXC5 | 16381 | 0.27 | 38.93 | NA | NA | 140 | 1.00 |
| HLA-DRB5 | 9410 | 0.15 | 204.20 | NA | 16 | 108 | 0.00 |
| JUNB | 45409 | 0.74 | 76.45 | NA | NA | 148 | 0.00 |
| MS4A1 | 1852 | 0.03 | 6.99 | NA | 3 | 441 | 1.00 |
| RPL13 | 61103 | 0.99 | 441.25 | NA | NA | 43 | 1.00 |
| RPL18 | 59543 | 0.97 | 515.77 | NA | NA | 42 | 0.00 |
| RPSA | 57248 | 0.93 | 827.86 | NA | NA | 41 | 0.00 |
| TCL1A | 1705 | 0.03 | 2.61 | 2 | 3 | 444 | 0.90 |
| ADGRL4 | 1554 | 0.03 | NA | NA | 12 | 244 | 1.00 |
| CALCRL | 1627 | 0.03 | 14.79 | NA | 12 | 240 | 1.00 |
| CD34 | 1451 | 0.02 | 25.07 | NA | 12 | 241 | 1.00 |
| CD36 | 7341 | 0.12 | 57.20 | NA | NA | 506 | 1.00 |
| COL4A1 | 2872 | 0.05 | 133.00 | 9 | 13 | 238 | 1.00 |
| COL4A2 | 3914 | 0.06 | 105.90 | 9 | 13 | 239 | 1.00 |
| GNG11 | 4278 | 0.07 | 69.70 | 13 | 12 | 246 | 1.00 |
| GSN | 19635 | 0.32 | 55.73 | NA | NA | 273 | 0.00 |
| HSPB1 | 36963 | 0.60 | 484.92 | NA | NA | 264 | 1.00 |
| HSPG2 | 4840 | 0.08 | 29.61 | NA | 12 | 245 | 0.52 |
| IFITM3 | 31570 | 0.51 | 851.68 | NA | NA | 272 | 1.00 |
| IL3RA | 965 | 0.02 | 8.85 | NA | NA | 236 | 1.00 |
| LAMC1 | 5053 | 0.08 | 38.98 | NA | NA | 268 | 1.00 |
| LDB2 | 2010 | 0.03 | 7.55 | NA | NA | 252 | 1.00 |
| MYL6 | 55384 | 0.90 | 736.20 | NA | NA | 265 | 0.00 |
| PECAM1 | 4646 | 0.08 | NA | NA | NA | 248 | 1.00 |
| PLVAP | 1729 | 0.03 | 58.85 | NA | 12 | 242 | 1.00 |
| PTPRB | 1457 | 0.02 | 6.80 | NA | NA | 250 | 1.00 |
| RAMP2 | 6464 | 0.11 | 48.26 | 13 | 12 | 247 | 1.00 |
| SOX18 | 2548 | 0.04 | 4.26 | NA | 12 | 243 | 1.00 |
| TMSB10 | 58659 | 0.95 | 4111.46 | NA | NA | 130 | 0.00 |
| TP53 | 8585 | 0.14 | 30.57 | NA | NA | 181 | 1.00 |
| ACTA2 | 4040 | 0.07 | 220.93 | 6 | 7 | 196 | 1.00 |
| AGR2 | 16023 | 0.26 | 804.89 | NA | 2 | 496 | 1.00 |
| AKT1 | 8094 | 0.13 | 73.42 | NA | NA | 385 | 1.00 |
| AP1M2 | 14150 | 0.23 | 88.88 | NA | NA | 493 | 1.00 |
| AR | 9560 | 0.16 | 18.62 | NA | NA | 479 | 1.00 |
| AZGP1 | 26024 | 0.42 | 826.74 | NA | NA | 334 | 1.00 |
| BAG1 | 23728 | 0.39 | 28.12 | NA | NA | 473 | 1.00 |
| BRAF | 3530 | 0.06 | 10.53 | NA | NA | 159 | 1.00 |
| CAPN13 | 3496 | 0.06 | 14.58 | NA | NA | 470 | 1.00 |
| CD9 | 33679 | 0.55 | 240.14 | NA | NA | 343 | 1.00 |
| CDH1 | 9805 | 0.16 | 195.48 | NA | NA | 387 | 1.00 |
| CDH3 | 2072 | 0.03 | 15.22 | NA | NA | 362 | 1.00 |

TABLE 1-continued

| Example Genes | | | | | | | |
|---|---|---|---|---|---|---|---|
| CDK7 | 6028 | 0.10 | 37.99 | NA | NA | 472 | 1.00 |
| CDKN2A | 8147 | 0.13 | 3.10 | NA | NA | 371 | 0.00 |
| CLDN4 | 22549 | 0.37 | 84.65 | NA | NA | 337 | 1.00 |
| CLU | 20780 | 0.34 | 410.40 | NA | 2 | 495 | 0.00 |
| COBL | 4823 | 0.08 | 10.99 | NA | NA | 468 | 1.00 |
| COL4A5 | 2390 | 0.04 | 16.77 | NA | NA | 499 | 1.00 |
| CRABP2 | 21302 | 0.35 | 837.82 | NA | 2 | 488 | 0.12 |
| EPCAM | 26242 | 0.43 | 210.19 | NA | NA | 342 | 1.00 |
| ERBB2 | 9322 | 0.15 | 203.23 | NA | NA | 164 | 1.00 |
| ERBB3 | 14008 | 0.23 | 91.26 | NA | NA | 141 | 1.00 |
| ERBB4 | 3414 | 0.06 | 8.87 | NA | NA | 156 | 1.00 |
| ESR1 | 7660 | 0.12 | 46.69 | NA | NA | 155 | 1.00 |
| FASN | 10025 | 0.16 | 122.60 | NA | NA | 388 | 1.00 |
| FGFR4 | 3124 | 0.05 | 14.36 | NA | NA | 464 | 1.00 |
| FN1 | 5444 | 0.09 | 756.99 | NA | NA | 210 | 0.00 |
| FOS | 45136 | 0.73 | 60.55 | NA | NA | 147 | 0.00 |
| FOXA1 | 13319 | 0.22 | 103.87 | NA | NA | 490 | 1.00 |
| FXYD3 | 25957 | 0.42 | 225.23 | NA | NA | 497 | 1.00 |
| GATA3 | 20149 | 0.33 | 238.45 | NA | NA | 491 | 1.00 |
| GPR160 | 13377 | 0.22 | 29.17 | NA | NA | 485 | 1.00 |
| GRB7 | 4156 | 0.07 | 46.96 | NA | NA | 165 | 1.00 |
| IGF1R | 5131 | 0.08 | 31.79 | NA | NA | 153 | 1.00 |
| KRAS | 14604 | 0.24 | 6.41 | NA | NA | 186 | 1.00 |
| KRT10 | 32764 | 0.53 | 1165.70 | NA | NA | 501 | 1.00 |
| KRT14 | 1604 | 0.03 | 457.35 | NA | NA | 357 | 1.00 |
| KRT17 | 2811 | 0.05 | 56.98 | NA | 8 | 374 | 1.00 |
| KRT18 | 31150 | 0.51 | 826.19 | NA | 2 | 339 | 1.00 |
| KRT19 | 33362 | 0.54 | 1372.77 | 1 | 2 | 340 | 1.00 |
| KRT7 | 22115 | 0.36 | 100.18 | NA | 2 | 333 | 1.00 |
| KRT8 | 32496 | 0.53 | 721.75 | 1 | 2 | 341 | 1.00 |
| LRP2 | 2703 | 0.04 | 8.39 | NA | NA | 154 | 1.00 |
| LTF | 7858 | 0.13 | 133.52 | NA | 11 | 367 | 0.15 |
| LYPD6B | 8392 | 0.14 | 10.93 | NA | NA | 508 | 1.00 |
| MAPK13 | 14537 | 0.24 | 45.73 | NA | NA | 330 | 1.00 |
| MAPK3 | 10994 | 0.18 | 35.97 | NA | NA | 229 | 1.00 |
| MDM2 | 8696 | 0.14 | 47.13 | NA | NA | 178 | 1.00 |
| MLPH | 15747 | 0.26 | 129.97 | NA | NA | 487 | 1.00 |
| MUC1 | 15457 | 0.25 | 410.78 | NA | NA | 481 | 1.00 |
| MYB | 5689 | 0.09 | 22.84 | NA | NA | 327 | 1.00 |
| MYO5B | 3685 | 0.06 | 18.67 | NA | NA | 467 | 1.00 |
| NAT1 | 5485 | 0.09 | 72.21 | NA | NA | 142 | 1.00 |
| NF1 | 6426 | 0.10 | 17.89 | NA | NA | 151 | 1.00 |
| NR3C1 | 13000 | 0.21 | 16.49 | NA | NA | 463 | 1.00 |
| PDZK1IP1 | 9442 | 0.15 | 37.49 | NA | NA | 365 | 1.00 |
| PGR | 975 | 0.02 | 8.83 | NA | NA | 137 | 1.00 |
| PI3 | 923 | 0.02 | 7.32 | NA | NA | 369 | 0.00 |
| PTEN | 10816 | 0.18 | 26.47 | NA | NA | 503 | 1.00 |
| S100A14 | 19684 | 0.32 | 318.66 | NA | 2 | 489 | 1.00 |
| S100A8 | 4806 | 0.08 | 211.65 | 7 | 9 | 75 | 0.00 |
| S100A9 | 6387 | 0.10 | 646.15 | 7 | 9 | 76 | 0.00 |
| SIAH2 | 16120 | 0.26 | 51.55 | NA | NA | 157 | 1.00 |

TABLE 1-continued

| Example Genes | | | | | | | |
|---|---|---|---|---|---|---|---|
| SLC39A6 | 18662 | 0.30 | 523.52 | NA | NA | 482 | 1.00 |
| SLPI | 10969 | 0.18 | 218.98 | NA | 11 | 366 | 1.00 |
| SPDEF | 17096 | 0.28 | 124.14 | NA | NA | 486 | 1.00 |
| TAGLN | 5232 | 0.09 | 173.16 | 6 | 7 | 195 | 1.00 |
| TFF1 | 13355 | 0.22 | 724.83 | NA | 2 | 483 | 1.00 |
| TFF3 | 20623 | 0.34 | 597.46 | NA | 2 | 484 | 0.00 |
| TIMP1 | 27660 | 0.45 | 495.32 | NA | NA | 477 | 1.00 |
| TMEM45B | 1576 | 0.03 | 13.14 | NA | NA | 162 | 1.00 |
| TSPAN1 | 13460 | 0.22 | 134.78 | NA | 2 | 494 | 1.00 |
| TTC6 | 3204 | 0.05 | 7.04 | NA | NA | 158 | 1.00 |
| XBP1 | 35420 | 0.58 | 1314.70 | NA | NA | 492 | 1.00 |
| ACTG2 | 1490 | 0.02 | 35.08 | NA | NA | 378 | 0.00 |
| ACTR3B | 8471 | 0.14 | 8.90 | NA | NA | 305 | 1.00 |
| ALDH1A3 | 927 | 0.02 | 11.41 | NA | NA | 348 | 1.00 |
| ANLN | 1795 | 0.03 | 17.54 | NA | NA | 395 | 1.00 |
| AURKA | 4112 | 0.07 | 18.10 | NA | NA | 400 | 1.00 |
| BCL2 | 8507 | 0.14 | 13.81 | NA | NA | 51 | 1.00 |
| BIRC5 | 6052 | 0.10 | 25.57 | NA | 1 | 409 | 1.00 |
| CCNB1 | 5612 | 0.09 | 39.54 | NA | 17 | 403 | 1.00 |
| CCND1 | 23851 | 0.39 | 132.48 | NA | NA | 310 | 1.00 |
| CCNE1 | 1835 | 0.03 | 4.37 | NA | NA | 424 | 1.00 |
| CCNE2 | 1899 | 0.03 | 12.47 | NA | NA | 426 | 1.00 |
| CD24 | 28773 | 0.47 | NA | NA | 2 | 336 | 1.00 |
| CD44 | 27531 | 0.45 | 92.78 | NA | NA | 129 | 1.00 |
| CDC20 | 4247 | 0.07 | 24.13 | NA | 17 | 402 | 1.00 |
| CDC6 | 2362 | 0.04 | 14.65 | NA | NA | 427 | 1.00 |
| CDK4 | 21514 | 0.35 | 90.49 | NA | NA | 423 | 1.00 |
| CDK6 | 5830 | 0.09 | 4.56 | NA | NA | 50 | 1.00 |
| CEACAM1 | 7057 | 0.11 | 12.95 | NA | NA | 308 | 1.00 |
| CENPF | 5977 | 0.10 | 14.95 | NA | 1 | 407 | 1.00 |
| CEP55 | 2198 | 0.04 | 10.30 | NA | NA | 398 | 1.00 |
| CSRP2 | 9703 | 0.16 | 21.68 | NA | NA | 280 | 1.00 |
| CTCF | 10309 | 0.17 | 34.13 | NA | NA | 183 | 1.00 |
| EFNA5 | 5887 | 0.10 | 4.54 | NA | NA | 325 | 1.00 |
| EGFR | 3312 | 0.05 | 9.11 | NA | NA | 286 | 1.00 |
| EIF3E | 46946 | 0.76 | 218.87 | NA | NA | 321 | 0.00 |
| ELF5 | 9298 | 0.15 | 6.58 | NA | NA | 294 | 1.00 |
| FABP7 | 8455 | 0.14 | 3.87 | NA | 10 | 296 | 1.00 |
| FAT1 | 3442 | 0.06 | 20.16 | NA | NA | 317 | 1.00 |
| FGFR1 | 3752 | 0.06 | 62.49 | NA | NA | 199 | 1.00 |
| FGFR2 | 6623 | 0.11 | 21.16 | NA | NA | 304 | 1.00 |
| FOXC1 | 4379 | 0.07 | 6.51 | NA | NA | 288 | 1.00 |
| ISG15 | 29811 | 0.49 | 314.82 | NA | NA | 291 | 0.00 |
| ITGA6 | 5905 | 0.10 | 31.91 | NA | NA | 234 | 1.00 |
| KIF23 | 2691 | 0.04 | 13.65 | NA | NA | 397 | 1.00 |
| KIT | 2565 | 0.04 | 9.35 | NA | NA | 283 | 1.00 |
| KRT15 | 8612 | 0.14 | 20.11 | NA | NA | 306 | 1.00 |
| KRT5 | 3824 | 0.06 | 325.47 | NA | NA | 354 | 1.00 |
| LAMA1 | 2029 | 0.03 | 0.56 | NA | NA | 284 | 1.00 |
| MELK | 2128 | 0.03 | 11.03 | NA | NA | 412 | 1.00 |
| MIA | 12195 | 0.20 | 9.69 | 8 | 10 | 302 | 1.00 |

TABLE 1-continued

| Example Genes | | | | | | | |
|---|---|---|---|---|---|---|---|
| MKI67 | 4924 | 0.08 | 12.99 | NA | 1 | 406 | 1.00 |
| MYBL2 | 2936 | 0.05 | 23.38 | NA | NA | 411 | 1.00 |
| MYC | 16787 | 0.27 | 33.46 | NA | NA | 318 | 1.00 |
| MYLK | 3223 | 0.05 | 14.89 | NA | NA | 192 | 1.00 |
| MYO10 | 10134 | 0.16 | 12.53 | NA | NA | 295 | 1.00 |
| NDC80 | 2513 | 0.04 | 9.97 | NA | NA | 396 | 1.00 |
| NDRG2 | 17199 | 0.28 | 32.16 | 8 | 10 | 300 | 0.00 |
| NOTCH1 | 9632 | 0.16 | 11.37 | NA | 10 | 298 | 1.00 |
| NUF2 | 3971 | 0.06 | 14.50 | NA | NA | 405 | 1.00 |
| OBP2B | 8289 | 0.13 | 18.33 | NA | NA | 312 | 1.00 |
| ORC6 | 4430 | 0.07 | 8.59 | NA | NA | 410 | 1.00 |
| PABPC1 | 51946 | 0.85 | 633.54 | NA | NA | 320 | 0.00 |
| PBK | 4472 | 0.07 | 17.20 | NA | NA | 420 | 1.00 |
| PDPN | 581 | 0.01 | 5.98 | NA | NA | 174 | 1.00 |
| PHGDH | 19609 | 0.32 | 22.33 | NA | NA | 281 | 1.00 |
| PIK3CA | 3669 | 0.06 | 16.78 | NA | NA | 115 | 1.00 |
| PRLR | 9801 | 0.16 | 26.24 | NA | NA | 328 | 1.00 |
| PTTG1 | 10185 | 0.17 | 36.78 | NA | NA | 401 | 1.00 |
| RB1 | 5687 | 0.09 | 26.03 | NA | NA | 85 | 1.00 |
| RRM2 | 4213 | 0.07 | 29.34 | NA | NA | 415 | 1.00 |
| SFRP1 | 7901 | 0.13 | 19.40 | NA | 10 | 307 | 1.00 |
| SLC2A1 | 9679 | 0.16 | 49.84 | NA | NA | 287 | 1.00 |
| SNAI2 | 2534 | 0.04 | 16.57 | NA | NA | 200 | 1.00 |
| SOX10 | 7201 | 0.12 | 0.85 | NA | 10 | 297 | 1.00 |
| SOX4 | 28102 | 0.46 | 52.63 | 8 | 10 | 299 | 1.00 |
| STMN1 | 27056 | 0.44 | 54.53 | NA | NA | 282 | 1.00 |
| TCF4 | 5571 | 0.09 | 11.01 | NA | NA | 237 | 1.00 |
| TFF2 | 11190 | 0.18 | 11.21 | 8 | 10 | 301 | 0.13 |
| THY1 | 2228 | 0.04 | 53.93 | NA | 6 | 211 | 1.00 |
| TPM2 | 7550 | 0.12 | 64.15 | NA | 7 | 194 | 0.00 |
| TTYH1 | 11787 | 0.19 | 0.95 | 8 | 10 | 303 | 0.11 |
| TYMS | 7127 | 0.12 | 57.47 | NA | NA | 416 | 1.00 |
| UBE2C | 6406 | 0.10 | 41.81 | NA | 1 | 408 | 1.00 |
| UBE2T | 10880 | 0.18 | 58.59 | NA | NA | 419 | 1.00 |
| VIM | 31444 | 0.51 | 343.22 | NA | NA | 132 | 1.00 |
| ZEB1 | 1836 | 0.03 | 14.85 | NA | NA | 231 | 1.00 |
| BGN | 5350 | 0.09 | 421.63 | NA | 6 | 212 | 0.00 |
| BICC1 | 624 | 0.01 | 5.76 | NA | NA | 218 | 1.00 |
| CDH11 | 1186 | 0.02 | 18.64 | NA | NA | 208 | 1.00 |
| COL1A1 | 5281 | 0.09 | 1261.39 | 5 | 6 | 215 | 0.00 |
| COL1A2 | 2791 | 0.05 | 1298.43 | 5 | 6 | 216 | 0.31 |
| COL3A1 | 2440 | 0.04 | 1066.16 | 5 | 6 | 217 | 0.00 |
| DCN | 2308 | 0.04 | 152.92 | 5 | 6 | 213 | 0.28 |
| FAP | 765 | 0.01 | 23.34 | NA | NA | 219 | 1.00 |
| IGFBP5 | 5420 | 0.09 | 249.55 | NA | NA | 138 | 1.00 |
| LGALS1 | 35276 | 0.57 | 694.80 | NA | NA | 263 | 0.00 |
| LUM | 2182 | 0.04 | 423.55 | 5 | 6 | 214 | 1.00 |
| MMP11 | 2286 | 0.04 | 118.67 | NA | NA | 202 | 1.00 |
| MT2A | 32342 | 0.53 | 370.60 | NA | NA | 381 | 0.00 |
| MYL9 | 9609 | 0.16 | 275.28 | 6 | 7 | 193 | 0.00 |
| SULF1 | 1145 | 0.02 | 51.87 | NA | NA | 209 | 1.00 |

TABLE 1-continued

| Example Genes | | | | | | | |
|---|---|---|---|---|---|---|---|
| APOC1 | 8453 | 0.14 | 3208.81 | NA | 5 | 92 | 1.00 |
| APOE | 18463 | 0.30 | 777.37 | NA | 5 | 91 | 1.00 |
| BLVRA | 17792 | 0.29 | 123.60 | NA | NA | 478 | 1.00 |
| C1QA | 4754 | 0.08 | 192.36 | 4 | 5 | 98 | 1.00 |
| C1QB | 4521 | 0.07 | 177.94 | 4 | 5 | 99 | 1.00 |
| CD274 | 420 | 0.01 | 2.31 | NA | NA | 428 | 1.00 |
| CD4 | 3663 | 0.06 | 32.25 | NA | NA | 126 | 1.00 |
| CD63 | 45264 | 0.74 | 442.47 | NA | NA | 474 | 0.00 |
| CD68 | 5192 | 0.08 | 174.93 | 4 | 5 | 97 | 1.00 |
| CSTB | 41355 | 0.67 | 423.25 | NA | NA | 351 | 0.00 |
| CTSL | 11823 | 0.19 | NA | NA | NA | 87 | 1.00 |
| FTL | 58868 | 0.96 | 6225.81 | NA | NA | 102 | 1.00 |
| GPNMB | 5886 | 0.10 | 121.74 | NA | 5 | 90 | 0.43 |
| HLA-DPA1 | 17181 | 0.28 | 209.80 | 12 | 16 | 109 | 0.00 |
| HLA-DRA | 20387 | 0.33 | 1184.50 | 12 | 16 | 111 | 1.00 |
| IL2RA | 529 | 0.01 | 1.98 | NA | NA | 46 | 1.00 |
| ITGAX | 1016 | 0.02 | 12.10 | NA | NA | 93 | 1.00 |
| LGMN | 12017 | 0.20 | 90.89 | NA | NA | 89 | 0.00 |
| MSR1 | 1906 | 0.03 | 17.75 | NA | 5 | 101 | 1.00 |
| STAT5A | 2643 | 0.04 | 13.58 | NA | NA | 128 | 1.00 |
| TFEC | 874 | 0.01 | 2.74 | NA | NA | 94 | 1.00 |
| TFRC | 7069 | 0.12 | 50.19 | NA | NA | 117 | 1.00 |
| TMSB4X | 60166 | 0.98 | 2036.49 | NA | 15 | 18 | 1.00 |
| AHR | 3563 | 0.06 | 32.64 | NA | NA | 123 | 1.00 |
| AIF1 | 6122 | 0.10 | 92.44 | 4 | 5 | 104 | 1.00 |
| C10orf54 | 7586 | 0.12 | 9.77 | NA | NA | 127 | 1.00 |
| CCL2 | 2206 | 0.04 | 96.45 | NA | NA | 86 | 0.00 |
| CCL3 | 7016 | 0.11 | 19.65 | NA | NA | 33 | 0.00 |
| CD14 | 6618 | 0.11 | 93.45 | NA | 5 | 96 | 0.00 |
| CD163 | 1539 | 0.03 | 40.02 | NA | 5 | 100 | 1.00 |
| CST3 | 39369 | 0.64 | 178.58 | NA | NA | 475 | 0.00 |
| FCGR3A | 4602 | 0.07 | 84.66 | NA | NA | 32 | 1.00 |
| FCN1 | 1607 | 0.03 | 6.42 | NA | 5 | 77 | 1.00 |
| HIF1A | 9537 | 0.16 | 62.36 | NA | NA | 262 | 1.00 |
| HLA-DRB1 | 20659 | 0.34 | 722.39 | 12 | 16 | 112 | 0.00 |
| ICAM1 | 3232 | 0.05 | 26.18 | NA | NA | 121 | 1.00 |
| JUN | 37213 | 0.61 | 50.03 | NA | NA | 146 | 0.00 |
| LGALS2 | 1717 | 0.03 | 7.21 | NA | 5 | 74 | 1.00 |
| LILRB1 | 1280 | 0.02 | 4.18 | NA | NA | 107 | 1.00 |
| LST1 | 5754 | 0.09 | 18.86 | 4 | 5 | 103 | 0.20 |
| LYZ | 6168 | 0.10 | 354.32 | 4 | 5 | 105 | 1.00 |
| MMP12 | 90 | 0.00 | 4.00 | NA | NA | 119 | 1.00 |
| MMP9 | 788 | 0.01 | 68.69 | NA | NA | 120 | 0.00 |
| NFKBIA | 28435 | 0.46 | 106.04 | NA | NA | 122 | 0.00 |
| SPP1 | 3771 | 0.06 | 521.50 | NA | NA | 350 | 1.00 |
| CCL4 | 11504 | 0.19 | 22.00 | 14 | 4 | 11 | 0.00 |
| CCL5 | 13852 | 0.23 | 38.21 | 14 | 4 | 9 | 1.00 |
| CD7 | 8480 | 0.14 | 5.21 | NA | NA | 24 | 1.00 |
| GNLY | 3683 | 0.06 | 9.51 | 10 | 14 | 40 | 1.00 |
| GZMB | 2959 | 0.05 | 5.27 | 10 | 14 | 39 | 1.00 |
| HLA-A | 54884 | 0.89 | 938.11 | 11 | 15 | 13 | 1.00 |

TABLE 1-continued

| Example Genes | | | | | | | |
|---|---|---|---|---|---|---|---|
| HLA-B | 53994 | 0.88 | 1628.64 | 11 | 15 | 15 | 1.00 |
| HLA-C | 55230 | 0.90 | 1060.50 | 11 | 15 | 14 | 1.00 |
| HLA-E | 41238 | 0.67 | 389.87 | NA | 15 | 12 | 0.00 |
| NCAM1 | 1168 | 0.02 | 1.42 | NA | NA | 22 | 1.00 |
| NKG7 | 10215 | 0.17 | 19.59 | 14 | 4 | 10 | 1.00 |
| PLEK | 5504 | 0.09 | 22.62 | NA | NA | 31 | 1.00 |
| PTPRC | 14444 | 0.24 | 31.03 | NA | NA | 19 | 1.00 |
| SKAP1 | 5992 | 0.10 | 20.33 | NA | NA | 6 | 1.00 |
| TBX21 | 1512 | 0.02 | 1.17 | NA | NA | 36 | 1.00 |
| TRDC | 2899 | 0.05 | 8.03 | NA | NA | 25 | 1.00 |
| XCL1 | 2659 | 0.04 | 1.56 | NA | NA | 26 | 1.00 |
| CD38 | 2414 | 0.04 | 3.90 | NA | NA | 453 | 1.00 |
| DERL3 | 3411 | 0.06 | 10.52 | NA | 18 | 457 | 0.47 |
| FCRL5 | 970 | 0.02 | 0.72 | NA | NA | 456 | 1.00 |
| IGHG1 | 7884 | 0.13 | 704.69 | 15 | 19 | 454 | 0.00 |
| IGHG4 | 5716 | 0.09 | 151.18 | 15 | 19 | 455 | 0.00 |
| IGHM | 8135 | 0.13 | 176.25 | NA | NA | 460 | 1.00 |
| IGKC | 21863 | 0.36 | 2768.58 | NA | NA | 461 | 1.00 |
| ISG20 | 20975 | 0.34 | 14.68 | NA | NA | 52 | 1.00 |
| MZB1 | 5867 | 0.10 | NA | NA | 18 | 458 | 1.00 |
| POU2AF1 | 1205 | 0.02 | 0.98 | NA | NA | 459 | 1.00 |
| SDC1 | 11037 | 0.18 | 165.69 | NA | NA | 352 | 1.00 |
| B2M | 59682 | 0.97 | 1902.68 | 11 | 15 | 16 | 1.00 |
| CD2 | 11451 | 0.19 | 19.50 | NA | 4 | 61 | 1.00 |
| CD3D | 11436 | 0.19 | 22.01 | 3 | 4 | 63 | 1.00 |
| CD3E | 9936 | 0.16 | 20.53 | NA | 4 | 60 | 1.00 |
| CD3G | 6586 | 0.11 | 3.39 | NA | NA | 59 | 1.00 |
| CD40LG | 2151 | 0.03 | 1.53 | NA | NA | 56 | 1.00 |
| CD5 | 1704 | 0.03 | 4.03 | NA | NA | 55 | 1.00 |
| CD8A | 4488 | 0.07 | 6.40 | NA | NA | 8 | 1.00 |
| CD96 | 3227 | 0.05 | 3.56 | NA | NA | 7 | 1.00 |
| CTLA4 | 342 | 0.01 | 2.15 | NA | NA | 45 | 1.00 |
| FOXP3 | 346 | 0.01 | 1.86 | NA | NA | 47 | 1.00 |
| ICOS | 1429 | 0.02 | 1.87 | NA | NA | 49 | 1.00 |
| IL32 | 19822 | 0.32 | 101.62 | 3 | 4 | 62 | 0.19 |
| IL7R | 5545 | 0.09 | 9.01 | NA | NA | 58 | 1.00 |
| LAG3 | 2888 | 0.05 | 3.52 | NA | NA | 3 | 1.00 |
| PDCD1 | 854 | 0.01 | 1.18 | NA | NA | 2 | 1.00 |
| S100A4 | 24765 | 0.40 | 192.92 | NA | NA | 17 | 0.00 |
| THEMIS | 1580 | 0.03 | 1.42 | NA | NA | 4 | 1.00 |
| TRAC | 13287 | 0.22 | 41.92 | 3 | 4 | 64 | 1.00 |
| ZNF571 | 1609 | 0.03 | 2.98 | NA | NA | 150 | 1.00 |

In certain embodiments, the invention provides an expression profile for distinguishing between a malignant epithelial cell, an endothelial cell, a fibroblast, a hepatocyte, a lymphocyte, a mesenchymal cell, a monocyte/macrophage, and other cells that reside in the metastatic tumor tissues of MBC, comprising one or more of the genes presented in Table 1.

Figure 4:
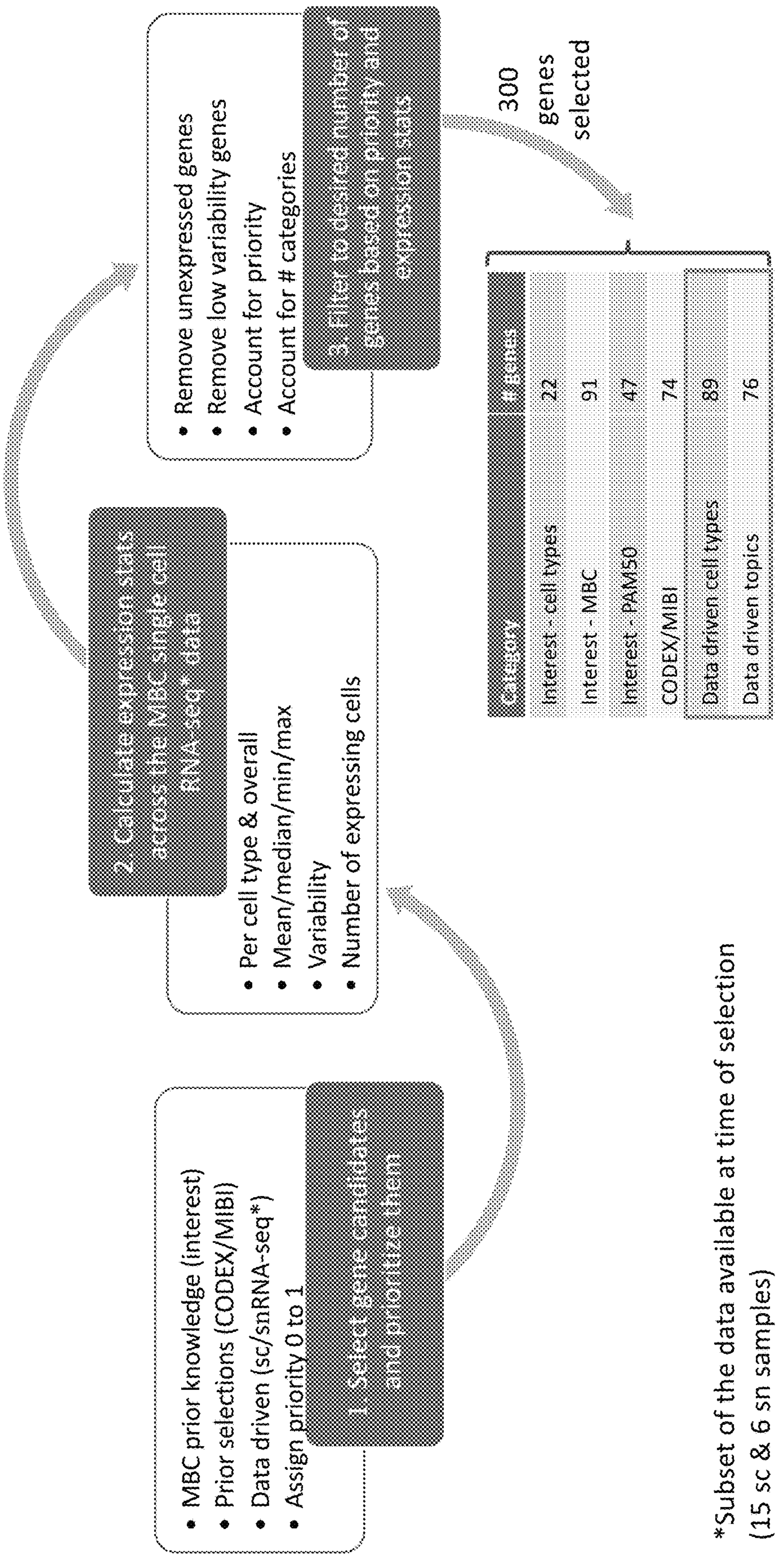
FIG. 4. A schematic flowchart showing the process of selecting genes for RNA based molecular spatial mapping. The process includes steps of selecting gene candidates and prioritizing them, calculating gene expression statistics across the MBC single-cell RNA sequencing data or single-nucleus RNA sequencing data, and filtering to desired number of genes based on priority and expression statistics. Using these processes, a distinct list of genes can be obtained for molecular spatial mapping of MBC tissue microenvironment.

In certain embodiments, the invention provides a method for selecting the genes, such as genes listed in Table 1 as shown in FIG. 4.

In certain embodiments, the invention provides an expression profile for distinguishing between an epithelial cell, an endothelial cell, a fibroblast, a T lymphocyte, a smooth muscle cell, a macrophage, and an adipocyte reside in the tumor tissues of DCIS, comprising one or more of the genes presented herein.

In certain embodiments, a method is disclosed for identifying subpopulations of epithelial cells in tissues of DCIS, comprising detecting the expression pattern of PIP, ESR1, PGR, ERBB2, and EGFR. In certain aspects, the epithelial cells comprise at least two subpopulations, and wherein a first subpopulation is characterized by the expression of PIP, and a second subpopulation is characterized by no or low levels of expression of PIP in comparison to normal ductal tissue of the breast.

In certain embodiments, an epithelial cell derived from DCIS is disclosed. This cell is characterized by expression of PIP gene or gene products, and the expression of one or more of genes or gene products comprising ESR1, PGR, ERBB2, and EGFR.

In certain embodiments, an epithelial cell derived from DCIS is disclosed. This cell is characterized by no or low levels of expression of PIP gene or gene products in comparison to the normal breast ductal tissue, and the expression of one or more of genes or gene products comprising ESR1, PGR, and ERBB2.

All gene name symbols refer to the gene as commonly known in the art. The examples described herein that refer to the human gene names are to be understood to also encompasses genes in any other organism (e.g., homologous, orthologous genes). Any reference to the gene symbol is a reference made to the entire gene or variants of the gene. Any reference to the gene symbol is also a reference made to the gene product (e.g., protein). The term, homolog, may apply to the relationship between genes separated by the event of speciation (e.g., ortholog). Orthologs are genes in different species that evolved from a common ancestral gene by speciation. Normally, orthologs retain the same function in the course of evolution. Gene symbols may be those referred to by the HUGO Gene Nomenclature Committee (HGNC) or National Center for Biotechnology Information (NCBI). The signature as described herein may encompass any of the genes described herein.

As used herein a "signature", a "gene expression profile" or "biological program" may encompass any gene or genes, protein or proteins, or epigenetic element(s) whose expression profile or whose occurrence is associated with a specific cell type, subtype, or cell state of a specific cell type or subtype within a population of cells (e.g., epithelial malignant cell). In certain embodiments, the signature is dependent on epigenetic modification of the genes or regulatory elements associated with the genes (e.g., methylation, ubiquitination). Thus, in certain embodiments, use of signature genes includes epigenetic modifications that may be detected or modulated. For ease of discussion, when discussing gene expression, any of gene or genes, protein or proteins, or epigenetic element(s) may be substituted. As used herein, the terms "signature", "biological program", "expression profile", "transcriptional program" or "expression program" may be used interchangeably. It is to be understood that also when referring to proteins (e.g. differentially expressed proteins), such may fall within the definition of "gene" signature.

As used herein the term "biological program" may further refer to a set of genes that share a role in a biological function (e.g., an activation program, cell differentiation program, proliferation program). Biological programs can include a pattern of gene expression that result in a corresponding physiological event or phenotypic trait. Biological programs can include up to several hundred genes that are expressed in a spatially and temporally controlled fashion. Expression of individual genes can be shared between biological programs. Expression of individual genes can be shared among different single cell types; however, expression of a biological program may be cell type specific or temporally specific (e.g., the biological program is expressed in a cell type at a specific time). Multiple biological programs may include the same gene, reflecting the gene's roles in different processes. Expression of a biological program may be regulated by a master switch, such as a nuclear receptor or transcription factor. As used herein, a biological program may be referred to as a "topic." The biological program can be modeled as a distribution over expressed genes.

In certain embodiments, genes are selected from a gene program. One method to identify biological programs in cells is non-negative matrix factorization (NMF) (see, e.g., Lee D D and Seung H S, Learning the parts of objects by non-negative matrix factorization, Nature. 1999 Oct. 21; 401(6755):788-91). As an alternative, a generative model based on latent Dirichlet allocation (LDA) (Blei, D. M., Ng, A. Y., and Jordan, M. I. (2003). Latent Dirichlet allocation. J Mach Learn Res 3, 993-1022), or "topic modeling" may be created. Topic modeling is a statistical data mining approach for discovering the abstract topics that explain the words occurring in a collection of text documents. Originally developed to discover key semantic topics reflected by the words used in a corpus of documents (Dumais, S. T., Furnas, G. W., Landauer, T. K., and Harshman, R. (1990). Indexing by Latent Semantic Analysis. Journal of the American Society for Information Science 41, 391-407), topic modeling can be used to explore gene programs ("topics") in each cell ("document") based on the distribution of genes ("words") expressed in the cell. A gene can belong to multiple programs, and its relative relevance in the topic is reflected by a weight. A cell is then represented as a weighted mixture of topics, where the weights reflect the importance of the corresponding gene program in the cell. Topic modeling using LDA has recently been applied to scRNA-seq data (see, e.g., Bielecki, Riesenfeld, Kowalczyk, et al., 2018 Skin inflammation driven by differentiation of quiescent tissue-resident ILCs into a spectrum of pathogenic effectors. bioRxiv 461228; and duVerle, D. A., Yotsukura, S., Nomura, S., Aburatani, H., and Tsuda, K. (2016). CellTree: an R/bioconductor package to infer the hierarchical structure of cell populations from single-cell RNA-seq data. BMC Bioinformatics 17, 363). Other approaches include word embeddings. Identifying cell programs can recover cell states and bridge differences between cells. Single cell types may span a range of continuous cell states (see, e.g., Shekhar et al., Comprehensive Classification of Retinal Bipolar Neurons by Single-Cell Transcriptomics Cell. 2016 Aug. 25; 166(5):1308-1323.e30; and Bielecki, et al., 2018).

Levels of expression or activity or prevalence of genes, gene signatures, or biological programs may be compared between different cells in order to characterize or identify, for instance, signatures specific for cell (sub)populations. Increased or decreased expression or activity or prevalence of signature genes may be compared between different cells in order to characterize or identify, for instance, specific cell (sub)populations. The detection of a signature in single cells may be used to identify and quantitate, for instance, specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell population or subpopulation. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor tissue or cancer tissue), thus allowing the discovery of novel cell subtypes or cell states that were previously invisible or unrecognized, for example, adult newborn neurons. The presence of subtypes or cell states may be determined by subtype specific or cell state specific signatures. The presence of these specific cell types or subtypes or cell states may be determined by applying the signature genes to bulk sequencing data in a sample. The signatures of the present invention may be microenvironment specific, such as their expression in a particular spatial or spatio-temporal context. In certain embodiments, signatures as discussed herein are specific to a particular developmental stage or pathological context. In certain embodiments, a combination of cell subtypes having a particular signature may indicate an outcome. The signatures may be used to deconvolute the network of cells present in a particular developmental stage or pathological condition. The presence of specific cells and cell subtypes may also be indicative of a particular developmental stage, a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular stages of development or particular pathological condition, or linked to a particular outcome or progression of the disease, or linked to a particular response to treatment of the disease (e.g. resistance to cancer therapy).

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell population or subpopulation if it is upregulated or only present, detected or detectable in that particular cell or cell population or subpopulation, or alternatively is downregulated or only absent, or undetectable in that particular cell or population or subpopulation. In this context, a signature consists of one or more differentially expressed genes/proteins or differential epigenetic elements when comparing different cells or cell population or subpopulation, including comparing different types of cells in tumor tissue microenvironment, for example, malignant cells, endothelial cells, fibroblasts, T cells, B cells, macrophages, as well as comparing immune cells or immune cell population or subpopulation with other immune cells or immune cell population or subpopulation. It is to be understood that "differentially expressed" genes/proteins include genes/proteins which are up- or down-regulated as well as genes/proteins which are turned on or off. When referring to up-or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a subpopulation of cells preferably refers to a particular subset of cells of a particular cell type (e.g., proliferating) which can be distinguished or are uniquely identifiable and set apart from other cells of this cell type. The cell subpopulation may be phenotypically characterized, and is preferably characterized by the signature as discussed herein. A cell subpopulation as referred to herein may constitute a subpopulation of cells of a particular cell type characterized by a specific cell state.

When referring to induction, or alternatively reducing or suppression of a particular signature, preferable is meant induction or alternatively reduction or suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signatures, and/or other genetic or epigenetic signatures based on single cell analyses (e.g. single cell RNA sequencing) or alternatively based on cell population analyses, as is defined herein elsewhere.

The invention further relates to various uses of the gene signatures, protein signature, and/or other genetic or epigenetic signature as defined herein. Particular advantageous uses include methods for identifying agents capable of suppressing tumorigenesis, tumor cell growth, or angiogenesis, or inducing apoptosis of tumor cells, particularly suppressing tumor cell subpopulations based on the gene signatures, protein signature, and/or other genetic or epigenetic signature as defined herein. The invention further relates to agents capable of inducing or suppressing particular cellular biological pathways and growth or invasion or mobility of subpopulations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular gene signature, protein signature, and/or other genetic or epigenetic signature may inhibit tumorigenesis, and/or malignant cell subpopulation composition or distribution, or functionality.

The signature genes of the present invention were discovered by analysis of expression profiles of single-cells within tumor cells, thus allowing the discovery of novel cell subtypes that were previously invisible or rare in a population of cells within the tumor tissue. The presence of subtypes may be determined by subtype specific signature genes. The presence of these specific cell types may be determined by applying the signature genes to bulk sequencing data in a patient. In one embodiment, the signature genes of the present invention are applied to bulk sequencing data from a sample obtained from a subject, such that information relating to disease outcome and personalized treatments is determined. Not being bound by a theory, many cells make up a microenvironment, whereby the cells communicate and affect each other in specific ways. As such, specific cell types within this microenvironment may express signature genes specific for this microenvironment. Not being bound by a theory the signature genes of the present invention may be microenvironment specific. The signature genes may indicate the presence of one particular cell type. In one embodiment, the expression may indicate the presence of proliferating cell types. Not being bound by a theory, a combination of cell subtypes in a subject may indicate an outcome.

In some embodiments, a heterogeneous cell types in tumor tissue microenvironment are used for analyzing gene expression profile at single cell level. Heterogeneous cell types are cells that are of mixed, diverse, different, assorted, or varied phenotypes. Such variations in cell phenotype in a single-cell-derived clone may result from asymmetric cell divisions that lead to different cell fate in a homogenous microenvironment. The heterogeneous population of cells may be derived from a section of a tumor tissue or a tumor from a subject. Accordingly, the term "cell population" or "population" can denote a set of cells having one or more characteristics in common, which may be, for example, source derivation. The section may be obtained by microdissection. The tissue may be tumor tissue or cancer tissue. The tumor tissue or cancer tissue maybe isolated from the breast, lung, bone, or any other tissues or organs. The heterogeneous population of cells may be a population of cells grown in tissue culture. The cells grown in tissue culture may be tumor cells or cancer cells. The cells grown in tissue culture may also be immune cells, endothelial cells, fibroblasts, macrophages, or any other types of cells that can be found in a tumor microenvironment.

Therapeutic Methods

The present invention provides methods and compositions for treating a subject with MBC or DCIS. In some embodiments, therapeutic agents disclosed herein for treating MBC and/or DCIS comprise immune cells specific for one or more targets (e.g., adoptive cell transfer), small molecules, antibodies or fragments thereof, genome editing systems. In some embodiments, the methods comprise administering a therapeutically effective amount of one or more of therapeutic agents targeting the expression or function of gene targets disclosed herein. In some embodiments, additional treating cancer agents are used. In some embodiments, a therapeutically effective amount of agent or agents are used for treating metastasis in the bone, breast, liver, spleen, lung, brain, pancreas, stomach, kidney, ovary, lymph nodes, colon, uterus, or any other tissues with metastasis of breast cancer. In some embodiments, a therapeutically effective amount of agent or agents are used for treating DCIS so as to prevent the disease from becoming invasive or metastatic. In some embodiments, a therapeutically effective amount of agent or agents can be used to specifically target the subpopulations that are responsible for invasiveness and metastasis as disclosed herein in MBC and DCIS.

In some embodiments, the present invention provides methods and compositions for treating MBC. In some aspects, methods for identifying therapeutic targets for MBC are provided. These targets can be used for developing, screening, and evaluating therapeutic agents for treating MBC.

Therapeutic Target Identification

In some embodiments, therapeutic targets identified in the present invention can be gene targets, protein targets, or any molecules or mechanisms that regulate the expression or function of the gene targets or protein targets. In certain embodiments, the targets are cell surface or secreted proteins or receptors for secreted or cell surface proteins. They can be one or more genes, one or more gene products, one or more proteins encoded by the gene targets, and factors that regulate the expression of the one or more gene targets. The "gene targets" herein refer to any gene or genes that are directly or indirectly associated with cellular functions comprising apoptosis, angiogenesis, immunity, immunotolerance, antigen presentation, extracellular matrix integrity, immunocytotoxicity, and any combination thereof, and have differentially expressed in tumors in comparison to that in normal tissues. For example, such gene target can be identified based on its higher expression levels in metastatic tumor tissue microenvironment of MBC than in normal counterpart tissues, and this gene has one or more functions related to apoptosis, angiogenesis, immunity, cytotoxicity, extracellular matrix degradation or synthesis, or any other related functions. For example, a gene encodes protein or proteins with functions of anti-apoptosis and has increased expression levels in metastatic tumor tissues of MBC in comparison to that in normal counterpart tissues, or a gene encodes protein or proteins with functions of stimulating angiogenesis and has increased expression levels in metastatic tumor tissue of MBC in comparison to that in normal counterpart tissues. An epigenetic modification of the target gene can also serve as a therapeutic target in the present invention.

Therapeutic Approaches

In some embodiments, the present invention provides therapeutic methods for treating MBC and DCIS. In some aspects, therapeutic agents used in the present invention are obtained by using the therapeutic targets disclosed herein for developing, screening, and evaluating agents comprising immune cells specific for one or more targets (e.g., adoptive cell transfer), small molecules, antibodies or antibody fragments thereof, genome editing systems, and any combinations thereof. Small molecules used for treating MBC or DCIS can target one or more of gene targets disclosed herein, or one or more of products of these gene targets disclosed herein. The small molecule agents comprise kinase inhibitor, apoptosis inducing agents, angiogenesis inhibitor, and senescence inducing agents. The small molecule agents can also target the regulatory mechanisms that modulate the expression or functions of the gene targets. The regulatory mechanisms include, but not limited to, epigenetic regulations, epigenomic regulations, lncRNA expression or functions that regulate the expression or function of the gene targets.

The therapeutic agents can also be antibodies or antibody fragments thereof. The antibody or fragments thereof used for treating MBC or DCIS are those capable of directly or indirectly regulating the expression or function of target genes. The antibody or fragment thereof can be monoclonal antibody, bispecific antibody, or fragments thereof.

The therapeutic agents can also be genome editing systems that are capable of directly or indirectly regulating the expression or function of the gene targets disclosed herein, for example, in Table 1 and/or the figures. The genome editing systems can modulate one or more of the gene targets listed in Table 1 and/or figures or disclosed otherwise in the present invention. In some embodiments, CRISPR-Cas system is used for genome editing. In some embodiments, transcription activator-like effector nucleases (TALEN) system is used for genome editing. In some embodiments, zinc finger nucleases (ZFN) is used for genome editing.

Methods and Compositions for Preventing DCIS from Becoming Invasive and Metastatic In some embodiments, the present invention provides methods and compositions for preventing DCIS becoming invasive and metastatic. In some embodiments, methods for identification of therapeutic targets for developing, screening, and evaluating agents for preventing DCIS are provided. In specific embodiments, a specific subpopulation of epithelial cells in DCIS is disclosed. This subpopulation of epithelial cells are characterized by no or low levels of expression of PIP gene or gene products, and the expression of ESR1, PGR, ERBB2, and EGFR. PIP gene encodes prolactin-induced protein (PIP). The expression of PIP is generally restricted to cells with apocrine properties. The expression of PIP is lower in advanced apocrine carcinomas and invasive carcinomas than in, respectively, in situ carcinomas and adjacent normal tissue. PIP gene expression decreased gradually along with higher stage and grade of breast cancer. In agreement with these data, it was shown that low levels or the lack of PIP expression are associated with a worse response of breast cancer cells to chemotherapy. It was proposed that PIP plays important role in the development and progression of breast cancer. PIP mRNA and protein expression in normal breast tissue were significantly higher than in breast cancer tissues. Significant downregulation of PIP was also observed in early stages of breast tumor progression (Parris et al. PIP, S100A8 and UBE2C molecular biomarkers improves outcome prediction in breast carcinoma. Int J Cancer. 2014; 134:1617-1629; Gangadharan et al. Prolactin induced protein (PIP) is a potential biomarker for early stage and malignant breast cancer. Breast. 2018; 39:101-109; Urbaniak et al. Prolactin-induced protein (PIP)-characterization and role in breast cancer progression. Am J Cancer Res. 2018; 8(11): 2150-2164). It has been shown that PIP gene expression is a prognostic factor for breast tumor invasion and metastasis.

In some embodiments, methods for identifying therapeutic targets include steps of identifying genes highly expressed in this subpopulation of epithelial cells in DCIS tissues and selecting therapeutic agents that are capable of inhibiting the expression or function of the gene targets. In some embodiments, targets can also be identified by identifying genes which expressions are inhibited in the subpopulation of epithelial cells in DCIS tissues and selecting therapeutic agents that are capable of enhancing or increasing the expression or function of the genes, whereby therapeutic agents are selected that are capable of inhibiting or reducing the growth of second subpopulation of epithelial cells or the volume of DCIS tumor, and preventing the DCIS tumor from becoming invasive.

In some embodiments, therapeutic agent for preventing DCIS from becoming invasive or metastatic can comprise those capable of inhibiting the specific subpopulation of epithelial cells with no or low expression of PIP. In some embodiments, the therapeutic agents can be those targeting genes or gene products highly expressed in this subpopulation of cells. In some embodiments, the therapeutic agents can be those capable of inhibiting the phenotype of subpopulation of cells.

As used in this context, to "treat" means to cure, ameliorate, stabilize, prevent, or reduce the severity of at least one symptom or a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term “in need of treatment” as used herein refers to a judgment made by a caregiver (e.g. physician, nurse, nurse practitioner, or individual in the case of humans; veterinarian in the case of animals, including non-human animals) that a subject requires or will benefit from treatment. This judgment is made based on a variety of factors that are in the realm of a caregiver’s experience, but that include the knowledge that the subject is ill, or will be ill, as the result of a condition that is treatable by the compositions and therapeutic agents described herein.

As used herein, “treatment” or “treating,” or “palliating” or “ameliorating” are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein “treating” includes ameliorating, curing, preventing it from becoming worse, slowing the rate of progression, or preventing the disorder from re-occurring (i.e., to prevent a relapse).

The term “effective amount” or “therapeutically effective amount” refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

Adoptive Cell Transfer

In certain embodiments, allogenic or autologous T cells targeting one or more of the signature genes described herein are used to treat breast cancer (e.g., MBC and DCIS). The T cells may be modified as described further herein. For example, the T cells may be modified to be resistant to immune suppression and/or include a T cell receptor or chimeric antigen receptor specific for a tumor antigen as described further herein. As used herein, “ACT”, “adoptive cell therapy” and “adoptive cell transfer” may be used interchangeably. In certain embodiments, Adoptive Cell Therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term “engraft” or “engraftment” refers to the process of cell incorporation into a tissue of interest in vivo through contact with existing cells of the tissue. Adoptive Cell Therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June;24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); x-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; 56 surviving; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGEl); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis (Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OacGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGEl); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAPi (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (57 survivin antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); CD70; and any combination thereof.

In certain embodiments, an antigen to be targeted in adoptive cell therapy (such as particularly CAR or TCR T cell therapy) of a disease (such as particularly of tumor or cancer) is a tumor-specific antigen (TSA).

In certain embodiments, an antigen to be targeted in adoptive cell therapy (such as particularly CAR or TCR T cell therapy) of a disease (such as particularly of tumor or cancer) is a neoantigen.

In certain embodiments, an antigen to be targeted in adoptive cell therapy (such as particularly CAR or TCR T cell therapy) of a disease (such as particularly of tumor or cancer) is a tumor-associated antigen (TAA).

In certain embodiments, an antigen to be targeted in adoptive cell therapy (such as particularly CAR or TCR T cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), and any combinations thereof.

In certain embodiments, an antigen (such as a tumor antigen) to be targeted in adoptive cell therapy (such as particularly CAR or TCR T cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B cell lymphomas, such as without limitation in diffuse large B cell lymphoma, primary mediastinal B cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; U.S. Pat. No. 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3): IEVMYPPPYLDNEKSNGTIIHVKGKHLCPSPLFPGPSKPFWVLVVVGGVLACYSLLVTVA FIIFWVRSKRSRLLHSDYMNMTPRRPGPTRKHYQPYAPPRDFAAYRS) (SEQ ID NO: 1).

Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ ID NO: 2) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002, Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 2) and continuing all the way to the carboxy-terminus of the protein. The sequence is reproduced herein: IEVMYPPPYLD-NEKSNGTIIHVKGKHLCPSPLFPGPSKPFWVLVVVGG VLACYSLLVTVA FIIFWVRSKRSRLLHSDYMNMT-PRRPGPTRKHYQPYAPPRDFAAYRS (SEQ ID NO: 1). Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in International Patent Publication No. WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T cell signaling domains (CD28-CD3ζ; 4-1BB-CD3ζ; CD27-CD3ζ; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T cell signaling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in International Patent Publication No. WO2012058460A2 (see also, Park et al., CD70 as a target for chimeric antigen receptor T cells in head and neck squamous cell carcinoma, Oral Oncol. 2018 March;78:145-150; and Jin et al., CD70, a novel target of CAR T cell therapy for gliomas, Neuro Oncol. 2018 Jan. 10; 20(1):55-65). CD70 is expressed by diffuse large B cell and follicular lymphoma and also by the malignant cells of Hodgkin's lymphoma, Waldenstrom's macroglobulinemia and multiple myeloma, and by HTLV-1- and EBV-associated malignancies. (Agathanggelou et al. Am. J. Pathol. 1995;147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T cell response. Some CARs may also comprise a "suicide switch" to induce cell death of the CAR T cells following treatment (Buddee et al., PloS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using $2^{nd}$ generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T cell receptors (TCRs) that are MHC restricted, CARs can potentially bind any cell surface-expressed antigen and can thus be more universally used to treat patients (see Irving et al., Engineering Chimeric Antigen Receptor T cells for Racing in Solid Tumors: Don't Forget the Fuel, Front. Immunol., 3 Apr. 2017, doi.org/10.3389/fimmu.2017.00267). In certain embodiments, in the absence of endogenous T cell infiltrate (e.g., due to aberrant antigen processing and presentation), which precludes the use of TIL therapy and immune checkpoint blockade, the transfer of CAR T cells may be used to treat patients (see, e.g., Hinrichs C S, Rosenberg S A. Exploiting the curative potential of adoptive T cell therapy for cancer. Immunol Rev (2014) 257(1):56-71. Doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T cell therapy and to support endogenous immunity (see, e.g., Irving et al., Engineering Chimeric Antigen Receptor T cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^1$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T cell manufacturing platform for "off-the-shelf" adoptive T cell immunotherapies, Cancer Res 75 (18): 3853; Ren et al., 2017, Multiplex genome editing to generate universal CAR T cells resistant to PD1 inhibition, Clin Cancer Res. 2017 May 1;23(9):2255-2266. Doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more IHC constituent proteins in a cell; to activate a T cell; to modulate cells such that the cells are resistant to exhaustion or dysfunction; and/or increase the differentiation and/or proliferation of functionally exhausted or dysfunctional CD8+ T cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T cell receptor, such as T cell receptor alpha locus (TRA) or T cell receptor beta locus (TRB), for example T cell receptor alpha constant (TRAC) locus, T cell receptor beta constant 1 (TRBC1) locus or T cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1;112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

International Patent Publication No. WO2014172606 relates to the use of MT1 and/or MT2 inhibitors to increase proliferation and/or activity of exhausted CD8+ T cells and to decrease CD8+ T cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, ILIORB, HMOX2, IL6R, IL6ST, EIF2AK4, CSK, PAG1, SIT1, FOXP3, PRDM1, BATF, VISTA, GUCY1A2, GUCYlA3, GUCYlB2, GUCYlB3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immune adherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/02m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR may be manufactured as described in WO2015120096, by a method comprising: enriching a population of lymphocytes obtained from a donor subject; stimulating the population of lymphocytes with one or more T cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/$m^2$/day.

Therapeutic Agents

In certain embodiments, the present invention provides for one or more therapeutic agents against the malignant cells or one or more gene signature genes identified herein. Targeting the identified cells or genes may provide for enhanced or otherwise previously unknown activity in the treatment of disease. In certain embodiments, one or more agents against one of the target cells or genes may be used in combination with a treatment already known or used clinically. In certain embodiments, the combination may require less of the known agent as compared to the current standard of care and provide for less toxicity and improved treatment. In certain embodiments, the one or more agents comprises a small molecule inhibitor, small molecule degrader (e.g., PROTAC), genetic modifying agent, antibody, antibody fragment, antibody-like protein scaffold, aptamer, protein, or any combination thereof.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

Small Molecules

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating a receptor by binding to a ligand binding site).

One type of small molecule applicable to the present invention is a degrader molecule. Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810).

Genetic Modifying Agents

In certain embodiments, the one or more agents is a genetic modifying agent. The genetic modifying agents may manipulate nucleic acids (e.g., genomic DNA or mRNA). The genetic modulating agent can be used to up- or down-regulate expression of a gene either by targeting a nuclease or functional domain to a DNA or RNA sequence. The genetic modifying agent may comprise an RNA-guided nuclease system (e.g., CRISPR system or IscB system), RNAi system, a zinc finger nuclease, a TALE, or a meganuclease.

CRISPR-Cas Modification

In some embodiments, a polynucleotide of the present invention described elsewhere herein can be modified using a CRISPR-Cas and/or Cas-based system (e.g., genomic DNA or mRNA, preferably, for a disease gene). The nucleotide sequence may be or encode one or more components of a CRISPR-Cas system. For example, the nucleotide sequences may be or encode guide RNAs. The nucleotide sequences may also encode CRISPR proteins, variants thereof, or fragments thereof.

In general, a CRISPR-Cas or CRISPR system as used herein and in other documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two classes are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

Figures 1A, 1B:
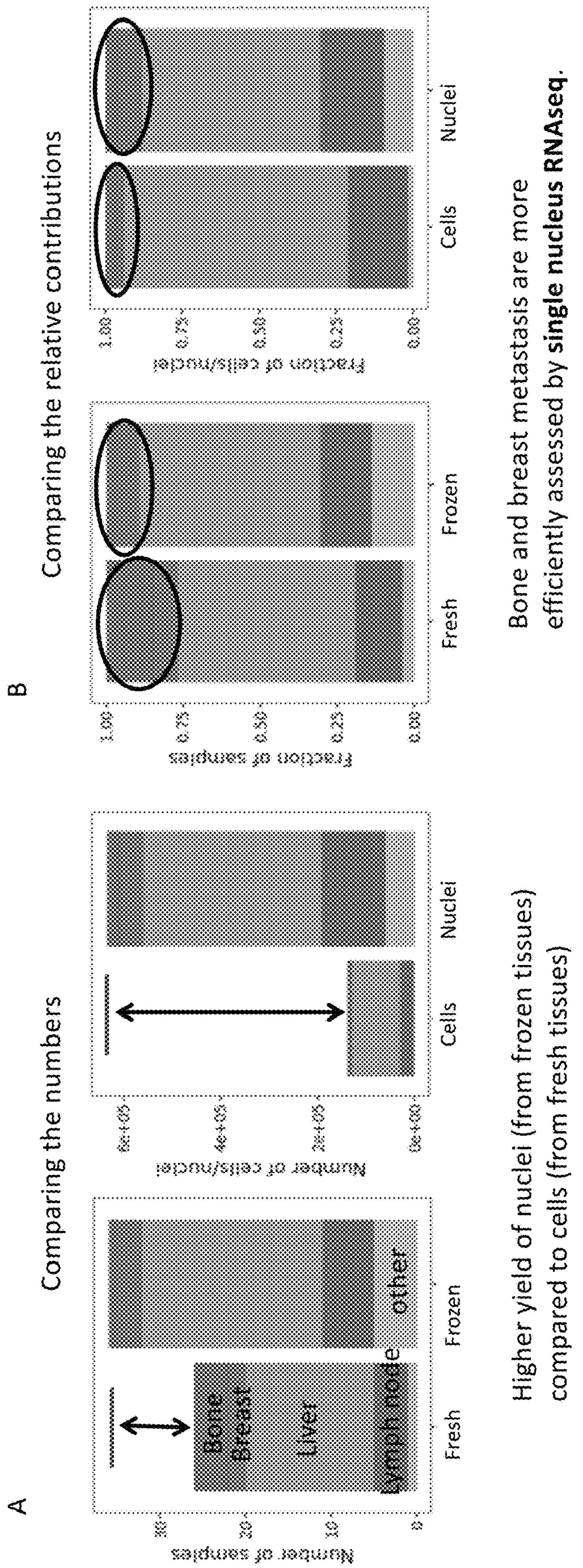
FIG. 1A-1B. 1A: The yield of nuclei is greater than that of single cells in a variety of metastatic tissues of MBC. The nuclei are prepared from frozen tissues, and the single cells are prepared from fresh tissues. 1B: Single-nucleus RNA sequencing provides better representation for bone and breast metastases of MBC than single-cell RNA sequencing does.
Figure 5B:
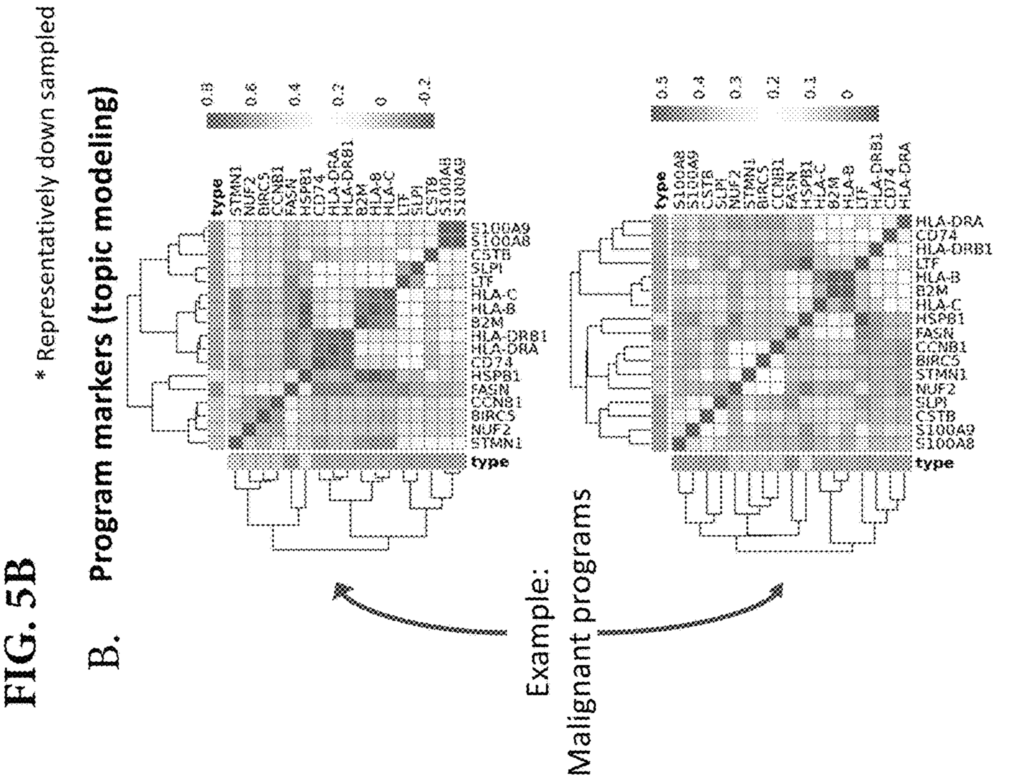
FIG. 5A-5B. The expression of selected genes in the cells and biological programs (topics) in metastatic tissues of MBC. 5A: Gene expression data were obtained using single-cell RNA sequencing or single-nucleus RNA sequencing. Cells were grouped by cell types. It shows the enrichment and capability of genes to discriminate the different types of cells in metastatic tissue of MBC using both RNA sequencing techniques. The gene expression data used for the heatmap are scaled. 5B: Exemplary malignant biological programs (topics) are well preserved in the larger datasets.
Figure 5A:
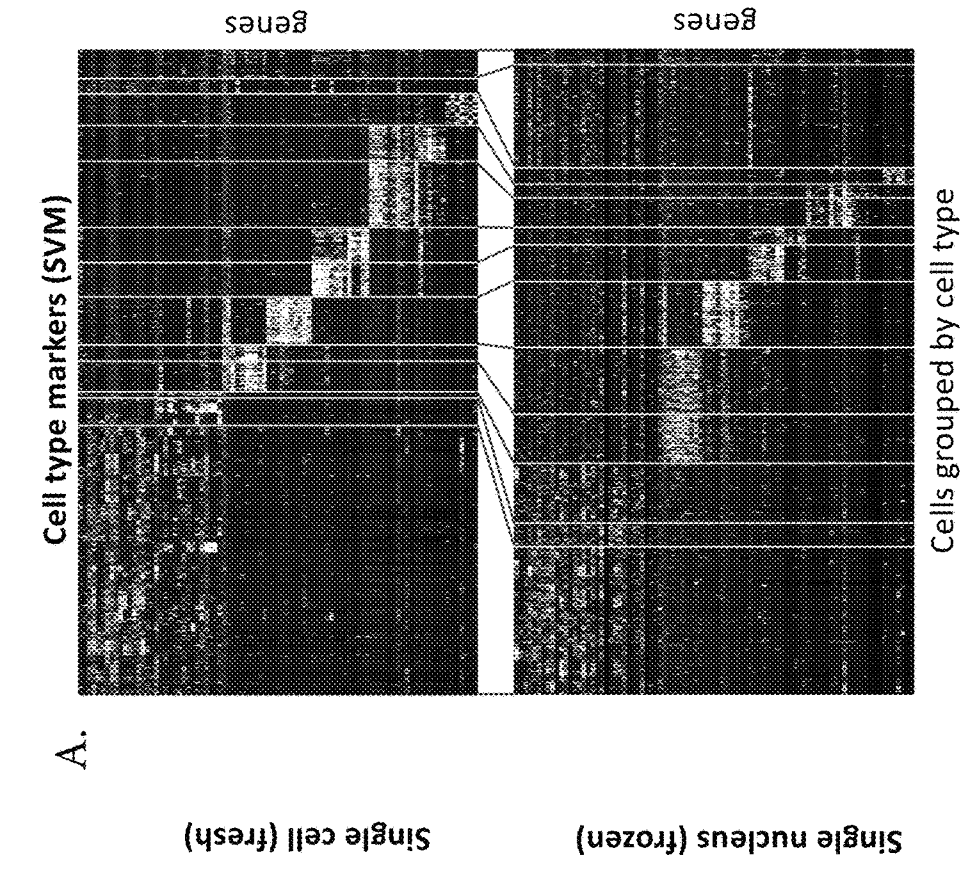
Figure 6:
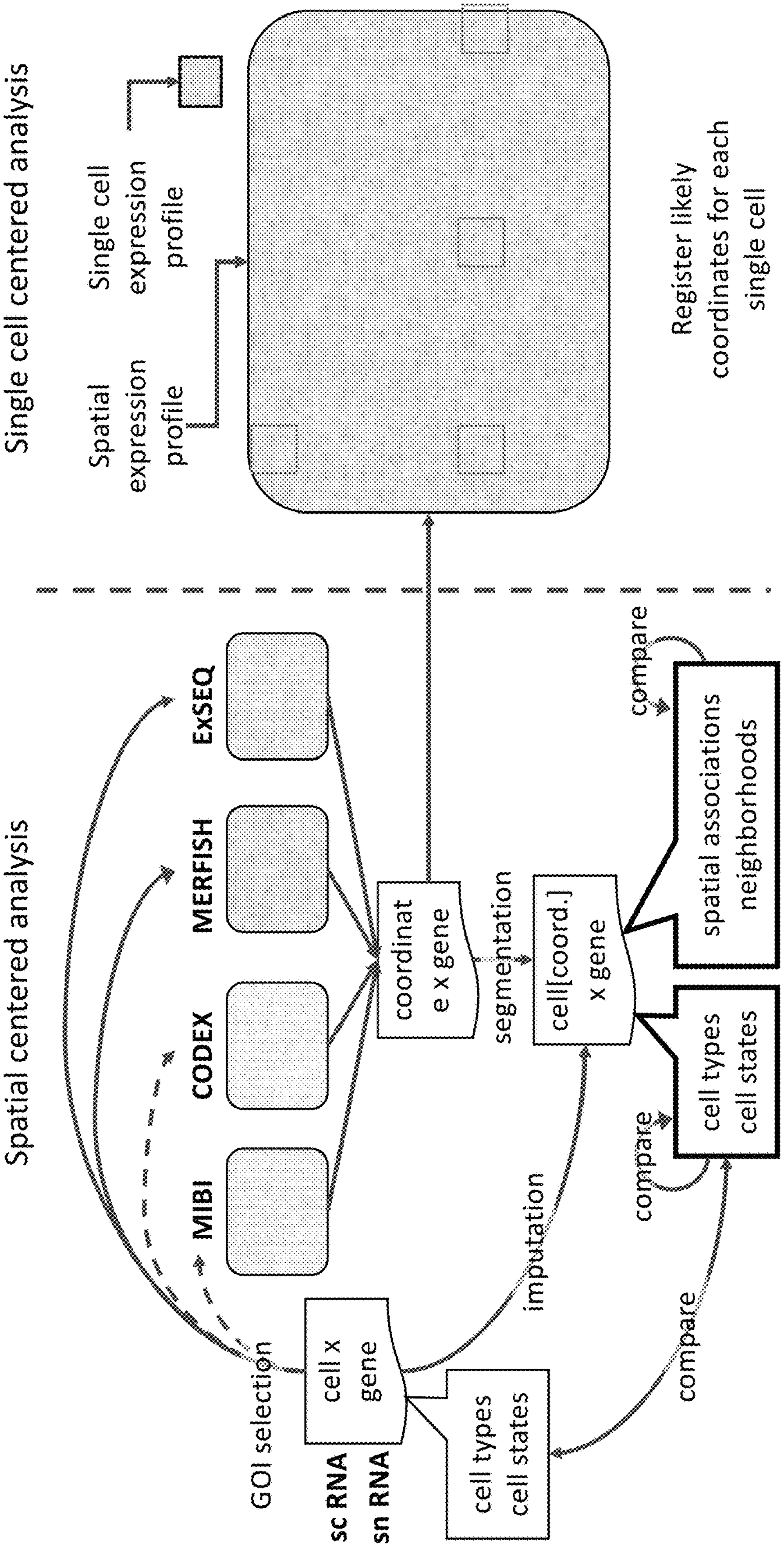
FIG. 6. A schematic flowchart showing the roadmap and power of molecular spatial mapping of metastatic tissue microenvironment. The spatial information together with single-cell and single-nucleus gene expression data produce rich information about cell types and states in a metastatic tissue microenvironment. The spatial data additionally present spatial associations that allow one to do neighborhood analysis. Single-cell or single-nucleus RNA sequencing are used to select genes for performing spatial mapping. In a spatial centered analysis, one can use the single-cell and single-nucleus gene expression data to impute the molecularly less rich spatial data. Furthermore, one can also compare within and between the methods of spatial mapping that will show the strengths of each method as well as obtain a more complete picture of the metastatic tissue microenvironment. Moreover, there is also the possibility for a more single-cell centered analysis in which the spatial data are used to add an additional layer of information to each single cell or nucleus by registering all likely spatial locations for this single cell and using that information to show the transcriptomic differences between cells of the same cell type at different locations.
Figure 7:
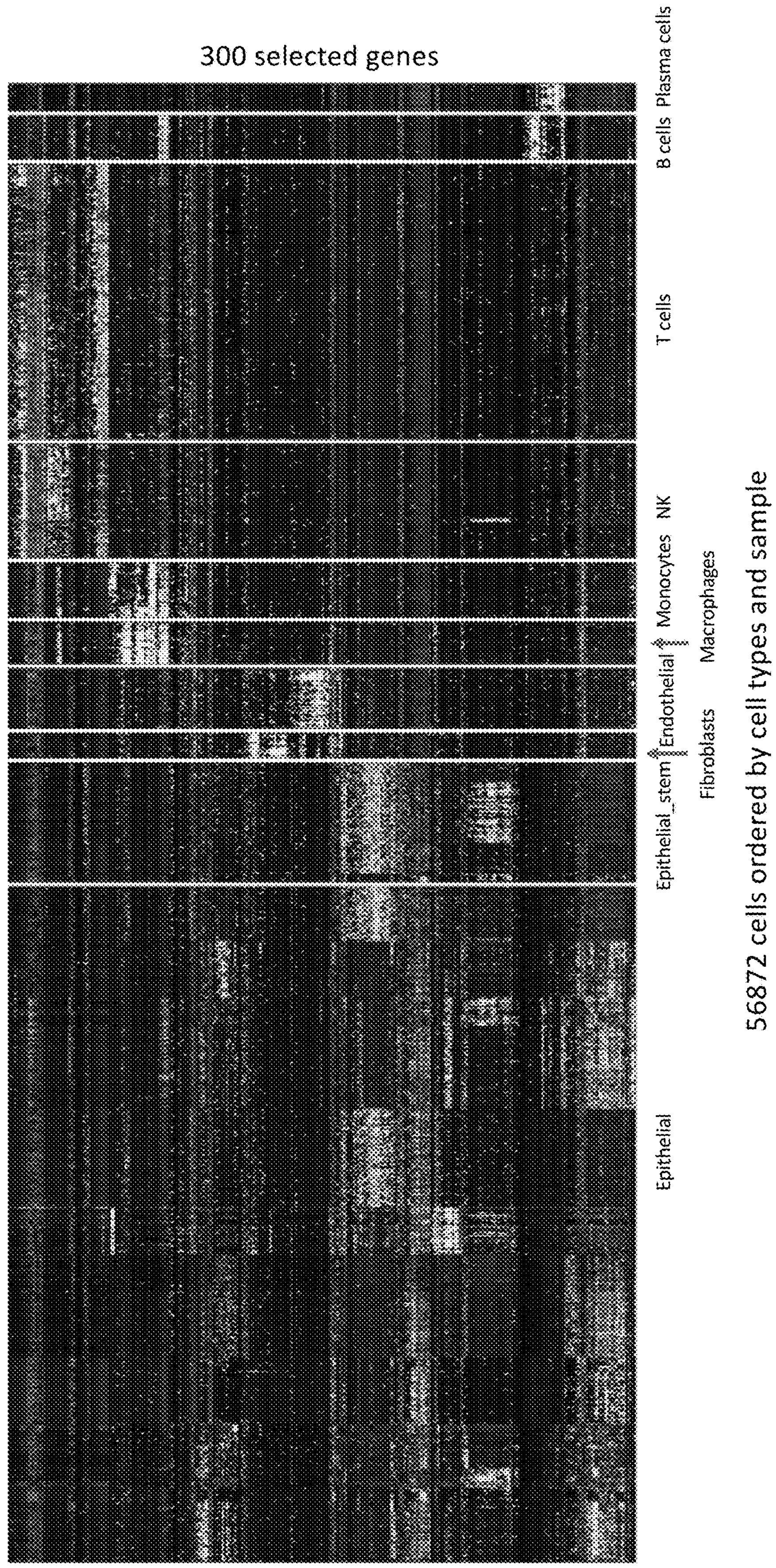
FIG. 7. The expression of selected genes across the cell types in metastatic tumor tissues of MBC. A total of 56872 cells are ordered by cell types and tissue samples based on their expression of 300 selected genes.
Figure 8:
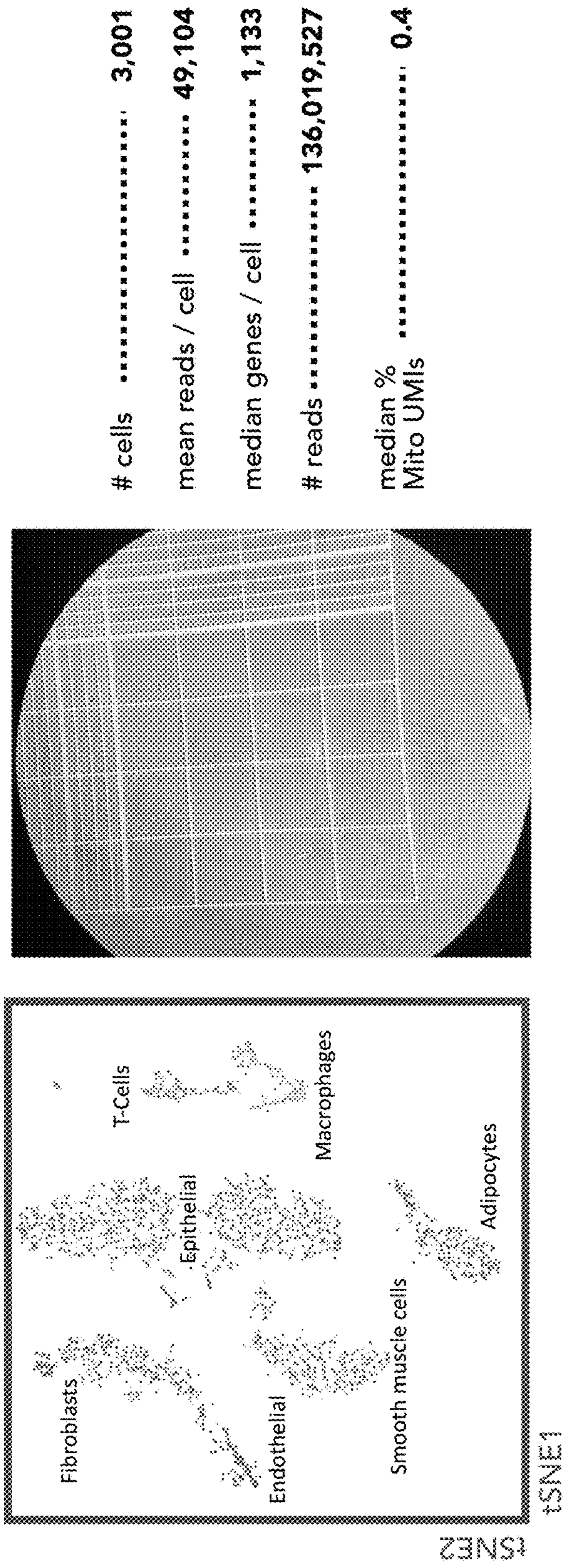
FIG. 8. Cells identified using single-nucleus RNA sequencing in frozen samples of ductal carcinoma in situ (DCIS) of the breast. Two subpopulations of epithelial cells are identified, together with other types of cells comprising fibroblasts, endothelial cells, smooth muscle cells, adipocytes, macrophages, and T cells.
Figure 9:
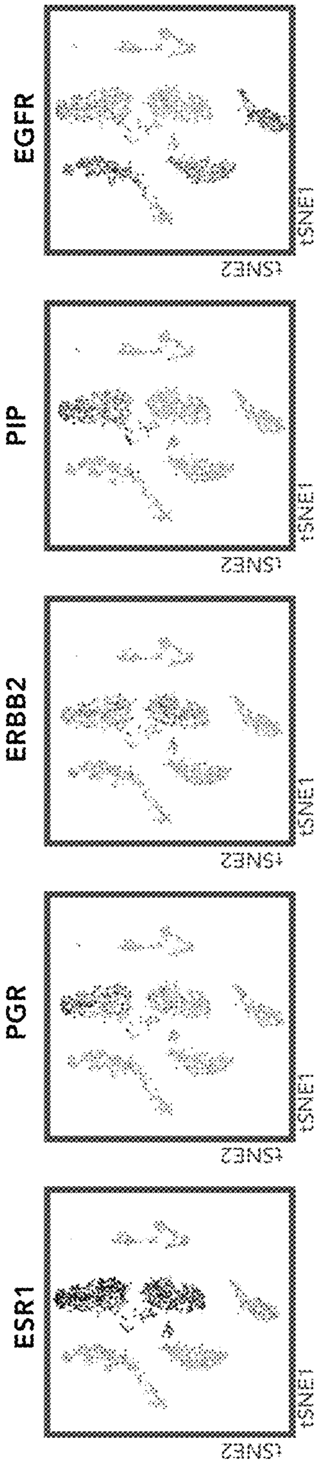
FIG. 9. The expression of breast cancer biomarker genes in ductal carcinoma in situ (DCIS) of the breast. Two subpopulations of malignant epithelial cells are detected: one population with high expression of PIP gene, and the other one with low or no expression of PIP gene. Also shown are the expression of ESR1, PGR, ERBB2, and EGFR genes in DCIS of the breast.

In some embodiments, the CRISPR-Cas system that can be used to modify a polynucleotide of the present invention described herein can be a Class 1 CRISPR-Cas system. Class 1 CRISPR-Cas systems are divided into Types I, II, and IV. Makarova et al. 2020. Nat. Rev. 18: 67-83, particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, IB, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, FIG. 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Figures 2A, 2B:
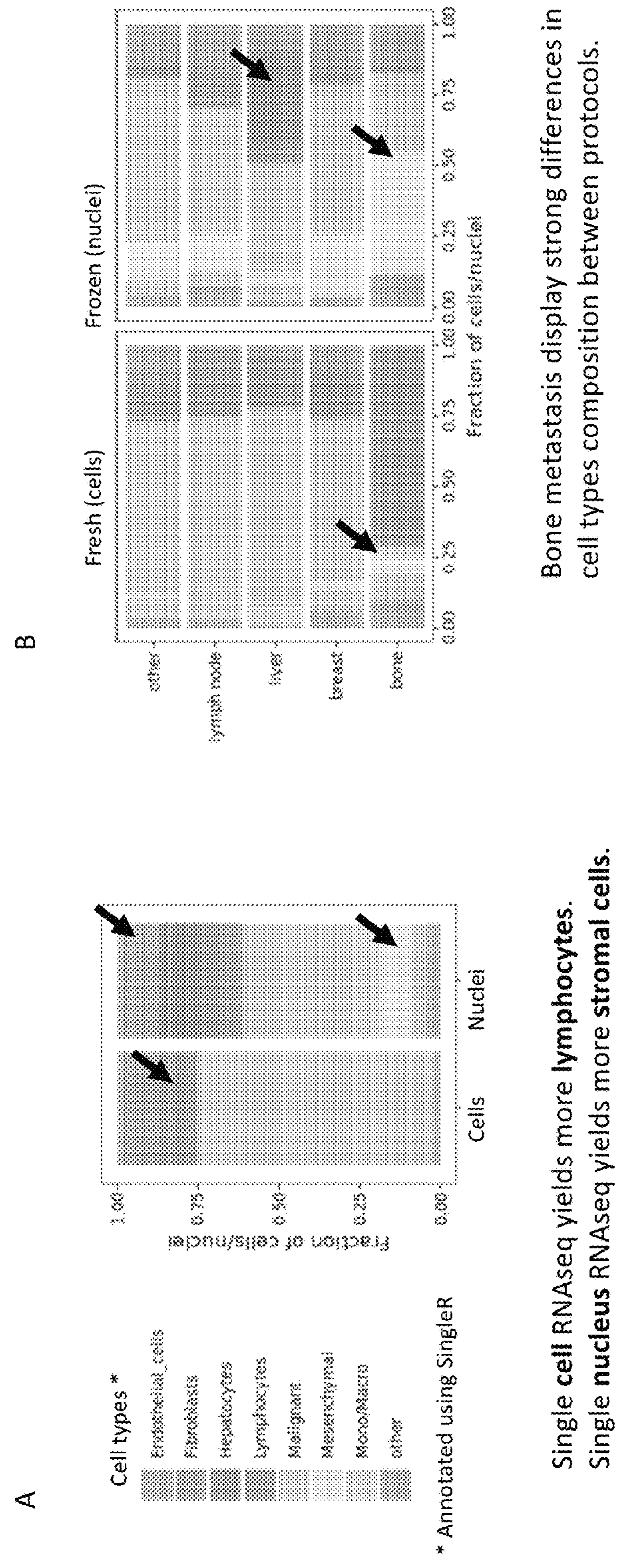
FIG. 2A-2B. Comparison between single-cell RNA sequencing and single-nucleus RNA sequencing data for their efficiency in capturing/representing the types of cells in metastatic tissues of MBC. 2A: Single-cell RNA sequencing captures more lymphocytes, while single-nucleus RNA sequencing captures more stromal cells. 2B: The efficiency of single-cell RNA sequencing and single-nucleus RNA sequencing in capturing different metastatic tissues of MBC. Single-nucleus RNA sequencing captures more malignant cells and stromal cells in bone metastasis, and more stromal cells in breast metastasis. It also captures more hepatocytes in liver metastasis, while single-cell RNA sequencing barely captures hepatocytes in liver metastasis.
Figures 3A, 3B, 3C:
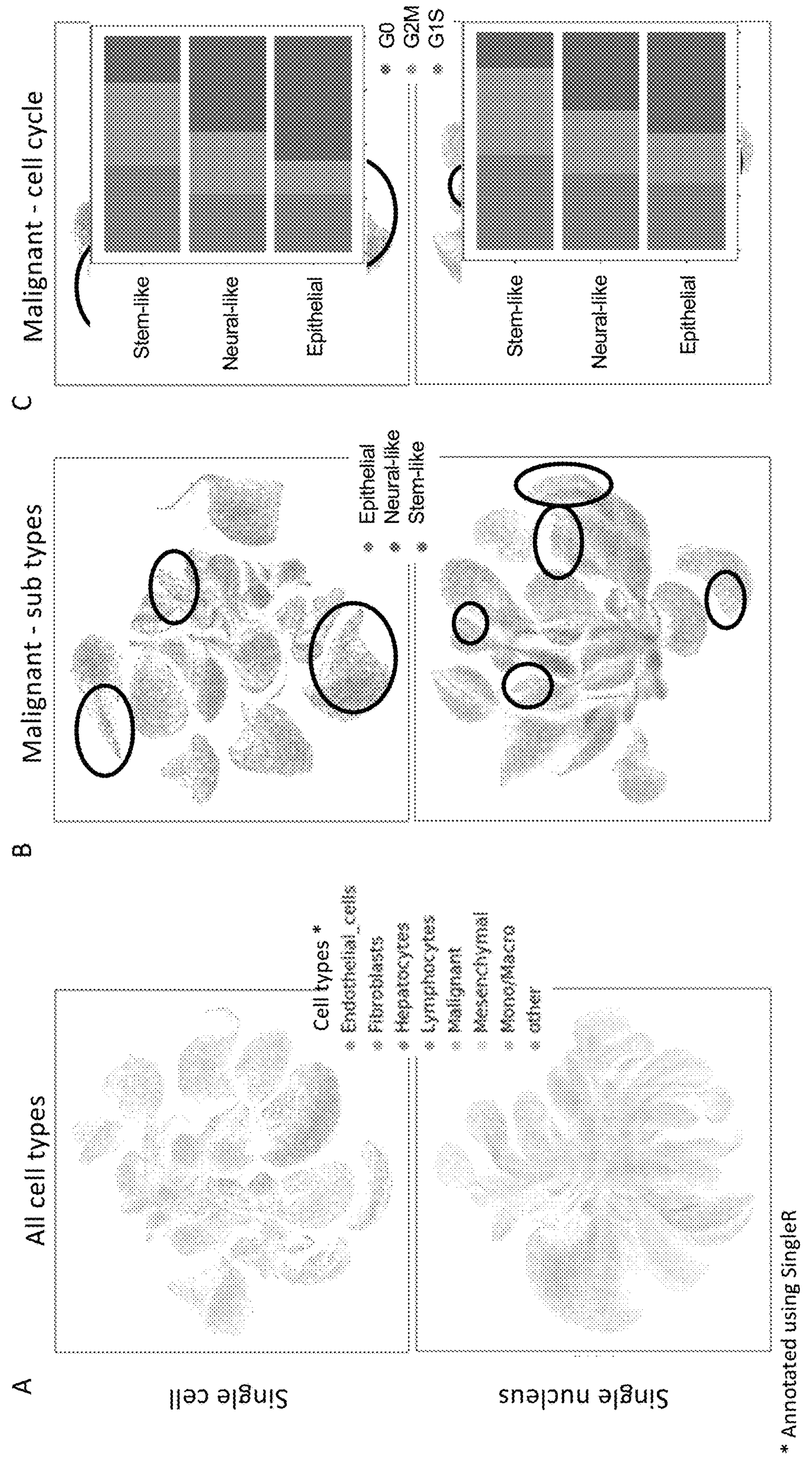
FIG. 3A-3C. Clustering of cells based on gene expression data derived from single-cell RNA sequencing and single-nucleus RNA sequencing. 3A: Clustering of eight cell types in MBC using gene expression data derived from single-cell RNA sequencing or single-nucleus RNA sequencing. Clustering is based on dimension reduction using Uniform Manifold Approximation and Projection (UMAP) technique. Gene expression data from both sequencing methods show the diversity of malignant cells. 3B: Clustering of malignant cells shows the existence of subtypes in the malignant cells. Here neural-like and stem-like malignant cells together with epithelial malignant cells are shown. 3C: Bar graph shows the distribution in cell cycle phase of different subtypes of malignant cells. Gene expression data from both single-cell RNA sequencing and single-nucleus RNA sequencing show that the majority of stem-like and neural-like malignant cells are in cycling phases (G1/S and G2/M). While gene expression data from single-cell RNA sequencing show that the majority of epithelial malignant cells are in quiescent state (G0), data from single-nucleus RNA sequencing show slightly more epithelial malignant cells are in cycling phases.

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374: 20180087, DOI: 10.1098/rstb.2018.0087 and Makarova et al. 2020.

Class 1 CRISPR-Cas system effector complexes can, in some embodiments, include a small subunit (for example, Cas11). See, e.g., FIGS. 1 and 2. Koonin E V, Makarova K S. 2019 Origins and Evolution of CRISPR-Cas systems. Phil. Trans. R. Soc. B 374: 20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1 (V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), CasX, and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d. Specialized Cas-based Systems In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sep. 12; 154(6):1380-1389), Cas12 (Liu et al. Nature Communications, 8, 2095 (2017)), and Cas13 (WO 2019/005884, WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Patent Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33(2): 139-142 and WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C·G base pair into a T·A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Rees and Liu. 2018. Nat. Rev. Genet. 19(12): 770-788, particularly at FIGS. 1*b*, 2*a*-2*c*, 3*a*-3*f*, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471. Base editors may be further engineered to optimize conversion of nucleotides (e.g. A:T to G:C). Richter et al. 2020. Nature Biotechnology. doi.org/10.1038/s41587-020-0453-z.

Other Example Type V base editing systems are described in WO 2018/213708, WO 2018/213726, PCT/US2018/067207, PCT/US2018/067225, and PCT/US2018/067307 which are incorporated by referenced herein.

In certain example embodiments, the base editing system may be a RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA based editor may be used to delete or introduce a post-translation modification site in the expressed mRNA. In contrast to DNA base editors, whose edits are permanent in the modified cell, RNA base editors can provide edits where finer temporal control may be needed, for example in modulating a particular immune response. Example Type VI RNA-base editing systems are described in Cox et al. 2017. Science 358: 1019-1027, WO 2019/005884, WO 2019/005886, WO 2019/071048, PCT/US20018/05179, PCT/US2018/067207, which are incorporated herein by reference. An example FnCas9 system that may be adapted for RNA base editing purposes is described in WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system (See e.g. Anzalone et al. 2019. Nature. 576: 149-157). Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion, and combinations thereof. Generally, a prime editing system, as exemplified by PE1, PE2, and PE3 (Id.), can include a reverse transcriptase fused or otherwise coupled or associated with an RNA-programmable nickase, and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRISPR-Cas systems along with few byproducts and greater or similar efficiency as compared to traditional CRISPR-Cas systems.

In some embodiments, the prime editing guide molecule can specify both the target polynucleotide information (e.g. sequence) and contain a new polynucleotide cargo that replaces target polynucleotides. To initiate transfer from the guide molecule to the target polynucleotide, the PE system can nick the target polynucleotide at a target side to expose a 3' hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576: 149-157, particularly at FIGS. 1*b*, 1*c*, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576: 149-157, particularly at pgs. 2-3, FIGS. 2*a*, 3*a*-3*f*, 4*a*-4*b*, Extended data FIGS. 3*a*-3*b*, 4.

The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576: 149-157, particularly at pg. 3, FIG. 2*a*-2*b*, and Extended Data FIG. 5*a*-*c*.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide, refer to polynucleotides capable of guiding Cas to a target genomic locus and are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAST, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in PCT US2019/045582, specifically paragraphs [0178]-[0333]. which is incorporated herein by reference.

Target Sequences, PAMs, and PFSs

Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table 2 below shows several Cas polypeptides and the PAM sequence they recognize.

TABLE 2

Example PAM Sequences

| Cas Protein | PAM Sequence |
|---|---|
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein HisA, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155(Pt. 3):733-740; Atschul et al. 1990. J. Mol. Biol. 215:403-410; Biswass et al. 2013 RNA Biol. 10:817-827; and Grissa et al. 2007. Nucleic Acid Res. 35:W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead, such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3' end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

IscBs

In some embodiments, the genetic modifying agent herein may be an IscB protein. An IscB protein may comprise an X domain and a Y domain as described herein. In some examples, the IscB proteins may form a complex with one or more guide molecules. In some cases, the IscB proteins may form a complex with one or more hRNA molecules which serve as a scaffold molecule and comprise guide sequences. In some examples, the IscB proteins are CRISPR-associated proteins, e.g., the loci of the nucleases are associated with an CRISPR array. In some examples, the IscB proteins are not CRISPR-associated.

In some examples, the IscB protein may be homolog or ortholog of IscB proteins described in Kapitonov V V et al., ISC, a Novel Group of Bacterial and Archaeal DNA Transposons That Encode Cas9 Homologs, J Bacteriol. 2015 Dec. 28; 198(5):797-807. Doi: 10.1128/JB.00783-15, which is incorporated by reference herein in its entirety.

In some embodiments, the IscBs may comprise one or more domains, e.g., one or more of a X domain (e.g., at N-terminus), a RuvC domain, a Bridge Helix domain, and a Y domain (e.g., at C-terminus). In some examples, the nucleic-acid guided nuclease comprises an N-terminal X domain, a RuvC domain (e.g., including a RuvC-I, RuvC-II, and RuvC-III subdomains), a Bridge Helix domain, and a C-terminal Y domain. In some examples, the nucleic-acid guided nuclease comprises In some examples, the nucleic-acid guided nuclease comprises an N-terminal X domain, a RuvC domain (e.g., including a RuvC-I, RuvC-II, and RuvC-III subdomains), a Bridge Helix domain, an HNH domain, and a C-terminal Y domain.

In some embodiments, the nucleic acid-guided nucleases may have a small size. For example, the nucleic acid-guided nucleases may be no more than 50, no more than 100, no more than 150, no more than 200, no more than 250, no more than 300, no more than 350, no more than 400, no more than 450, no more than 500, no more than 550, no more than 600, no more than 650, no more than 700, no more than 750, no more than 800, no more than 850, no more than 900, no more than 950, or no more than 1000 amino acids in length.

In some examples, the IscB protein shares at least 80%, at least 85%, at least 90%, at least 95%, at least 99%, or 100% sequence identity with a IscB protein selected from Table 3.

TABLE 3

<table>
<tr><th>No.</th><th>Proteins</th><th>Sequences</th></tr>
<tr><td>1</td><td>IscB(-HNH)<br>EFH81386</td><td>1 mstdatlirt tpshaeadat dtivatplmp prrvispwpg pgegqslmri pvvdirgmal<br>61 mpctpakarh llksgnarpk rnklglfyvq lsyeqepdnq slvagvdpgs kleglsvvgt<br>121 kdtvlnlmve apdhvkgavq trrtmrrarr qrkwrrpkrf hnrlnrmqri ppstrsrwea<br>181 karivahlrt ilpftdvvve dvqavtrkgk ggtwngsfsp vqvgkehlyr llramgltlh<br>241 lregwqtkel reqhglkktk skskqsfesh avdswvlaas isgaehptct rlwymvpail<br>301 hrrqlhrlqa skggvrkpyg gtrslgvkrg tlvehkkygr ctvggvdrkr ntislheyrt<br>361 ntrltqaakv etcrvltwls wrswllrgkr tsskgkgshs s (SEQ ID NO: 3)</td></tr>
<tr><td>2</td><td>IscB(+HNH)<br>TAE54104.1</td><td>1 mqpakqqnwv fqingdkqpl dminpgrcre lqnrgklasf rrfpyvviqq qtienpqtke<br>61 yilkidpgsq wtgfaiqcgn dilfraelnh rgeaikfdlv krawfrrgrr srnlryrkkr<br>121 lnrakpegwl apsirhrvlt vetwikrfmr ycpiawieie qvrfdtqkla npeidgveyq<br>181 qgelqgyevr eyllqkwgrk caycgtenvp levehiqsks kggssrignl tlachvcnvk<br>241 kgnldvrdfl akspdilnqv lenstkplkd aaavnstrya ivkmaksice nvkcssgart<br>301 kmnrvrqgle kthsldaacv gesgasirvl tdrpllitck ghgsrqsirv nasgfpavkn<br>361 aktvfthiaa gdvvrftigk drkkaqagty tarvktptpk gfevlidgar islstmsnvv<br>421 fvhrsdgygy el (SEQ ID NO: 4)</td></tr>
<tr><td>3</td><td>IscB(+HNH)<br>WP_038093640.1</td><td>1 mavfvidkhk rplmpcsekr arlllergra vvhrqvpfvi rlkdrtvqhs avqplrvald<br>61 pgsratgmal vrekntvdtg tgevyreria lnlfelvhrg hrireqldqr rnfrrrrrga<br>121 nlryraprfd nrrrppgwla pslqhrvdtt mawvrrlcrw apasaigiet vrfdtqrlqn<br>181 peisgveyqq galagcevre yllekwgrkc aycgaenvpl eiehivpksr ggsdrvsnla<br>241 lacracnqak gnrdvrafla dqperlaril aqakaplkda aavnatrwal yralvdtglp<br>301 veagtggrtk wnrtrlglpk thaldalcvg qvdqvrhwrv pvlgircagr gsyrrtrltr<br>361 hgfprgyltr nksafgfqtg dliravvtkg kkagtylgri airasgsfni qtpmgvvqgi<br>421 hhrfctllqr adgygyfvqp kpteaalssp rlkagvssag n (SEQ ID NO: 5)</td></tr>
<tr><td>4</td><td>IscB(+HNH)<br>WP_052490348.1</td><td>1 mttnvvfvid tnqkplqpcs aavarklllr gkaamfrryp aviilkkevd svgkpkielr<br>61 idpgskytgf alvdskdnad fiiwgteleh rgaaickelt krsairrsrr nrktryrkkr<br>121 ferrkpegwl apslqhrvdt tltwvkrick fvpimsisve qvkfdlqkle nsdiqgieyq<br>181 qgtlagytlr eallehwgrk caycdvenvf leiehiypks kggsdkfsnl tlachkcnin<br>241 kgnksidefl lsdhkrleqi klhqkktlkd aaavnatrkk lvttlqektf lnvlvsdgas<br>301 tkmtrlsssl akrhwidagc vnttlivilk tlqplqvkcn ghgnkqfvtm daygfprksy<br>361 epkkvrkdwk agdiirvtkk dgtmlmgrvk kaakklvyip fggkeasfss enakaihrsd<br>421 gyrysfaaid sellqkmat (SEQ ID NO: 6)</td></tr>
<tr><td>5</td><td>IscB(+HNH)<br>WP_015325818.1</td><td>1 mpnkyafvld skgklldptk skkawylirk gkaslveeyp liiklkrevp kdqvnsdkli<br>61 lgiddgtkkv gfalvqkcqt knkvlfkavm eqrqdvskkm eerrgyrryr rshkryrpar<br>121 fdnrssskrk grippsilqk kqailrvvnk lkkyiridki vledvsidir kltegrelyn<br>181 weyqesnrld enlrkatlyr ddctcqlcgt tetmlhahhi mprrdggads iynlitlcka<br>241 chkdkvdnne yqykdqflai idskelsdlk sashvmqgkt wlrdklskia qleitsggnt<br>301 ankridyeie kshsndaict tgllpvdnid dikeyyikpl rkkskakike lkcfrqrdlv<br>361 kytkrngety tgyitslrik nnkynskvcn fstlkgkifr gygfrnltll nrpkglmiv<br>(SEQ ID NO: 7)</td></tr>
<tr><td>6</td><td>sp|G3ECR1|<br>CAS9_STRTR</td><td>1 mlfnkciiis inldfsnkek cmtkpysigl digtnsvgwa vitdnykvps kkmkvlgnts<br>61 kkyikknllg vllfdsgita egrrlkrtar rrytrrrnri lylqeifste matlddaffq<br>121 rlddsflvpd dkrdskypif gnlveekvyh defptiyhlr kyladstkka dlrlvylala<br>181 hmikyrghfl iegefnsknn diqknfqdfl dtynaifesd lslenskqle eivkdkiskl<br>241 ekkdrilklf pgeknsgifs eflklivgnq adfrkcfnld ekaslhfske sydedletll<br>301 gyigddysdv flkakklyda illsgfltvt dneteaplss amikrynehk edlallkeyi<br>361 rnislktyne vfkddtkngy agyidgktnq edfyvylknl laefegadyf lekidredfl<br>421 rkqrtfdngs ipyqihlqem raildkqakf ypflaknker iekiltfrip yyvgplargn<br>481 sdfawsirkr nekitpwnfe dvidkessae afinrmtsfd lylpeekvlp khsllyetfn<br>541 vyneltkvrf iaesmrdyqf ldskqkkdiv rlyfkdkrkv tdkdiieylh aiygydgiel<br>601 kgiekqfnss lstyhdllni indkefldds sneaiieeii htltifedre mikqrlskfe</td></tr>
</table>

TABLE 3-continued

| | | | |
|---|---|---|---|
| | | 661 | nifdksvlkk lsrrhytgwg klsaklingi rdeksgntil dyliddgisn rnfmqlihdd |
| | | 721 | alsfkkkiqk aqiigdedkg nikevvkslp gspaikkgil qsikivdelv kvmggrkpes |
| | | 781 | ivvemarenq ytnqgksnsq qrlkrleksl kelgskilke nipaklskid nnalqndrly |
| | | 841 | lyylqngkdm ytgddldidr lsnydidhii pqaflkdnsi dnkvlvssas nrgksddfps |
| | | 901 | levvkkrktf wyqllkskli sqrkfdnltk aergglped kagfiqrqlv etrqitkhva |
| | | 961 | rlldekfnnk kdennravrt vkiitlkstl vsqfrkdfel ykvreindfh hahdaylnav |
| | | 1021 | iasallkkyp klepefvygd ypkynsfrer ksatekvyfy snimnifkks isladgrvic |
| | | 1081 | rplievneet gesvwnkesd latvrrvlsy pqvnvvkkve eqnhgldrgk pkglfnanls |
| | | 1141 | skpkpnsnen lvgakeyldp kkyggyagis nsfavlvkgt iekgakkkit nvlefqgisi |
| | | 1201 | ldrinyrkdk lnfllekgyk dieliielpk yslfelsdgs rrmlasilst nnkrgeihkg |
| | | 1261 | nqiflsqlfv kllyhakris ntinenhrky venhkkefee lfyyilefne nyvgakkngk |
| | | 1321 | llnsafqswq nhsidelcss figptgserk glfeltsrgs aadfeflgvk ipryrdytps |
| | | 1381 | sllkdatlih qsvtglyetr idlaklgeg (SEQ ID NO: 8) |
| 7 | sp\|J7RUA5\| CAS9_STAAU | 1 | mkrnyilgld igitsvgygi idyetrdvid agvrlfkean vennegrrsk rgarrlkrrr |
| | | 61 | rhriqrvkkl lfdynlltdh selsginpye arvkglsqkl seeefsaall hlakrrgvhn |
| | | 121 | vneveedtgn elstkeqisr nskaleekyv aelqlerlkk dgevrgsinr fktsdyvkea |
| | | 181 | kqllkvqkay hqldqsfidt yidlletrrt yyegpgegsp fgwkdikewy emlmghctyf |
| | | 241 | peelrsykya ynadlynaln dlnnlvitrd enekleyyek fqiienvfkq kkkptlkqia |
| | | 301 | keilvneedi kgyrvtstgk peftnlkvyh dikditarke iienaelldq iakiltiyqs |
| | | 361 | sediqeeltn lnseltqeei eqisnlkgyt gthnlslkai nlildelwht ndnqiaifnr |
| | | 421 | lklvpkkvdl sqqkeipttl vddfilspvv krsfiqsikv inaiikkygl pndiiielar |
| | | 481 | eknskdaqkm inemqkrnrq tnerieeiir ttgkenakyl iekiklhdmq egkclyslea |
| | | 541 | ipledllnnp fnyevdhiip rsvsfdnsfn nkvlvkqeen skkgnrtpfq ylsssdskis |
| | | 601 | yetfkkhiln lakgkgrisk tkkeylleer dinrfsvqkd finrnlvdtr yatrglmnll |
| | | 661 | rsyfrvnnld vkvksinggf tsflrrkwkf kkernkgykh haedaliian adfifkewkk |
| | | 721 | ldkakkvmen qmfeekqaes mpeieteqey keifitphqi khikdfkdyk yshrvdkkpn |
| | | 781 | relindtlys trkddkgntl ivnnlnglyd kdndklkkli nkspekllmy hhdpqtyqkl |
| | | 841 | klimeqygde knplykyyee tgnyltkysk kdngpvikki kyygnklnah ldittddypns |
| | | 901 | rnkvvklslk pyrfdvyldn gvykfvtvkn ldvikkenyy evnskcyeea kklkkisnqa |
| | | 961 | efiasfynnd likingelyr vigvnndlln rievnmidit yreylenmnd krppriikti |
| | | 1021 | asktqsikky stdilgnlye vkskkhpqii kkg (SEQ ID NO: 9) |
| 8 | *Streptococcus_ pyogenes*_SF370 | 1 | kysigldigt nsvgwavitd eykvpskkfk vlgntdrhsi kknligallf dsgetaeatr |
| | | 61 | lkrtarrryt rrknricylq eifsnemakv ddsffhrlee sflveedkkh erhpifgniv |
| | | 121 | devayhekyp tiyhlrkklv dstdkadlrl iylalahmik frghfliegd lnpdnsdvdk |
| | | 181 | lfiqlvqtyn qlfeenpina sgvdakails arlsksrrle nliaqlpgek knglfgnlia |
| | | 241 | lslgltpnfk snfdlaedak lqlskdtydd dldnllaqig dqyadlflaa knlsdaills |
| | | 301 | dilrvnteit kaplsasmik rydehhqdlt llkalvrqql pekykeiffd qskngyagyi |
| | | 361 | dggasqeefy kfikpilekm dgteellvkl nredllrkqr tfdngsiphq ihlgelhail |
| | | 421 | rrqedfypfl kdnrekieki ltfripyyvg plargnsrfa wmtrkseeti tpwnfeevvd |
| | | 481 | kgasaqsfie rmtnfdknlp nekvlpkhsl lyeyftvyne ltkvkyvteg mrkpaflsge |
| | | 541 | qkkaivdllf ktnrkvtvkq lkedyfkkie cfdsveisgv edrfnaslgt yhdllkiikd |
| | | 601 | kdfldneene diledivltl tlfedremie erlktyahlf ddkvmkqlkr rrytgwgrls |
| | | 661 | rklingirdk qsgktildfl ksdgfanrnf mqlihddslt fkediqkaqv sgqgdslheh |
| | | 721 | ianlagspai kkgilqtvkv vdelvkvmgr hkpeniviem arenqttqkg qknsrermkr |
| | | 781 | ieegikelgs qilkehpven tqlqneklyl yylqngrdmy vdqeldinrl sdydvdhivp |
| | | 841 | qsflkddsid nkvltrsdkn rgksdnvpse evvkkmknyw rqllnaklit qrkfdnltka |
| | | 901 | ergglseldk agfikrqlve trqitkhvaq ildsrmntky dendklirev kvitlksklv |
| | | 961 | sdfrkdfqfy kvreinnyhh ahdaylnavv gtalikkypk lesefvygdy kvydvrkmia |
| | | 1021 | kseqeigkat akyffysnim nffkteitla ngeirkrpli etngetgeiv wdkgrdfatv |
| | | 1081 | rkvlsmpqvn ivkktevqtg gfskesilpk rnsdkliark kdwdpkkygg fdsptvaysv |
| | | 1141 | lvvakvekgk skklksvkel lgitimerss feknpidfle akgykevkkd liiklpkysl |
| | | 1201 | felengrkrm lasagelqkg nelalpskyv nflylashye klkgspedne qkqlfveqhk |
| | | 1261 | hyldeiieqi sefskrvila danldkvlsa ynkhrdkpir eqaeniihlf tltnlgapaa |
| | | 1321 | fkyfdttidr krytstkevl datlihqsit glyetridls qlggd (SEQ ID NO: 10) |

| No. | Proteins | Domains and amino acid positions |
|---|---|---|
| 1 | IscB(-HNH) EFH81386 | X domain: 51-97<br>RuvC-I: 104-118<br>Bridge Helix: 140-160<br>RuvC-II: 169-212<br>RuvC-III: 226-278 |
| 2 | IscB(+HNH) TAE54104.1 | X domain: 11-56<br>RuvC-I: 63-77<br>Bridge Helix: 100-121<br>RuvC-II: 129-172<br>HNH: 211-243<br>RuvC-III: 279-321 |
| 3 | IscB(+HNH) WP_038093640.1 | X domain: 4-50<br>RuvC-I: 57-71<br>Bridge Helix: 108-129<br>RuvC-II: 138-181<br>HNH: 220-252<br>RuvC-III: 288-330 |

TABLE 3-continued

| | | |
|---|---|---|
| 4 | IscB(+HNH) WP_052490348.1 | X domain: 7-52<br>RuvC-I: 59-73<br>Bridge Helix: 100-121<br>RuvC-II: 129-172<br>HNH: 211-243<br>RuvC-III: 279-322 |
| 5 | IscB(+HNH) WP_015325818.1 | X domain: 7-52<br>RuvC-I: 61-75<br>Bridge Helix: 101-121<br>RuvC-II: 132-175<br>HNH: 215-247<br>RuvC-III: 284-327 |
| 6 | sp\|G3ECR1\| CAS9_STRTR | RuvC-I: 28-42<br>Bridge Helix: 85-108<br>Rec: 118-736<br>RuvC-II: 750-799<br>HNH: 864-896<br>RuvC-III: 957-1019<br>PAM Interaction (PI): 1119-1409 |
| 7 | sp\|J7RUA5\| CAS9_STAAU | RuvC-I: 7-21<br>Bridge Helix: 49-72<br>Rec: 80-433<br>RuvC-II: 445-493<br>HNH: 553-585<br>RuvC-III: 654-709<br>PAM Interaction (PI): 789-1053 |
| 8 | *Streptococcus_ pyogenes*_SF370 | RuvC-I: 4-18<br>Bridge Helix: 61-84<br>Rec: 94-718<br>RuvC-II: 725-774<br>HNH: 833-865<br>RuvC-III: 926-988<br>PAM Interaction (PI): 1099-1365 |

X Domains

In some embodiments, the IscB proteins comprise an X domain, e.g., at its N-terminal.

In certain embodiments, the X domain include the X domains in Table 3. Examples of the X domains also include any polypeptides a structural similarity and/or sequence similarity to a X domain described in the art. In some examples, the X domain may have an amino acid sequence that share at least 50%, at least 55%, at least 60%, at least 50%, at least 70%, at least 750%, at least 80%, at least 85%, at least 90%, at least 95%, at least 99%, or 100% o sequence identity with X domains in Table 3.

In some examples, the X domain may be no more than 10, no more than 20, no more than 30, no more than 40, no more than 50, no more than 60, no more than 70, no more than 80, no more than 90, or no more than 100 amino acids in length. For example, the X domain may be no more than 50 amino acids in length, such as comprising 2 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

Y Domain

In some embodiments, the IscB proteins comprise a Y domain, e.g., at its C-terminal.

In certain embodiments, the X domain include Y domains in Table 3. Examples of the Y domain also include any polypeptides a structural similarity and/or sequence similarity to a Y domain described in the art. In some examples, the Y domain may have an amino acid sequence that share at least 50%, at least 55%, at least 60%, at least 5%, at least 70%, at least 75%, at least 80%, at least 85%, at least 90%, at least 95%, at least 99%, or 100% sequence identity with Y domains in Table 3.

RuvC Domain

In some embodiments, the IscB proteins comprises at least one nuclease domain. In certain embodiments, the IscB proteins comprise at least two nuclease domains. In certain embodiments, the one or more nuclease domains are only active upon presence of a cofactor. In certain embodiments, the cofactor is Magnesium (Mg). In embodiments where more than one nuclease domain is present and the substrate is a double-strand polynucleotide, the nuclease domains each cleave a different strand of the double-strand polynucleotide. In certain embodiments, the nuclease domain is a RuvC domain.

The IscB proteins may comprise a RuvC domain. The RuvC domain may comprise multiple subdomains, e.g., RuvC-I, RuvC-II and RuvC-III. The subdomains may be separated by interval sequences on the amino acid sequence of the protein.

In certain embodiments, examples of the RuvC domain include those in Table 3. Examples of the RuvC domain also include any polypeptides a structural similarity and/or sequence similarity to a RuvC domain described in the art. For example, the RuvC domain may share a structural similarity and/or sequence similarity to a RuvC of Cas9. In some examples, the RuvC domain may have an amino acid sequence that share at least 50%, at least 55%, at least 60%, at least 5%, at least 70%, at least 75%, at least 80%, at least 85%, at least 90%, at least 95%, at least 99%, or 100% sequence identity with RuvC domains in Table 3.

Bridge Helix

The IscB proteins comprise abridge helix (BH) domain. The bridge helix domain refers to a helix and arginine rich polypeptide. The bridge helix domain may be located next to anyone of the amino acid domains in the nucleic-acid guided nuclease. In some embodiments, the bridge helix domain is next to a RuvC domain, e.g., next to RuvC-I, RuvC-II, or RuvC-III subdomain. In one example, the bridge helix domain is between a RuvC-1 and RuvC2 subdomains.

The bridge helix domain may be from 10 to 100, from 20 to 60, from 30 to 50, e.g., 35, 36, 37, 38, 39, 40, 41, 42, 43, 44, 45, 46 or 47, 48, 49, or 50 amino acids in length. Examples of bridge helix includes the polypeptide of amino acids 60-93 of the sequence of *S. pyogenes* Cas9.

In certain embodiments, examples of the BH domain include those in Table 3. Examples of the BH domain also include any polypeptides a structural similarity and/or sequence similarity to a BH domain described in the art. For example, the BH domain may share a structural similarity and/or sequence similarity to a BH domain of Cas9. In some examples, the BH domain may have an amino acid sequence that share at least 50%, at least 55%, at least 60%, at least 5%, at least 70%, at least 75%, at least 80%, at least 85%, at least 90%, at least 95%, at least 99%, or 100% sequence identity with BH domains in Table 3.

HNH Domain

The IscB proteins comprise an HNH domain. In certain embodiments, at least one nuclease domain shares a substantial structural similarity or sequence similarity to a HNH domain described in the art.

In some examples, the nucleic acid-guided nuclease comprises a HNH domain and a RuvC domain. In the cases where the RuvC domain comprises RuvC-I, RuvC-II, and RuvC-III domain, the HNH domain may be located between the Ruv C II and RuvC III subdomains of the RuvC domain.

In certain embodiments, examples of the HNH domain include those in Table 3. Examples of the HNH domain also include any polypeptides a structural similarity and/or sequence similarity to a HNH domain described in the art. For example, the HNH domain may share a structural similarity and/or sequence similarity to a HNH domain of Cas9. In some examples, the HNH domain may have an amino acid sequence that share at least 50%, at least 55%, at least 60%, at least 5%, at least 70%, at least 75%, at least 80%, at least 85%, at least 90%, at least 95%, at least 99%, or 100% sequence identity with HNH domains in Table 3.

hRNA

In some examples, the IscB proteins capable of forming a complex with one or more hRNA molecules. The hRNA complex can comprise a guide sequence and a scaffold that interacts with the IscB polypeptide. An hRNA molecules may form a complex with an IscB polypeptide nuclease or IscB polypeptide and direct the complex to bind with a target sequence. In certain example embodiments, the hRNA molecule is a single molecule comprising a scaffold sequence and a spacer sequence. In certain example embodiments, the spacer is 5' of the scaffold sequence. In certain example embodiments, the hRNA molecule may further comprise a conserved nucleic acid sequence between the scaffold and spacer portions.

As used herein, a heterologous hRNA molecule is an hRNA molecule that is not derived from the same species as the IscB polypeptide nuclease, or comprises a portion of the molecule, e.g. spacer, that is not derived from the same species as the IscB polypeptide nuclease, e.g. IscB protein. For example, a heterologous hRNA molecule of a IscB polypeptide nuclease derived from species A comprises a polynucleotide derived from a species different from species A, or an artificial polynucleotide.

Zinc Finger Nucleases

In some embodiments, the polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

TALE Nucleases

In some embodiments, a TALE nuclease or TALE nuclease system can be used to modify a polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$—($X_{12}X_{13}$)—$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as ($X_{1-11}$—($X_{12}X_{13}$)—$X_{14-33}$ or 34 or $35)_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                        (SEQ ID NO: 11)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N
```

An exemplary amino acid sequence of a C-terminal capping region is:

```
                                        (SEQ ID NO: 12)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

In some embodiments, a meganuclease or system thereof can be used to modify a polynucleotide. Meganucleases, which are endodeoxyribonucleases characterized by a large recognition site (double-stranded DNA sequences of 12 to 40 base pairs). Exemplary methods for using meganucleases can be found in U.S. Pat. Nos. 8,163,514, 8,133,697, 8,021,867, 8,119,361, 8,119,381, 8,124,369, and 8,129,134, which are specifically incorporated by reference.

Sequences Related to Nucleus Targeting and Transportation

In some embodiments, one or more components (e.g., the Cas protein and/or deaminase, Zn Finger protein, TALE, or meganuclease) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO: 13) or PKKKRKVEAS (SEQ ID NO: 14); the NLS from nucleoplasmin (e.g., the nucleoplasmin bipartite NLS with the sequence KRPAATKKAGQAKKKK (SEQ ID NO: 15)); the c-myc NLS having the amino acid sequence PAAKRVKLD (SEQ ID NO: 16) or RQRRNELKRSP (SEQ ID NO: 17); the hRNPA1 M9 NLS having the sequence NQSSNFGPMKGGNFGGRSSGPYGGGGQYFAK-PRNQGGY (SEQ ID NO: 18); the sequence RMRIZFKNKGKDTAELRRRRVEVSVELRKAKKD-EQILKRRNV (SEQ ID NO: 19) of the IBB domain from importin-alpha; the sequences VSRKRPRP (SEQ ID NO: 20) and PPKKARED (SEQ ID NO: 21) of the myoma T protein; the sequence PQPKKKPL (SEQ ID NO: 22) of human p53; the sequence SALIKKKKKMAP (SEQ ID NO: 23) of mouse c-abl IV; the sequences DRLRR (SEQ ID NO: 24) and PKQKKRK (SEQ ID NO: 25) of the influenza virus NS1; the sequence RKLKKKIKKL (SEQ ID NO: 26) of the Hepatitis virus delta antigen; the sequence REKKKFLKRR (SEQ ID NO: 27) of the mouse Mx1 protein; the sequence KRKGDEVDGVDEVAKKKSKK (SEQ ID NO: 28) of the human poly(ADP-ribose) polymerase; and the sequence RKCLQAGMNLEARKTKK (SEQ ID NO: 29) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting, as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to an nucleotide deaminase or catalytic domain thereof. When such a guide forms a CRISPR complex (e.g., CRISPR-Cas protein binding to guide and target) the adapter proteins bind and, the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+nucleotide deaminase (e.g. due to steric hindrance within the three dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include sequence that corresponds to both, a first site on the target sequence that is cleaved in a first Cas protein mediated event, and a second site on the target sequence that is cleaved in a second Cas protein mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration In a non-coding sequence, e.g., an alteration in an exon or in a "or" non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may be designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

In certain embodiments, a template nucleic acid for correcting a mutation may be designed for use with a homology-independent targeted integration system. Suzuki et al. describe in vivo genome editing via CRISPR/Cas9 mediated homology-independent targeted integration (2016, Nature 540:144-149). Schmid-Burgk, et al. describe use of the CRISPR-Cas9 system to introduce a double-strand break (DSB) at a user-defined genomic location and insertion of a universal donor DNA (Nat Commun. 2016 Jul. 28; 7:12338). Gao, et al. describe "Plug-and-Play Protein Modification Using Homology-Independent Universal Genome Engineering" (Neuron. 2019 Aug. 21; 103(4):583-597).

RNAi

In some embodiments, the genetic modulating agents may be interfering RNAs. In certain embodiments, diseases caused by a dominant mutation in a gene is targeted by silencing the mutated gene using RNAi. In some cases, the nucleotide sequence may comprise coding sequence for one or more interfering RNAs. In certain examples, the nucleotide sequence may be interfering RNA (RNAi). As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

In certain embodiments, a modulating agent may comprise silencing one or more endogenous genes. As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA", used interchangeably herein, are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al. Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Antibodies

In certain embodiments, the one or more agents is an antibody. The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, VHH and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, IgM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, V1-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains. The "variable" domains of an antibody light chain are referred to interchangeably as "light chain variable regions", "light chain variable domains", "VL" regions or "VL" domains. The "variable" domains of an antibody heavy chain are referred to interchangeably as "heavy chain constant regions", "heavy chain constant domains", "VH" regions or "VH" domains.

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 μM. Antibodies with affinities greater than 1×107 M-1 (or a dissociation coefficient of 1 M or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term “affinity” refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term “monoclonal antibody” refers to an antibody derived from a clonal population of antibody-producing cells (e.g., B lymphocytes or B cells) which is homogeneous in structure and antigen specificity. The term “polyclonal antibody” refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term “binding portion” of an antibody (or “antibody portion”) includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

“Humanized” forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CHI domain; (v) the Fv fragment having the VL and VH domains of a single arm of an antibody; (vi) the dAb fragment (Ward et al., 341 Nature 544 (1989)) which consists of a VH domain or a VL domain that binds antigen; (vii) isolated CDR regions or isolated CDR regions presented in a functional framework; (viii) F(ab')2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) “diabodies” with two antigen binding sites, comprising a heavy chain variable domain (VH) connected to a light chain variable domain (VL) in the same polypeptide chain (see, e.g., EP 404,097; WO 93/11161; Hollinger et al., 90 PNAS 6444 (1993)); (xi) “linear antibodies” comprising a pair of tandem Fd segments (VH-Ch1-VH-Ch1) which, together with complementary light chain polypeptides, form a pair of antigen binding regions (Zapata et al., Protein Eng. 8(10):1057-62 (1995); and U.S. Pat. No. 5,641,870).

As used herein, a “blocking” antibody or an antibody “antagonist” is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4):1786-1794 (1998); Zhu et al., Cancer Res. 58(15):3209-3214

(1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Bi-Specific Antibodies

In certain embodiments, the one or more therapeutic agents can be bi-specific antigen-binding constructs, e.g., bi-specific antibodies (bsAb) or BiTEs, that bind two antigens (see, e.g., Suurs et al., A review of bispecific antibodies and antibody constructs in oncology and clinical challenges. Pharmacol Ther. 2019 September;201:103-119; and Huehls, et al., Bispecific T cell engagers for cancer immunotherapy. Immunol Cell Biol. 2015 March; 93(3): 290-296). The bi-specific antigen-binding construct includes two antigen-binding polypeptide constructs, e.g., antigen binding domains, wherein at least one polypeptide construct specifically binds to a tumor surface protein. In some embodiments, the antigen-binding construct is derived from known antibodies or antigen-binding constructs. In some embodiments, the antigen-binding polypeptide constructs comprise two antigen binding domains that comprise antibody fragments. In some embodiments, the first antigen binding domain and second antigen binding domain each independently comprises an antibody fragment selected from the group of: an scFv, a Fab, and an Fe domain. The antibody fragments may be the same format or different formats from each other. For example, in some embodiments, the antigen-binding polypeptide constructs comprise a first antigen binding domain comprising an scFv and a second antigen binding domain comprising a Fab. In some embodiments, the antigen-binding polypeptide constructs comprise a first antigen binding domain and a second antigen binding domain, wherein both antigen binding domains comprise an scFv. In some embodiments, the first and second antigen binding domains each comprise a Fab. In some embodiments, the first and second antigen binding domains each comprise an Fc domain. Any combination of antibody formats is suitable for the bi-specific antibody constructs disclosed herein.

In certain embodiments, immune cells can be engaged to tumor cells. In certain embodiments, tumor cells are targeted with a bsAb having affinity for both the tumor and a payload. In certain embodiments, two targets are disrupted on a tumor cell by the bsAb (e.g., Table 1). By means of an example, an agent, such as a bi-specific antibody, capable of specifically binding to a gene product expressed on the cell surface of the immune cells (e.g., CD3, CD8, CD28, CD16) and a tumor cell may be used for targeting polyfunctional immune cells to tumor cells. Immune cells targeted to a tumor may include T cells or Natural Killer cells.

Antibody Drug Conjugates

The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8.

In certain embodiments, the ADC specifically binds to a gene product expressed on the cell surface of a tumor cell. By means of an example, an agent, such as an antibody, capable of specifically binding to a gene product expressed on the cell surface of the tumor cells may be conjugated with a therapeutic or effector agent for targeted delivery of the therapeutic or effector agent to the immune cells.

Examples of such therapeutic or effector agents include immunomodulatory classes as discussed herein, such as without limitation a toxin, drug, radionuclide, cytokine, lymphokine, chemokine, growth factor, tumor necrosis factor, hormone, hormone antagonist, enzyme, oligonucleotide, siRNA, RNAi, photoactive therapeutic agent, anti-angiogenic agent and pro-apoptotic agent.

Non-limiting examples of drugs that may be included in the ADCs are mitotic inhibitors (e.g., maytansinoid DM4), antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

Example toxins include ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, or *Pseudomonas* endotoxin.

Example radionuclides include $^{103m}Rh$, $^{103}Ru$, $^{105}Rh$, $^{105}Ru$, $^{107}Hg$, $^{109}Pd$, $^{109}Pt$, $^{111}Ag$, $^{111}In$, $^{113m}In$ $^{119}Sb$, $^{11}C$, $^{121m}Te$, $^{122m}Te$, $^{125}I$, $^{125m}Te$, $^{126}I$, $^{131}I$, $^{133}I$, $^{13}N$, $^{142}Pr$, $^{143}Pr$, $^{149}Pm$, $^{152}Dy$, $^{153}Sm$, $^{15}O$, $^{161}Ho$ $^{161}Tb$, $^{165}Tm$, $^{166}Dy$, $^{166}Ho$, $^{167}Tm$, $^{168}Tm$, $^{169}Er$, $^{169}Yb$ $^{177}Lu$, $^{186}Re$, $^{188}Re$, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo or $^{99m}$Tc. Preferably, the radionuclide may be an alpha-particle-emitting radionuclide.

Example enzymes include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase or acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-NH2), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to, those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer containing any modification as described herein.

Administration

The administration of compositions, agents, cells, or populations of cells, as disclosed herein may be carried out in any convenient manner including by aerosol inhalation, injection, ingestion, transfusion, implantation or transplantation. The agents described herein may be administered to a patient subcutaneously, intradermally, intratumorally, intranodally, intramedullary, intramuscularly, intrathecally, by intravenous or intralymphatic injection, or intraperitoneally.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isethionate, triethiodide, lactate, panoate, valerate, and the like which can be used as a dosage form for modifying the solubility or hydrolysis characteristics or can be used in sustained release or prodrug formulations. It will be understood that, as used herein, references to specific agents also include the pharmaceutically acceptable salts thereof.

Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules, minicells, polymers, capsules, tablets, and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art as disclosed, for example, in U.S. Pat. Nos. 4,837,028 and 4,737,323. In yet another embodiment, the pharmacological compositions can be delivered in a controlled release system including, but not limited to, a delivery pump (see, for example, Saudek, et al., New Engl. J. Med. 321: 574 (1989)) and a semi-permeable polymeric material (see, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. In certain embodiments, suitable dosage ranges for intravenous administration of the agent are generally about 5-500 micrograms (g) of active compound per kilogram (Kg) body weight. Suitable dosage ranges for intranasal administration are generally about 0.01 pg/kg body weight to 1 mg/kg body weight. In certain embodiments, a composition containing an agent of the present invention is subcutaneously injected in adult patients with dose ranges of approximately 5 to 5000 μg/human and preferably approximately 5 to 500 μg/human as a single dose. It is desirable to administer this dosage 1 to 3 times daily. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately, the attending physician will decide on the appropriate duration of therapy using compositions of the present invention. Dosage will also vary according to the age, weight and response of the individual patient.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In preferred embodiments, antibodies are used as agonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like; d) peptides and proteins, such as aspartame, human serum albumin, gelatin, and the like; e) alditols, such mannitol, xylitol, and the like; and f) polycationic polymers, such as chitosan or a chitosan salt or derivative.

For dermal application, the antibodies of the present invention may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabens, such as methyl, ethyl, propyl, p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and bezylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives, wool fats, wool alcohols, sorbitan esters, monoglycerides, fatty alcohols, fatty acid esters (e.g. triglycerides of fatty acids), and mixtures thereof.

Examples of suspending agents are, e.g., celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Examples of gel bases, viscosity-increasing agents or components which are able to take up exudate from a wound are liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carrageenans, hyaluronates (e.g. hyaluronate gel optionally containing sodium chloride), and alginates including propylene glycol alginate.

Examples of ointment bases are, e.g., beeswax, paraffin, cetanol, cetyl palmitate, vegetable oils, sorbitan esters of fatty acids (Span), polyethylene glycols, and condensation products between sorbitan esters of fatty acids and ethylene oxide, e.g., polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmellose, sodium carmellose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanil glucoside, collagen, carrageenan, hyaluronates and alginates and chitosans.

The dose of antibody required in humans to be effective in the treatment or prevention of a condition differs with the type and severity of the condition to be treated, the age and condition of the patient, etc. Typical doses of antibody to be administered are in the range of 1 μg to 1 g, preferably 1-1000 μg, more preferably 2-500 μg, even more preferably 5-50 μg, most preferably 10-20 μg per unit dosage form. In certain embodiments, infusion of antibodies of the present invention may range from 10-500 mg/m2.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

In another aspect, provided is a pharmaceutical pack or kit, comprising one or more containers filled with one or more of the ingredients of the pharmaceutical compositions.

Diagnostic Methods

In certain embodiments, one or more biomarkers is detected in a subject having, at risk for, or having a history of, breast cancer as described herein (e.g., MBC or DCIS). The invention provides biomarkers (e.g., biological programs, signature genes) for the identification, diagnosis, prognosis and manipulation of disease phenotypes (e.g., immune state, metastatic state, proliferation state), for use in a variety of diagnostic and/or therapeutic indications. Biomarkers in the context of the present invention encompasses, without limitation nucleic acids, proteins, reaction products, and metabolites, together with their polymorphisms, mutations, variants, modifications, subunits, fragments, and other analytes or sample-derived measures. In certain embodiments, biomarkers include the signature genes or signature gene products, and/or cells as described herein.

In certain embodiments, the invention provides uses of the biomarkers for predicting risk for a certain phenotype (e.g., MCB, DCIS). In certain embodiments, the invention provides uses of the biomarkers for selecting a treatment. In certain embodiments, a subject having a disease can be classified based on severity of the disease.

In certain embodiments, provided herein are gene expression profiles and genes selected for RNA visualization for distinguishing between cells comprising a malignant cell, a endothelial cell, a fibroblast, a T cell, a B cell, and a macrophage. As described herein, an expression profile may encompass any gene or genes, protein or proteins, or epigenetic element(s) whose expression profile or whose occurrence is associated with a specific cell type, subtype, or cell state of a specific cell type or subtype within a population of cells (e.g., malignant cell).

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The biomarkers of the present invention are useful in methods of identifying specific patient populations based on a detected level of expression, activity and/or function of one or more biomarkers. These biomarkers are also useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The biomarkers provided herein are useful for selecting a group of patients at a specific state of a disease with accuracy that facilitates selection of treatments.

The term "monitoring" generally refers to the follow-up of a disease or a condition in a subject for any changes which may occur over time.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Hence, the methods may rely on comparing the quantity of biomarkers, or gene or gene product signatures measured in samples from patients with reference values, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favorable or unfavorable prognoses for such disease or condition.

Such comparison may generally include any means to determine the presence or absence of at least one difference and optionally of the size of such difference between values being compared. A comparison may include a visual inspection, an arithmetical or statistical comparison of measurements. Such statistical comparisons include, but are not limited to, applying a rule.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or 1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

Detection of Biomarkers

In one embodiment, one or more of the signature genes are detected by immunofluorescence, immunohistochemistry (IHC), fluorescence activated cell sorting (FACS), mass spectrometry (MS), mass cytometry (CyTOF), RNA-seq, single cell RNA-seq (described further herein), quantitative RT-PCR, single cell qPCR, ExSeq (expansion-seq), RNA-FISH, MERFISH (multiplex (in situ) RNA FISH) and/or by in situ hybridization. Detection may comprise primers and/or probes or fluorescently bar-coded oligonucleotide probes for hybridization to RNA (see e.g., Geiss G K, et al., Direct multiplexed measurement of gene expression with color-coded probe pairs. Nat Biotechnol. 2008 March;26(3):317-25). Other methods including absorbance assays and colorimetric assays are known in the art and may be used herein.

In one embodiment, cells are stained for specific signature genes. In one embodiment, the cells are fixed. In another embodiment, the cells are formalin fixed and paraffin embedded. In certain embodiments, the cell types may be quantitated in a tissue section and the number of cells indicates an outcome and personalized treatment. In certain embodiments, an immune response is diagnosed, prognosed, or monitored. For example, a tissue sample may be obtained and analyzed for specific cell markers (IHC) or specific transcripts (e.g., RNA-FISH). In one embodiment, a tissue sample is stained for cell subtype specific signature genes. Not being bound by a theory, the presence of the immune cell subtypes indicate outcome and personalized treatments.

The present invention also includes a kit with one or more detection reagents for the one or more biomarkers.

Sequencing

In some embodiments, provided herein discloses a method of single-cell RNA sequencing (scRNA-seq) for measuring the levels of gene transcripts. scRNA-seq measures gene transcripts at single-cell level. In some embodiments, provided herein discloses a method of single-nucleus RNA sequencing (snRNA-seq) for measuring the levels of gene transcripts. snRNA-seq measures gene transcripts at single-nucleus level. In some aspects, snRNA-seq measures both pre-RNA and mRNA.

In one embodiment, single-cell or single-nuclei RNA analysis is performed by digital polymerase chain reactions (PCR), e.g., Fluidigm C. Digital polymerase chain reaction (digital PCR, DigitalPCR, dPCR, or dePCR) is a refinement of conventional polymerase chain reaction methods that can be used to directly quantify and clonally amplify nucleic acids including DNA, cDNA or RNA. The key difference between dPCR and traditional PCR lies in that PCR carries out one reaction per single sample and dPCR carries out a single reaction within samples separated into a large number of partitions wherein the reactions are carried out in each partition individually. A sample is partitioned so that individual nucleic acid molecules within the sample are localized and concentrated within many separate regions. The capture or isolation of individual nucleic acid molecules may be effected in micro well plates, capillaries, the dispersed phase of an emulsion, and arrays of miniaturized chambers, as well as on nucleic acid binding surfaces.

In a preferred embodiment, single cell or single nuclei analysis is performed using microfluidics. Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 201202 19947 and PCT publication No. WO20 14085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 108 samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012,12, 2146-2155.

In certain embodiments, sequencing is used to identify the expression of signature genes or biological programs in single cells. In certain embodiments, sequencing comprises high-throughput (formerly "next-generation") technologies to generate sequencing reads. Methods for constructing sequencing libraries are known in the art (see, e.g., Head et al., Library construction for next-generation sequencing: Overviews and challenges. Biotechniques. 2014; 56(2): 61-77). A "library" or "fragment library" may be a collection of nucleic acid molecules derived from one or more nucleic acid samples, in which fragments of nucleic acid have been modified, generally by incorporating terminal adapter sequences comprising one or more primer binding sites and identifiable sequence tags. In certain embodiments, the library members (e.g., cDNA) may include sequencing adaptors that are compatible with use in, e.g., Illumina's reversible terminator method, long read nanopore sequencing, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Schneider and Dekker (Nat Biotechnol. 2012 Apr. 10; 30(4):326-8); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92:255-64), which are incorporated by reference for the general descriptions of the methods and the particular steps of the methods, including all starting products, reagents, and final products for each of the steps.

In certain embodiments, the invention involves detection of signature genes or biological programs by single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the present invention involves single cell RNA sequencing (scRNA-seq). In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January;12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; Gierahn et al., "Seq-Well: portable, low-costRNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October;14(10):955-958; International Patent Application No. PCT/US2016/059239, published as WO2017164936 on Sep. 28, 2017; International Patent Application No. PCT/US2018/060860, published as WO/2019/094984 on May 16, 2019; International Patent Application No. PCT/US2019/055894, published as WO/2020/077236 on Apr. 16, 2020; and Drokhlyansky, et al., "The enteric nervous system of the human and mouse colon at a single-cell resolution," bioRxiv 746743; doi: doi.org/10.1101/746743, which are herein incorporated by reference in their entirety.

In some embodiments, the invention provides methods of producing a molecular spatial map for MBC and DCIS. The methods use a set of genes selected from gene expression data obtained using scRNA-seq and/or snRNA-seq. The method may comprise treating tumor tissues with different enzymes, buffers, and other components to dissociate cells from a tissue, and isolate nuclei from a tissue, a cell, or a plurality of cells. The cells and nuclei are placed into individual reaction vessels or wells for scRNA-seq and snRNA-seq, respectively.

As outlined in the Examples, the Applicants have unexpectedly determined that single nuclei comprising a portion of the rough endoplasmic reticulum (RER) can be isolated and the resulting nuclei provides for improved RNA recovery and single cell expression profiling. In some embodiments, the methods provide for isolation of single nuclei with partially intact outer membrane containing RER. In some embodiments, the methods allow for isolation of single nuclei with partially intact outer membrane and partially intact RER with ribosomes. In some embodiments, the methods allow for isolation of single nuclei with partially intact outer membrane, RER and mitochondria.

In specific embodiments, the method further comprises sequencing the RNA from the isolated single cells from tumor tissue microenvironment as described herein, or isolated single nucleus, whereby single cell gene expression data are obtained for heterogenous types of cells in tumor tissue microenvironment. In certain embodiments, the invention provides single-nucleus RNA sequencing, as described herein.

The invention provides for a method of single-cell sequencing comprising: extracting nuclei from a population of cells under conditions that preserve: (1) a portion of the outer nuclear envelope with attached ribosomes, or (2) a portion of the outer nuclear membrane and a portion of the rough endoplasmic reticulum (RER) with ribosomes, or (3) a portion of the outer nuclear membrane, a portion of the rough endoplasmic reticulum (RER), and a portion of mitochondria; isolated single nuclei are placed into separate reaction vessels; extracting RNA from the single nuclei; generating a cDNA library; and sequencing the library, whereby gene expression data from single cells is obtained. In some embodiments, the reaction vessels may be single cell droplets.

In certain embodiments, the invention involves the Assay for Transposase Accessible Chromatin using sequencing (ATAC-seq) as described. (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. Nature 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22;348(6237): 910-4. doi: 10.1126/science.aab1601. Epub 2015 May 7; US20160208323A1; US20160060691A1; and WO2017156336A1).

Single Cell HiC

In certain embodiments, epigenetic features can be chromatin contact domains, chromatin loops, superloops, or chromatin architecture data, such as obtained by single cell HiC (see, e.g., Rao et al., Cell. 2014 Dec. 18; 159(7):1665-80; and Ramani, et al., Sci-Hi-C: A single-cell Hi-C method for mapping 3D genome organization in large number of single cells Methods. 2020 Jan. 1; 170: 61-68).

Single Cell Proteomics

In certain embodiments, single cell proteomics can be used to generate the single cell data. In certain embodiments, the single cell proteomics data is combined with single cell transcriptome data. Non-limiting examples include multiplex analysis of single cell constituents (US20180340939A), single-cell proteomic assay using aptamers (US20180320224A1), and methods of identifying multiple epitopes in cells (US20170321251A1).

Multimodal Technology

In certain embodiments, SHARE-Seq (Ma, S. et al. Chromatin potential identified by shared single cell profiling of RNA and chromatin. bioRxiv 2020.06.17.156943 (2020) doi:10.1101/2020.06.17.156943) is used to generate single cell RNA-seq and chromatin accessibility data. In certain embodiments, CITE-seq (Stoeckius, M. et al. Simultaneous epitope and transcriptome measurement in single cells. Nat. Methods 14, 865-868 (2017)) (cellular proteins) is used to generate single cell RNA-seq and proteomics data. In certain embodiments, Patch-seq (Cadwell, C. R. et al. Electrophysiological, transcriptomic and morphologic profiling of single neurons using Patch-seq. Nat. Biotechnol. 34, 199-203 (2016)) is used to generate single cell RNA-seq and patch-clamping electrophysiological recording and morphological analysis of single neurons data (e.g., for the brain or enteric nervous system (ENS)) (see, e.g., van den Hurk, et al., Patch-Seq Protocol to Analyze the Electrophysiology, Morphology and Transcriptome of Whole Single Neurons Derived From Human Pluripotent Stem Cells, Front Mol Neurosci. 2018; 11: 261).

In certain embodiments, the present invention provides methods for determining expression profiles for single cells comprising malignant cells, endothelial cells, fibroblasts, T cells, B cells, and macrophages. The method may further comprise determining an expression profile for each identified cell or cell subtype/subpopulation based on the gene expression data.

The gene expression data may be obtained from scRNA-seq or snRNA-seq. The snRNA-seq may comprise: treating the heterogeneous population of cells with a reagent that stabilizes RNA; extracting nuclei from the cells; sorting single nuclei into separate reaction vessels; extracting RNA from the single nuclei; generating a cDNA library; and sequencing the library, whereby gene expression data from single cells is obtained. The single nuclei may be sorted into single wells of a plate by FACS or MACS or any appropriate techniques. The sorting single nuclei into separate reaction vessels may comprise microfluidics. The single nuclei may be sorted into individual chambers on a microfluidic chip.

In certain embodiments, the present invention provides a method for producing at least one high resolution map for visualizing different cell subtypes or cell states in a heterogeneous population of cells comprising: performing dimensionality reduction on single cell gene expression data or single nucleus gene expression data obtained from the heterogeneous population of cells; producing a first set of clusters of cells by a method comprising measuring the dissimilarity between sets of genes in the dimensionality reduced single cell gene expression data and applying a first metric, wherein the clusters are in a dimensionality reduced space and the clusters comprise cells in a tissue microenvironment; producing a set of informative genes by a method comprising scoring genes based on their expression across the first set of clusters of cells, wherein the informative genes are uniquely expressed in cells embedded in close proximity in the dimensionality reduced space; and producing at least one second set of clusters of cells by a method comprising measuring the dissimilarity between the set of informative genes and applying a second metric, whereby visualization of a map of the second set of clusters indicate cell subtypes or cell states.

In some embodiments, variable genes are identified using Seurat's FindVaribleGenes. Principal components analysis (PCA) is performed over these genes for each cell, followed by non-linear dimensionality reduction by t-stochastic neighbor embedding (tSNE). Clusters are identified in the linear PC space using K-nearest neighbor (KNN) clustering, and cluster assignments are visualized on the non-linear tSNE space. In some embodiments, uniform manifold approximation and projection (UMAP) is used for dimension reduction.

In certain embodiments, dimension reduction is used to cluster single cells based on differentially expressed genes. In certain embodiments, the dimension reduction technique may be, but is not limited to, Uniform Manifold Approximation and Projection (UMAP) or t-SNE (see, e.g., Becht et al., Evaluation of UMAP as an alternative to t-SNE for single-cell data, bioRxiv 298430; doi.org/10.1101/298430; and Becht et al., 2019, Dimensionality reduction for visualizing single-cell data using UMAP, Nature Biotechnology volume 37, pages 38-44).

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an $F(ab')_2$ fragment, a single chain antibody fragment, an Fv fragment, a single chain Fv fragment, a nucleic acid, a lectin, a ligand-binding receptor, affibodies, nanobodies, ankyrins, domain antibodies, alternative antibody scaffolds (e.g. diabodies etc.) imprinted polymers, avimers, peptidomimetics, peptoids, peptide nucleic acids, threose nucleic acid, a hormone receptor, a cytokine receptor, and synthetic receptors, and modifications and fragments of these.

Immunoassays

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Hybridization Assays

Hybridization assays may be used to detect biomarkers. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1 SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

In certain embodiments, a subject can be categorized based on signature genes or gene programs expressed by a tissue sample obtained from the subject. In certain embodiments, the tissue sample is analyzed by bulk sequencing. In certain embodiments, subtypes can be determined by determining the percentage of specific cell subtypes expressing the identified biomarkers in the sample that contribute to the phenotype. In certain embodiments, gene expression associated with the cells are determined from bulk sequencing reads by deconvolution of the sample. For example, deconvoluting bulk gene expression data can include defining the relative frequency of a set of cell types in a sample from the bulk gene expression data using cell type specific gene expression.

Spatial Localization of Cells and Cell Populations in Tissue Microenvironment

In some embodiments, the present invention comprises mapping the spatial location of the tumor microenvironment cells and cell populations and subpopulations using one or more signature genes as described herein. In certain embodiments, mapping the spatial location is by performing RNA in situ hybridization (ISH) or RNA in situ sequencing on whole tissue sections comprising said cells or cell populations or cell subpopulations using probes specific for genes expressed in the cells, cell populations, or cell subpopulations, whereby the spatial location of cells, cell populations, and/or cell subpopulations is visualized in a biological sample. The methods may further comprise mapping the spatial location of the cell subtypes or cells having a cell state by comparing gene expression data for each cell type to landmark gene expression patterns in tissue samples, whereby the spatial location of cell subtypes is visualized in a biological sample. In certain embodiments, one or more of the signature genes described herein are analyzed. In certain embodiments, a tissue is analyzed using a selected gene by ExSeq or MERFISH. In certain embodiments, the present invention provides for a kit for analyzing the spatial localization using one or more of the signature genes described herein.

In certain embodiments, the markers selected for using the methods herein are used to link high resolution single cell RNA sequencing data to a spatial map. For example, the markers are used in a spatial location method and the gene expression from single cell types expressing the markers (e.g., scRNA-seq, snRNA-seq) are used to assign the gene expression to the spatial data. In certain embodiments, the single cell data is obtained from a single cell atlas. In certain embodiments, single cell data is obtained for the same tissue used for determining the spatial data (e.g., part of the tissue is used for single cell/nuclei RNA-seq and another part is used for spatial analysis).

Cell Atlas

In certain embodiments, the data can be obtained from a single cell atlas or cell atlas. As used herein "single cell atlas" refers to any collection of single cell data from any tissue sample of interest having a phenotype of interest (see, e.g., Rozenblatt-Rosen O, Stubbington M J T, Regev A, Teichmann S A., The Human Cell Atlas: from vision to reality, Nature. 2017 Oct. 18; 550(7677):451-453; and Regev, A. et al. The Human Cell Atlas Preprint available at bioRxiv at dx.doi.org/10.1101/121202 (2017)). In preferred embodiments, single cell data is obtained from one or more tissue samples, more preferably, one or more tissue samples from one or more subjects. The subjects preferably include one or more subjects having a phenotype and one or more control subjects. The single cell data can include, but is not limited to transcriptome, chromatin accessibility, epigenetic data, or any combination thereof. A single cell atlas can refer to any collection of single cell data from any tissue sample. The number of cells analysed in the atlas may be about 1,000, 2,000, 5,000, 10,000, 20,000, 50,000, 100,000, 500,000, or more than a million cells. The single cell atlas can also include biological and medical information for the subjects where the tissue samples were obtained.

A single cell atlas for a tissue may be constructed by measuring single cell transcriptomes. The single cell atlas can be used as a roadmap for any phenotype present in or associated with a specific tissue (e.g., a "Google Map" of patient tissue samples). The atlas can be generated by providing: (1) biological information, including medical records, histology, single cell profiles, and genetic information, and (2) data, including multiplexed ion beam imaging (MIBI) (see, e.g., Angelo et al., Nat Med. 2014 April; 20(4): 436-442), NanoString (DSP, digital spatial profiling) (see e.g., Geiss G K, et al., Direct multiplexed measurement of gene expression with color-coded probe pairs. Nat Biotechnol. 2008 March;26(3):317-25), microbiome, immunoprofiling, and sequencing (e.g., bulk and single cell sequencing). Pathology of tissue samples can be performed. Tissue samples can be dissociated for scRNA-seq, flow cytometry and cell culture. Tissues can also be snap frozen for analysis of DNA by WES, bulk RNA-seq, and epigenetics. Tissue can also be OCT frozen for multiplex imaging. The data obtained can be computationally analyzed.

Non-limiting examples of a single cell atlas applicable to the present invention are disclosed in U.S. Ser. No. 16/072,674, WO 2018/191520, WO 2018/191558, U.S. Ser. No. 16/348,911, WO 2019/018440, U.S. Ser. No. 15/844,601, and U.S. 62/888,347. See, also, Darmanis, S. et al. Proc. Natl Acad. Sci. USA 112, 7285-7290 (2015); Lake, B. B. et al. Science 352, 1586-1590 (2016); Pollen, A. A. et al. Nature Biotechnol. 32, 1053-1058 (2014); Tasic, B. et al. Nature Neurosci. 19, 335-346 (2016); Zeisel, A. et al. Science 347, 1138-1142 (2015); Grun. D. et al Nature 525, 251-255 (2015); Shekhar, K. et al. Cell 166, 1308-1323 (2016); Villani, A. C. et al. Science 356, eaah4573 (2017); Lonnberg, T. et al. Sci. Immunol. 2, eaa12192 (2017); Tirosh, I. et al. Science 352, 189-196 (2016); Venteicher A S, et al., Decoupling genetics, lineages, and microenvironment in IDH-mutant gliomas by single-cell RNA-seq., Science. 2017 Mar. 31; 355(6332); Tirosh, I. et al. Single-cell RNA-seq supports a developmental hierarchy in human oligodendroglioma. Nature. 2016 Nov. 10; 539(7628):309-313; Drokhlyansky et al., The enteric nervous system of the human and mouse colon at a single-cell resolution. bioRxiv 746743; doi: doi.org/10.1101/746743; Smillie C S. et al., Intra- and Inter-cellular Rewiring of the Human Colon during Ulcerative Colitis. Cell. 2019 Jul. 25; 178(3):714-730.e22; Montoro D T. et al., A revised airway epithelial hierarchy includes CFTR-expressing ionocytes. Nature. 2018 August; 560(7718):319-324; and Haber A L, et al., A single-cell survey of the small intestinal epithelium. Nature. 2017 Nov. 16; 551(7680):333-339. Smillie et al. shows a cell atlas of UC, a complex disease atlas. Smillie et al. further shows that the atlas can be built from involved and uninvolved tissue in patients, in comparison to the healthy reference from a human cell atlas. A relatively small number of individuals provides a robust catalog (i.e., atlas).

In certain embodiments, single cell transcriptomes are included in the cell atlas. As used herein the term "transcriptome" refers to the set of transcripts molecules. In some embodiments, transcript refers to RNA molecules, e.g., messenger RNA (mRNA) molecules, small interfering RNA (siRNA) molecules, transfer RNA (tRNA) molecules, ribosomal RNA (rRNA) molecules, and complimentary sequences, e.g., cDNA molecules. In some embodiments, a transcriptome refers to a set of mRNA molecules. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells. In some embodiments, a transcriptome refers to 50%, 55, 60, 65, 70, 75, 80, 85, 90, 91, 92, 93, 94, 95, 96, 97, 98, 99, 99.9, or 100% of transcripts from a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

In certain embodiments, a single cell atlas includes single cell epigenetic data that can be mapped to spatial data using the markers herein. For example, the epigenetic states of the markers can be used or a combination of epigenetic markers and single cell RNA-seq data can be used. A single cell atlas for a tissue may be constructed by measuring epigenetic marks on chromatin in single cells. The epigenetic marks can indicate genomic loci that are in active or silent chromatin states (see, e.g., Epigenetics, Second Edition, 2015, Edited by C. David Allis; Marie-Laure Caparros; Thomas Jenuwein; Danny Reinberg; Associate Editor Monika Lachlan). In certain embodiments, single cell ChIP-seq can be used to determine chromatin states in single cells (see, e.g., Rotem, et al., Single-cell ChIP-seq reveals cell subpopulations defined by chromatin state. Nat Biotechnol. 2015 November; 33(11): 1165-1172). In certain embodiments, single cell ChIP-seq is used to determine genomic loci that are occupied by histone modifications, histone variants, transcription factors and/or chromatin modifying enzymes. In certain embodiments, epigenetic features can be chromatin contact domains, chromatin loops, superloops, or chromatin architecture data, such as obtained by single cell HiC (see, e.g., Rao et al., Cell. 2014 Dec. 18; 159(7):1665-80; and Ramani, et al., Sci-Hi-C: A single-cell Hi-C method for mapping 3D genome organization in large number of single cells Methods. 2020 Jan. 1; 170: 61-68).

Gene Selection

In some embodiments, methods for selecting genes for molecular spatial mapping are provided herein. The genes can be selected based on literature, relevance to tumorigenesis and metastasis, biological functions comprising apoptosis, angiogenesis, immunity, immunotolerance, immunocytotoxicity, autophagy, extracellular matrix degradation, or any functions related to cell proliferation, cell mobility, cell killing, or cell growth. The genes can also be selected based on mammary cells types and lineages, estrogen receptor (ER) signature, treatment resistance, and cancer related cellular programs comprising senescence, stemness, and immune evasion. The genes can be selected based on PAM50 model for breast cancer subtype classification, and refined for application in single cell gene expression data.

The genes can be selected based on proprietary knowledge for MBC single cell and single nucleus gene expression data. These proprietary knowledge of scRNA-seq and snRNA-seq datasets include, but not limited to, cell type specific gene expression, genes capable of predicting treatment response and prognosis, and genes reflecting cellular or biological programs within cell types.

In certain embodiments, the genes can be selected based on the panels of proteins/gene products previously used for CODEX and multiplexed ion beam imaging (MIBI) experiments (see, e.g., Angelo et al., Nat Med. 2014 April; 20(4): 436-442). The genes can also be selected based on prior selection of function genes. Data driven approach can also be employed in selecting genes. Data driven approach includes, but not limited to, selecting genes with differential expression in metastatic tumor tissues in comparison to normal counterpart tissues. Subsequently, the genes selected can be prioritized and used for calculating expression statistics across single cells isolated from metastatic tumor tissues of MBC or DCIS tissues using scRNA-seq and/or snRNA-seq data. The expression statistics can be calculated per cell type and in overall cell populations. The expression statistics can include values of mean, median, minimum level, and maximum level. Variability of gene expression can be calculated. Also, the number of cells with positive expression of a given gene and number of cells with negative expression of a given gene can be calculated. Those genes with no or low levels of expression in the single cells can be removed from the list. Redundant genes can be unified. The number of categories can be calculated. With these steps, a desired number of genes can be obtained for use of molecular spatial mapping.

RNA In Situ Hybridization

In some embodiments, RNA in situ hybridization method MERFISH is performed for determining spatial location of RNA molecules in tissue samples. The MERFISH method is a highly multiplexed smFISH imaging method that substantially increases the number of RNA species that can be simultaneously imaged in single cells by using combinatorial labeling and sequential imaging with error-robust encoding schemes (Chen et al., Spatially resolved, highly multiplexed RNA profiling in single cells. Science, 2015, 348: aaa6090; and Xia et al., Multiplexed detection of RNA using MERFISH and branched DNA amplification. Sci Rep. 2019 May 22;9(1):7721. doi: 10.1038/s41598-019-43943-8). MERFISH has been shown to be able to simultaneously measuring 140 RNA species with an encoding scheme that can both detect and correct errors and 1001 RNA species with an encoding scheme that can detect but not correct errors. Correlation analyses of the copy number variations and spatial distributions of these genes allowed one to identify groups of genes that are coregulated and groups of genes that share similar spatial distribution patterns inside the cell.

RNA In Situ Sequencing

In some embodiments, RNA in situ sequencing (ExSEQ) is performed for spatial localizing RNA molecules in tissue samples. ExSEQ (U.S. Pat. No. 10,059,990) is an in situ nucleic acid sequencing technique conducted in biological specimens that have been physically expanded (see also, Chen F. et al. Science 347, 543-548 (2015); and Lee J. H. et al. Science 343, 1360-1363 (2014)). This technique leverages the techniques for expansion microscopy to provide methods for in situ sequencing of nucleic acids as well as methods for fluorescent in situ sequencing in a process referred to herein as "expansion sequencing" and also referred to herein as "ExSEQ". ExSEQ comprises steps of (a) linking target nucleic acids present in the biological sample with a small molecule linker or a nucleic acid adaptor capable of linking to a target nucleic acid and to a swellable material; (b) embedding the biological sample comprising the target nucleic acids and attached small molecule linker or nucleic acid adaptor in a swellable material wherein the small molecule linker or the nucleic acid adaptor is linked to the target nucleic acids present in the sample and to the swellable material; (c) digesting proteins present in the biological sample; (d) swelling the swellable material to form a first enlarged biological sample that is enlarged as compared to the biological sample; (e) re-embedding the first enlarged sample in a non-swellable material; (f) modifying the target nucleic acids or the nucleic acid adaptor to form a nucleic acid adaptor useful for sequencing; and (g) sequencing the nucleic acids present in the first enlarged sample.

Slide-Seq

In some embodiments, Slide-seq is performed for determining spatial location of RNA molecules in tissue samples (see, e.g., Rodriques et al., Slide-seq: A Scalable Technology for Measuring Genome-Wide Expression at High Spatial Resolution. bioRxiv preprint first posted online Feb. 28, 2019; doi: dx.doi.org/10.1101/563395). In Slide-seq, RNA is transferred from freshly frozen tissue sections onto a surface covered in DNA-barcoded beads with known positions, allowing the spatial locations of the RNA to be inferred by sequencing.

High-Definition Spatial Transcriptomics

In some embodiments, high-definition spatial transcriptomics (HDST) is performed for determining spatial location of RNA molecules in tissue samples (see, e.g., Vickovic et al., High-definition spatial transcriptomics for in situ tissue profiling. Nat Methods. 2019 October;16(10):987-990). HDST captures RNA from histological tissue sections on a dense, spatially barcoded bead array. Each experiment recovers several hundred thousand transcript-coupled spatial barcodes at 2-μm resolution.

Histology

The methods and systems provided herein can also be used to align single cell resolution spatial maps with histological samples. In certain embodiments, only a few features need to be determined by histological methods because those features will be shared with a genome wide spatially resolved map of the present invention, such that the system can align single cells to the histological data (e.g., 1, 2, 3, 4, 5, 6, 7, 8, 9 or 10 features). For example, a spatial map can be used to bridge single cell data to a histological sample of the same tissue or anatomical region. In certain embodiments, the spatial map is registered on an anatomically annotated common coordinate framework (CCF) (see, e.g., Wang, et al., The Allen Mouse Brain Common Coordinate Framework: A 3D Reference Atlas, Cell. 2020 May 14;181(4):936-953.e20; Lein E, et al. Genome-wide atlas of gene expression in the adult mouse brain. Nature, 2007; 445:168-76; and Allen Mouse Brain Atlas: mouse.brain-map.org/). As used herein, an "anatomically annotated common coordinate framework" refers to a common reference map that uniquely and reproducibly defines any location in an organism (e.g., human) (see, e.g., Rood, et al., Toward a Common Coordinate Framework for the Human Body, Cell, 2019 Dec. 12;179(7):1455-1467). A CCF may use coordinate systems and the use of common landmarks for the integration of reference maps at differing scales in one common framework. The CCF is preferably a 3D framework.

Histology, also known as microscopic anatomy or microanatomy, is the branch of biology which studies the microscopic anatomy of biological tissues. Histology is the microscopic counterpart to gross anatomy, which looks at larger structures visible without a microscope. Although one may divide microscopic anatomy into organology, the study of organs, histology, the study of tissues, and cytology, the study of cells, modern usage places these topics under the field of histology. In medicine, histopathology is the branch of histology that includes the microscopic identification and study of diseased tissue. Biological tissue has little inherent contrast in either the light or electron microscope. Staining is employed to give both contrast to the tissue as well as highlighting particular features of interest. When the stain is used to target a specific chemical component of the tissue (and not the general structure), the term histochemistry is used. Antibodies can be used to specifically visualize proteins, carbohydrates, and lipids. This process is called immunohistochemistry, or when the stain is a fluorescent molecule, immunofluorescence. This technique has greatly increased the ability to identify categories of cells under a microscope. Other advanced techniques, such as nonradioactive in situ hybridization, can be combined with immunochemistry to identify specific DNA or RNA molecules with fluorescent probes or tags that can be used for immunofluorescence and enzyme-linked fluorescence amplification.

Spatial Data Technology

The spatial data used in the present invention can be any spatial data. Methods of generating spatial data of varying resolution are known in the art, for example, ISS (Ke, R. et al. In situ sequencing for RNA analysis in preserved tissue and cells. Nat. Methods 10, 857-860 (2013)), MERFISH (Chen, K. H., Boettiger, A. N., Moffitt, J. R., Wang, S. & Zhuang, X. Spatially resolved, highly multiplexed RNA profiling in single cells. Science 348, (2015)), smFISH (Codeluppi, S. et al. Spatial organization of the somatosensory cortex revealed by cyclic smFISH. biorxiv.org/lookup/doi/10.1101/276097 (2018) doi:10.1101/276097), osmFISH (Codeluppi, S. et al. Spatial organization of the somatosensory cortex revealed by osmFISH. Nat. Methods 15, 932-935 (2018)), STARMap (Wang, X. et al. Three-dimensional intact-tissue sequencing of single-cell transcriptional states. Science 361, eaat5691 (2018)), Targeted ExSeq (Alon, S. et al. Expansion Sequencing: Spatially Precise In Situ Transcriptomics in Intact Biological Systems. biorxiv.org/lookup/doi/10.1101/2020.05.13.094268 (2020) doi:10.1101/2020.05.13.094268), seqFISH+(Eng, C.-H. L. et al. Transcriptome-scale super-resolved imaging in tissues by RNA seqFISH+. Nature (2019) doi:10.1038/s41586-019-1049-y), Spatial Transcriptomics methods (e.g., Spatial Transcriptomics (ST))(Stihl, P. L. et al. Visualization and analysis of gene expression in tissue sections by spatial transcriptomics. Science 353, 78-82 (2016)) (now available commercially as Visium), Slide-seq (Rodriques, S. G. et al. Slide-seq: A scalable technology for measuring genome-wide expression at high spatial resolution. Science 363, 1463-1467 (2019)), or High Definition Spatial Transcriptomics (Vickovic, S. et al. High-definition spatial transcriptomics for in situ tissue profiling. Nat. Methods 16, 987-990 (2019)). In certain embodiments, proteomics and spatial patterning using antenna networks is used to spatially map a tissue specimen and this data can be further used to align single cell data to a larger tissue specimen (see, e.g., US20190285644A1). In certain embodiments, the spatial data can be immunohistochemistry data or immunofluorescence data.

Use of Shared Features

The spatial methods described herein share features with the single cell methods in order to generate the single cell resolution maps of the present invention. In certain embodiments, gene expression or transcriptome data (e.g., genes) can be shared between the single cell data and spatial data. Shared genes can advantageously allow multimodal data that includes gene expression to be spatially aligned. For example chromatin accessibility data, proteomics data, patch-clamp and morphological data can be spatially aligned to single cells. Shared regions of accessible chromatin can be used to spatially align genome wide accessibility to a specimen. Shared regions of epigenetic marks can be used to spatially align genome wide chromatin modifications to a specimen. In certain embodiments, multiple single-Chip data sets for different markers may be used to determine spatially resolved chromatin patterns. In certain embodiments, specific regions of a genome may be labeled in spatial data and chromatin accessibility or epigenetic marks determined for those regions. These shared regions with single cell data can be used to generate a genome wide spatially resolved map. In certain embodiments, CITE-seq can be used to align spatial data that includes gene expression and/or surface labeled proteins. For example, CITE-seq can be used to align transcriptome data to spatially data that only includes surface marker labeling.

Screening for Modulating Agents

In certain embodiments, the invention provides for screening of therapeutic agents capable of modulating gene signatures and/or biological programs. In certain embodiments, agents capable of modulating the tumor microenvironment are screened. In certain embodiments, the method comprises: a) applying a candidate agent to a cell population comprising tumor cells and/or immune cells; and b) detecting modulation of one or more phenotypic aspects of the cell population by the candidate agent (e.g., selected genes, Table 1), thereby identifying the agent. The phenotypic aspects of the cell population that is modulated may be a gene signature or biological program specific to a cell type or cell phenotype or phenotype specific to a population of cells (e.g., an immune phenotype). In certain embodiments, steps can include administering candidate modulating agents to cells, detecting identified cell (sub)populations for changes in signatures, or identifying relative changes in cell (sub) populations which may comprise detecting relative abundance of particular gene signatures. The phenotype may be a change in secretion of cytokines associated with an anti-tumor response. In certain embodiments, candidate agents are screened in vivo models (e.g., mouse tumor models).

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

Aspects of the present disclosure relate to the correlation of an agent with the spatial proximity and/or epigenetic profile of the nucleic acids in a sample of cells. In some embodiments, the disclosed methods can be used to screen chemical libraries for agents that modulate spatial gene expression profiles, and/or relationships thereof. In some embodiments, the disclosed methods can be used to screen chemical libraries for agents that modulate chromatin architecture epigenetic profiles, and/or relationships thereof.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, agents capable of shifting the signatures are screened. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

In certain embodiments, Cmap is used to screen for in silico for agents capable of shifting a signature. The Connectivity Map (Cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention in silico.

Further embodiments are illustrated in the following Examples which are given for illustrative purposes only and are not intended to limit the scope of the invention.

EXAMPLES

The following examples are included for illustrative purposes only and are not intended to limit the scope of the invention.

Example 1. Single Cell RNA Sequencing and Single Nucleus RNA Sequencing

Freshly dissected tissue samples were placed in ice cold PBS and kept cold during microdissection. Microdissections were performed under a stereomicroscope as described elsewhere. Dissected subregions were placed into ice-cold RNAlater (Ambion, RNAlater, #7020) and stored at 4° C. overnight. Then samples were processed for nuclei isolation immediately or stored in −80° C. Nuclei were isolated by sucrose gradient centrifugation with two modifications: RNAse inhibitor (Clontech, Recombinant Ribonuclease Inhibitor, #2313A, 40 units/μl) was added to the resuspension buffer (final 1 U/μl), and nuclei were filtered through a 35 μm cell strainer (Falcon, #352235) before sorting. Nuclei were labeled with ruby dye (Thermo Fisher Scientific, Vybrant DyeCycle Ruby Stain, #V-10309) added to the resuspension buffer at a concentration of 1:800. Nuclei were kept on ice until sorting using Fluorescence Activated Cell Sorting into 96 well plates containing 5 μl of TCL lysis buffer (Qiagen, #1031576) added with 10% 2-mercaptoethanol. FACS gating was set on FSC, SSC, and on fluorescent channels to include only Ruby+ or Ruby+GFP+ nuclei (for nuclei tagged by GFP-KASH or EdU-GFP). Each 96 well plate included an empty well as a negative control and a population well of 50-100 nuclei as a positive control.

Single nucleus RNA was first purified using RNAClean XP beads (Beckman Coulter, Agencourt RNA-Clean XP, #A63987) at 2.2× beads to sample volume ratio. Single nucleus derived cDNA libraries were generated following a modified Smart-seq2 method. Briefly, beads were eluted into 4 μl elution mix made of 1 μl RT primer (10 μm), 1 μl dNTP mix (10 mM each, Thermo Fisher Scientific, #R0191), 1 μl RNAse inhibitor diluted at 1:10 in water (final 1 U/μl), and 1 μl $H_2O$. Eluted samples were incubated at 72° C. for 3 min and immediately placed on ice. Each sample was added with 7 μl reverse transcription (RT) mix made of 0.75 μl $H_2O$, 01 μl Maxima RNase-minus RT (Thermo Fisher Scientific, Maxima Reverse Transcriptase, #EP0752), 2 μl 5× Maxima RT buffer, 2 μl Betaine (Sigma Aldrich, 5M, #B0300), 0.9 μl MgCl2 (Sigma Aldrich, 100 mM, #M1028), 1 μl TSO primer (10 μm), 0.25 μl RNase inhibitor (40 U/μl). The RT reaction was incubated at 42° C. for 90 min and followed by 10 cycles of (50° C. for 2 min, 42° C. for 2 min), then heat inactivated at 70° C. for 15 min. Samples were then amplified with an addition of 14 μl polymerase chain reaction (PCR) mix made of 1 μl $H_2O$, 0.5 μl ISPCR primer (10 μm), 12.5 μl KAPA HiFi HotStart ReadyMix (KAPA Biosystems, #KK2602). The PCR reaction was performed as follows: 98° C. for 3 min, 21 cycles of (98° C. for 15 sec, 67° C. for 20 sec, 72° C. for 6 min), and final extension at 72° C. for 5 min. PCR product was purified using AMPure XP (Beckman Coulter, Agencourt AMPure XP, #A63880) twice and eluted in TE buffer (Thermo Fisher Scientific, #AM9849). Purified cDNA libraries were analyzed on Agilent 2100 Bioanalyzer (Agilent, Agilent High Sensitivity DNA Kit, #5067-4626) and quantified using picogreen (Thermo Fisher Scientific, Quant-iT PicoGreen dsDNA Assay Kit, #P11496) on a plate reader (Biotek, Synergy H4, wavelength at 485 nm, 528 nm with 20 nm bandwidth). Sequencing libraries were prepared using Nextera XT kit (Illumina, #FC-131-1024) as described previously [42]. Single nucleus cDNA libraries were sequenced on an Illumina NextSeq 500 to an average depth of 632,169 reads.

Drop-seq has previously been developed for generating single cell libraries. The major advantages are speed, numbers and cost. The cell number is at least 10× greater than was possible with previous methods, and the cost per library is about 100× lower than that of previous methods. In addition, nuclear RNAs are enriched for recently transcribed genes, which facilitates detection of transcriptional changes following a stimulus. The current drawback is that the number of nuclei than can be profiled is limited. Applicants therefore used a hybrid method, Dronc-seq, that combines the strengths of its two parents.

The Drop-seq method (Macosko et al., 2015) uses a microfluidic device to co-encapsulate individual cells in reverse emulsion aqueous droplets in an oil medium together with one uniquely barcoded mRNA-capture bead. The oligonucleotides on the bead are each comprised of four parts: a constant sequence (identical on all primers) for use as a priming site for PCR and sequencing; a “cell barcode” that is the same across all the primers on the surface of any one bead, but different from the cell barcodes on all other beads; a random sequence that enables reads from the same mRNA transcript to be identified computationally (UMI); and an oligo dT sequence for capturing polyadenylated mRNAs. Once the cell and bead are co-encapsulated, the cell lyses and its mRNA is captured on the bead. The emulsion is then broken, and the mRNAs are reverse-transcribed, amplified, and sequenced in a single reaction. The barcodes are used to correct for PCR amplification bias and to infer each transcript’s cell of origin. The clusters included all major cell classes and, for several classes, multiple cell types within several of the classes. The analysis also predicted markers of new types that Applicants validated immunohistochemically. Applicants have therefore begun purifying these classes by FACS prior to Drop-Seq. Applicants recently profiled 13,000 bipolar cells, and have been able to double the number of types in the initial dataset.

Recent studies demonstrated the feasibility of sequencing pre-mRNAs from isolated nuclei. Applicants have now adapted these methods for both full-length and 3' directed single-nuclei mRNA-seq of intact nuclei. Our method robustly produces RNA libraries from single nuclei in the adult mammalian brain. The improved RNA libraries, consistently detect 4,000-7,000 genes per cell, while reducing the required sequencing depth. Applicants re-assembled the transcriptome from population libraries and show that Applicants' polyA nuclear RNAs are similar to cytoplasmic RNAs in structure (largely spliced), but also reveal new splice isoforms and potential lincRNAs.

Analysis of nuclei clusters. Clustering analysis partitions nuclei into groups, such that nuclei from the same group share more similarity than nuclei from different groups. The quality of the grouping can be measured using the Dunn index $$DB = \frac{\min_{1 \le i < j \le n} d(i, j)}{\max_{1 \le k \le n} d'(k)},$$

where d(i, j) represents the inter-group distance between group i and j, and d'(k) represents the intragroup distance of group k.

Applicants expect that the coherent structure in transcriptomes of cells of high similarity generates observations that lie on a low-dimensional manifold in the high-dimensional measurement space [52]. In this case, data points for cells belonging to the same group would lie on a continuous smooth low-dimensional manifold, and data points for cells from different groups would lie on different manifold structures. Applicants confine distances used in calculating the Dunn index to the low-dimensional manifold structure and define the distance d'(k) as $$\hat{\Phi}_{pq} = \underset{\Phi_{pq}}{\operatorname{argmin}} \max\{d_{mn} \mid d_{mn} \in \Phi_{pq}\}$$

$$d'(k) = \max\left\{d_{mn} \mid d_{mn} \in \bigcup_{p,q} \hat{\Phi}_{pq}\right\},$$

where p, q, m, and n are data points belonging to the group k, dmn represents the pairwise distance of data points m and n, and _p q represents a path connecting p and q through data points belonging to the group k. Applicants define the distance d(i, j) similarly to d'(k) and confine p, q, m, and n to be data points belonging to the union of the groups i and j.

Here, Applicants describe a pipeline of techniques to obtain nuclei clusters. Applicants first normalize data, then Applicants estimate false negatives and reduce their impact on the calculation of dmn. Next, Applicants perform modified PCA and tSNE to map the low-dimensional structures to a 2-D space, where dmn and _p q in the 2-D space represent their high-dimensional counterparts. The mapping transforms each of the low dimensional manifold structures to dense data clouds in the 2-D space, permitting grouping of cells by a density clustering technique. This non-linear mapping is particularly useful for data sets, where the scales of d'(k) for different cell groups are very different and d'(k) are affected by large noises in the original high dimensional space. Finally, Applicants identify cell sub-clusters within each cell cluster by the biSNE algorithm. The PCA-tSNE, biSNE, and density clustering are applied hierarchically to each cell clusters to obtain clusters at finer level. In each iteration, the Dunn index with the defined local distances d'(k) can be used to evaluate the quality of the clustering assignment.

Normalization. Each library of single nuclei was prepared individually. Biases exist among libraries due to inevitable differences in lysis efficiency, priming rate at RT, amplification efficiency during the initial PCR, the equalization for tagmentation, and ratios in the final sequencing pooling. Although several experimental methods have been developed to mitigate biases, including, for example, adding spike-in or using unique molecular identifiers, Applicants note that these methods would only help to reduce, at best, the amount of bias introduced after the initial PCR step, however significant amount of bias occurs before that step. Applicants assume that cells of the same type should highly express a set of genes that are tightly regulated and exhibit small "real" intercellular variability. An example of such a gene set includes ribosomal and cytoskeleton genes in stem cells or housekeeping genes in dendritic cells that was previously used to normalize single cell sequencing data. Using only a small set of highly expressed and lowly variable genes, as opposed to using all genes or genes within the middle quantile, provides robustness against noise, because measurements of highly expressed genes are resistant to sampling noise, and lowly variable measurements unlikely to have been corrupted by large noise. In addition, small intercellular variance enables simple statistical models, such as Gaussian model, to yield good estimates. Similar reasoning underlies previously described normalized methods such as TMM and DESeq. However, these methods are designed for population RNA-Seq data, and Applicants empirically found that they not compatible with single cell data. A modified DESeq normalization which takes into account of massive false negatives common to single cell data did give comparable performance to Applicants' procedure.

To identify the set of genes for normalization, Applicants first calculate differences and averages of log transformed expression level of each gene between a given pair of cells, and plot the distribution of differences by averages on an MA plot. Then, gene density in this distribution is estimated and genes within the most densely plotted regions are selected. Applicants calculate a scaling factor as the average of the log expression differences of selected genes. The second cell is normalized with respect to the first cell by dividing gene expressions of the second cell by the scaling factor. Specifically, the log expression difference of gene j between two cells is given by $$r_{12\_j} = \log(e_{2j}) - \log(e_{1j}),$$

and the average of log expression of gene j is given by $$a_{12\_j} = [\log(e_{1j}) + \log(e_{2j})]/2.$$

where $e_{ij}$ denotes the expression level of gene j in cell i. Gene j is selected into the gene set SJ, if $r_{i2\_j}$ and $a_{12\_j}$, coordinates of gene j, are within the region having density above the top 70 percentile in the MA plot. The scaling factor is obtained by $$s = \sum_{j, j \in 3_J} r_{12\_j} / |\mathbb{S}_J|.$$

Then the second cell is normalized as $$e'_{2j}=e_{2j}/s.$$

To normalize single cells of different types, cells are first clustered into separate groups, each of which contains cells of a similar type. This step ensures that normalization complies with Applicants' assumption that cells are of the same type. Then normalization is performed for each group separately. Within each group, scaling factors are estimated for each cell with respect to multiple reference cells, which are chosen based on the number of genes detected, for example, cells having number of genes detected around the 80 percentile. Although any particular reference cell could be affected by erroneous measurements to various degrees, using multiple reference cells reduces the effect of these errors in the normalization.

Specifically, for a given group of cells {i|i∈Cg and g∈G}, a set of cells that have number of genes detected above 80 percentile are selected as reference cells {r|r∈Cgr and Cgr⊂Cg}. The scaling factor sir for each cell i with respect to each reference cell r is calculated. To relate sir obtained with different reference cells, Applicants solve the optimization problem $$\{\hat{a}_r \mid r \in \mathbb{C}_{gr}\} = \underset{a_r, r\in\mathbb{C}_{gr}}{\operatorname{argmax}} \sum_{i\in\mathbb{C}_g} \underset{r\in\mathbb{C}_{gr}}{Var}[\log(s_{ir}) - \log(a_r)].$$

and scaling factors are estimated as $$s_i = \underset{r\in\mathbb{C}_{gr}}{\operatorname{median}}\left(\frac{S_{ir}}{\hat{a}_r}\right).$$

To normalize cells from different groups, Applicants use group scaling factors estimated for each group aggregates, which are obtained by averaging all cells within a same group. Cells from a same group are normalized using their group scaling factor. Specifically, for each group g E G, the group aggregate is calculated as $$e_{gj} = \sum_{i\in\mathbb{C}_g} e'_{ij},$$

where $e_{gj}$ denotes the expression level of gene j in group g, and e'ij is the normalized expression level of gene g in cell i. Multiple reference group aggregates are selected for the estimation of group scaling factors.

Comparison of Applicants' normalization method with TMM and DESeq. Applicants consider a model for observed expression level eij given true expression level $$x_{ij}, e_{ij}=s_i \cdot \epsilon_{ij} \cdot x_{ij}.$$

where si represents the scaling factor of cell i, $\epsilon_{ij}$ represents the technical noise of gene j measured in cell i, and xij represents the true expression level of gene j measured in cell i. Rewrite eij on log scale, log(eij)=log(si)+log(∈ij)+log (xij). In Applicants' normalization, the normalization factor is obtained by averaging, between cell i1 and i2, the differences in the expression of selected subset of genes SJ.

$$\sum_{j\in S_J}(\log(e_{1j})-\log(e_{2j}))/|\mathbb{S}_J| = \log(s_1)-\log(s_2) + \sum_{j\in S_J}(\log(\epsilon_{1j})-\log(\epsilon_{2j}))/|\mathbb{S}_J| + \sum_{j\in S_J}(\log(x_{1j})-\log(x_{2j}))/|\mathbb{S}_J|.$$

As ∈ij for j∈SJ is assumed to be lognormally distributed with zero mean (modeling PCR and sampling noise), and genes within SJ are not differentially expressed on average, it follows that $$\log(s_1)-\log(s_2) = \sum_{j\in S_J}(\log(e_{1j})-\log(e_{2j}))/|\mathbb{S}_J|.$$

In TMM normalization, the SJ is replaced by $$S_Q=\{j|e_{ij}\in[e_{qa},e_{qb}]\},$$

where $e_{qa}$ and $e_{qb}$ are $a_{th}$ and $b_{th}$ quantiles of $e_{ij}$. Applicants find the assumption that $$\Sigma_{j\in S_Q}[\log(x_{1j})-\log(x_{2j})]=0$$

might not hold true for single cell RNA-Seq data. In DESeq normalization, $e_{ij}$ is first normalized by its geometric mean across all cells, $$\log(e_{ij}) - \sum_i \log(e_{ij})/|I| = \log(s_i) - \sum_i \log(s_i)/|I| + \log(\epsilon_{ij}) - \sum_i \log(\epsilon_{ij})/|I| + \log(x_{ij}) - \sum_i \log(x_{ij})/|I|.$$

Then median is taken over all genes, $$\underset{j}{median}\left(\log(e_{ij}) - \sum_i \log(e_{ij})/|I|\right) = \log(s_i) - \sum_i \log(s_i)/|I| + \underset{j}{median}\left(\log(\epsilon_{ij}) - \sum_i \log(\epsilon_{ij})/|I|\right) + \underset{j}{median}\left(\log(x_{ij}) - \sum_i \log(x_{ij})/|I|\right).$$

Assume that the median of $\epsilon_{ij}$ can be replaced by the mean of $\epsilon_{ij}$, $$\underset{j}{median}\left(\log(\epsilon_{ij}) - \sum_i \log(\epsilon_{ij})/|I|\right) = \sum_j\left(\log(\epsilon_{ij}) - \sum_i \log(\epsilon_{ij})\right)\Big/|I||J| = \sum_j \log(\epsilon_{ij})/|J| - \sum_i \frac{1}{|I|}\sum_j \log(\epsilon_{ij})/|J|.$$

It shows that the median of normalized eij is a good estimator for the scaling factor si only if $$\sum_i \log(\epsilon_{ij}) = 0 \text{ and } \underset{j}{median}\left(\log(x_{ij}) - \sum_i \log(x_{ij})/|I|\right) = 0.$$

However, because single cell RNA-Seq data contains substantial amount of false negative measurements, as discussed in the next section, these conditions might not hold true generally. Applicants propose a modified DESeq normalization, which gives comparable performance to Applicants' normalization method when applied to synthetic test data. In the modified DESeq normalization, the geometric mean and median are taken over only genes whose measured expression level eij>0. This leads to $$\underset{j,e_{ij}\neq 0}{median}\left(\log(e_{ij}) - \sum_i \log(e_{ij})/|I|\right) = \log(s_i) - \sum_i \log(s_i)/|I| + \underset{j,e_{ij}\neq 0}{median}\left(\log(\epsilon_{ij}) - \sum_i \log(\epsilon_{ij})/|I|\right) + \underset{j,e_{ij}\neq 0}{median}\left(\log(x_{ij}) - \sum_i \log(x_{ij})/|I|\right).$$

In this formulation, the expression level $\epsilon_{ij}$ for {j|eij>0} is not subjected to false negative, and is assumed to be lognormally distributed with zero mean. Therefore, the median of ϵij for {j|eij>0} is $$\underset{j,e_{ij}\neq 0}{median}\left(\log(\epsilon_{ij}) - \sum_i \log(\epsilon_{ij})/|I|\right) = \sum_{j,e_{ij}\neq 0} \log(\epsilon_{ij})/|J| - \sum_i \frac{1}{|I|} \sum_{j,e_{ij}\neq 0} \log(\epsilon_{ij})/|J| = 0.$$

And further assume that there exist some genes that are not differentially expressed among all cells, then the median is a robust measure to find one such gene, $$\underset{j,e_{ij}>0}{median}\left(\log(x_{ij}) - \sum_i \log(x_{ij})/|I|\right) = 0.$$

Therefore, Applicants can obtain the scaling factor by $$\log(s_i) - \sum_i \log(s_i) = \underset{j,e_{ij}>0}{median}\left(\log(e_{ij}) - \sum_i \log(e_{ij})/|I|\right).$$

Estimation of missed detection probability. Single nuclei transcriptome libraries are amplified from extremely small input materials. As such, Applicants expect that some transcripts that are lowly expressed will not be detected (false negatives). The probability of such missed detection increases for lowly expressed transcripts and lower quality libraries. Such false negatives are detrimental to various analyses. For example, they invalidate the normal distribution assumption underlying typically used Student's t-test, leaving the statistical test unjustified. In addition, false negatives confound the identification of bimodally expressed genes, such as cell type specific markers. Previous studies accounted for such false negatives by combining estimation of cell quality and gene expression. These methods were based on parametric estimation of gene expression distribution. However, distribution of gene expression cannot be readily fitted by a single parametric function. In contrast to these methods, Applicants developed a Bayesian method to estimate the likelihood of an observed zero measurement being a missed detection. Our approach is based on a non-parametric estimation for gene expression distribution.

In some embodiments, the method used herein is based on two observations: a) Detection rates depend on expression level. The higher a gene is expressed, the more likely it can be detected. b) Detection rates depend on library quality. Genes are more likely to be detected in libraries of high quality. Applicants model these two observations as:

- prior distributions: distributions of expression levels for each gene in cells of the same type
- sampling probabilities: detection probabilities at different expression levels for each cell.

For each observed eij=0 of gene j in cell i, Applicants then estimate the posterior distribution for two mutually exclusive hypotheses that eij is a missed detection or that gene j is not expressed in cell i. Specifically, the distribution of expression level of gene j is calculated as mixture of two distributions. The first one is the probability that gene j is not expressed $$p_j(x=0) = \frac{\sum_{i\in\{e_{ij}=0\}} 1}{\sum_i 1},$$

where x denotes the true expression level. The second one is a conditional distribution of expression levels of gene j given that gene j is expressed. This distribution is estimated using a KDE based method [59] using gene expression levels $e_{ij}$ from cells i, {i|$e_{ij}$>0}. Combining two parts yields $$p_j(x)=p_j(x=0)+[1-p_j(x=0)]p_{j\_KDE}(x),$$

where x denotes the expression level. The detection probability (1−dropout probability) for a cell i is modeled using a geometric distribution parameterized by βi, as it captures the Poisson sampling process, mechanism underlying detection stochasticity $$\Lambda(x,\beta_i) = 1 - e^{-t},\ t = \beta_i\begin{bmatrix}1\\x\end{bmatrix} = \beta_{i0} + \beta_{i1}x$$

$$0 \le \Lambda(x,\beta_i) \le 1,$$

where x denotes expression level. Given observed data eij, the expected value of the log likelihood function is given by $$E[L] = \sum_{j\in\{e_{ij}>0\}} \log(1\cdot\Lambda(e_{ij},\beta_i)) + \sum_{j\in\{e_{ij}=0\}}\sum_x p_j(x)\log(p_j(x)(1-\Lambda(x,\beta_i))).$$

In each iteration, the log likelihood function is maximized using gradient descent.

$$\hat{\beta}_i = \underset{\beta_i}{\mathrm{argmax}}\,E[L]$$

$$\frac{\partial E[L]}{\partial \beta_i} = \sum_{j\in\{e_{ij}>0\}} \frac{1}{\Lambda(e_{ij},\beta_i)}\frac{\partial\Lambda(e_{ij},\beta_i)}{\partial\beta_i} + \sum_{j\in\{e_{ij}=0\}}\sum_x p_j(x)\frac{1}{1-\Lambda(x,\beta_i)}(-1)\frac{\partial\Lambda(x,\beta_i)}{\partial\beta_i}.$$

Because _(x, β) is constrained to be non-negative, its derivative is modified with a rectifier so that _(x, β) is differentiable for any x, $$h(x)=\frac{\log(\exp(x\cdot N)+1)}{N},\text{ where } N \text{ is a large number}$$

$$\frac{\partial\Lambda}{\partial\beta}\approx\frac{\partial h}{\partial\Lambda}\frac{\partial\Lambda}{\partial\beta}=\frac{1}{1+\exp(-\Lambda(x,\beta)\cdot N)}\cdot e^{-t}\begin{bmatrix}1\\x\end{bmatrix}.$$

Then the distribution of expression levels are updated by $$p(e_{ij}=0\mid x_{ij}>0)=\sum_x p_j(x)\left(1-\Lambda\left(x,\hat{\beta}_i\right)\right)$$

$$p(x_{ij}=0\mid e_{ij}=0)=\frac{p_j(x_{ij}=0)}{p_j(x_{ij}=0)+p(e_{ij}=0\mid x_{ij}>0)}$$

$$p_j(x=0)=\frac{\sum_{j\in\{e_{ij}=0\}}p(x_{ij}=0\mid e_{ij}=0)}{\sum_{j\in\{e_{ij}=0\}}p(x_{ij}=0\mid e_{ij}=0)+\sum_{j\in\{e_{ij}>0\}}1}$$

$$p_j(x)=p_j(x=0)+[1-p_j(x=0)]p_{j\_KDE}(x),$$

where p ($x_{ij}=0|e_{ij}=0$) denotes the probability that gene j is not expressed in cell i. Applicants implemented an expectation-maximization (EM) algorithm that alternates between performing an expectation step for L, and a maximization step for searching the maximizer $\hat{\beta}_i$ of E[L]. The probability p ($x_{ij}=0|e_{ij}=0$) is incorporated in calculations of summary statistics and distances to weight zero measurements. The higher the probability, the more likely that an observed zero represents an truly unexpressed gene in a cell, and the more Applicants weight the contribution of the zero. Conversely, the lower the probability, the higher the chance that it is false negative, and the lower Applicants weight its contribution in an analysis.

Specifically, Applicants weight summary statistics, Euclidean distance, Pearson correlation coefficient, and cosine similarity in the following ways.

I. the weighted gene expression mean: where $$u_j=\sum_i e_{ij}\omega_{ij}\Big/\sum_i\omega_{ij},$$

$$\omega_{ij}=\begin{cases}p(x_{ij}=0\mid e_{ij}=0) & \text{if } e_{ij}=0\\ 1 & \text{if } e_{ij}>0\end{cases}.$$

II. the weighted Euclidean distance between two cells x, y:

$$\omega_j=\omega_{xj}\omega_{yj}$$

$$d_{xy}=\frac{\sum_j(e_{xj}-e_{yj})^2\omega_j}{\sum_j\omega_j}.$$

III. the weighted Pearson correlation coefficient between two cells x, y:

$$\hat{e}_x=e_x-u_x,\quad \hat{e}_y=e_y-u_y$$

$$S_{xy}=\sum_j\hat{e}_{xj}\hat{e}_{yj}\omega_j,\quad S_{xx}=\sum_j\hat{e}_{xj}^2\omega_j,\quad S_{yy}=\sum_j\hat{e}_{yj}^2\omega_j$$

$$p_{xy}=\frac{S_{xy}}{\sqrt{S_{xx}S_{yy}}}.$$

IV. the weighted cosine similarity is calculated in a similar way except no data centering.

V. the weighted Euclidean distance between two cells x, y under a linear transformation of linear combinations of genes, Y=XA, where X is an i×j matrix, and A is a j×k transformation matrix, is given by $$\omega_j=\omega_{xj}\omega_{yj}$$

$$d_{xy}=\sum_k\left(\frac{\sum_j a_{jk}(e_{xj}-e_{yj})\omega_j}{\sum_j\omega_j}\right)^2.$$

VI. the weighted Pearson correlation coefficient between two cells x, y under a linear transformation of linear combinations of genes as above is given by $$u_x=\frac{1}{|K|}\sum_k\frac{\sum_j a_{jk}e_{xj}\omega_j}{\sum_j\omega_j},\quad u_y=\frac{1}{|K|}\sum_k\frac{\sum_j a_{jk}e_{yj}\omega_j}{\sum_j\omega_j}$$

$$\hat{e}_{xk}=\frac{\sum_j a_{jk}e_{xj}\omega_j}{\sum_j\omega_j}-u_x,\quad \hat{e}_{yk}=\frac{\sum_j a_{jk}e_{yj}\omega_j}{\sum_j\omega_j}-u_y$$

$$S_{xy}=\sum_k\hat{e}_{xk}\hat{e}_{yk},\quad S_{xx}=\sum_k\hat{e}_{xk}^2,\quad S_{yy}=\sum_k\hat{e}_{yk}^2$$

$$\rho_{xy}=\frac{S_{xy}}{\sqrt{S_{xx},S_{yy}}}.$$

VII. the weighted cosine similarity is calculated similarly as the weighted correlation coefficient except no data centering.

VIII. the weighted covariance between two genes under a linear transformation of linear combinations of genes as above is given by $$u_{xk}=\frac{\sum_i\sum_j a_{jk}\hat{e}_{ij}\omega_{ij}}{\sum_i\sum_j\omega_{ij}}=\frac{\sum_j a_{jk}\sum_i\hat{e}_{ij}\omega_{ij}}{\sum_i\sum_j\omega_{ij}}=0,$$

$\hat{e}$ is centered along $i$

-continued $$\mathrm{cov}(k,k') = \frac{\sum_i \left(\sum_j a_{jk}\hat{e}_{ij}\omega_{ij}\right)\left(\sum_j a_{jk'}\hat{e}_{ij}\omega_{ij}\right)}{\sum_i \left(\sum_j \omega_{ij}\right)^2}.$$

PCA and tSNE. To project cells to two dimensional space, Applicants first perform principal component analysis (PCA) to project original data to reduce linear dimensions, where most significant variance of the data is preserved as determined based on the largest eigenvalue gap. Applicants then calculate the cosine distance of cells on the PCA reduced dimensional space. Finally, Applicants use t-distributed Stochastic Neighbor Embedding (tSNE) [53, 61, 62] with the cosine distance to further map cells to two dimensions, where Euclidean distances of closely projected cells represent their cosine distances. The cosine distance depends the angle between two vectors defined by gene expressions in the high dimensional space. It is preferred in Applicants' analysis over Euclidean distance and correlation distance, because it is more robust to noise than Euclidean distance and it is invariant under rotational transformations, such as PCA.

I. weighted PCA. The PCA analysis is performed usually using singular value decomposition (SVD) or eigenvalue decomposition (EVD) on the covariance matrix, which scales quadratically with the number of genes. Given large number of genes, more than 25,000, in Applicants' data, it is computational costly to directly perform SVD or EVD on the large covariance matrix. In order to get principal components, or the transformation matrix A, while accounting for weights, Applicants first center the original data matrix E across genes to get $\vec{E}$, where eij is the expression level of gene j in cell i. Next, Applicants perform SVD on centered data matrix $\vec{E}$ to get A*. Applicants calculate the weighted covariance matrix Cw on $\vec{E}$ under the linear transformation defined by the matrix A*. Applicants then perform SVD or EVD on Cw to get A.

II. tSNE with cosine distance. Applicants modified the original tSNE to allow dimensionality reduction based on a weighted cosine similarity. The original tSNE technique projects data in a non-linear way to low dimensional space, such that Euclidean distances between neighboring data points in the low dimensional space overall represent distances between these neighboring data points, or local distances, in the high dimensional space. The input to tSNE is a distance matrix, describing all pairwise distances in the high dimensional space. In order to apply tSNE, Applicants first transform the weighted cosine similarity to cosine distance by exploring relationships between the two measures on the closest data points. Specifically, given a cell and its gene expression measurements denoted by a n dimensional vector x, the measurements of its neighbor y is modeled as $$y=k(x+d),$$

where k is a scaling factor and d denotes the distance between x and y. Under the null hypothesis that x and y are measured from two cells of the same type, d is drawn from a Gaussian distribution with zero mean and variance σ. Our goal is to estimate the distance magnitude |d|, given the measured angle ϕ between x and y. Geometrically, the vector d lies on a hypersphere defined by radius |d|. The volume and surface area of a hypersphere of dimension n (n-sphere) has the following properties $$S_n=(n+1)V_{n+1}$$

$$dS_n=(n+1)dV_{n+1}$$

the volume element is $$\begin{aligned} dV_{n+1} &= |d|^n \sin^{n-1}(\phi_1)\sin^{n-2}(\phi_2)\ \dots\ \sin(\phi_{n-1})d|d|d\phi_1 d\phi_2\ \dots\ d\phi_n \\ &= \sin^{n-1}(\phi_1)d\phi_1 \cdot g(|d|, \phi_2, \dots, \phi_n) \\ dS_n &= \sin^{n-1}(\phi_1)d\phi_1 \cdot (n+1)g(|d|, \phi_2, \dots, \phi_n). \end{aligned}$$

The probability of drawing d in a n-sphere of radius |d| with an angle ϕ from x scales as sinn−1(ϕ). When n is large, most of d lie perpendicular to x, thus there exists a unique mapping between |d| and ϕ.

$$\cos(\phi) = \frac{1}{\sqrt{(1+|d|)^2+1}}$$

$$|d| = \sqrt{\frac{1}{\cos^2(\phi)} - 1}$$

Differential gene expression and pathway analysis. Applicants use an adjusted Welch's t-test for identifying differentially expressed genes. Applicants applied weights in the calculation of summary statistics, such as sample mean, sample variance, and effective degrees of freedom, used in Welch's t-test. Specifically, to find the significance level of gene j between cells in group X and cells in group Y, $$u_{xj} = \sum_{i,i\in\mathbb{X}} \omega_{ij},\quad n_{yj} = \sum_{i,i\in\mathbb{Y}} \omega_{ij},$$

$$u_{xj} = \sum_{i,i\in\mathbb{X}} e_{ij}\omega_{ij}/n_{xj},\quad u_{yj} = \sum_{i,i\in\mathbb{Y}} e_{ij}\omega_{ij}/n_{yj},$$

$$S_{xj} = \sum_{i,i\in\mathbb{X}} (e_{ij}-u_{xj})^2\omega_{ij}/(n_{xj}-1),$$

$$S_{yj} = \sum_{i,i\in\mathbb{Y}} (e_{ij}-u_{yj})^2\omega_{ij}/(n_{yj}-1),$$

$$t \text{ statistic } t_j = \frac{u_{xj}-u_{yj}}{\sqrt{\frac{S_{xj}}{n_{xj}} + \frac{S_{yj}}{n_{yj}}}},$$

$$\text{degree of freedom } v_j \approx \frac{(S_{xj}/n_{xj} + S_{yj}/n_{yj})^2}{S_{xj}^2/[n_{xj}^2(n_{xj}-1)] + S_{yj}^2/[n_{yj}^2(n_{yj}-1)]}.$$

The false discovery rate (FDR) is calculated for each differentially expressed gene in multiple hypothesis testing using Benjamini and Hochberg procedure [63].

Density clustering and selection of the number of clusters. Applicants used a density based clustering method [54] to partition cells embedded in the 2-D space. The method searches cluster centers that are characterized by two quantities: (1) high local density pi and (2) large distance δi from points of higher density, which are centers of other clusters. Applicants unify the two quantities into a single metric by taking the product of the two quantities, si=pi·δi.

To select cluster centers, Applicants rank each data points by their si in descending order. For a given n, the number of desired clusters, Applicants select the top ranked n cluster centers, and perform the cluster assignment as described previously [54]. To evaluate the quality of the clustering, Applicants calculate the Dunn index for each n with d(i, j) and d'(k) defined as local distances. The calculation of the Dunn index can be operated in O(N3), where N is the number of total data points.

---

Algorithm: Identification of maximum steps on shortest paths (MaxStep)

Input: pairwise distance of data points (D)
Output: the pairwise shortest link (D')
D' := D
n := # of data points
for k := 1 to n do
| for i := 1 to n−1 do
| | for j := i+1 to n do
| | | D'(i,j) = min(D'(i,j), max(D'(i,k), D'(k,j)))
| | end
| end
end
return D'

---

Algorithm: Calculation of the Dunn index defined on local distances (DunnLocal)

Input: pairwise distance of data points in the 2-D embedding (D), clustering assignment (Cl)
Output: the Dunn index (θ)
cl_uiq := unique(Cl)
n := # of cl_uiq
d'$_k$ := empty array with a length of n
d$_{ij}$ := empty matrix with a size of (n, n)
for i := 1 to n do
| ii := index of data whose clustering assignment is cl_uiq(i)
| d'$_k$(i) := max(MaxStep(D(ii,ii)))
end
for i := 1 to n−1 do
| for j := i+1 to n do
| | ii := index of data whose clustering assignment is either cl_uiq(i) or cl_uiq(j)
| | d$_{ij}$(i,j) := max(MaxStep(D(ii,ii)))
| end
end
θ := min(d$_{ij}$)/ max(d'$_k$)
return θ

---

Large scale comparison between RNA-Seq data and ISH data. Applicants selected genes differentially expressed between any bipartition of DG, CA1, CA2, CA3 clusters in RNA-Seq data. For example, a gene is selected if it is differentially expressed between cells in a combined DG and CA2 cluster, and cells in a combined CA1 and CA3 cluster. Specifically, the differential expression was tested using the adjusted t-test between cells ∈C1, C1⊂{DG, CA1, CA2, CA3} and cells ∈C2, C2={DG, CA1, CA2, CA3}\C1. Gene j is selected if

| difference in mean | $m_{C_1,j} - m_{C_2,j} > 1$ |
|---|---|
| mean of cells ∈ $\mathbb{C}_1$ | $m_{C_1,j} > 20$ TPM |
| mean of cells ∈ $\mathbb{C}_2$ | $m_{C_2,j} < 5$ TPM |
| p values of t-test | $p_j < 0.01$. |

The quantified ISH data [64] with 200 μm resolution was downloaded from Allen Brain Atlas (Website: 2015 Allen Institute for Brain Science. Allen Mouse Brain Atlas [Internet]. Available from: mouse.brain-map.org.) Mean expression level of ISH data was calculated as averaged energy level for each of the DG, CA1, CA2, CA3 regions. Specifically, averaged energy level eG for grids in a region G is given by $$e_G = \sum_{g,g \in G} d_g \cdot i_g / |G|,$$

where dg is the quantified expression density for grid g, and ig is the quantified expression intensity for grid g. The Indices for DG, CA1, CA2, CA3 regions are 726, 382, 423, 463. Applicants obtained two vectors e∈R4 comprising averaged expression levels of DG, CA1, CA2, CA3 regions for each gene, one from RNA-Seq data, and another from ISH data. Pearson correlation coefficient was calculated between these two vectors for each selected gene.

BiSNE. Cells positioned in proximity in the tSNE mapping coexpress a set of genes that are not expressed by distal cells. These set of genes could be used to distinguish different cell subpopulations. These genes are coexpressed in the cells grouped in proximity, and therefore they have localized expression patterns in the tSNE mapping.

Statistics for scoring expression patterns. Motivated by this observation, Applicants use two different statistics to identify genes with significantly localized expression patterns in the tSNE mapping and then perform PCA-tSNE using the union of these identified genes to cluster cells.

I. Moran's I. Moran's I scores correlation between a measurement on a set of mapping positions and pairwise distances of these mapping positions. Given tSNE coordinates, the Moran's I for gene k is given by $$I(k) = \frac{\sum_i \sum_j Q_{ij}(e_{ik} - u_k)(e_{jk} - u_k)\omega_{ik}\omega_{jk} / \sum_i \sum_j Q_{ij}\omega_{ik}\omega_{jk}}{\sum_i (e_{ik} - u_k)^2 \omega_{ik} / \sum_i \omega_{ik}},$$

where Qij denotes the pairwise similarity transformed from dij, the Euclidean distances between cell i and j in the tSNE mapping. Applicants obtain Q$_{ij}$ from d$_{ij}$ using the Gaussian function, $$Q_{ij} = \frac{1}{\sigma\sqrt{2\pi}}\exp\left(-\frac{d_{ij}^2}{2\sigma^2}\right).$$

Applicants choose u to set the minimal size of localized expressed pattern, as dij≈σ weights around 60% and dij≈2σ weights around 13.5%. The statistical significance of the pattern of gene k is tested by converting I(k) to a z score, $$E[I] = -1/(N-1), \text{ where } N \text{ is the length of } e_k$$

$$V[I] = \frac{1}{S_0^2(N^2-1)(N^2S_1 - NS_2 + 3S_0^2)} - E[I]^2$$

$$S_0 = 2\sum_i\sum_j Q_{ij},\quad S_1 = 2\sum_i\sum_j Q_{ij}^2,\quad S_2 = 4\sum_i\left(\sum_j Q_{ij}\right)^2$$

$$z = -\frac{I - E[I]}{\sqrt{V[I]}}.$$

Moran's I uses gene expression levels in its calculation. When identifying marker genes, only the information about whether a gene is expressed or not is necessary. Applicants use a modified Moran's I on binarized gene expression levels. Specifically, Applicants binarize gene expression level by a threshold, $$\hat{e}_{ij} = \begin{cases} 1 & \text{if } e_{ij} > 3\ TPM \\ 0 & \text{if } e_{ij} \le 3\ TPM \end{cases}.$$

Applicants then calculate the modified Moran's I by, $$I(k) = \frac{\sum_i\sum_j Q_{ij}(\hat{e}_{ik} - \hat{u}_k)(\hat{e}_{jk} - \hat{u}_k)\omega_{ik}\omega_{jk}}{\sum_i\sum_j Q_{ij}\omega_{ik}\omega_{jk}}.$$

Moran's I is a global measure. It has biases towards genes that are widely expressed. To reduce false positives, Applicants filtered out genes expressed in more than 80% of cells.

II. Manhattan distance and order statistics. The Manhattan distance is an alternative to the Euclidean distance in quantifying proximity. The advantage of using Manhattan distance is that x and y coordinates can be tested independently using order statistics. Assume a given set of cells that express gene j and their positions z on a coordinate z, z is defined as the normalized z such that $$\bar{z}_i = (z_i - \min(z))/(\max(z) - \min(z)), i \in \{i \mid e_{ij} > \text{TPM3}\},$$

and $\hat{z}$ is defined as the ordered list of $\bar{z}$, such that $\hat{z}_i < \hat{z}_{i+1}$. The range $w_z$ is defined as $w_z = \hat{z}_n - \hat{z}_i$. Assume that $\hat{z}$ is a vector of i.e. samples from a uniform distribution, the significance level p of $w_z$ can be found using order statistics.

$$\text{PDF of } w\ f_w(w) n(n-1)\int_{-\infty}^{+\infty}[F(x+w) - F(w)]^{(n-2)} f(x) f(x+w)\,dx$$

where f(x) and F(x) are PDF and CDF of z $$\text{CDF of } F_w(w) = w^{n-1}[n-(n-1)w], \text{ under null hypothesis}$$

$$p_z = F_w(w_x),$$

where PDF is the probability density function and CDF is the cumulative density function. To robustly estimate w in the presence of outliers, the distribution of z is fitted using the Gaussian distribution with robust estimators of mean and variance.

$$u_z = \text{median}(z)$$

$$S_z = 1.1926\,\underset{i}{median}\left(\underset{j}{median}(|z_i - z_j|)\right)$$

$$p_i = \Phi\left(-\left|\frac{z_i - u_z}{S_z}\right|\right),$$

where Φ denotes the CDF of the standard normal distribution. Samples with pi<ϵ, a predefined threshold, are considered outliers and are excluded from the estimation of w. A single p value is calculated for each gene by taking the product of px and py, the p values obtained for x and y coordinates, respectively. It measures the overall significance level of each gene in both coordinates.

Selection of significant genes. For each statistic, Applicants rank genes based on their significance. Genes ranked high are likely to be informative for clustering cells, whereas genes ranked low are more likely to be noises that suppress clustering separation. Applicants use a cut off rank to select informative genes, chosen based on the statistic of eigenvalues of random matrices, which states that inclusion of a noisy row (gene) in a data matrix would lead to a reduction in the maximum eigenvalue gap of the matrix. Conversely, inclusion of an informative row (gene) would lead to an increase in the maximum eigenvalue gap, as the variance it introduces aligns with variances of some other genes. Therefore, the change in the maximum eigenvalue gap measures the extent a gene being informative. After genes are ranked, Applicants start with a data matrix containing the top ranked genes, and add subsequent genes with lower rank incrementally. For each addition, Applicants calculate the change in the maximum eigenvalue gap before and after adding the gene. Additionally, Applicants randomly permute measurements of this gene across cells and calculate the change in the maximum eigenvalue gap induced by adding this permuted gene. Applicants then select a cut off rank, below which there is no difference in the change of the maximum eigenvalue gap between adding a gene or its permuted counterpart. The selection cut-off can also be formally tested using minimum hypergeometric test. Specifically, for a data matrix E1, j−1 and a gene j, Applicants form a new matrix $$E_{1,j} = \begin{bmatrix} E_{1,j-1} \\ e_j, \end{bmatrix}$$

and we obtain the eigenvalues of $E_{1,j-1}E_{1,j-1}^T$ using weighted SVD. The eigenvalues are normalized and sorted in order $$\lambda_1 > \lambda_2 > \ldots > \lambda_n, \text{ and } \sum_i \lambda_i = 1.$$

The distribution density (Marchenko-Pastur distribution) of higher order eigenvalues can be approximated by a linear function, and its cumulative distribution can be approximated by a quadratic polynomial. The sorted eigenvalues follow the inverse function of the cumulative distribution, and are fitted by $$\hat{\lambda}_i = f(i) = \alpha_0 + \alpha_1\sqrt{\frac{i}{n}},\ \alpha_0 \text{ and } \alpha_1 \in \mathbb{R}.$$

The eigenvalue gap is approximated as $$\Delta_j = \sum_{i=1}^{n} (\lambda_i - \hat{\lambda}_i).$$

For permutation comparison, expression of gene j is permuted, $\tilde{e}_j$:$\tilde{e}_{ij}$=$e_{i'j}$, i' is drawn without replacement from [1, n]

$$\tilde{E}_{1,j} = \begin{bmatrix} E_{1,j-1} \\ \tilde{e}_j \end{bmatrix},$$

where i' denotes randomly permuted cell index. The eigenvalue gap ~_j is obtained for the permuted matrix ~E 1,j. A cut off rank is chosen at k, if the change in the eigenvalue gap _'-~_' is not significant for genes ranked below k. To combine top genes, Applicants take the union of genes selected by different statistics. Clustering of gene signatures using cross correlation. To cluster genes into gene signatures while taking into account of the similarity between cells expressing these genes, Applicants compute cross correlations between high scoring genes while taking account of the proximity of cells expressing these genes, convert the correlation coefficient to distances, and cluster these genes using t-SNE and density clustering. Specifically, spatial cross correlation between gene k and k' is given by $$I(k, k') = \frac{\sum_i \sum_j Q_{ij}(e_{ik} - u_k)(e_{jk'} - u_k)\omega_{ik}\omega_{jk'} \Big/ \sum_i \sum_j Q_{ij}\omega_{ik}\omega_{jk'}}{\sqrt{\left(\sum_i (e_{ik} - u_{k'})^2\omega_{ik} \Big/ \sum_i \omega_{ik}\right)\left(\sum_i (e_{ik'} - u_{k'})^2\omega_{ik'} \Big/ \sum_i \omega_{ik'}\right)}}.$$

It has been noted that the range of I is not [−1, 1], unlike Pearson's correlation coefficient. Applicants empirically found that I is positively biased in the tSNE mapping. The positive bias may underestimate the strength of anti-correlation genes having complementary patterns. A scalar transformation of I that has the exact range [−1, 1] has been proposed.

$W=(n\ddot{w})^{-1}H^TWH$, where $\ddot{W}$ is a (n−1)×(n−1) matrix, and $$\tilde{\omega} = \sum_{i,j=1}^{n} \epsilon_i j / n^2$$

$H=(h_1, \ldots, h_{n-1})$ is defined based on Helmert orthogonal matrix $h_i^T=(1_i^T-i,0_{n-i-1}^T)/\sqrt{i(n+1)}$, for i=1, . . . , n−1.

The scalar transformation of Moran's I is given by $$I_M = \begin{cases} [(n-1)I+1]/[|(n-1)\lambda_{(1)}+1|] & \text{if } (n-1)I+1<0 \\ [(n-1)I+1]/[(n-1)\lambda_{(n-1)}+1] & \text{if } (n-1)I+1 \geq 0 \end{cases}.$$

where $\lambda_{(1)}$ and $\lambda_{(n-1)}$ are the smallest and largest eigenvalues of the matrix $\tilde{W}$.

The calculation of spatial cross correlation has a computational complexity that scales quadratically with the number of gene and cells as of O(N2M2), where N is the number of cells and M is the number of genes. When the number of cells and the number of genes are large, it becomes impractical to calculate the spatial cross correlation. However, for clustering genes using tSNE, only the information about k nearest neighbor (knn) data points is necessary, requiring a linear complexity as of O(N2MK). The data with knn defined on a metric space can be developed a conversion between spatial correlation coefficient and a metric.

Theorem For a given similarity I(k, k'), I(k, k')∈[−B, B], B∈R and B>0, define g(k, k')

$$g(k, k') = \begin{cases} 0 & \text{if } k = k' \\ \sqrt{a - I(k, k')} & \text{if } k \neq k' \end{cases}$$

with a>5/3B, and g(I(k, k')) is a metric.

Proof: For k=k', the proof is trivial For k≠k', 1. non-negativity, $g(k, k')=\sqrt{a-I(k,k')}>\sqrt{2/3B}>0$
2. coincidence, $g(k, k')=\sqrt{a-I(k,k')}>0$
3. symmetry, $g(k, k')=\sqrt{a-I(k,k')}=\sqrt{a-I(k',k)}=g(k', k)$
4. triangle inequality, $g(k, k'')+g(k'', k')\geq 2\sqrt{a-B}\geq\sqrt{a-(-B)}>g(k, k')$ Selection of principal components. Applicants chose top principal components (PCs) based on the largest Eigen value gap. Comparison of biSNE and generalized linear model. Applicants used an in-house implemented generalized linear model (GLM) to select highly variable genes in the GABAergic nuclei data. Three different set of genes were chosen based on three significance levels. PCA-tSNE embeddings were performed on the nuclei data using each of the chosen sets of genes. The cluster assignments were obtained on the PCA-tSNE embedding that corresponds to the most stringent significance level. Applicants used biSNE to select three sets of correlated highly variable genes in the same nuclei data. Each set contains the same number of genes as that in the corresponding set selected by GLM. PCA-tSNE embedding and the cluster assignments were performed using each of sets of genes.

Validations of glia sub-types expression signatures. Differentially expressed marker genes were found for each of the glia sub-clusters and for the neuronal clusters. Differential genes were averaged across each glia cluster and averaged across all neuronal clusters combined. Spearman correlation was calculated between these average expression patterns and cell type specific bulk RNA-Seq performed in the cerebral cortex. The published dataset was log transformed.

Identification of nuclei identity based on a single marker gene. Applicants performed in silico cell sorting based on Pvalb expression, and found that the sorted cells constitute a subset of the identified Pvalb interneurons. This demonstrates that cell type identification based on the expression level of a single marker gene can suffer from false negatives, if only because of "drop outs" in single cell RNA-Seq or Nuc-Seq. Fortunately, the Pvalb expressing interneurons also share similarity in the expression of many other genes, enabling the recovery of genes commonly expressed by Pvalb interneurons, providing a robust way to determine cell type.

Localization of subclusters to anatomical regions. Localizing subclusters requires a spatial reference map of a few landmark genes and the expression level of these landmark genes in each subcluster. Applicants first created a spatial reference map by dividing an anatomical region into a grid. Applicants manually scored the expression levels of known landmark genes in this grid as not expressed, weakly, or highly expressed in these grids. Next, Applicants generated for each subcluster a "landmark profile" by the percentage of cells expressing each landmark in this subcluster. Applicants developed an approach similar to Seurat to infer whether a given landmark gene is expressed in each cell by exploiting information from all non-landmark genes. Our anatomical alignment method is similar to Seurat in concept. Unlike Seurat, however, Applicants' method can accommodate situations when far fewer landmark genes are available (a common situation in many systems unlike the heavily-studied zebrafish embryo, on which Applicants demonstrated Seurat). Applicants calculated the percentage of inferred expressing cells in each subcluster. To relate the subclusters to the reference map, Applicants evaluated the correlation between each subcluster's landmark profile and the profile of landmark genes in each part of the reference map. Applicants positioned each of the subclusters to the highly correlated parts of the map. The accuracy of this spatial mapping is dependent on the quality of ISH images of landmark genes from the Allan brain atlas. To obtain a training data set for a given marker gene j, Applicants ranked subclusters by weighted mean expression of the marker gene, and select cells expressing the marker gene above TPM 8 in the top ranked three subclusters as positive training samples. Applicants selected cells not expressing or lowly (less than TPM 3) expressing the marker gene in the bottom ranked three subclusters as negative training samples. Specifically, Applicants use all genes except marker genes as feature data z in an L1-regularized L2-loss support vector machine $$z_{ik} = \begin{cases} 1 - p(x_{ik} = 0 \mid e_{ik} = 0) & \text{if } e_{ik} = 0 \\ 1 & \text{if } e_{ik} > 0 \end{cases}$$

$$y_{ij} = \begin{cases} 0 & \text{if } i \in \text{negative training samples} \\ 1 & \text{if } i \in \text{positive training samples} \end{cases},$$

where k$\notin$ markers, and i$\in$ training cells. Applicants solved the unconstrained optimization problem using liblinear package [75]

$$\min_{\omega_j} \|w_j\|_1 + C\sum_{i=1}^{l} (\max(0, 1 - y_{ij} w_j^T z_i^T))^2$$

where C denotes the penalty parameter. Applicants performed coarse search followed by fine search using 5-fold cross validation for parameter C that yielded the best accuracy for training data. To predict whether the marker gene is expressed in cells not included in the training samples, Applicants used the decision function $$\hat{y}_{ij} sgn(w_j^T z_j^T).$$

The fraction of cells expressing marker gene j in a subcluster C is given by $$f_{\mathbb{C}j} = \sum_{i,i\in\mathbb{C}} \hat{y}_{ij} / |\mathbb{C}|.$$

Applicants predicted expression of all marker genes in this way and calculate Pearson correlation coefficient between subclusters and subregions using fC and manually quantified expression intensity. To test whether the subclusters were driven by the selected landmark genes, Applicants excluded the landmark genes from PCA-tSNE and biSNE steps, and repeated the clustering. Applicants consistently obtained the same clustering.

Indexing cells along a trajectory on projected continuum. To obtain the ranking of cells along a given trajectory, Applicants treat the indexing as a traveling salesman problem (TSP). Cells at the start and the end points of a given trajectory are manually selected. The Euclidean distances between cells on the projected space are calculated, and normalized to integers.

$$\hat{d}=[10d/\min(d)]$$

The distance between start and points is set to 0. The normalized distances are used in Lin-Kernighan heuristic (LKH) solver for TSP. The obtained ordering of cells is shifted, so that the manually selected start cell is indexed the first.

Example 2. Single Molecule In Situ Hybridization Tissue Assay

For in situ hybridization (ISH) assay, it is performed using QuantiGene ViewRNA ISH Tissue 2-plex Assay Kit (Affymetrix, #QVT0012) with proprietary probes designed for the list of genes listed in Table 1 and the figures herein. The assay is optimized based on the manufacturer's protocol for fresh and frozen samples. Images were taken using fluorescent microscopy (Zeiss microscope and Hamamatsu camera C11440-22CU) and were processed in Matlab. Image background due to non-uniform illumination was removed using Matlab function strel('disk', 25). The image brightness and contrast were adjusted to obtain the maximum dynamic range.

Example 3. Nuclei Purification Protocols

Nuclei purification protocol: method A: This method may be used for Nuc-Seq or Div-Seq. Reference: In vivo interrogation of gene function in the mammalian brain using CRISPR-Cas9. Swiech L, Heidenreich M, Banerjee A, Habib N, Li Y, Trombetta J, Sur M, Zhang F. Nat Biotechnol. 2015 January;33(1):102-6. doi: 10.1038/nbt.3055. Epub 2014 Oct. 19.

TABLE 4

| Buffer 1: | | | | |
|---|---|---|---|---|
| | Stocks | 25 ml For 2 samples (+spare) | 50 ml For 4 samples (+spare) | 75 ml For 6 samples (+spare) |
| 320 mM Sucrose | 1M | 8 ml | 16 ml | 24 ml |
| 5 mM CaCl | 1M | 125 ul | 250 ul | 375 ul |
| 3 mM Mg(Ac)2 | 1M | 75 ul | 150 ul | 225 ul |

TABLE 4-continued

Buffer 1:

| | Stocks | 25 ml For 2 samples (+spare) | 50 ml For 4 samples (+spare) | 75 ml For 6 samples (+spare) |
|---|---|---|---|---|
| 10 mM Tris pH 7.8 | 1M | 250 ul | 500 ul | 750 ul |
| 0.1 mM EDTA | 0.5M | 5 ul | 10 ul | 15 ul |
| 0.1 mM PMSF | 100 mM | 25 ul | 50 ul | 75 ul |
| 0.1% NP40 | 10% | 250 ul | 500 ul | 750 ul |
| 1 mM β-mercapto | 500 mM | 50 ul | 100 ul | 150 ul |
| $H_2O$ | | 16.2 ml | 32.4 ml | 48.6 ml |

TABLE 5

Working solution (×6):

| | Stocks | 5 ml For 2 samples (+spare) | 10 ml For 4 samples (+spare) |
|---|---|---|---|
| 30 mM CaCl | 1M | 150 ul | 300 ul |
| 18 mM Mg(Ac)2 | 1M | 90 ul | 180 ul |
| 60 mM Tris | 1M | 300 ul | 600 ul |
| 0.6 mM PMSF | 100 mM | 30 ul | 60 ul |
| 6 mM β-mercapto | 500 mM | 60 ul | 120 ul |
| $H_2O$ | | 4.370 ml | 8.740 ml |

TABLE 6

50% Optiprep solution:

| 1:6 | 1 sample | 2 samples-25 ml | 4 samples-50 ml |
|---|---|---|---|
| Working solution | 2 ml | 5 ml | 8.35 ml |
| Optiprep | 8 ml | 25 ml | 41.68 ml |

TABLE 7

29% Optiprep solution:

| | 1 sample | 4 samples-50 ml |
|---|---|---|
| 50% Optiprep | 5.8 ml | 29 |
| Buffer 1 | 4.2 ml | 21 |

TABLE 8

Resuspension buffer RB:

| | Stocks | 10 ml For 4 samples |
|---|---|---|
| 340 mM Sucrose | 1M | 3.4 ml |
| 2 mM MgCl2 | 1M | 10 ul |
| 25 mM KCl | 2M | 125 ul |
| 65 mM glycerophosphate | 1M | 650 ul |
| 5% glycerol | 100% | 500 ul |

Before Starting:

1. Make fresh buffers
2. All: buffers, tubes, homogenizer should be on ice at all times Protocol:

1. Dounce homogenize tissue in 2 ml Buffer 1+0.1% NP40 (25 times with a, 25 times with b), transfer to a 15 ml tube 1. Rinse homogenizer with 3 ml Buffer 1 to get final 5 ml, and collect in the same tube
2. Keep on ice 5 min
3. Add 5 ml 50% Optiprep, invert 10× (final volume 10 ml)
4. Keep on ice 5 min
5. While waiting, prepare an ultracentrifuge tube with 10 ml of 29% Optiprep.
6. Transfer the lysate to the ultracentrifuge tube carefully on top of the 10 ml 29% Optiprep solution, to form a gradient
7. Centrifuge at 7500 rpm 4c for 30 min
8. Carefully remove supernatant
9. Add ~300 ul/hp buffer RB, keep on ice 5-15 min 10. Resuspend carefully by slow vortex & pipette 10× with a 1 ml tip, then transfer to tubes (for FACS, filter through a membrane to get better purity)
11. Counterstain nuclei with Ruby Dye 1:500-1:1000 (check for clumps in the microscope before sorting)

Nuclei Purification Protocol: Method B

This method is particularly suitable for Dronc-Seq.

EZ NUCLEI ISOLATION PROTOCOL FROM TISSUE (Using EZ PREP NUC-101, Sigma)

Procedure for frozen/fixed tissue: Dounce homogenize tissue in 2 ml of ice-cold Nuclei EZ lysis buffer (25 times with a, 25 times with b), transfer to a 15 ml tube.

1. Rinse homogenizer with 2 ml of ice-cold Nuclei EZ lysis buffer to get final 4 ml, and collect in the same tube.
2. Mix well and set on ice for 5 minutes.
3. Collect the nuclei by centrifugation at 500×g for 5 minutes at 4° C. Carefully aspirate the clear supernatant from each tube and set the nuclei pellet on ice. Note: The supernatant contains cytoplasmic components and can be saved for later analysis or use.
4. Resuspend. Add 1 ml cold Nuclei EZ lysis buffer and mix by pipetting gently with a 1 ml tip to completely suspend nuclei pellet. Add the remaining 3 ml of Nuclei EZ lysis buffer, mix well and set on ice for 5 minutes.
5. Collect washed nuclei by centrifugation as in step 3. Carefully aspirate the clear supernatant and set the nuclei pellet on ice.
6. Optional: Wash. Resuspend in 4 ml 0.01% PBS BSA or Resuspension buffer (RB*). Collect washed nuclei by centrifugation as in step 3.
7. Resuspend with ~500 µl Resuspension buffer (RB*) or 0.01% PBS BSA+RNAse inhibitor carefully by slow vortex & pipette 10× with a 1 ml tip, then transfer to tubes for FACS, filter through a membrane to get better purity.
8. Counterstain nuclei with Ruby Dye 1:500-1:1000 (check for clumps in the microscope before sorting).

Resuspension Buffer

—based on the original nuclei resuspension buffer from Swiech et al. 2015:

TABLE 9

| | Stocks | For 10 ml |
|---|---|---|
| 340 mM Sucrose | 1M | 3.4 ml |
| 2 mM MgCl2 | 1M | 10 ul |
| 25 mM KCl | 2M | 125 ul |
| 65 mM glycerophosphate | 1M | 650 ul |
| 5% glycerol | 100% | 500 ul |

Example 4. SMART-Seq2 Protocol Full-Length mRNA-Seq for Single Nuclei or Small Amounts of RNA Samples Tissue, Cells & Nuclei Prep Tissue should be stored in RNA-later in 4c for 24 hours and then moved to the −80 (removing the RNA-later), or immediately frozen and stored at −80° C.

Prep cells/nuclei short time before sorting. Use RNAse free reagents.

Sorting

Sort single cells/nuclei into 96-well plate, 5 µL TCL in each well (with bME, and optional RNAse inhibitor)

Immediately spin for 1-2 min, 2500 RPM

Snap freeze on dry ice, store at −80° C.

Prep Work

RNase-ZAP work surfaces and equipment 30 minutes prior to purification, let RNA-SPRI beads equilibrate to room temperature Thaw cell plates on ice and spin down for 1 min, 2500 RPM RNA Purification Add 11 µL (2.2×) RNA-SPRI beads to each well, mix Let at room temp for 10 minutes, place plate on magnet for 5 minutes Remove supernatant Wash in 100 µL 80% EtOH three times Completely remove supernatant, let dry for 8-10 minutes on magnet Elute in 4 µL Mix #1

Continue immediately

TABLE 10

| Mix #1 | | | |
|---|---|---|---|
| Reagent | 1 sample (µL) | 96 samples (µL) | 96 for Bravo (µL) |
| RT primer (10 µM) | 1.0 | 115.2 | 120 |
| dNTP mix (10 mM each) | 1.0 | 115.2 | 120 |
| RDil (10% RNase-Inhib, final of 4 U/µL) | 1.0 | 115.2 | 120 |
| $H_2O$ | 1.0 | 115.2 | 120 |
| Total | 4.0 | 460.8 | 480 |

RT

Incubate eluted plate at 72° for 3 min, immediately place on ice

TABLE 11

| Mix #2 | | |
|---|---|---|
| Reagent | 1 sample (µL) | 96 samples (µL) |
| $H_2O$ | 0.75 | 86.4 |
| 5 × Maxima RT buffer | 2.0 | 230.4 |
| Betaine (5M) | 2.0 | 230.4 |
| $MgCl_2$ (100 mM) | 0.9 | 103.68 |
| TSO (10 µM) | 1.0 | 115.2 |
| RNase Inhibitor (40 U/µL) | 0.25 | 28.8 |
| Maxima RNaseH-minus RT (200 U/µL) | 0.10 | 11.52 |
| Total | 7.0 | 806.4 |

Add 7 ul of Mix #2 (mix well & spin down)

RT PROGRAM: Incubate at 42° for 90 minutes, followed by 10 cycles of (50° for 2 min, 42° for 2 min), then heat inactivation at 70° for 15 min.

Transfer plate in only when machine is ready at 42° C.

TABLE 12

| PCR Preamplification Mix #3 | | | |
|---|---|---|---|
| Reagent | 1 sample (µL) | 96 samples (µL)-x1.2 | x1.1 |
| $H_2O$ | 1.0 | 115.2 | 105.6 |
| ISPCR Primer (10 µM) | 0.5 | 57.6 | 52.8 |
| KAPA HiFi HotStart ReadyMix | 12.5 | 1440 | 1320 |
| Total | 14 | 1612.8 | 1478.4 |

Add 14 µL of Mix #3 to each well

Cycle the PCR as follows: 98° for 3 min, 21 cycles of (98° for 15 sec, 67° for 20 sec, 72° for 6 min), final extension at 72° for 5 min.

PCR Pre-Amplification Clean Up

Purify the PCR products with a 0.8× AMPure XP SPRI cleanup

Add 20 µL AMPure XP SPRI beads, let sit for 5 min place plate on magnet for 6 min pipette off supernatant Wash beads by adding 100 µL fresh 70% EtOH and magnet switching Pipette off supernatant and repeat wash remove all EtOH and let dry on magnet for 10 min Elute material in 20 µL TE Post-PCR Pre-Amplification QC 1. Bio Analyze test quality
2. PICO-green in the plate reader—QC & quant Nextera-XT (Modified Protocol)

Make NTA:

2.5 ul TD buffer per well 1.25 ul sample (diluted to 0.15-0.2 ng/ul per well)

1.25 ul ATM

Put cover, bang to mix & spin down briefly

Incubate 10 min at 55° C. ("make NTA" program, hold at 10° C.)

Spin down

Neutralize:

Add 1.25 NT buffer to neutralize

Spin down

Incubate on bench for 5 min

PCR:

3.75 ul NPM 2.5 ul of index array primers (1.25 ul of each primer)

Cover & bang to mix & spin down

PCR (NTA PCR program, following the Nextera XT protocol)

1. Perform PCR using the following program on a thermal cycler (with heated lid, program "Nextera PCR" on machine D):
   - a. 72° C. for 3 minutes
   - b. 95° C. for 30 seconds
   - c. 12 cycles of:
     - i. 95° C. for 10 seconds
     - ii. 55° C. for 30 seconds
     - iii. 72° C. for 30 seconds
     - iv. 72° C. for 5 minutes
   - d. Hold at 4° C.

Pull & Cleanup:

Pull together 2.5 ul from each well and SPRI clean twice (in each SPRI wash twice with ETOH 70%):

1st cleanup: Add 0.9× beads (240 ul samples, 216 ul beads), elute in 50 ul TE

2nd cleanup: Add 0.9× beads, elute in 20-25 ul

Post Nextera QC: BioA/Tape-station and quant pool with qubit. Store at −20.

Example 5. sNucER-Seq

Previously, Applicants developed single nucleus RNA sequencing (sNuc-seq) as a method to profile the expression of single cells. The outer membrane of the nucleus is continuous with the rough endoplasmic reticulum (RER). The RER is a site of RNA translation. Preserving a portion of it with the nucleus would improve RNA recovery and single cell expression profiling. The compositions of nuclei isolation solutions that worked best preserve a portion of the nuclear outer membrane/RER along with ribosomes as determined by electron microscopy. This method is referred to as single nucleus and rough endoplasmic reticulum (sNucER)-seq.

Detergents: Applicants conducted a screen to optimize single nucleus RNA profiling of cells from tissues. Applicants tested a range of detergents that have previously been reported for nuclei extraction (Tween-20, Nonidet P-40/IGEPAL CA-630, Digitonin), and not reported (CHAPS). Applicants also compared a commercial nuclei extraction reagent (Nuclei EZ lysis buffer, SIGMA).

Based on the published literature it was not clear which concentrations of detergents would be optimal for nuclei extraction for sNuc-seq. Additionally, there was no data on CHAPS. Applicants chose to include CHAPS to increase detergent diversity. Tween-20, and Nonidet P-40/IGEPAL CA-630 are both non-ionic detergents. CHAPS is a zwitterionic detergent; as a note, CHAPS performed the best, and it is likely other zwitterionic detergents could do equally well.

Applicants chose the detergent concentrations based on the critical micelle concentration (CMC) for each detergent. Applicants then varied it either above or below the CMC.

Buffers: As part of the screen, Applicants also tested different buffers that have been used in the literature (Tris, Tricine, and HEPES). Although Tris performed the best, it is likely that the buffer choice is less critical than the detergents.

Salts: Applicants chose fixed salts concertation for the tests, although Applicants did try hypotonic solutions. The salts concentration was based on cellular concentrations of salts and what has been previously reported. Applicants used 146 mM NaCl, 1 mM $CaCl_2$), and 21 mM $MgCl_2$. The NaCl concertation can likely be varied up to 300 mM, or completely eliminated, and replaced with another salt such as KCl (as has been done in various biochemistry preparations as needed). Similar, $CaCl_2$) can likely be replaced with other calcium containing salts and concentrations can be increased to 20 mM or more. The same is true for varying $MgCl_2$ or adding in other salts.

CST with 0.49% CHAPS was the top extraction solution with the highest ENS score and lowest contamination. The nuclei have a nuclear membrane (not double membrane in all places), the membrane contiguous with RER and has ribosomes, and mitochondrial contamination was reduced.

Applicants found that the CST buffer has a lower intron/exon ratio compared to nuclei-only preps with EZ lysis reagent supporting more spliced RNA. The Intron/Exon ratio for each were as follows: CST=1.27904; EZ frozen=1.642955; and EZ chop=2.081659.

Example 6. Isolation of Nuclei

All buffers were used to extract nuclei by chopping tissue with scissors for 10 minutes in the respective buffer. Subsequently, extracted nuclei were filtered through a 40 micron filter, and washed once. The compositions of the four buffers used are shown in Table 28. Reagents used to make buffers were procured from VWR, Sigma, and other vendors.

TABLE 13

Compositions of Buffers

| Buffer | Buffer Concentration | Detergent | Detergent Concentration (%) | Salt and Concentration | Additives and Concentration |
|---|---|---|---|---|---|
| Tris | 10 mM | NP40 | 0.2 | 146 mM NaCl, 1 mM $CaCl_2$, 21 mM $MgCl_2$ | |
| Tris | 10 mM | CHAPS | 0.49 | 146 mM NaCl, 1 mM $CaCl_2$, 21 mM $MgCl_2$ | |
| Tris | 10 mM | Tween-20 | 0.03 | 146 mM NaCl, 1 mM $CaCl_2$, 21 mM $MgCl_2$ | |
| Tricine | 20 mM | NP40 | 0.2 | 146 mM NaCl, 1 mM $CaCl_2$, 21 mM $MgCl_2$ | 0.15 mM spermine and 0.5 mM spermidine |

The buffers were compared to two different preparations of Sigma's EZ nuclei extraction reagent. One preparation was EZ chop, which was generated by chopping tissue with scissors in accordance with the previously described protocol. The other, EZ frozen, entailed first fracturing the tissue in liquid nitrogen and then using a Dounce homogenizer. The cell quality score is defined by the average score of 'quality' expressed genes that were expected. Since all of the nuclei were sorted from the enteric nervous system, Applicants used genes that are expected to be expressed in the neurons and glia of the enteric nervous system.

Example 7. Freezing of Samples

Pieces of tissue should be small; ~100-200 mg, about 1 $cm^3$, or half an almond. If tissue is limited, one can go as low as 25 mg. More than this is not needed for one preparation and smaller pieces are generally better because it is hard to cut larger pieces without freeze thawing and ruining the remainder of the tissue.

Tissue should not be allowed to freeze in liquid. It is recommended to take tissue pieces from the petri dish and wiping it on the side of the container. It should then be placed on the side of a cryotube. If it sticks on the side of the tube, then the tube can be closed and buried in dry ice. If it does not stick, but rather slides to the bottom, then it will likely end up in a pool of liquid and damage the tissue upon freezing. If it slides down, then the tissue should be removed and placed on the side of new cryotube. Also, tissue should not be patted dry as this may damage it. Clear tubes should be used rather than colored tubes, so the tissue can be seen prior to processing. Once the tissue is in a closed tube, the tube should be buried fully in dry ice and moved to −80° C. when possible for longer term storage.

Example 8. Protocol for Isolation of Nuclei from Tissues

All steps are performed on ice or at 4° C. Pre-cool all plates/tubes. Alternative buffer component concentrations that deviate from the buffers below may be used. In certain embodiments, tricine may improve small molecule diffusion. Regarding buffering agents (e.g., Tris, Tricine, HEPES, PIPES) if a tissue is neutral pH then the buffer concentration may be close to zero (e.g. 1 mM). Regarding detergents, Applicants tested down to 0.0012 for tween-20. In certain embodiments, the concentration for detergents is between 0.001 or 0.0005%. In certain embodiments, detergent concentration is up to 1-2%. Regarding salts, the buffer may be adjusted down to 10 mM for NaCl, 0.1 mM for $CaCl_2$, and 1 mM for $MgCl_2$. Regarding polyamines, the buffer may be adjusted down to 0.1 mM for both spermidine and spermine.

1. Place tissue (25 mg-300 mg) into 1 mL of either CST, NST, NSTnPo, or TST. Applicants use 1 well of a 6-well dish.
2. Manually disaggregate with sharp dissection scissors for 10 min.
3. Filter into 50 mL tube through 40 micron nylon cell strainer (Falcon 352340).
4. Wash well with 1 mL of CST, NST, NSTnPo, or TST and put through cell strainer.
5. Add 3 mL of ST to cell strainer.
6. Transfer 5 mL of nuclei extract to 15 mL tube.
7. Spin down at 500×g for 5 minutes.
8. Remove ALL supernatant.
9. Re-suspend in ST (50 uL-200 uL).
10. Filter into polystyrene tube with 35 uM nylon strainer cap (Falcon 352235).
11. Count nuclei and dilute as needed for 10× or FACS.

TABLE 14

Compositions of Buffers.

| Composition | Buffer | Buffer conc. | Detergent | Detergent concentration (%) | Salt conc. | Additives concentration |
|---|---|---|---|---|---|---|
| ST | Tris | 10 mM | | | 146 mM NaCl, 1 mM $CaCl_2$, 21 mM $MgCl_2$ | |
| CST | Tris | 10 mM | CHAPS | 0.49 | 146 mM NaCl, 1 mM $CaCl_2$, 21 mM $MgCl_2$ | 0.01% BSA |
| TST | Tris | 10 mM | Tween-20 | 0.03 | 146 mM NaCl, 1 mM $CaCl_2$, 21 mM $MgCl_2$ | 0.01% BSA |
| NSTnPo | Tricine | 20 mM | NP40 | 0.2 | 146 mM NaCl, 1 mM $CaCl_2$, 21 mM $MgCl_2$ | 0.15 mM spermine 0.5 mM spermidine 0.01% BSA |
| NST | Tris | 10 mM | NP40 | 0.2 | 146 mM NaCl, 1 mM $CaCl_2$, 21 mM $MgCl_2$ | 0.01% BSA |

Example 9. Selecting Genes for ExSeq and MERFISH Using Single Cell RNA-Seq

Figure 10:
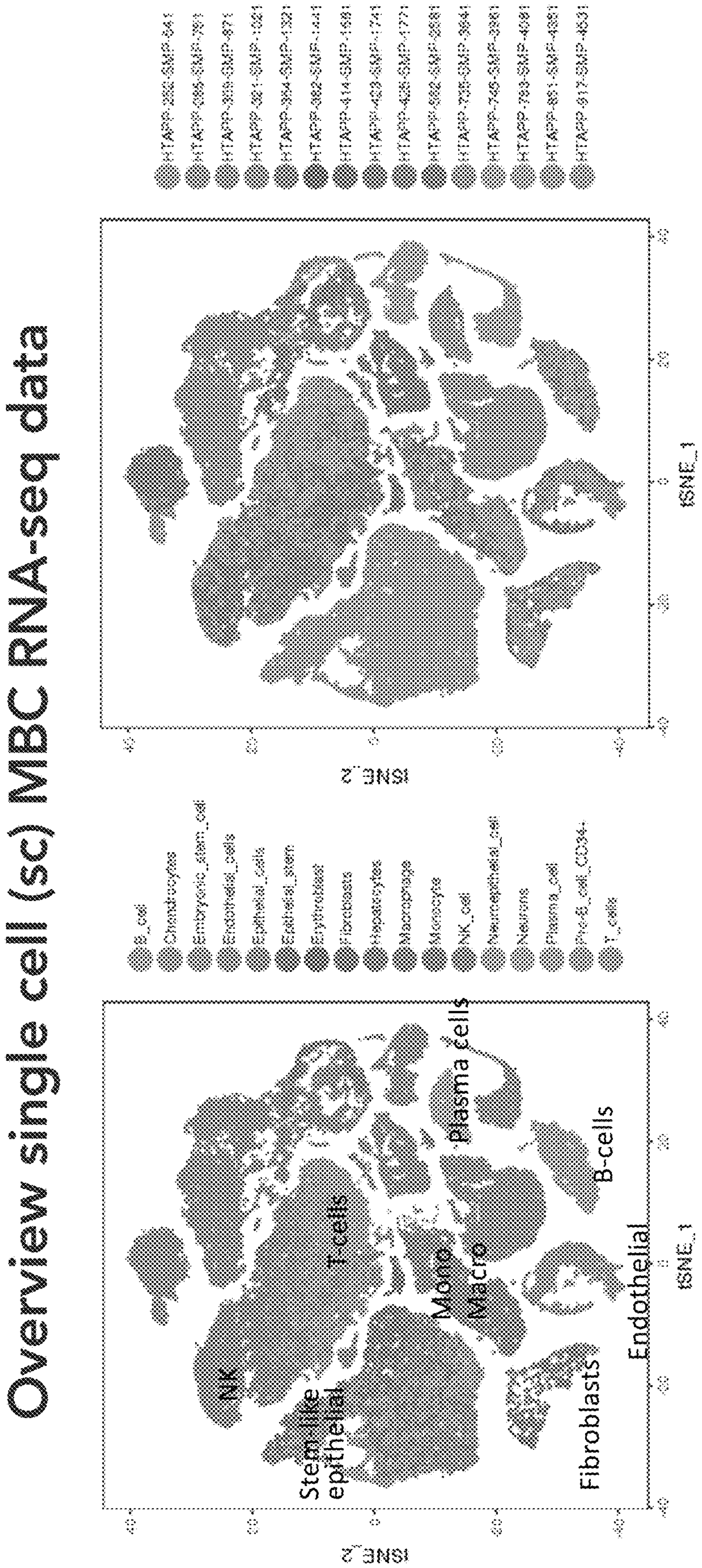
FIG. 10. tSNE plots of single cells using single cell RNA-seq labeled by cell type and sample.
Figure 11:
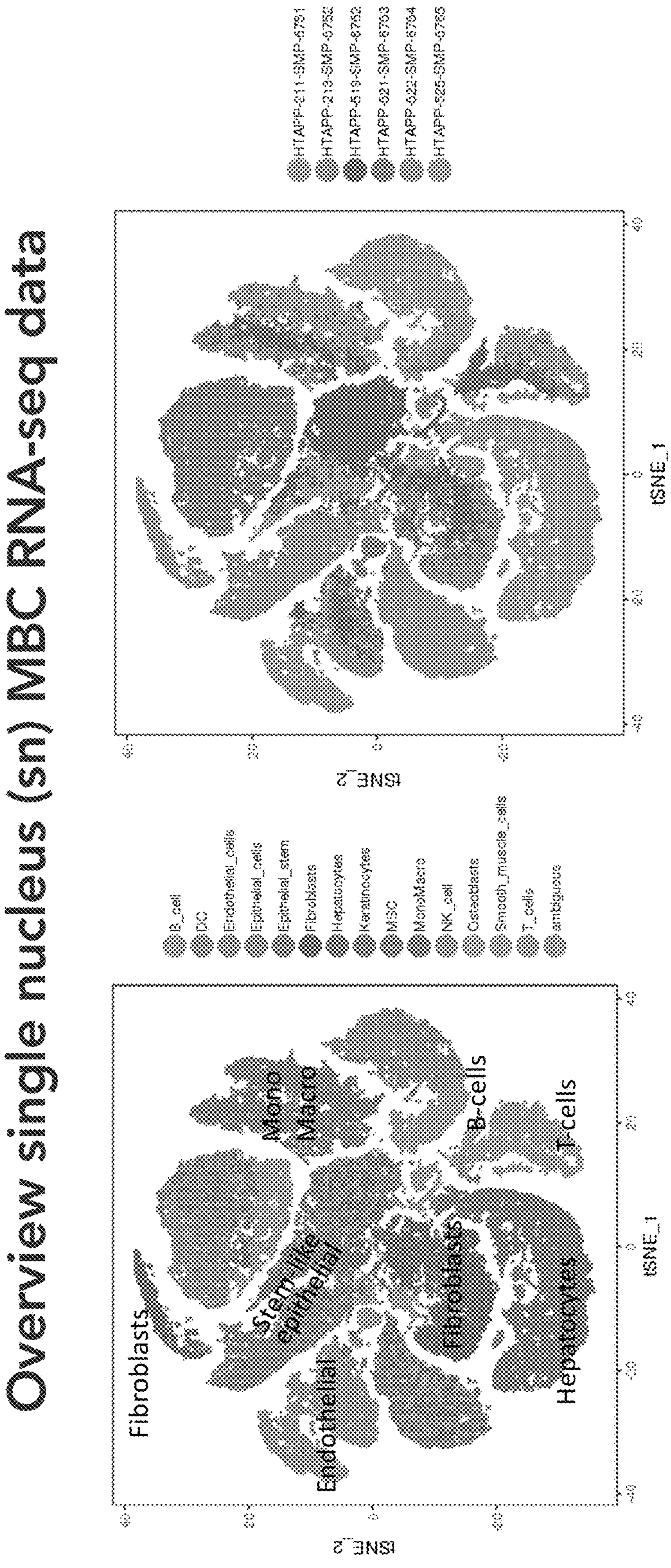
FIG. 11. tSNE plots of single cells using single nucleus RNA-seq labeled by cell type and sample.
Figure 12:
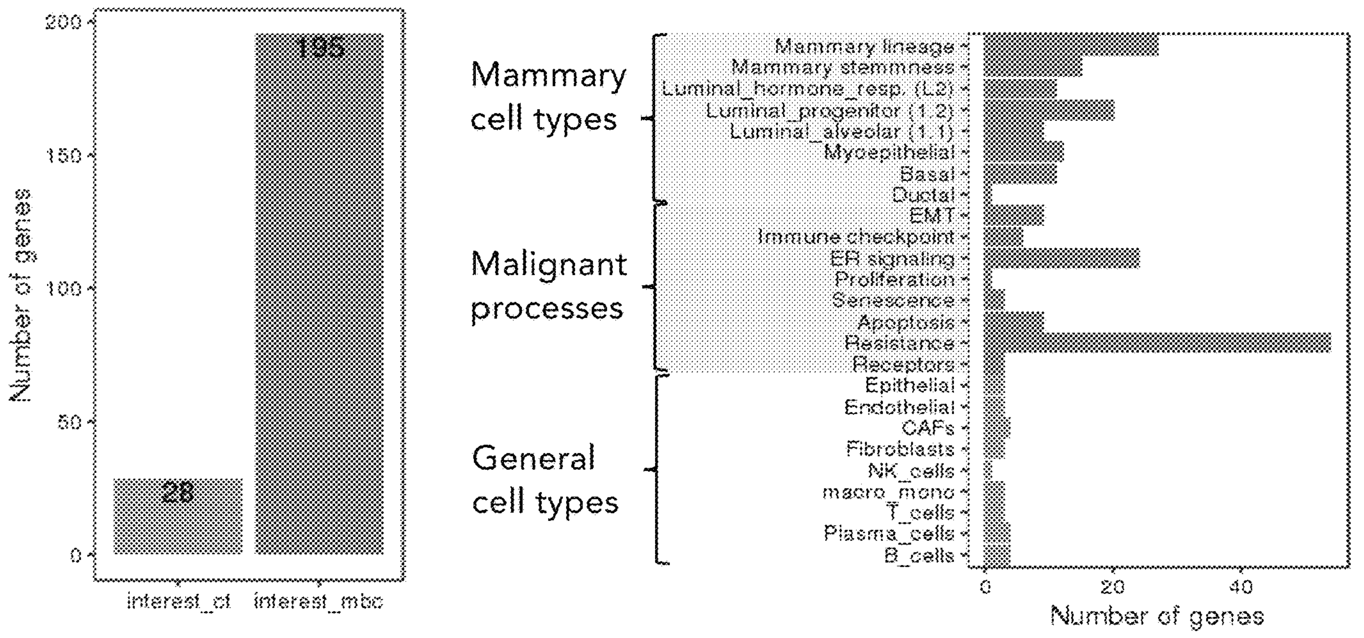
FIG. 12. Graphs showing genes of interest for metastatic breast cancer (MBC).
Figure 13:
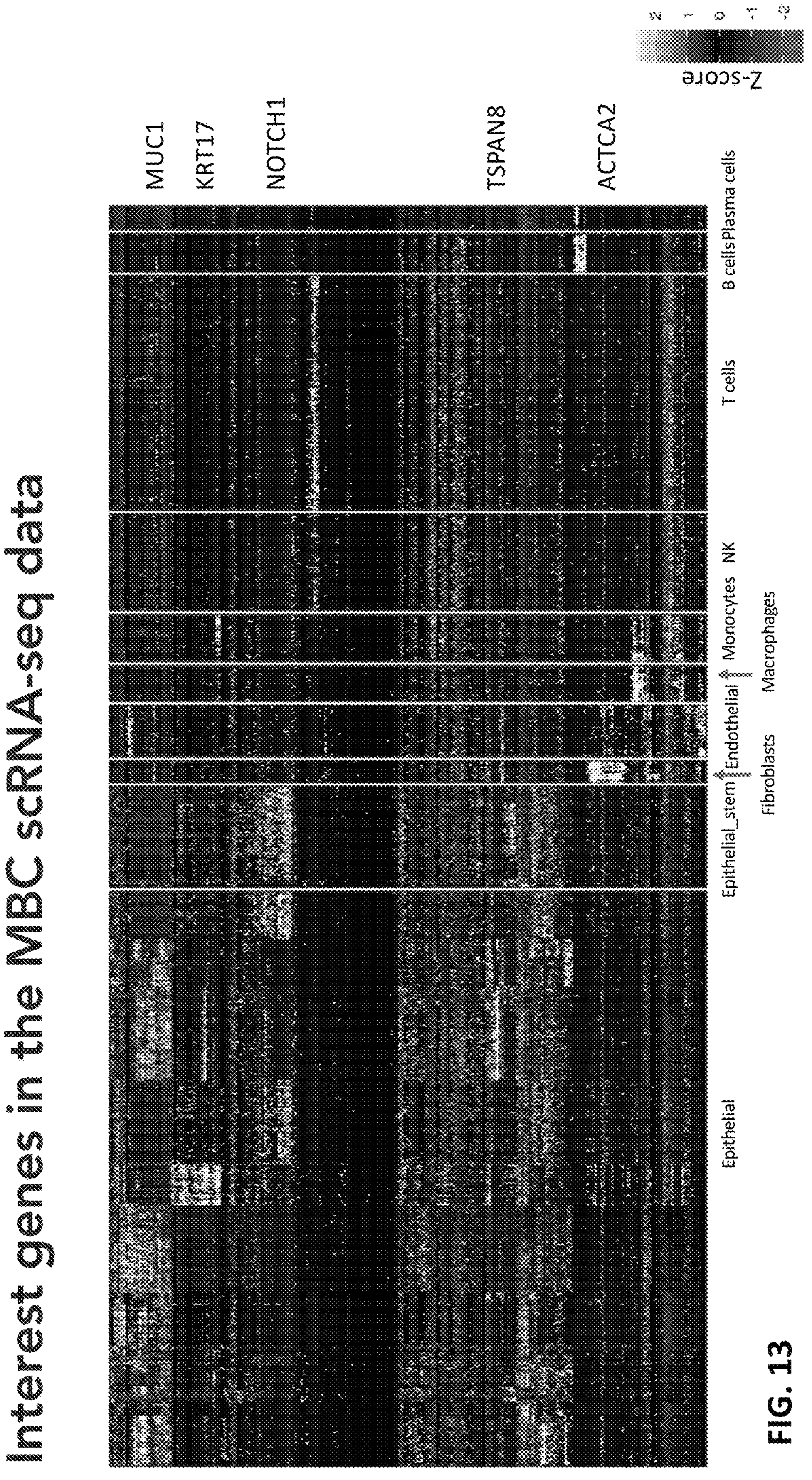
FIG. 13. Heat map showing expression of genes of interest in single cells from MBC and labeled by the cell type.
Figure 15:
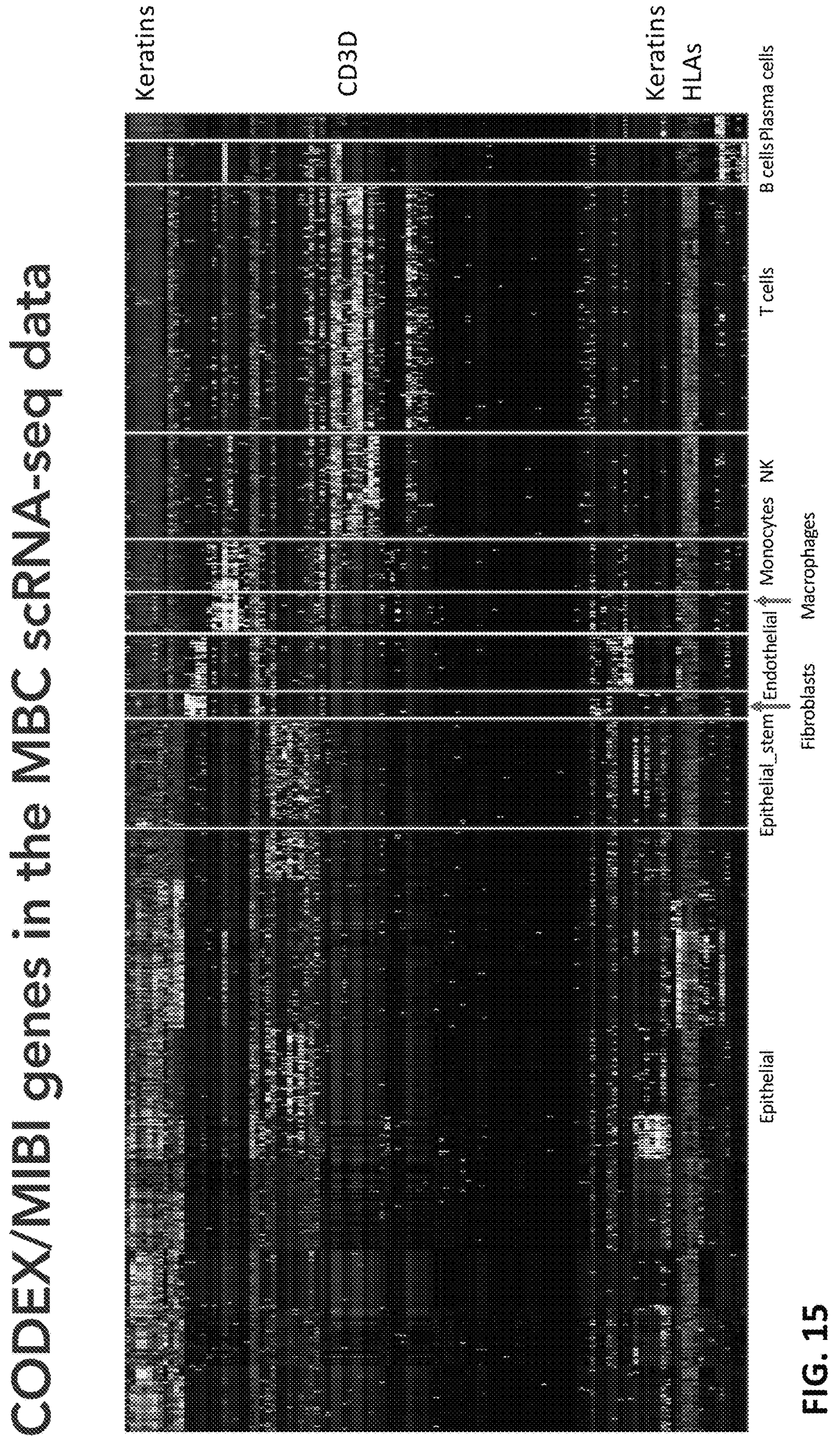
FIG. 15. Heat map showing expression of CODEX/MIBI genes in single cells from MBC and labeled by the cell type.
Figure 16:
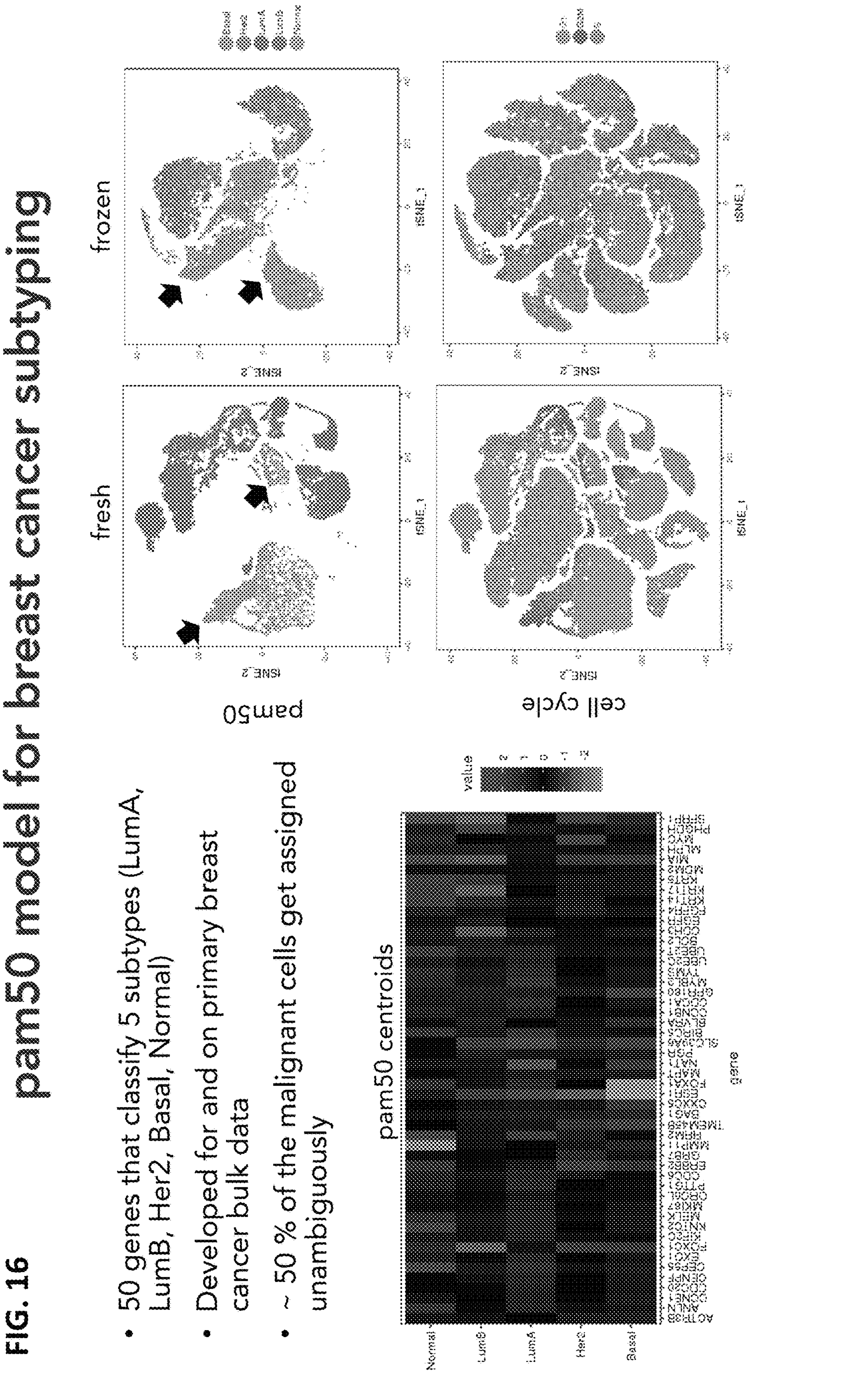
FIG. 16. Heatmap showing expression of pam50 genes in the breast cancer subtypes. tSNE plots of single cells from fresh and frozen tissue with pam50 subtypes and cell cycle projected.

Applicants selected genes that can be used on spatial gene expression platforms and spatial methods to identify cell types in a tissue sample (e.g., ExSeq and MERFISH) (Table 1, FIGS. 41-45). Applicants performed single cell and single nuclei RNA-seq on metastatic breast cancer (MBC) tissue samples and analyzed cell type specific gene expression (FIGS. 10-11, 34). Applicants analyzed fresh and frozen tissue samples (see, e.g., FIG. 19). Applicants analyzed genes using literature, CODEX/MIBI panels, pam50 model and data driven models (e.g., topics) to select for the genes (FIGS. 12-31 and 35-49). Applicants used the selected genes in ExSeq to provide for high resolution spatial maps of cell types in metastatic breast cancer (FIGS. 32-33).

Example 10. Select Data Driven Program Genes

The following example illustrates selecting genes from gene programs. In an exemplary embodiment the following method can be used to select data driven program genes:

- Run topic modeling on each of 8 cell types separately
  - T, NK, B, Plasma, MonoMacro, Fibroblasts, Endothelial, Epithelial(malignant)
  - Downsampled to max 4000 cells per cell type (runtime)
  - Remove mitochondrial and ribosomal genes
  - Select "best" number of topics for each cell type by the measure of lowest BIC
- Run GO-term enrichment (biological processes) on top 30 driving genes per topic
- Manually select "interesting" topics to include
- Select genes that lead to enrichment of the respective GO-terms
  - Among those, assign priority 1 to genes with highest topic weight
  - Assign priority 0 to all other enrichment relevant genes

REFERENCES

The following references apply to the above descriptions and examples and are incorporated herein by reference:

Parris T Z, Kovics A, Aziz L, Hajizadeh S, Nemes S, Semaan M, Forssell-Aronsson E, Karlsson P, Helou K. Additive effect of the AZGP1, PIP, S100A8 and UBE2C molecular biomarkers improves outcome prediction in breast carcinoma. Int J Cancer. 2014; 134:1617-1629.

Gangadharan A, Nyirenda T, Patel K, Jaimes-Delgadillo N, Coletta D, Tanaka T, Walland A C, Jameel Z, Vedantam S, Tang S, Mannion C, Lee G Y, Goy A, Pecora A, Suh K S. Prolactin induced protein (PIP) is a potential biomarker for early stage and malignant breast cancer. Breast. 2018; 39:101-109.

Anna Urbaniak, Karolina Jablonska, Marzenna Podhorska-Okolow, Maciej Ugorski,1,4 and Piotr Dziegiel. Prolactin-induced protein (PIP)-characterization and role in breast cancer progression. Am J Cancer Res. 2018; 8(11): 2150-2164.

Hsu P D, Lander E S, Zhang F. Development and applications of CRISPR-Cas9 for genome engineering. Cell. 2014 Jun. 5; 157(6):1262-78. doi: 10.1016/j.cell.2014.05.010.

Macosko E Z, Basu A, Satija R, Nemesh J, Shekhar K, Goldman M, Tirosh I, Bialas A R, Kamitaki N, Martersteck E M, Trombetta J J, Weitz D A, Sanes J R, Shalek A K, Regev A, McCarroll S A. Highly Parallel Genome-wide Expression Profiling of Individual Cells Using Nanoliter Droplets. Cell. 2015 May 21;161(5):1202-1214. doi: 10.1016/j.cell.2015.05.002.

U.S. Pat. No. 10,059,990 In situ nucleic acid sequencing of expanded biological samples.

US 2019/0285644 Proteomics and spatial patterning using antenna networks.

US 2019/0218276 Methods for determining spatial and temporal gene expression dynamics in single cells.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of producing a molecular spatial map for visualizing a tissue microenvironment of a lesion, wherein the lesion is a metastatic breast cancer (MBC), the method comprising:

identifying the location of epithelial stem cells on an MBC tissue from the MBC lesion by performing RNA visualization on the MBC tissue for the combination of RNA molecules consisting of CCND1, CSRP2, EFNA5, FABP7, KIF23, MYO10, OBP2B, PBK, PHGDH, SOX4, TFF2, TTYH1, and UBE2C, whereby a molecular spatial map comprising the location of epithelial stem cells for the MBC tissue microenvironment is obtained.

2. The method of claim 1, wherein the tissue microenvironment of MBC comprises a heterogeneous population of cells.

3. The method of claim 1, wherein the RNA visualization is performed using methods comprising RNA in situ sequencing methods and RNA in situ hybridization methods.

4. The method of claim 1, wherein the method further comprises identifying therapeutic targets for MBC, comprising:

selecting one or more genes visualized on the molecular spatial map, wherein the genes are highly expressed in metastatic tumor tissues of MBC in comparison to normal tissues, and wherein the genes have functions comprising inhibiting apoptosis, stimulating angiogenesis, promoting cell proliferation, inhibiting cytotoxic immune cells, inhibiting antigen presenting cells, stimulating regulatory T cells and immunotolerance, degrading extracellular matrix, and any combination thereof, whereby the one or more genes can be used as therapeutic target or targets for developing, screening, or evaluating therapeutic agents for treating MBC.

5. The method of claim 1, further comprising obtaining gene expression data from the MBC lesion via scRNA-seq or snRNA-seq.

6. The method of claim 3, wherein the RNA in situ sequencing methods comprise expansion sequencing (ExSEQ) method.

7. The method of claim 3, wherein the RNA in situ hybridization methods comprise multiplexed error-robust fluorescence in situ hybridization (MERFISH), SLIDE-Seq, or high-definition spatial transcriptomics (HDST).

8. The method of claim 1, further comprising contacting a candidate therapeutic agent to one or more cells of the MBC lesion and detecting modulation of one or more phenotypic aspects of the MBC lesion by the candidate agent.

9. The method of claim 8, wherein detecting modulation comprises identifying the location of epithelial stem cells on an MBC tissue sample from the MBC lesion contacted with the candidate therapeutic agent by performing RNA visualization on the MBC tissue sample for the combination of RNA molecules consisting of CCND1, CSRP2, EFNA5, FABP7, KIF23, MYO10, OBP2B, PBK, PHGDH, SOX4, TFF2, TTYH1, and UBE2C, whereby a molecular spatial map comprising the location of epithelial stem cells for the MBC tissue microenvironment contacted with the candidate therapeutic agent is obtained.

10. The method of claim 8, wherein detecting modulation comprises obtaining gene expression data on an MBC tissue sample from the MBC lesion contacted with the candidate therapeutic agent via scRNA-seq or snRNA-seq.

11. The method of claim 9, wherein the RNA visualization is performed using methods comprising RNA in situ sequencing methods and RNA in situ hybridization methods.

12. The method of claim 11, wherein the RNA in situ sequencing methods comprise expansion sequencing (ExSEQ) method.

13. The method of claim 11, wherein the RNA in situ hybridization methods comprise multiplexed error-robust fluorescence in situ hybridization (MERFISH), SLIDE-Seq, or high-definition spatial transcriptomics (HDST).

14. The method of claim 1, wherein the molecular spatial map comprises information about cell types, cell state, and cell location.

15. The method of claim 1, wherein the molecular spatial map further comprises information about expression levels of one or more genes in one or more locations, one or more cell types, and one or more cell states in the MBC tissue microenvironment.

16. The method of claim 1, wherein the MBC tissue comprises bone, brain, breast, lung, liver, lymph node, stomach, spleen, pancreas, kidney, ovary, uterus, or any combination thereof.

* * * * *

SEQUENCE LISTING

```
<160> NUMBER OF SEQ ID NOS: 29

<210> SEQ ID NO 1
<211> LENGTH: 107
<212> TYPE: PRT
<213> ORGANISM: Homo sapiens

<400> SEQUENCE: 1

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105


<210> SEQ ID NO 2
<211> LENGTH: 9
<212> TYPE: PRT
<213> ORGANISM: Homo sapiens

<400> SEQUENCE: 2

Ile Glu Val Met Tyr Pro Pro Pro Tyr
1               5


<210> SEQ ID NO 3
<211> LENGTH: 401
<212> TYPE: PRT
<213> ORGANISM: Ktedonobacter racemifer DSM 44963

<400> SEQUENCE: 3

Met Ser Thr Asp Ala Thr Leu Ile Arg Thr Thr Pro Ser His Ala Glu
1               5                   10                  15

Ala Asp Ala Thr Asp Thr Leu Val Ala Thr Pro Leu Met Pro Pro Arg
```

-continued

```
            20                  25                  30

Arg Val Ile Ser Pro Trp Pro Gly Pro Gly Glu Gly Gln Ser Leu Met
        35                  40                  45

Arg Ile Pro Val Val Asp Ile Arg Gly Met Ala Leu Met Pro Cys Thr
    50                  55                  60

Pro Ala Lys Ala Arg His Leu Leu Lys Ser Gly Asn Ala Arg Pro Lys
65                  70                  75                  80

Arg Asn Lys Leu Gly Leu Phe Tyr Val Gln Leu Ser Tyr Glu Gln Glu
                85                  90                  95

Pro Asp Asn Gln Ser Leu Val Ala Gly Val Asp Pro Gly Ser Lys Phe
            100                 105                 110

Glu Gly Leu Ser Val Val Gly Thr Lys Asp Thr Val Leu Asn Leu Met
        115                 120                 125

Val Glu Ala Pro Asp His Val Lys Gly Ala Val Gln Thr Arg Arg Thr
    130                 135                 140

Met Arg Arg Ala Arg Arg Gln Arg Lys Trp Arg Arg Pro Lys Arg Phe
145                 150                 155                 160

His Asn Arg Leu Asn Arg Met Gln Arg Ile Pro Pro Ser Thr Arg Ser
                165                 170                 175

Arg Trp Glu Ala Lys Ala Arg Ile Val Ala His Leu Arg Thr Ile Leu
            180                 185                 190

Pro Phe Thr Asp Val Val Val Glu Asp Val Gln Ala Val Thr Arg Lys
        195                 200                 205

Gly Lys Gly Gly Thr Trp Asn Gly Ser Phe Ser Pro Val Gln Val Gly
    210                 215                 220

Lys Glu His Leu Tyr Arg Leu Leu Arg Ala Met Gly Leu Thr Leu His
225                 230                 235                 240

Leu Arg Glu Gly Trp Gln Thr Lys Glu Leu Arg Glu Gln His Gly Leu
                245                 250                 255

Lys Lys Thr Lys Ser Lys Ser Lys Gln Ser Phe Glu Ser His Ala Val
            260                 265                 270

Asp Ser Trp Val Leu Ala Ala Ser Ile Ser Gly Ala Glu His Pro Thr
        275                 280                 285

Cys Thr Arg Leu Trp Tyr Met Val Pro Ala Ile Leu His Arg Arg Gln
    290                 295                 300

Leu His Arg Leu Gln Ala Ser Lys Gly Gly Val Arg Lys Pro Tyr Gly
305                 310                 315                 320

Gly Thr Arg Ser Leu Gly Val Lys Arg Gly Thr Leu Val Glu His Lys
                325                 330                 335

Lys Tyr Gly Arg Cys Thr Val Gly Gly Val Asp Arg Lys Arg Asn Thr
            340                 345                 350

Ile Ser Leu His Glu Tyr Arg Thr Asn Thr Arg Leu Thr Gln Ala Ala
        355                 360                 365

Lys Val Glu Thr Cys Arg Val Leu Thr Trp Leu Ser Trp Arg Ser Trp
    370                 375                 380

Leu Leu Arg Gly Lys Arg Thr Ser Ser Lys Gly Lys Gly Ser His Ser
385                 390                 395                 400

Ser
```

<210> SEQ ID NO 4
<211> LENGTH: 432
<212> TYPE: PRT
<213> ORGANISM: Oscillatoriales cyanobacterium

<400> SEQUENCE: 4

```
Met Gln Pro Ala Lys Gln Gln Asn Trp Val Phe Gln Ile Asn Gly Asp
1               5                   10                  15

Lys Gln Pro Leu Asp Met Ile Asn Pro Gly Arg Cys Arg Glu Leu Gln
            20                  25                  30

Asn Arg Gly Lys Leu Ala Ser Phe Arg Arg Phe Pro Tyr Val Val Ile
        35                  40                  45

Gln Gln Gln Thr Ile Glu Asn Pro Gln Thr Lys Glu Tyr Ile Leu Lys
    50                  55                  60

Ile Asp Pro Gly Ser Gln Trp Thr Gly Phe Ala Ile Gln Cys Gly Asn
65                  70                  75                  80

Asp Ile Leu Phe Arg Ala Glu Leu Asn His Arg Gly Glu Ala Ile Lys
                85                  90                  95

Phe Asp Leu Val Lys Arg Ala Trp Phe Arg Arg Gly Arg Arg Ser Arg
            100                 105                 110

Asn Leu Arg Tyr Arg Lys Lys Arg Leu Asn Arg Ala Lys Pro Glu Gly
        115                 120                 125

Trp Leu Ala Pro Ser Ile Arg His Arg Val Leu Thr Val Glu Thr Trp
    130                 135                 140

Ile Lys Arg Phe Met Arg Tyr Cys Pro Ile Ala Trp Ile Glu Ile Glu
145                 150                 155                 160

Gln Val Arg Phe Asp Thr Gln Lys Leu Ala Asn Pro Glu Ile Asp Gly
                165                 170                 175

Val Glu Tyr Gln Gln Gly Glu Leu Gln Gly Tyr Glu Val Arg Glu Tyr
            180                 185                 190

Leu Leu Gln Lys Trp Gly Arg Lys Cys Ala Tyr Cys Gly Thr Glu Asn
        195                 200                 205

Val Pro Leu Glu Val Glu His Ile Gln Ser Lys Ser Lys Gly Gly Ser
    210                 215                 220

Ser Arg Ile Gly Asn Leu Thr Leu Ala Cys His Val Cys Asn Val Lys
225                 230                 235                 240

Lys Gly Asn Leu Asp Val Arg Asp Phe Leu Ala Lys Ser Pro Asp Ile
                245                 250                 255

Leu Asn Gln Val Leu Glu Asn Ser Thr Lys Pro Leu Lys Asp Ala Ala
            260                 265                 270

Ala Val Asn Ser Thr Arg Tyr Ala Ile Val Lys Met Ala Lys Ser Ile
        275                 280                 285

Cys Glu Asn Val Lys Cys Ser Ser Gly Ala Arg Thr Lys Met Asn Arg
    290                 295                 300

Val Arg Gln Gly Leu Glu Lys Thr His Ser Leu Asp Ala Ala Cys Val
305                 310                 315                 320

Gly Glu Ser Gly Ala Ser Ile Arg Val Leu Thr Asp Arg Pro Leu Leu
                325                 330                 335

Ile Thr Cys Lys Gly His Gly Ser Arg Gln Ser Ile Arg Val Asn Ala
            340                 345                 350

Ser Gly Phe Pro Ala Val Lys Asn Ala Lys Thr Val Phe Thr His Ile
        355                 360                 365

Ala Ala Gly Asp Val Val Arg Phe Thr Ile Gly Lys Asp Arg Lys Lys
    370                 375                 380

Ala Gln Ala Gly Thr Tyr Thr Ala Arg Val Lys Thr Pro Thr Pro Lys
385                 390                 395                 400

Gly Phe Glu Val Leu Ile Asp Gly Ala Arg Ile Ser Leu Ser Thr Met
                405                 410                 415
```

```
Ser Asn Val Val Phe Val His Arg Ser Asp Gly Tyr Gly Tyr Glu Leu
            420                 425                 430


<210> SEQ ID NO 5
<211> LENGTH: 461
<212> TYPE: PRT
<213> ORGANISM: Acidihalobacter prosperus

<400> SEQUENCE: 5

Met Ala Val Phe Val Ile Asp Lys His Lys Arg Pro Leu Met Pro Cys
1               5                   10                  15

Ser Glu Lys Arg Ala Arg Leu Leu Leu Glu Arg Gly Arg Ala Val Val
            20                  25                  30

His Arg Gln Val Pro Phe Val Ile Arg Leu Lys Asp Arg Thr Val Gln
        35                  40                  45

His Ser Ala Val Gln Pro Leu Arg Val Ala Leu Asp Pro Gly Ser Arg
    50                  55                  60

Ala Thr Gly Met Ala Leu Val Arg Glu Lys Asn Thr Val Asp Thr Gly
65                  70                  75                  80

Thr Gly Glu Val Tyr Arg Glu Arg Ile Ala Leu Asn Leu Phe Glu Leu
                85                  90                  95

Val His Arg Gly His Arg Ile Arg Glu Gln Leu Asp Gln Arg Arg Asn
            100                 105                 110

Phe Arg Arg Arg Arg Arg Gly Ala Asn Leu Arg Tyr Arg Ala Pro Arg
        115                 120                 125

Phe Asp Asn Arg Arg Arg Pro Pro Gly Trp Leu Ala Pro Ser Leu Gln
    130                 135                 140

His Arg Val Asp Thr Thr Met Ala Trp Val Arg Arg Leu Cys Arg Trp
145                 150                 155                 160

Ala Pro Ala Ser Ala Ile Gly Ile Glu Thr Val Arg Phe Asp Thr Gln
                165                 170                 175

Arg Leu Gln Asn Pro Glu Ile Ser Gly Val Glu Tyr Gln Gln Gly Ala
            180                 185                 190

Leu Ala Gly Cys Glu Val Arg Glu Tyr Leu Leu Glu Lys Trp Gly Arg
        195                 200                 205

Lys Cys Ala Tyr Cys Gly Ala Glu Asn Val Pro Leu Glu Ile Glu His
    210                 215                 220

Ile Val Pro Lys Ser Arg Gly Gly Ser Asp Arg Val Ser Asn Leu Ala
225                 230                 235                 240

Leu Ala Cys Arg Ala Cys Asn Gln Ala Lys Gly Asn Arg Asp Val Arg
                245                 250                 255

Ala Phe Leu Ala Asp Gln Pro Glu Arg Leu Ala Arg Ile Leu Ala Gln
            260                 265                 270

Ala Lys Ala Pro Leu Lys Asp Ala Ala Ala Val Asn Ala Thr Arg Trp
        275                 280                 285

Ala Leu Tyr Arg Ala Leu Val Asp Thr Gly Leu Pro Val Glu Ala Gly
    290                 295                 300

Thr Gly Gly Arg Thr Lys Trp Asn Arg Thr Arg Leu Gly Leu Pro Lys
305                 310                 315                 320

Thr His Ala Leu Asp Ala Leu Cys Val Gly Gln Val Asp Gln Val Arg
                325                 330                 335

His Trp Arg Val Pro Val Leu Gly Ile Arg Cys Ala Gly Arg Gly Ser
            340                 345                 350

Tyr Arg Arg Thr Arg Leu Thr Arg His Gly Phe Pro Arg Gly Tyr Leu
```

```
        355                 360                 365

Thr Arg Asn Lys Ser Ala Phe Gly Phe Gln Thr Gly Asp Leu Ile Arg
    370                 375                 380

Ala Val Val Thr Lys Gly Lys Lys Ala Gly Thr Tyr Leu Gly Arg Ile
385                 390                 395                 400

Ala Ile Arg Ala Ser Gly Ser Phe Asn Ile Gln Thr Pro Met Gly Val
                405                 410                 415

Val Gln Gly Ile His His Arg Phe Cys Thr Leu Leu Gln Arg Ala Asp
            420                 425                 430

Gly Tyr Gly Tyr Phe Val Gln Pro Lys Pro Thr Glu Ala Ala Leu Ser
        435                 440                 445

Ser Pro Arg Leu Lys Ala Gly Val Ser Ser Ala Gly Asn
    450                 455                 460


<210> SEQ ID NO 6
<211> LENGTH: 439
<212> TYPE: PRT
<213> ORGANISM: Tolypothrix campylonemoides

<400> SEQUENCE: 6

Met Thr Thr Asn Val Val Phe Val Ile Asp Thr Asn Gln Lys Pro Leu
1               5                   10                  15

Gln Pro Cys Ser Ala Ala Val Ala Arg Lys Leu Leu Leu Arg Gly Lys
            20                  25                  30

Ala Ala Met Phe Arg Arg Tyr Pro Ala Val Ile Ile Leu Lys Lys Glu
        35                  40                  45

Val Asp Ser Val Gly Lys Pro Lys Ile Glu Leu Arg Ile Asp Pro Gly
    50                  55                  60

Ser Lys Tyr Thr Gly Phe Ala Leu Val Asp Ser Lys Asp Asn Ala Asp
65                  70                  75                  80

Phe Ile Ile Trp Gly Thr Glu Leu Glu His Arg Gly Ala Ala Ile Cys
                85                  90                  95

Lys Glu Leu Thr Lys Arg Ser Ala Ile Arg Arg Ser Arg Arg Asn Arg
            100                 105                 110

Lys Thr Arg Tyr Arg Lys Lys Arg Phe Glu Arg Arg Lys Pro Glu Gly
        115                 120                 125

Trp Leu Ala Pro Ser Leu Gln His Arg Val Asp Thr Thr Leu Thr Trp
    130                 135                 140

Val Lys Arg Ile Cys Lys Phe Val Pro Ile Met Ser Ile Ser Val Glu
145                 150                 155                 160

Gln Val Lys Phe Asp Leu Gln Lys Leu Glu Asn Ser Asp Ile Gln Gly
                165                 170                 175

Ile Glu Tyr Gln Gln Gly Thr Leu Ala Gly Tyr Thr Leu Arg Glu Ala
            180                 185                 190

Leu Leu Glu His Trp Gly Arg Lys Cys Ala Tyr Cys Asp Val Glu Asn
        195                 200                 205

Val Phe Leu Glu Ile Glu His Ile Tyr Pro Lys Ser Lys Gly Gly Ser
    210                 215                 220

Asp Lys Phe Ser Asn Leu Thr Leu Ala Cys His Lys Cys Asn Ile Asn
225                 230                 235                 240

Lys Gly Asn Lys Ser Ile Asp Glu Phe Leu Leu Ser Asp His Lys Arg
                245                 250                 255

Leu Glu Gln Ile Lys Leu His Gln Lys Lys Thr Leu Lys Asp Ala Ala
            260                 265                 270
```

```
Ala Val Asn Ala Thr Arg Lys Lys Leu Val Thr Thr Leu Gln Glu Lys
        275                 280                 285

Thr Phe Leu Asn Val Leu Val Ser Asp Gly Ala Ser Thr Lys Met Thr
    290                 295                 300

Arg Leu Ser Ser Ser Leu Ala Lys Arg His Trp Ile Asp Ala Gly Cys
305                 310                 315                 320

Val Asn Thr Thr Leu Ile Val Ile Leu Lys Thr Leu Gln Pro Leu Gln
                325                 330                 335

Val Lys Cys Asn Gly His Gly Asn Lys Gln Phe Val Thr Met Asp Ala
            340                 345                 350

Tyr Gly Phe Pro Arg Lys Ser Tyr Glu Pro Lys Lys Val Arg Lys Asp
        355                 360                 365

Trp Lys Ala Gly Asp Ile Ile Arg Val Thr Lys Lys Asp Gly Thr Met
    370                 375                 380

Leu Met Gly Arg Val Lys Lys Ala Ala Lys Lys Leu Val Tyr Ile Pro
385                 390                 395                 400

Phe Gly Gly Lys Glu Ala Ser Phe Ser Ser Glu Asn Ala Lys Ala Ile
                405                 410                 415

His Arg Ser Asp Gly Tyr Arg Tyr Ser Phe Ala Ala Ile Asp Ser Glu
            420                 425                 430

Leu Leu Gln Lys Met Ala Thr
        435


<210> SEQ ID NO 7
<211> LENGTH: 419
<212> TYPE: PRT
<213> ORGANISM: Halobacteroides halobius

<400> SEQUENCE: 7

Met Pro Asn Lys Tyr Ala Phe Val Leu Asp Ser Lys Gly Lys Leu Leu
1               5                   10                  15

Asp Pro Thr Lys Ser Lys Lys Ala Trp Tyr Leu Ile Arg Lys Gly Lys
            20                  25                  30

Ala Ser Leu Val Glu Glu Tyr Pro Leu Ile Ile Lys Leu Lys Arg Glu
        35                  40                  45

Val Pro Lys Asp Gln Val Asn Ser Asp Lys Leu Ile Leu Gly Ile Asp
    50                  55                  60

Asp Gly Thr Lys Lys Val Gly Phe Ala Leu Val Gln Lys Cys Gln Thr
65                  70                  75                  80

Lys Asn Lys Val Leu Phe Lys Ala Val Met Glu Gln Arg Gln Asp Val
                85                  90                  95

Ser Lys Lys Met Glu Glu Arg Arg Gly Tyr Arg Arg Tyr Arg Arg Ser
            100                 105                 110

His Lys Arg Tyr Arg Pro Ala Arg Phe Asp Asn Arg Ser Ser Ser Lys
        115                 120                 125

Arg Lys Gly Arg Ile Pro Pro Ser Ile Leu Gln Lys Lys Gln Ala Ile
    130                 135                 140

Leu Arg Val Val Asn Lys Leu Lys Lys Tyr Ile Arg Ile Asp Lys Ile
145                 150                 155                 160

Val Leu Glu Asp Val Ser Ile Asp Ile Arg Lys Leu Thr Glu Gly Arg
                165                 170                 175

Glu Leu Tyr Asn Trp Glu Tyr Gln Glu Ser Asn Arg Leu Asp Glu Asn
            180                 185                 190

Leu Arg Lys Ala Thr Leu Tyr Arg Asp Asp Cys Thr Cys Gln Leu Cys
        195                 200                 205
```

Gly Thr Thr Glu Thr Met Leu His Ala His His Ile Met Pro Arg Arg
210 215 220

Asp Gly Gly Ala Asp Ser Ile Tyr Asn Leu Ile Thr Leu Cys Lys Ala
225 230 235 240

Cys His Lys Asp Lys Val Asp Asn Asn Glu Tyr Gln Tyr Lys Asp Gln
245 250 255

Phe Leu Ala Ile Ile Asp Ser Lys Glu Leu Ser Asp Leu Lys Ser Ala
260 265 270

Ser His Val Met Gln Gly Lys Thr Trp Leu Arg Asp Lys Leu Ser Lys
275 280 285

Ile Ala Gln Leu Glu Ile Thr Ser Gly Gly Asn Thr Ala Asn Lys Arg
290 295 300

Ile Asp Tyr Glu Ile Glu Lys Ser His Ser Asn Asp Ala Ile Cys Thr
305 310 315 320

Thr Gly Leu Leu Pro Val Asp Asn Ile Asp Asp Ile Lys Glu Tyr Tyr
325 330 335

Ile Lys Pro Leu Arg Lys Lys Ser Lys Ala Lys Ile Lys Glu Leu Lys
340 345 350

Cys Phe Arg Gln Arg Asp Leu Val Lys Tyr Thr Lys Arg Asn Gly Glu
355 360 365

Thr Tyr Thr Gly Tyr Ile Thr Ser Leu Arg Ile Lys Asn Asn Lys Tyr
370 375 380

Asn Ser Lys Val Cys Asn Phe Ser Thr Leu Lys Gly Lys Ile Phe Arg
385 390 395 400

Gly Tyr Gly Phe Arg Asn Leu Thr Leu Leu Asn Arg Pro Lys Gly Leu
405 410 415

Met Ile Val

<210> SEQ ID NO 8
<211> LENGTH: 1409
<212> TYPE: PRT
<213> ORGANISM: Streptococcus thermophilus

<400> SEQUENCE: 8

Met Leu Phe Asn Lys Cys Ile Ile Ile Ser Ile Asn Leu Asp Phe Ser
1 5 10 15

Asn Lys Glu Lys Cys Met Thr Lys Pro Tyr Ser Ile Gly Leu Asp Ile
20 25 30

Gly Thr Asn Ser Val Gly Trp Ala Val Ile Thr Asp Asn Tyr Lys Val
35 40 45

Pro Ser Lys Lys Met Lys Val Leu Gly Asn Thr Ser Lys Lys Tyr Ile
50 55 60

Lys Lys Asn Leu Leu Gly Val Leu Leu Phe Asp Ser Gly Ile Thr Ala
65 70 75 80

Glu Gly Arg Arg Leu Lys Arg Thr Ala Arg Arg Arg Tyr Thr Arg Arg
85 90 95

Arg Asn Arg Ile Leu Tyr Leu Gln Glu Ile Phe Ser Thr Glu Met Ala
100 105 110

Thr Leu Asp Asp Ala Phe Phe Gln Arg Leu Asp Asp Ser Phe Leu Val
115 120 125

Pro Asp Asp Lys Arg Asp Ser Lys Tyr Pro Ile Phe Gly Asn Leu Val
130 135 140

Glu Glu Lys Val Tyr His Asp Glu Phe Pro Thr Ile Tyr His Leu Arg
145 150 155 160

-continued

```
Lys Tyr Leu Ala Asp Ser Thr Lys Lys Ala Asp Leu Arg Leu Val Tyr
                165                 170                 175

Leu Ala Leu Ala His Met Ile Lys Tyr Arg Gly His Phe Leu Ile Glu
            180                 185                 190

Gly Glu Phe Asn Ser Lys Asn Asn Asp Ile Gln Lys Asn Phe Gln Asp
        195                 200                 205

Phe Leu Asp Thr Tyr Asn Ala Ile Phe Glu Ser Asp Leu Ser Leu Glu
    210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
            260                 265                 270

Phe Arg Lys Cys Phe Asn Leu Asp Glu Lys Ala Ser Leu His Phe Ser
        275                 280                 285

Lys Glu Ser Tyr Asp Glu Asp Leu Glu Thr Leu Leu Gly Tyr Ile Gly
    290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                325                 330                 335

Pro Leu Ser Ser Ala Met Ile Lys Arg Tyr Asn Glu His Lys Glu Asp
            340                 345                 350

Leu Ala Leu Leu Lys Glu Tyr Ile Arg Asn Ile Ser Leu Lys Thr Tyr
        355                 360                 365

Asn Glu Val Phe Lys Asp Asp Thr Lys Asn Gly Tyr Ala Gly Tyr Ile
    370                 375                 380

Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
            420                 425                 430

Tyr Gln Ile His Leu Gln Glu Met Arg Ala Ile Leu Asp Lys Gln Ala
        435                 440                 445

Lys Phe Tyr Pro Phe Leu Ala Lys Asn Lys Glu Arg Ile Glu Lys Ile
    450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495

Trp Asn Phe Glu Asp Val Ile Asp Lys Glu Ser Ser Ala Glu Ala Phe
            500                 505                 510

Ile Asn Arg Met Thr Ser Phe Asp Leu Tyr Leu Pro Glu Glu Lys Val
        515                 520                 525

Leu Pro Lys His Ser Leu Leu Tyr Glu Thr Phe Asn Val Tyr Asn Glu
    530                 535                 540

Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575
```

-continued

```
Lys Arg Lys Val Thr Asp Lys Asp Ile Ile Glu Tyr Leu His Ala Ile
            580                 585                 590

Tyr Gly Tyr Asp Gly Ile Glu Leu Lys Gly Ile Glu Lys Gln Phe Asn
        595                 600                 605

Ser Ser Leu Ser Thr Tyr His Asp Leu Leu Asn Ile Ile Asn Asp Lys
    610                 615                 620

Glu Phe Leu Asp Asp Ser Ser Asn Glu Ala Ile Ile Glu Glu Ile Ile
625                 630                 635                 640

His Thr Leu Thr Ile Phe Glu Asp Arg Glu Met Ile Lys Gln Arg Leu
                645                 650                 655

Ser Lys Phe Glu Asn Ile Phe Asp Lys Ser Val Leu Lys Lys Leu Ser
            660                 665                 670

Arg Arg His Tyr Thr Gly Trp Gly Lys Leu Ser Ala Lys Leu Ile Asn
        675                 680                 685

Gly Ile Arg Asp Glu Lys Ser Gly Asn Thr Ile Leu Asp Tyr Leu Ile
    690                 695                 700

Asp Asp Gly Ile Ser Asn Arg Asn Phe Met Gln Leu Ile His Asp Asp
705                 710                 715                 720

Ala Leu Ser Phe Lys Lys Lys Ile Gln Lys Ala Gln Ile Ile Gly Asp
                725                 730                 735

Glu Asp Lys Gly Asn Ile Lys Glu Val Val Lys Ser Leu Pro Gly Ser
            740                 745                 750

Pro Ala Ile Lys Lys Gly Ile Leu Gln Ser Ile Lys Ile Val Asp Glu
        755                 760                 765

Leu Val Lys Val Met Gly Gly Arg Lys Pro Glu Ser Ile Val Val Glu
    770                 775                 780

Met Ala Arg Glu Asn Gln Tyr Thr Asn Gln Gly Lys Ser Asn Ser Gln
785                 790                 795                 800

Gln Arg Leu Lys Arg Leu Glu Lys Ser Leu Lys Glu Leu Gly Ser Lys
                805                 810                 815

Ile Leu Lys Glu Asn Ile Pro Ala Lys Leu Ser Lys Ile Asp Asn Asn
            820                 825                 830

Ala Leu Gln Asn Asp Arg Leu Tyr Leu Tyr Tyr Leu Gln Asn Gly Lys
        835                 840                 845

Asp Met Tyr Thr Gly Asp Asp Leu Asp Ile Asp Arg Leu Ser Asn Tyr
    850                 855                 860

Asp Ile Asp His Ile Ile Pro Gln Ala Phe Leu Lys Asp Asn Ser Ile
865                 870                 875                 880

Asp Asn Lys Val Leu Val Ser Ser Ala Ser Asn Arg Gly Lys Ser Asp
                885                 890                 895

Asp Phe Pro Ser Leu Glu Val Val Lys Lys Arg Lys Thr Phe Trp Tyr
            900                 905                 910

Gln Leu Leu Lys Ser Lys Leu Ile Ser Gln Arg Lys Phe Asp Asn Leu
        915                 920                 925

Thr Lys Ala Glu Arg Gly Gly Leu Leu Pro Glu Asp Lys Ala Gly Phe
    930                 935                 940

Ile Gln Arg Gln Leu Val Glu Thr Arg Gln Ile Thr Lys His Val Ala
945                 950                 955                 960

Arg Leu Leu Asp Glu Lys Phe Asn Asn Lys Lys Asp Glu Asn Asn Arg
                965                 970                 975

Ala Val Arg Thr Val Lys Ile Ile Thr Leu Lys Ser Thr Leu Val Ser
            980                 985                 990

Gln Phe Arg Lys Asp Phe Glu Leu  Tyr Lys Val Arg Glu  Ile Asn Asp
```

```
        995                1000                1005

Phe His  His Ala His Asp Ala  Tyr Leu Asn Ala Val  Ile Ala Ser
    1010                 1015                 1020

Ala Leu  Leu Lys Lys Tyr Pro  Lys Leu Glu Pro Glu  Phe Val Tyr
    1025                 1030                 1035

Gly Asp  Tyr Pro Lys Tyr Asn  Ser Phe Arg Glu Arg  Lys Ser Ala
    1040                 1045                 1050

Thr Glu  Lys Val Tyr Phe Tyr  Ser Asn Ile Met Asn  Ile Phe Lys
    1055                 1060                 1065

Lys Ser  Ile Ser Leu Ala Asp  Gly Arg Val Ile Glu  Arg Pro Leu
    1070                 1075                 1080

Ile Glu  Val Asn Glu Glu Thr  Gly Glu Ser Val Trp  Asn Lys Glu
    1085                 1090                 1095

Ser Asp  Leu Ala Thr Val Arg  Arg Val Leu Ser Tyr  Pro Gln Val
    1100                 1105                 1110

Asn Val  Val Lys Lys Val Glu  Glu Gln Asn His Gly  Leu Asp Arg
    1115                 1120                 1125

Gly Lys  Pro Lys Gly Leu Phe  Asn Ala Asn Leu Ser  Ser Lys Pro
    1130                 1135                 1140

Lys Pro  Asn Ser Asn Glu Asn  Leu Val Gly Ala Lys  Glu Tyr Leu
    1145                 1150                 1155

Asp Pro  Lys Lys Tyr Gly Gly  Tyr Ala Gly Ile Ser  Asn Ser Phe
    1160                 1165                 1170

Ala Val  Leu Val Lys Gly Thr  Ile Glu Lys Gly Ala  Lys Lys Lys
    1175                 1180                 1185

Ile Thr  Asn Val Leu Glu Phe  Gln Gly Ile Ser Ile  Leu Asp Arg
    1190                 1195                 1200

Ile Asn  Tyr Arg Lys Asp Lys  Leu Asn Phe Leu Leu  Glu Lys Gly
    1205                 1210                 1215

Tyr Lys  Asp Ile Glu Leu Ile  Ile Glu Leu Pro Lys  Tyr Ser Leu
    1220                 1225                 1230

Phe Glu  Leu Ser Asp Gly Ser  Arg Arg Met Leu Ala  Ser Ile Leu
    1235                 1240                 1245

Ser Thr  Asn Asn Lys Arg Gly  Glu Ile His Lys Gly  Asn Gln Ile
    1250                 1255                 1260

Phe Leu  Ser Gln Lys Phe Val  Lys Leu Leu Tyr His  Ala Lys Arg
    1265                 1270                 1275

Ile Ser  Asn Thr Ile Asn Glu  Asn His Arg Lys Tyr  Val Glu Asn
    1280                 1285                 1290

His Lys  Lys Glu Phe Glu Glu  Leu Phe Tyr Tyr Ile  Leu Glu Phe
    1295                 1300                 1305

Asn Glu  Asn Tyr Val Gly Ala  Lys Lys Asn Gly Lys  Leu Leu Asn
    1310                 1315                 1320

Ser Ala  Phe Gln Ser Trp Gln  Asn His Ser Ile Asp  Glu Leu Cys
    1325                 1330                 1335

Ser Ser  Phe Ile Gly Pro Thr  Gly Ser Glu Arg Lys  Gly Leu Phe
    1340                 1345                 1350

Glu Leu  Thr Ser Arg Gly Ser  Ala Ala Asp Phe Glu  Phe Leu Gly
    1355                 1360                 1365

Val Lys  Ile Pro Arg Tyr Arg  Asp Tyr Thr Pro Ser  Ser Leu Leu
    1370                 1375                 1380

Lys Asp  Ala Thr Leu Ile His  Gln Ser Val Thr Gly  Leu Tyr Glu
    1385                 1390                 1395
```

```
Thr Arg  Ile Asp Leu Ala Lys  Leu Gly Glu Gly
    1400                 1405


<210> SEQ ID NO 9
<211> LENGTH: 1053
<212> TYPE: PRT
<213> ORGANISM: Staphylococcus aureus

<400> SEQUENCE: 9

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
```

-continued

```
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780
```

Asn Asp Thr Leu Tyr Ser Thr Arg Lys Asp Asp Lys Gly Asn Thr Leu
785 790 795 800

Ile Val Asn Asn Leu Asn Gly Leu Tyr Asp Lys Asp Asn Asp Lys Leu
805 810 815

Lys Lys Leu Ile Asn Lys Ser Pro Glu Lys Leu Leu Met Tyr His His
820 825 830

Asp Pro Gln Thr Tyr Gln Lys Leu Lys Leu Ile Met Glu Gln Tyr Gly
835 840 845

Asp Glu Lys Asn Pro Leu Tyr Lys Tyr Tyr Glu Glu Thr Gly Asn Tyr
850 855 860

Leu Thr Lys Tyr Ser Lys Lys Asp Asn Gly Pro Val Ile Lys Lys Ile
865 870 875 880

Lys Tyr Tyr Gly Asn Lys Leu Asn Ala His Leu Asp Ile Thr Asp Asp
885 890 895

Tyr Pro Asn Ser Arg Asn Lys Val Val Lys Leu Ser Leu Lys Pro Tyr
900 905 910

Arg Phe Asp Val Tyr Leu Asp Asn Gly Val Tyr Lys Phe Val Thr Val
915 920 925

Lys Asn Leu Asp Val Ile Lys Lys Glu Asn Tyr Tyr Glu Val Asn Ser
930 935 940

Lys Cys Tyr Glu Glu Ala Lys Lys Leu Lys Lys Ile Ser Asn Gln Ala
945 950 955 960

Glu Phe Ile Ala Ser Phe Tyr Asn Asn Asp Leu Ile Lys Ile Asn Gly
965 970 975

Glu Leu Tyr Arg Val Ile Gly Val Asn Asn Asp Leu Leu Asn Arg Ile
980 985 990

Glu Val Asn Met Ile Asp Ile Thr Tyr Arg Glu Tyr Leu Glu Asn Met
995 1000 1005

Asn Asp Lys Arg Pro Pro Arg Ile Ile Lys Thr Ile Ala Ser Lys
1010 1015 1020

Thr Gln Ser Ile Lys Lys Tyr Ser Thr Asp Ile Leu Gly Asn Leu
1025 1030 1035

Tyr Glu Val Lys Ser Lys Lys His Pro Gln Ile Ile Lys Lys Gly
1040 1045 1050

<210> SEQ ID NO 10
<211> LENGTH: 1365
<212> TYPE: PRT
<213> ORGANISM: Streptococcus pyogenes

<400> SEQUENCE: 10

Lys Tyr Ser Ile Gly Leu Asp Ile Gly Thr Asn Ser Val Gly Trp Ala
1 5 10 15

Val Ile Thr Asp Glu Tyr Lys Val Pro Ser Lys Lys Phe Lys Val Leu
20 25 30

Gly Asn Thr Asp Arg His Ser Ile Lys Lys Asn Leu Ile Gly Ala Leu
35 40 45

Leu Phe Asp Ser Gly Glu Thr Ala Glu Ala Thr Arg Leu Lys Arg Thr
50 55 60

Ala Arg Arg Arg Tyr Thr Arg Arg Lys Asn Arg Ile Cys Tyr Leu Gln
65 70 75 80

Glu Ile Phe Ser Asn Glu Met Ala Lys Val Asp Asp Ser Phe Phe His
85 90 95

Arg Leu Glu Glu Ser Phe Leu Val Glu Glu Asp Lys Lys His Glu Arg

-continued

```
            100                 105                 110

His Pro Ile Phe Gly Asn Ile Val Asp Glu Val Ala Tyr His Glu Lys
        115                 120                 125

Tyr Pro Thr Ile Tyr His Leu Arg Lys Lys Leu Val Asp Ser Thr Asp
    130                 135                 140

Lys Ala Asp Leu Arg Leu Ile Tyr Leu Ala Leu Ala His Met Ile Lys
145                 150                 155                 160

Phe Arg Gly His Phe Leu Ile Glu Gly Asp Leu Asn Pro Asp Asn Ser
                165                 170                 175

Asp Val Asp Lys Leu Phe Ile Gln Leu Val Gln Thr Tyr Asn Gln Leu
            180                 185                 190

Phe Glu Glu Asn Pro Ile Asn Ala Ser Gly Val Asp Ala Lys Ala Ile
        195                 200                 205

Leu Ser Ala Arg Leu Ser Lys Ser Arg Arg Leu Glu Asn Leu Ile Ala
    210                 215                 220

Gln Leu Pro Gly Glu Lys Lys Asn Gly Leu Phe Gly Asn Leu Ile Ala
225                 230                 235                 240

Leu Ser Leu Gly Leu Thr Pro Asn Phe Lys Ser Asn Phe Asp Leu Ala
                245                 250                 255

Glu Asp Ala Lys Leu Gln Leu Ser Lys Asp Thr Tyr Asp Asp Asp Leu
            260                 265                 270

Asp Asn Leu Leu Ala Gln Ile Gly Asp Gln Tyr Ala Asp Leu Phe Leu
        275                 280                 285

Ala Ala Lys Asn Leu Ser Asp Ala Ile Leu Leu Ser Asp Ile Leu Arg
    290                 295                 300

Val Asn Thr Glu Ile Thr Lys Ala Pro Leu Ser Ala Ser Met Ile Lys
305                 310                 315                 320

Arg Tyr Asp Glu His His Gln Asp Leu Thr Leu Leu Lys Ala Leu Val
                325                 330                 335

Arg Gln Gln Leu Pro Glu Lys Tyr Lys Glu Ile Phe Phe Asp Gln Ser
            340                 345                 350

Lys Asn Gly Tyr Ala Gly Tyr Ile Asp Gly Gly Ala Ser Gln Glu Glu
        355                 360                 365

Phe Tyr Lys Phe Ile Lys Pro Ile Leu Glu Lys Met Asp Gly Thr Glu
    370                 375                 380

Glu Leu Leu Val Lys Leu Asn Arg Glu Asp Leu Leu Arg Lys Gln Arg
385                 390                 395                 400

Thr Phe Asp Asn Gly Ser Ile Pro His Gln Ile His Leu Gly Glu Leu
                405                 410                 415

His Ala Ile Leu Arg Arg Gln Glu Asp Phe Tyr Pro Phe Leu Lys Asp
            420                 425                 430

Asn Arg Glu Lys Ile Glu Lys Ile Leu Thr Phe Arg Ile Pro Tyr Tyr
        435                 440                 445

Val Gly Pro Leu Ala Arg Gly Asn Ser Arg Phe Ala Trp Met Thr Arg
    450                 455                 460

Lys Ser Glu Glu Thr Ile Thr Pro Trp Asn Phe Glu Glu Val Val Asp
465                 470                 475                 480

Lys Gly Ala Ser Ala Gln Ser Phe Ile Glu Arg Met Thr Asn Phe Asp
                485                 490                 495

Lys Asn Leu Pro Asn Glu Lys Val Leu Pro Lys His Ser Leu Leu Tyr
            500                 505                 510

Glu Tyr Phe Thr Val Tyr Asn Glu Leu Thr Lys Val Lys Tyr Val Thr
        515                 520                 525
```

```
Glu Gly Met Arg Lys Pro Ala Phe Leu Ser Gly Glu Gln Lys Lys Ala
    530                 535                 540

Ile Val Asp Leu Leu Phe Lys Thr Asn Arg Lys Val Thr Val Lys Gln
545                 550                 555                 560

Leu Lys Glu Asp Tyr Phe Lys Lys Ile Glu Cys Phe Asp Ser Val Glu
                565                 570                 575

Ile Ser Gly Val Glu Asp Arg Phe Asn Ala Ser Leu Gly Thr Tyr His
            580                 585                 590

Asp Leu Leu Lys Ile Ile Lys Asp Lys Asp Phe Leu Asp Asn Glu Glu
        595                 600                 605

Asn Glu Asp Ile Leu Glu Asp Ile Val Leu Thr Leu Thr Leu Phe Glu
    610                 615                 620

Asp Arg Glu Met Ile Glu Glu Arg Leu Lys Thr Tyr Ala His Leu Phe
625                 630                 635                 640

Asp Asp Lys Val Met Lys Gln Leu Lys Arg Arg Arg Tyr Thr Gly Trp
                645                 650                 655

Gly Arg Leu Ser Arg Lys Leu Ile Asn Gly Ile Arg Asp Lys Gln Ser
            660                 665                 670

Gly Lys Thr Ile Leu Asp Phe Leu Lys Ser Asp Gly Phe Ala Asn Arg
        675                 680                 685

Asn Phe Met Gln Leu Ile His Asp Asp Ser Leu Thr Phe Lys Glu Asp
    690                 695                 700

Ile Gln Lys Ala Gln Val Ser Gly Gln Gly Asp Ser Leu His Glu His
705                 710                 715                 720

Ile Ala Asn Leu Ala Gly Ser Pro Ala Ile Lys Lys Gly Ile Leu Gln
                725                 730                 735

Thr Val Lys Val Val Asp Glu Leu Val Lys Val Met Gly Arg His Lys
            740                 745                 750

Pro Glu Asn Ile Val Ile Glu Met Ala Arg Glu Asn Gln Thr Thr Gln
        755                 760                 765

Lys Gly Gln Lys Asn Ser Arg Glu Arg Met Lys Arg Ile Glu Glu Gly
    770                 775                 780

Ile Lys Glu Leu Gly Ser Gln Ile Leu Lys Glu His Pro Val Glu Asn
785                 790                 795                 800

Thr Gln Leu Gln Asn Glu Lys Leu Tyr Leu Tyr Tyr Leu Gln Asn Gly
                805                 810                 815

Arg Asp Met Tyr Val Asp Gln Glu Leu Asp Ile Asn Arg Leu Ser Asp
            820                 825                 830

Tyr Asp Val Asp His Ile Val Pro Gln Ser Phe Leu Lys Asp Asp Ser
        835                 840                 845

Ile Asp Asn Lys Val Leu Thr Arg Ser Asp Lys Asn Arg Gly Lys Ser
    850                 855                 860

Asp Asn Val Pro Ser Glu Glu Val Val Lys Lys Met Lys Asn Tyr Trp
865                 870                 875                 880

Arg Gln Leu Leu Asn Ala Lys Leu Ile Thr Gln Arg Lys Phe Asp Asn
                885                 890                 895

Leu Thr Lys Ala Glu Arg Gly Gly Leu Ser Glu Leu Asp Lys Ala Gly
            900                 905                 910

Phe Ile Lys Arg Gln Leu Val Glu Thr Arg Gln Ile Thr Lys His Val
        915                 920                 925

Ala Gln Ile Leu Asp Ser Arg Met Asn Thr Lys Tyr Asp Glu Asn Asp
    930                 935                 940
```

-continued

```
Lys Leu Ile Arg Glu Val Lys Val Ile Thr Leu Lys Ser Lys Leu Val
945                 950                 955                 960

Ser Asp Phe Arg Lys Asp Phe Gln Phe Tyr Lys Val Arg Glu Ile Asn
                965                 970                 975

Asn Tyr His His Ala His Asp Ala Tyr Leu Asn Ala Val Val Gly Thr
            980                 985                 990

Ala Leu Ile Lys Lys Tyr Pro Lys  Leu Glu Ser Glu Phe  Val Tyr Gly
        995                 1000                 1005

Asp Tyr  Lys Val Tyr Asp Val  Arg Lys Met Ile Ala  Lys Ser Glu
    1010                 1015                 1020

Gln Glu  Ile Gly Lys Ala Thr  Ala Lys Tyr Phe Phe  Tyr Ser Asn
    1025                 1030                 1035

Ile Met  Asn Phe Phe Lys Thr  Glu Ile Thr Leu Ala  Asn Gly Glu
    1040                 1045                 1050

Ile Arg  Lys Arg Pro Leu Ile  Glu Thr Asn Gly Glu  Thr Gly Glu
    1055                 1060                 1065

Ile Val  Trp Asp Lys Gly Arg  Asp Phe Ala Thr Val  Arg Lys Val
    1070                 1075                 1080

Leu Ser  Met Pro Gln Val Asn  Ile Val Lys Lys Thr  Glu Val Gln
    1085                 1090                 1095

Thr Gly  Gly Phe Ser Lys Glu  Ser Ile Leu Pro Lys  Arg Asn Ser
    1100                 1105                 1110

Asp Lys  Leu Ile Ala Arg Lys  Lys Asp Trp Asp Pro  Lys Lys Tyr
    1115                 1120                 1125

Gly Gly  Phe Asp Ser Pro Thr  Val Ala Tyr Ser Val  Leu Val Val
    1130                 1135                 1140

Ala Lys  Val Glu Lys Gly Lys  Ser Lys Lys Leu Lys  Ser Val Lys
    1145                 1150                 1155

Glu Leu  Leu Gly Ile Thr Ile  Met Glu Arg Ser Ser  Phe Glu Lys
    1160                 1165                 1170

Asn Pro  Ile Asp Phe Leu Glu  Ala Lys Gly Tyr Lys  Glu Val Lys
    1175                 1180                 1185

Lys Asp  Leu Ile Ile Lys Leu  Pro Lys Tyr Ser Leu  Phe Glu Leu
    1190                 1195                 1200

Glu Asn  Gly Arg Lys Arg Met  Leu Ala Ser Ala Gly  Glu Leu Gln
    1205                 1210                 1215

Lys Gly  Asn Glu Leu Ala Leu  Pro Ser Lys Tyr Val  Asn Phe Leu
    1220                 1225                 1230

Tyr Leu  Ala Ser His Tyr Glu  Lys Leu Lys Gly Ser  Pro Glu Asp
    1235                 1240                 1245

Asn Glu  Gln Lys Gln Leu Phe  Val Glu Gln His Lys  His Tyr Leu
    1250                 1255                 1260

Asp Glu  Ile Ile Glu Gln Ile  Ser Glu Phe Ser Lys  Arg Val Ile
    1265                 1270                 1275

Leu Ala  Asp Ala Asn Leu Asp  Lys Val Leu Ser Ala  Tyr Asn Lys
    1280                 1285                 1290

His Arg  Asp Lys Pro Ile Arg  Glu Gln Ala Glu Asn  Ile Ile His
    1295                 1300                 1305

Leu Phe  Thr Leu Thr Asn Leu  Gly Ala Pro Ala Ala  Phe Lys Tyr
    1310                 1315                 1320

Phe Asp  Thr Thr Ile Asp Arg  Lys Arg Tyr Thr Ser  Thr Lys Glu
    1325                 1330                 1335

Val Leu  Asp Ala Thr Leu Ile  His Gln Ser Ile Thr  Gly Leu Tyr
```

```
    1340                1345                1350

Glu Thr  Arg Ile Asp Leu Ser  Gln Leu Gly Gly Asp
    1355                1360                1365


<210> SEQ ID NO 11
<211> LENGTH: 288
<212> TYPE: PRT
<213> ORGANISM: Artificial Sequence
<220> FEATURE:
<223> OTHER INFORMATION: Synthetic N-terminal capping region

<400> SEQUENCE: 11

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285


<210> SEQ ID NO 12
<211> LENGTH: 183
<212> TYPE: PRT
<213> ORGANISM: Artificial Sequence
<220> FEATURE:
<223> OTHER INFORMATION: Synthetic C-terminal capping region

<400> SEQUENCE: 12
```

-continued

```
Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180
```

<210> SEQ ID NO 13
<211> LENGTH: 7
<212> TYPE: PRT
<213> ORGANISM: Simian virus 40

<400> SEQUENCE: 13

```
Pro Lys Lys Lys Arg Lys Val
1               5
```

<210> SEQ ID NO 14
<211> LENGTH: 10
<212> TYPE: PRT
<213> ORGANISM: Simian virus 40

<400> SEQUENCE: 14

```
Pro Lys Lys Lys Arg Lys Val Glu Ala Ser
1               5                   10
```

<210> SEQ ID NO 15
<211> LENGTH: 16
<212> TYPE: PRT
<213> ORGANISM: Artificial Sequence
<220> FEATURE:
<223> OTHER INFORMATION: Synthetic nucleoplasmin bipartite NLS

<400> SEQUENCE: 15

```
Lys Arg Pro Ala Ala Thr Lys Lys Ala Gly Gln Ala Lys Lys Lys Lys
1               5                   10                  15
```

<210> SEQ ID NO 16
<211> LENGTH: 9
<212> TYPE: PRT
<213> ORGANISM: Homo sapiens

<400> SEQUENCE: 16

```
Pro Ala Ala Lys Arg Val Lys Leu Asp
1               5


<210> SEQ ID NO 17
<211> LENGTH: 11
<212> TYPE: PRT
<213> ORGANISM: Homo sapiens

<400> SEQUENCE: 17

Arg Gln Arg Arg Asn Glu Leu Lys Arg Ser Pro
1               5                   10


<210> SEQ ID NO 18
<211> LENGTH: 38
<212> TYPE: PRT
<213> ORGANISM: Homo sapiens

<400> SEQUENCE: 18

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35


<210> SEQ ID NO 19
<211> LENGTH: 42
<212> TYPE: PRT
<213> ORGANISM: Homo sapiens

<400> SEQUENCE: 19

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40


<210> SEQ ID NO 20
<211> LENGTH: 8
<212> TYPE: PRT
<213> ORGANISM: Homo sapiens

<400> SEQUENCE: 20

Val Ser Arg Lys Arg Pro Arg Pro
1               5


<210> SEQ ID NO 21
<211> LENGTH: 8
<212> TYPE: PRT
<213> ORGANISM: Homo sapiens

<400> SEQUENCE: 21

Pro Pro Lys Lys Ala Arg Glu Asp
1               5


<210> SEQ ID NO 22
<211> LENGTH: 8
<212> TYPE: PRT
<213> ORGANISM: Homo sapiens

<400> SEQUENCE: 22

Pro Gln Pro Lys Lys Lys Pro Leu
```

1 5

<210> SEQ ID NO 23
<211> LENGTH: 12
<212> TYPE: PRT
<213> ORGANISM: Mus sp.

<400> SEQUENCE: 23

Ser Ala Leu Ile Lys Lys Lys Lys Lys Met Ala Pro
1 5 10

<210> SEQ ID NO 24
<211> LENGTH: 5
<212> TYPE: PRT
<213> ORGANISM: Influenza virus

<400> SEQUENCE: 24

Asp Arg Leu Arg Arg
1 5

<210> SEQ ID NO 25
<211> LENGTH: 7
<212> TYPE: PRT
<213> ORGANISM: Influenza virus

<400> SEQUENCE: 25

Pro Lys Gln Lys Lys Arg Lys
1 5

<210> SEQ ID NO 26
<211> LENGTH: 10
<212> TYPE: PRT
<213> ORGANISM: Hepatitis D virus

<400> SEQUENCE: 26

Arg Lys Leu Lys Lys Lys Ile Lys Lys Leu
1 5 10

<210> SEQ ID NO 27
<211> LENGTH: 10
<212> TYPE: PRT
<213> ORGANISM: Mus sp.

<400> SEQUENCE: 27

Arg Glu Lys Lys Lys Phe Leu Lys Arg Arg
1 5 10

<210> SEQ ID NO 28
<211> LENGTH: 20
<212> TYPE: PRT
<213> ORGANISM: Homo sapiens

<400> SEQUENCE: 28

Lys Arg Lys Gly Asp Glu Val Asp Gly Val Asp Glu Val Ala Lys Lys
1 5 10 15

Lys Ser Lys Lys
20

<210> SEQ ID NO 29
<211> LENGTH: 17
<212> TYPE: PRT
<213> ORGANISM: Homo sapiens -continued

```
<400> SEQUENCE: 29

Arg Lys Cys Leu Gln Ala Gly Met Asn Leu Glu Ala Arg Lys Thr Lys
1               5                   10                  15

Lys
```